US012138305B2

(12) United States Patent
Weissman et al.

(10) Patent No.: US 12,138,305 B2
(45) Date of Patent: Nov. 12, 2024

(54) NUCLEOSIDE-MODIFIED RNA FOR INDUCING AN ADAPTIVE IMMUNE RESPONSE

(71) Applicant: The Trustees of the University of Pennsylvania, Philadelphia, PA (US)

(72) Inventors: Drew Weissman, Wynnewood, PA (US); Norbert Pardi, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 93 days.

(21) Appl. No.: 17/705,837

(22) Filed: Mar. 28, 2022

(65) Prior Publication Data
US 2022/0226461 A1  Jul. 21, 2022

Related U.S. Application Data

(63) Continuation of application No. 15/569,546, filed as application No. PCT/US2016/029572 on Apr. 27, 2016, now abandoned.

(60) Provisional application No. 62/153,143, filed on Apr. 27, 2015.

(51) Int. Cl.
| | |
|---|---|
| A61K 39/12 | (2006.01) |
| A61K 9/00 | (2006.01) |
| A61K 9/127 | (2006.01) |
| A61K 31/7115 | (2006.01) |
| A61K 31/712 | (2006.01) |
| A61K 39/00 | (2006.01) |
| A61K 39/002 | (2006.01) |
| A61K 39/02 | (2006.01) |
| A61K 39/145 | (2006.01) |
| A61P 31/16 | (2006.01) |
| A61P 31/18 | (2006.01) |
| C07C 219/08 | (2006.01) |
| C07D 295/13 | (2006.01) |
| C12N 15/11 | (2006.01) |
| A61P 35/00 | (2006.01) |

(52) U.S. Cl.
CPC ............ *A61K 39/12* (2013.01); *A61K 9/0019* (2013.01); *A61K 9/127* (2013.01); *A61K 31/7115* (2013.01); *A61K 31/712* (2013.01); *A61K 39/0011* (2013.01); *A61K 39/002* (2013.01); *A61K 39/02* (2013.01); *A61K 39/145* (2013.01); *A61P 31/16* (2018.01); *A61P 31/18* (2018.01); *C07C 219/08* (2013.01); *C07D 295/13* (2013.01); *C12N 15/11* (2013.01); *A61K 2039/51* (2013.01); *A61K 2039/55555* (2013.01); *A61P 35/00* (2018.01)

(58) Field of Classification Search
None
See application file for complete search history.

(56) References Cited

U.S. PATENT DOCUMENTS

| | | |
|---|---|---|
| 2,856,420 A | 10/1958 | Crawford, Jr. |
| 3,340,299 A | 9/1967 | Weintraub |
| 3,931,430 A | 1/1976 | Tada |
| 6,034,137 A | 3/2000 | Belloni |
| 6,333,433 B1 | 12/2001 | Banerjee |
| 6,458,381 B1 | 10/2002 | Sourovoi |
| 8,278,036 B2 | 10/2012 | Kariko |
| 8,748,089 B2 | 6/2014 | Kariko |
| 8,835,108 B2 | 9/2014 | Kariko |
| 9,352,042 B2 | 5/2016 | Heyes |
| 9,737,619 B2 | 8/2017 | Ansell |
| 9,738,593 B2 | 8/2017 | Ansell |
| 9,750,824 B2 | 9/2017 | Kariko |
| 9,795,566 B2 | 10/2017 | Oya |
| 10,106,490 B2 | 10/2018 | Du |
| 10,144,725 B2 | 12/2018 | Brown |
| 10,166,298 B2 | 1/2019 | Ansell |
| 10,221,127 B2 | 3/2019 | Du |
| 10,723,692 B2 | 7/2020 | Ansell |
| 2003/0153081 A1 | 8/2003 | Tagawa |
| 2005/0032730 A1 | 2/2005 | Von |
| 2005/0059624 A1 | 3/2005 | Hoerr |
| 2005/0250723 A1 | 11/2005 | Hoerr |
| 2006/0100177 A1 | 5/2006 | Nishimura |
| 2006/0188490 A1 | 8/2006 | Hoerr |
| 2008/0025944 A1 | 1/2008 | Hoerr |
| 2009/0324584 A1 | 12/2009 | Hoerr |
| 2010/0189729 A1 | 7/2010 | Hoerr |

(Continued)

FOREIGN PATENT DOCUMENTS

| | | |
|---|---|---|
| EP | 1083232 A1 | 3/2001 |
| EP | 2567951 | 3/2013 |

(Continued)

OTHER PUBLICATIONS

"Hepacivirus C", UniprotKB, (Mar. 21, 2012), Database accession No. H2FJ05_9HEPC, XP055535308, 4 pages.

Akinc et al., "A combinatorial library of lipid-like materials for delivery of RNAi therapeutics," Nature Biotechnology 26 (5):561-569, May 2008.

(Continued)

*Primary Examiner* — Nicole Kinsey White
(74) *Attorney, Agent, or Firm* — Riverside Law LLP

(57) ABSTRACT

The present invention relates to compositions and methods for inducing an adaptive immune response in a subject. In certain embodiments, the present invention provides a composition comprising a nucleoside-modified nucleic acid molecule encoding an antigen, adjuvant, or a combination thereof. For example, in certain embodiments, the composition comprises a vaccine comprising a nucleoside-modified nucleic acid molecule encoding an antigen, adjuvant, or a combination thereof.

13 Claims, 50 Drawing Sheets
Specification includes a Sequence Listing.

(56) References Cited

U.S. PATENT DOCUMENTS

| | | |
|---|---|---|
| 2010/0203076 A1 | 8/2010 | Fotin-Mleczek |
| 2010/0291156 A1 | 11/2010 | Barner |
| 2010/0305196 A1 | 12/2010 | Probst |
| 2011/0150921 A1 | 6/2011 | Roingeard |
| 2011/0250225 A1 | 10/2011 | Fotin-Mleczek |
| 2011/0256175 A1 | 10/2011 | Hope |
| 2011/0300205 A1 | 12/2011 | Geall |
| 2011/0305770 A1 | 12/2011 | Zhao |
| 2012/0021043 A1 | 1/2012 | Kramps |
| 2012/0276209 A1 | 11/2012 | Cullis |
| 2012/0288510 A1 | 11/2012 | Ambrosino |
| 2013/0129754 A1 | 5/2013 | Thess |
| 2013/0259879 A1 | 10/2013 | Baumhof |
| 2013/0261172 A1 | 10/2013 | Kariko |
| 2013/0266640 A1 | 10/2013 | De Fougerolles |
| 2013/0280283 A1 | 10/2013 | Lorenz |
| 2013/0280305 A1 | 10/2013 | Kuboyama |
| 2013/0295043 A1 | 11/2013 | Kallen |
| 2013/0336998 A1 | 12/2013 | Kallen |
| 2014/0134175 A1 | 5/2014 | Ambrosino |
| 2014/0323548 A1 | 10/2014 | Budzik |
| 2015/0037326 A1 | 2/2015 | Butler-Ransohoff |
| 2015/0050302 A1 | 2/2015 | Thess |
| 2015/0057340 A1 | 2/2015 | Thess |
| 2015/0093413 A1 | 4/2015 | Thess |
| 2015/0118183 A1 | 4/2015 | Baumhof |
| 2015/0118264 A1 | 4/2015 | Baumhof |
| 2015/0165006 A1 | 6/2015 | Thess |
| 2015/0184195 A1 | 7/2015 | Thess |
| 2015/0203446 A1 | 7/2015 | Manoharan |
| 2015/0218554 A1 | 8/2015 | Thess |
| 2015/0306249 A1 | 10/2015 | Baumhof |
| 2015/0376115 A1 | 12/2015 | Ansell |
| 2016/0130345 A1 | 5/2016 | Fotin-Mleczek |
| 2016/0166668 A1 | 6/2016 | Kallen |
| 2016/0166678 A1 | 6/2016 | Kallen |
| 2016/0166710 A1 | 6/2016 | Baumhof |
| 2016/0166711 A1 | 6/2016 | Schnee |
| 2016/0168207 A1 | 6/2016 | Kramps |
| 2016/0168227 A1 | 6/2016 | Kallen |
| 2016/0235864 A1 | 8/2016 | Schlake |
| 2016/0304883 A1 | 10/2016 | Grund |
| 2016/0331828 A1 | 11/2016 | Ciaramella |
| 2016/0361411 A1 | 12/2016 | Gindy |
| 2016/0376224 A1 | 12/2016 | Du |
| 2017/0029847 A1 | 2/2017 | Thess |
| 2017/0119904 A1 | 5/2017 | Ansell |
| 2017/0157268 A1 | 6/2017 | Ansell |
| 2017/0252430 A1 | 9/2017 | Fotin-Mleczek |
| 2017/0283367 A1 | 10/2017 | Ansell |
| 2017/0326225 A1 | 11/2017 | Rauch |
| 2018/0044687 A1 | 2/2018 | Thess |
| 2018/0125952 A1 | 5/2018 | Fotin-Mleczek |
| 2018/0126003 A1 | 5/2018 | Hoerr |
| 2018/0148727 A1 | 5/2018 | Grund |
| 2018/0214537 A1 | 8/2018 | Mutzke |
| 2018/0237786 A1 | 8/2018 | Schlake |
| 2018/0296663 A1 | 10/2018 | Hipp |
| 2018/0312545 A1 | 11/2018 | Baumhof |
| 2019/0022247 A1 | 1/2019 | Ansell |
| 2019/0024096 A1 | 1/2019 | Schmid |
| 2019/0160164 A1 | 5/2019 | Rauch |
| 2019/0270697 A1 | 9/2019 | Ansell |
| 2019/0274968 A1 | 9/2019 | Weissman |
| 2019/0314524 A1 | 10/2019 | Ansell |
| 2019/0359556 A1 | 11/2019 | Du |
| 2020/0046838 A1 | 2/2020 | Ansell |
| 2020/0121809 A1 | 4/2020 | Hope |
| 2020/0163878 A1 | 5/2020 | Baumhof |
| 2020/0172472 A1 | 6/2020 | Du |
| 2020/0283372 A1 | 9/2020 | Du |
| 2021/0107861 A1 | 4/2021 | Ansell |

FOREIGN PATENT DOCUMENTS

| | | |
|---|---|---|
| EP | 3289083 | 3/2018 |
| JP | 2001338416 | 12/2001 |
| JP | 5331118 | 12/2010 |
| WO | 1987007183 | 12/1987 |
| WO | 1997003939 | 2/1997 |
| WO | 1999005094 | 2/1999 |
| WO | 2000030444 | 6/2000 |
| WO | 2003053409 | 7/2003 |
| WO | 2005004910 | 1/2005 |
| WO | 2005060934 | 7/2005 |
| WO | 2006138380 A2 | 12/2006 |
| WO | 2007024708 | 3/2007 |
| WO | 2011143230 | 11/2011 |
| WO | 2011153493 | 12/2011 |
| WO | 2012016184 | 2/2012 |
| WO | 2012068176 | 5/2012 |
| WO | 2013016058 | 1/2013 |
| WO | 2013086373 | 6/2013 |
| WO | 2013143555 | 10/2013 |
| WO | 2014028487 | 2/2014 |
| WO | 2014160243 | 10/2014 |
| WO | 2014160284 | 10/2014 |
| WO | 2015164674 A1 | 10/2015 |
| WO | 2015177752 A1 | 11/2015 |
| WO | 2015199952 | 12/2015 |
| WO | 2016176330 | 11/2016 |
| WO | 2017006182 | 1/2017 |
| WO | 2017021546 | 2/2017 |
| WO | 2017048770 | 3/2017 |
| WO | 2017049245 | 3/2017 |
| WO | 2017075531 A1 | 5/2017 |
| WO | 2017140905 | 8/2017 |
| WO | 2017173054 | 10/2017 |
| WO | 2017182634 | 10/2017 |
| WO | 2018191657 | 10/2018 |

OTHER PUBLICATIONS

Akinc et al., 2010, "Targeted delivery of RNAi therapeutics with endogenous and exogenous ligand-based mechanisms." Mol Ther., 18(7): 1357-1364.

Alabi C.A, et al., PNAS, vol. 110, No. 32, doi: 1-.1073/PNAS. 1306529110, ISSN 0027-8424, pp. 12881-12886, Aug. 6, 2013.

Alexandros N. Alexidis, et al., Journal of Pharmacy and Pharmacology, (Mar. 28, 1995), vol. 47, No. 2, doi: 10.1111/j.2042-7158. 1995.tb05765.X, ISSN 0022-3573, pp. 131-137.

Anderson et al., 2010, "Incorporation of pseudouridine into mRNA enhances translation by diminishing PKR activation." Nucleic Acids Res 38:5884-5892.

Anderson et al., 2011. Nucleoside modifications in RNA limit activation of 2'-5'-oligoadenylate synthetase and increase resistance to cleavage by RNase L. Nucleic Acids Research 39:9329-9338.

Ansell et al., "Novel Lipids and Lipid Nanoparticle Formulations for Delivery of Nucleic Acids," U.S. Appl. No. 17/317,517, filed May 11, 2021.

Basha et al., 2011, "Influence of cationic lipid composition on gene silencing properties of lipid nanoparticle formulations of siRNA in antigen-presenting cells." Mol Ther, 19(12): 2186-2200.

Belliveau et al., 2012, "Microfluidic Synthesis of Highly Potent Limit-size Lipid Nanoparticles for in Vivo Delivery of siRNA." Mol Ther Nucleic Acids, 1: e37, 9 pages.

Bhattacharya et al., "Synthesis, Thermotropic Behavior, and Permeability Properties of Vesicular Membranes Composed of Cationic Mixed-Chain Surfactants," Langmuir 11:4748-4757, 1995.

Brito et al: 'Self-Amplifying mRNA Vaccines,' Adv Genet, 2015;89:179-233.

Cattanach C.J, et al., Journal of the Chemical Society C: Organic, (Jan. 1, 1968), doi: 10.1039/j39680001235, ISSN 0022-4852, 9 pages.

Chen et al., "Influence of particle size on the in vivo potency of lipid nanoparticle formulations of siRNA," Journal of Controlled Release 235:236-244, 2016.

Cook CJ, et al., "Synthesis and characterization of cis-dioxomolybdenum(VI) complexes with sterically bulky tripodal tetradentate ligands," Onorganica Chimica Acta (Jan. 1, 1988), pp. 81-87.

(56) References Cited

OTHER PUBLICATIONS

D.N. Nguyen et al: "Lipid-derived nanoparticles for immunostimulatory RNA adjuvant delivery", Proceedings of the National Academy of Sciences of the United States of America, vol. 109, No. 14, Apr. 3, 2012 (Apr. 3, 2012), pp. E797-E803.
Durbin et al., "RNAs Containing Modified Nucleotides Fail to Trigger RIG-I Conformational Changes for Innate Immune Signaling," mBio 7(5):e00833-16, 2016 (11 pages).
Ernsting et al., "Factors controlling the pharmacokinetics, biodistribution and intratumoral penetration of nanoparticles," Journal of Controlled Release 172:782-794, 2013.
Falcone et al., "Both the 5' Untranslated Region and the Sequences Surrounding the Start Site Contribute to Efficient Initiation of Translation in Vitro," Molecular and Cellular Biology 11(5):2656-2664, 1991.
Frish, et al.; "A New Triantennary Galatose-Targeted PEGylated Gene Carrier, Characterization of Its Complex with DNA, and Transfection of Hepatoma Cells", Bioconjugate Chem., 2004, vol. 15, p. 754-764.
Han et al., "Synthesis and Properties of Di-Chain Esterquat Surfactants," J. Surfact Deterg. 18: 91-95, 2015.
Hekele et al., "Rapidly produced SAM® vaccine against H7N9 influenza is immunogenic in mice," Emerging Microbes and Infections 2:e52, 2013 (7 pages).
Hsu et al., "Hepatitis C virus glycoproteins mediate pH-dependent cell entry of pseudotyped retroviral particles," Proc Natl Acad Sci U S A, Jun. 10, 2003;100(12):7271-6.
Jayaraman, M et al., "Maximizing the Potency of siRNA Lipid Nanoparticles for Hepatic Gene Silencing in Vivo.", Angewandte Chemie, (Jul. 10, 2012), vol. 51, No. 34, pp. 8529-8533, XP055063645.
Karikó et al., "Incorporation of Pseudouridine Into mRNA Yields Superior Nonimmunogenic Vector With Increased Translational Capacity and Biological Stability," Mol Ther, vol. 16, Issue 11, Nov. 2008, pp. 1833-1840.
Karikó et al., "Suppression of RNA Recognition by Toll-like Receptors: The Impact of Nucleoside Modification and the Evolutionary Origin of RNA," Immunity, Aug. 2005, vol. 23, 165-175.
Kariko et al., 2011. Generating the optimal mRNA for therapy: HPLC purification eliminates immune activation and improves translation of nucleosidemodified, protein-encoding mRNA. Nucleic Acids Research 39(21):e142, pp. 1-10.
Karikó et al., 2012, "Increased Erythropoiesis in Mice Injected with Submicrogram Quantities of Pseudouridine-containing mRNA Encoding Erythropoietin." Mol Ther 20:948-953.
Kathryn A Whitehead et al: "Synergistic Silencing: Combinations of Lipid-like Materials for Efficacious siRNA Delivery", Molecular Therapy, vol. 19, No. 9, Sep. 1, 2011 (Sep. 1, 2011), pp. 1688-1694.
Krol et al., "Anti-Hepatitis C Virus Activity of Uridine Derivatives of 2-Deoxy Sugars," Molecules 2018, 23(7), 1547.
Lee et al., 2012, "Lipid nanoparticle siRNA systems for silencing the androgen receptor in human prostate cancer in vivo." Int J Cancer., 131(5): E781-90.
Leroueil et al., "Wide Varieties of Cationic Nanoparticles Induce Defects in Supported Lipid Bilayers," Nano Letters 8 (2):420-424, 2008.
Leung et al., "Microfluidic Mixing: A General Method for Encapsulating Macromolecules in Lipid Nanoparticle Systems," J. Phys. Chem. B 119:8698-8706, 2015.
Leung et al., 2012, "Lipid Nanoparticles Containing siRNA Synthesized by Microfluidic Mixing Exhibit an Electron-Dense Nanostructured Core." J Phys Chem C Nanomater Interfaces, 116(34): 18440-18450.
Liu et al., "Spontaneous clearance of primary acute hepatitis C virus infection correlated with high initial viral RNA level and rapid HVR1 evolution." Hepatology, Jun. 2012;55(6):1684-91.
Luis A Brito et al: "A Cationic Nanoemulsion for the Delivery of Next-generation RNA Vaccines", Molecular Therapy, vol. 22, No. 12, Jul. 16, 2014 (Jul. 16, 2014) pp. 2118-2129.
Maier et al., 2013, "Biodegradable lipids enabling rapidly eliminated lipid nanoparticles for systemic delivery of RNAi therapeutics." Mol Ther., 21(8): 1570-1578, XP055551712, ISSN: 1525-0016.
Masuda et al., "Envelope-type lipid nanoparticles incorporating a short PEG-lipid conjugate for improved control of intracellular trafficking and transgene transcription," Biomaterials 30:4806-4814, 2009.
Mui et al., 2013, "Influence of Polyethylene Glycol Lipid Desorption Rates on Pharmacokinetics and Pharmacodynamics of siRNA Lipid Nanoparticles." Mol Ther Nucleic Acids. 2, e139, 8 pages.
Pardi et al., "Expression kinetics of nucleoside-modified mRNA delivered in lipid nanoparticles to mice by various routes," Journal of Controlled Release vol. 217, Nov. 10, 2015, pp. 345-351.
Petsch et al., "Protective efficacy of in vitro synthesized, specific mRNA vaccines against influenza A virus infection," Nature Biotechnology 30:1210-1216, 2012.
Rajesh et al., "Dramatic Influence of the Orientation of Linker between Hydrophilic and Hydrophobic Lipid Moiety in Liposomal Gene Delivery," Journal of the American Chemical Society 129(37):11408-11420, 2007.
Schnee et al., "An mRNA Vaccine Encoding Rabies Virus Glycoprotein Induces Protection against Lethal Infection in Mice and Correlates of Protection in Adult and Newborn Pigs," PLoS Negl. Trop. Dis. 10(6):e0004746, 2016, 20 pages.
Semple et al., 2010, "Rational design of cationic lipids for siRNA delivery." Nat Biotechnol., 28(2):172-176.
Szebeni et al., "Activation of complement by therapeutic liposomes and other lipid excipient-based therapeutic products: Prediction and prevention," Advanced Drug Delivery Reviews 63:1020-1030, 2011.
Szebeni et al., "Complement activation as a bioequivalence issue relevant to the development of generic liposomes and other nanoparticulate drugs," Biochemical and Biophysical Research Communications 468:490-497, 2015.
Szebeni, "Complement activation-related pseudoallergy: A stress reaction in blood triggered by nanomedicines and biologicals," Molecular Immunology 61:163-173, 2014.
Tam et al., "Advances in Lipid Nanoparticles for siRNA Delivery," Pharmaceutics 5:498-507, 2013.
Tam et al., 2013, "Small molecule ligands for enhanced intracellular delivery of lipid nanoparticle formulations of siRNA." Nanomedicine, 9(5): 665-74.
Tomokazu Yoshimura et al., Journal of Oleo Science, (Jan. 1, 2013), vo. 62, No. 4, doi: 10.5650/jos.62.213, ISSN 1345-8957, pp. 213-221.
Torrecilla, J et al., "Lipid Nanoparticles as Carriers for RNAi against Viral infections: Current Status and Future Perspectives.", BioMed Research International., (Aug. 12, 2014), vol. 2014, No. 2014, pp. 1-18, XP055326069.
Vanderah et al, "Oligo(ethylene oxide) Self-Assembled Monolayers with Self-Limiting Packing Densities for the Inhibition of Nonspecific Protein Adsorption," Langmuir 25(9):5026-5030, 2009.
Xue et al., "Lipid-Based Nanocarriers for RNA Delivery," Current Pharmaceutical Design 21:3140-3147, 2015.
Zeisel et al: 'Hepatitis C virus entry into hepatocytes: Molecular mechanisms and targets for antiviral therapies.' J Hepatol, Mar. 2011;54(3):566-76.

SEQUENCE LISTING

<160> NUMBER OF SEQ ID NOS: 8

<210> SEQ ID NO 1
<211> LENGTH: 2544
<212> TYPE: DNA
<213> ORGANISM: Human immunodeficiency virus
<220> FEATURE:
<221> NAME/KEY: misc_feature
<222> LOCATION: (1507)..(1509)
<223> OTHER INFORMATION: n is a, c, g, t or u

<400> SEQUENCE: 1

| | | | | | |
|---|---|---|---|---|---|
| atgagagtga | agggcatccg | gcgcaactgc | cagcggtggt | ggaagtgggg | aatcatgctg | 60 |
| ctgggcatcc | tgatgatctg | caacgccgag | cagctgtggg | tcaccgtgta | ctacggcgtg | 120 |
| cccgtgtgga | agaggccac | caccaccctg | ttctgcgcca | cgacgccaa | gggccacgac | 180 |
| accgaggccc | acaacgtgtg | gccaccac | gcctgcgtgc | ccaccgaccc | caaccccag | 240 |
| gaaatcgtgc | tggaaaacgt | gaccgagaac | ttcaacatgt | ggaagaacaa | catggtggaa | 300 |
| cagatgcacg | aggacgtgat | cagcctgtgg | gaccagagcc | tgaagccctg | cgtgaagctg | 360 |
| acccccttct | gcgtgaccct | gaactgcacc | gacgtgatga | caacgtgaa | caccaccaca | 420 |
| aacagcagcg | agcggatgat | caagaagggc | gagatcaaga | actgcagctt | caacatcaac | 480 |
| accaacatgc | ggacaaggt | gcagaagaag | cacgccctgt | ctacaagct | ggacgtggtg | 540 |
| cccatcgaca | caccagcta | cagactgatc | agctgcaaca | ccagcgtgat | cacccaggcc | 600 |
| tgccccaagg | tgtccttcga | gcccatcccc | atccactact | gcgcccccgc | cggcttcgcc | 660 |
| atcctgaagt | gccgggacaa | gaagttcaac | ggcaccggcc | cctgcaccaa | cgtgagcacc | 720 |
| gtgcagtgca | cccacggcat | cagacccgtg | gtgagcaccc | agctgctgtt | caacggcagc | 780 |
| ctggccgagg | aggacgtcgt | gatcaagagc | gccaacttca | gcgacaacgc | caagaccatc | 840 |
| ctggtgcagc | tgaacgagac | agtcgtgatc | aactgcacca | gacccggcaa | caacacccgg | 900 |
| aaaagagtga | cactgggccc | cggccgggtg | tactacacca | ccggccagat | catcggcgac | 960 |
| atccggaagg | cccactgcaa | cctgagcaga | gccggctgga | caacacccct | ggaacggatc | 1020 |
| gccatcaagc | tgagagagca | gttccagaac | aagacaatcg | ccttcaacca | gagcagcgga | 1080 |
| ggcgacccg | agatcaccaa | gatcagcttc | aactgcggcg | gcgagttctt | ctactgcaac | 1140 |
| agcacacagc | tgttcaacgg | aacctggaac | ggcacatggc | tggacgtgaa | gcagggcgac | 1200 |
| ggcaccatca | ccctgccctg | cagaatcaag | cagatcatca | acctgtggca | ggaagtgggc | 1260 |
| aaggccatgt | acgccccccc | catcagcgga | cagatccggt | gcagcagcaa | catcaccggc | 1320 |
| ctgctgctga | ccagacggg | cggcaccagc | aacgagacaa | ccaccaccga | gacattccgg | 1380 |
| cccggaggag | gaaacatgaa | ggacaactgg | cgcagcgagc | tgtaccggta | caaagtgatc | 1440 |
| aagatcgagc | cctgggcgt | ggcccccaca | aaggcccgga | gaagggtggt | gcagcgcgag | 1500 |
| aaaagannng | ccgtgggaat | cggcgccgtg | ttcctgggct | tcctgggagc | cgccggaagc | 1560 |
| acaatgggcg | ccgccagcat | gaccctgacc | gtgcaggcca | gacagctgct | gagcggcatc | 1620 |
| gtgcagcagc | agaccaacct | gctgagagcc | atcgaggcac | agcagcagct | gctgaaactg | 1680 |
| accgtgtggg | gcatcaagca | gctgcagaca | agagtgctgg | ccgtggaaag | atacctgaag | 1740 |
| gaccagcagc | tgctgggaat | ctgggcctgc | agcggcaaac | tgatctgcac | caccaacgtg | 1800 |
| ccctggaaca | ccagctggag | caacaagagc | atgcaccaga | tttgggacaa | catgacctgg | 1860 |
| atgcagtggg | agagagagat | cgacaactac | acaggcctga | tctacagcct | gatcgaggaa | 1920 |
| agccagaacc | agcaggaaaa | gaacgaacag | gaactgctgg | ccctggacga | gtgggccagc | 1980 |

```
ctgtggaact ggttcgacat caccaagtgg ctgcggtaca tcaagatatt catcatcatc   2040
gtgggcggcc tgatcggcct gcggatcgtg ttcaccgtgc tgagcatcgt gaacagagtg   2100
cggaagggct acagcccct  gagcttccag accagactgc ccacacccag aggccccgac   2160
agacccggcg catcgagga  ggaaggcggc gacagagaca gggacggctc cggccccctc   2220
gtgaacggct tcctggccat catctgggtg gacctgcgga gcctgtgcct gttcagctac   2280
cacagactgc gggacctgct gctgatcgtg gccagaatcg tggaactgct gggcagaagg   2340
ggctgggagg ccctgaagta ctggtggaac ctgctgcagt actggtccca ggaactgaag   2400
aacagcgccg tgtccctgct gaacgccatc gccatcgccg tggccgaggg caccgacaga   2460
gtgatcgaag tgctgcagag agccggacgg gccatcctgc catccccag  aagaatccgg   2520 cagggcctgg aaagggccct gctg                                          2544
```

<210> SEQ ID NO 2
<211> LENGTH: 2960
<212> TYPE: DNA
<213> ORGANISM: Human immunodeficiency virus
<220> FEATURE:
<221> NAME/KEY: misc_feature
<222> LOCATION: (1653)..(1655)
<223> OTHER INFORMATION: n is a, c, g, t or u

<400> SEQUENCE: 2

```
ggaataaaag tctcaacaca acatatacaa acaaacgaa  tctcaagcaa tcaagcattc     60
tacttctatt gcagcaattt aaatcatttc ttttaaagca aaagcaattt tctgaaaatt    120
ttcaccattt acgaacgata gcgctgatga gagtgaaggg catccggcgc aactgccagc    180
ggtggtggaa gtggggaatc atgctgctgg gcatcctgat gatctgcaac gccgagcagc    240
tgtgggtcac cgtgtactac ggcgtgcccg tgtggaaaga ggccaccacc accctgttct    300
gcgccagcga cgccaaggc  cacgacaccc aggcccacaa cgtgtgggcc acccacgcct    360
gcgtgcccac cgaccccaac ccccaggaaa tcgtgctgga aaacgtgacc gagaacttca    420
acatgtggaa gaacaacatg gtggaacaga tgcacgagga cgtgatcagc ctgtgggacc    480
agagcctgaa gccctgcgtg aagctgaccc ccttctgcgt gaccctgaac tgcaccgacg    540
tgatgaacaa cgtgaacacc accacaaaca gcagcgagcg gatgatcaag aagggcgaga    600
tcaagaactg cagcttcaac atcaacacca acatgcggaa caaggtgcag aagaagcacg    660
ccctgttcta caagctggac gtggtgccca tcgacaacac cagctacaga ctgatcagct    720
gcaacaccag cgtgatcacc caggcctgcc ccaaggtgtc cttcgagccc atccccatcc    780
actactgcgc ccccgccggc ttcgccatcc tgaagtgccg ggacaagaag ttcaacggca    840
ccggcccctg caccaacgtg agcaccgtgc agtgcaccca cggcatcaga cccgtggtga    900
gcacccagct gctgttcaac ggcagcctgg ccgaggagga cgtcgtgatc aagagcgcca    960
acttcagcga caacgccaag accatcctgg tgcagctgaa cgagacagtc gtgatcaact   1020
gcaccagacc cggcaacaac acccggaaaa gagtgacact gggccccggc cgggtgtact   1080
acaccaccgg ccagatcatc ggcgacatcc ggaaggccca ctgcaacctg agcagagccg   1140 gctgaacaa  caccctggaa cggatcgcca tcaagctgag agagcagttc cagaacaaga   1200
caatcgcctt caaccagagc agcggaggcg accccgagat caccaagatc agcttcaact   1260
gcggcggcga gttcttctac tgcaacagca cacagctgtt caacgaacc  tggaacggca   1320 catggctgga cgtgaagcag ggcgacggca ccatcacccct gccctgcaga atcaagcaga   1380
```

```
tcatcaacct gtggcaggaa gtgggcaagg ccatgtacgc ccccccccatc agcggacaga    1440 tccggtgcag cagcaacatc accgccctgc tgctgaccag agacggcggc accagcaacg    1500
agacaaccac caccgagaca ttccggcccg aggaggaaa catgaaggac aactggcgca     1560
gcgagctgta ccggtacaaa gtgatcaaga tcgagcccct gggcgtggcc ccacaaagg    1620 cccggagaag ggtggtgcag cgcgagaaaa gannngccgt gggaatcggc gccgtgttcc    1680
tgggcttcct gggagccgcc ggaagcacaa tgggcgccgc cagcatgacc ctgaccgtgc    1740
aggccagaca gctgctgagc ggcatcgtgc agcagcagac caacctgctg agagccatcg    1800
aggcacagca gcagctgctg aaactgaccg tgtggggcat caagcagctg cagacaagag    1860
tgctggccgt ggaaagatac ctgaaggacc agcagctgct gggaatctgg ggctgcagcg    1920
gcaaactgat ctgcaccacc aacgtgccct ggaacaccag ctggagcaac aagagcatgc    1980
accagatttg ggacaacatg acctggatgc agtgggagag agagatcgac aactacacag    2040
gcctgatcta cagcctgatc gaggaaagcc agaaccagca ggaaaagaac gaacaggaac    2100
tgctggccct ggacgagtgg gccagcctgt ggaactggtt cgacatcacc aagtggctgc    2160
ggtacatcaa gatattcatc atcatcgtgg gcggcctgat cggcctgcgg atcgtgttca    2220
ccgtgctgag catcgtgaac agagtgcgga agggctacag ccccctgagc ttccagacca    2280
gactgcccac acccagaggc cccgacagac ccggcggcat cgaggaggaa ggcggcgaca    2340
gagacaggga cggctccggc cccctcgtga acggcttcct ggccatcatc tgggtggacc    2400
tgcggagcct gtgcctgttc agctaccaca gactgcggga cctgctgctg atcgtggcca    2460
gaatcgtgga actgctgggc agaagggggct gggaggccct gaagtactgg tggaacctgc    2520
tgcagtactg gtcccaggaa ctgaagaaca gcgccgtgtc cctgctgaac gccatcgcca    2580
tcgccgtggc cgagggcacc gacagagtga tcgaagtgct gcagagagcc ggacgggcca    2640
tcctgcacat ccccagaaga atccggcagg gcctggaaag ggccctgctg taaactagta    2700
gtgactgact aggatctggt taccactaaa ccagcctcaa gaacacccga atggagtctc    2760
taagctacat aataccaact tacacttaca aaatgttgtc ccccaaaatg tagccattcg    2820
tatctgctcc taataaaaag aaagtttctt cacattctaa aaaaaaaaa aaaaaaaaa     2880 aaaaaaaaaa aaaaaaaaaa aaaaaaaaaa aaaaaaaaaa aaaaaaaaaa aaaaaaaaaa    2940
aaaaaaaaaa aaaaaaaaac                                                 2960
```

<210> SEQ ID NO 3
<211> LENGTH: 565
<212> TYPE: PRT
<213> ORGANISM: Influenza virus

<400> SEQUENCE: 3

```
Met Lys Ala Asn Leu Leu Val Leu Leu Ser Ala Leu Ala Ala Ala Asp
1               5                   10                  15

Ala Asp Thr Ile Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Ser His Asn Gly Lys Leu Cys Arg Leu Lys Gly Ile
    50                  55                  60

Ala Pro Leu Gln Leu Gly Lys Cys Asn Ile Ala Gly Trp Leu Leu Gly
65                  70                  75                  80

Asn Pro Glu Cys Asp Pro Leu Leu Pro Val Arg Ser Trp Ser Tyr Ile
                85                  90                  95
```

```
Val Glu Thr Pro Asn Ser Glu Asn Gly Ile Cys Tyr Pro Gly Asp Phe
            100                 105                 110

Ile Asp Tyr Glu Glu Leu Arg Glu Gln Leu Ser Ser Val Ser Ser Phe
            115                 120                 125

Glu Arg Phe Glu Ile Phe Pro Lys Glu Ser Ser Trp Pro Asn His Asn
            130                 135                 140

Thr Asn Gly Val Thr Ala Ala Cys Ser His Glu Gly Lys Ser Ser Phe
145                 150                 155                 160

Tyr Arg Asn Leu Leu Trp Leu Thr Glu Lys Glu Gly Ser Tyr Pro Lys
                    165                 170                 175

Leu Lys Asn Ser Tyr Val Asn Lys Lys Gly Lys Glu Val Leu Val Leu
                180                 185                 190

Trp Gly Ile His His Pro Pro Asn Ser Lys Glu Gln Gln Asn Leu Tyr
            195                 200                 205

Gln Asn Glu Asn Ala Tyr Val Ser Val Val Thr Ser Asn Tyr Asn Arg
            210                 215                 220

Arg Phe Thr Pro Glu Ile Ala Glu Arg Pro Lys Val Arg Asp Gln Ala
225                 230                 235                 240

Gly Arg Met Asn Tyr Tyr Trp Thr Leu Leu Lys Pro Gly Asp Thr Ile
                    245                 250                 255

Ile Phe Glu Ala Asn Gly Asn Leu Ile Ala Pro Met Tyr Ala Phe Ala
            260                 265                 270

Leu Ser Arg Gly Phe Gly Ser Gly Ile Ile Thr Ser Asn Ala Ser Met
            275                 280                 285

His Glu Cys Asn Thr Lys Cys Gln Thr Pro Leu Gly Ala Ile Asn Ser
            290                 295                 300

Ser Leu Pro Tyr Gln Asn Ile His Pro Val Thr Ile Gly Glu Cys Pro
305                 310                 315                 320

Lys Tyr Val Arg Ser Ala Lys Leu Arg Met Val Thr Gly Leu Arg Asn
                    325                 330                 335

Thr Pro Ser Ile Gln Ser Arg Gly Leu Phe Gly Ala Ile Ala Gly Phe
                340                 345                 350

Ile Glu Gly Gly Trp Thr Gly Met Ile Asp Gly Trp Tyr Gly Tyr His
            355                 360                 365

His Gln Asn Glu Gln Gly Ser Gly Tyr Ala Ala Asp Gln Lys Ser Thr
            370                 375                 380

Gln Asn Ala Ile Asn Gly Ile Thr Asn Lys Val Asn Thr Val Ile Glu
385                 390                 395                 400

Lys Met Asn Ile Gln Phe Thr Ala Val Gly Lys Glu Phe Asn Lys Leu
                    405                 410                 415

Glu Lys Arg Met Glu Asn Leu Asn Lys Lys Val Asp Asp Gly Phe Leu
                420                 425                 430

Asp Ile Trp Thr Tyr Asn Ala Glu Leu Leu Val Leu Leu Glu Asn Glu
            435                 440                 445

Arg Thr Leu Asp Phe His Asp Ser Asn Val Lys Asn Leu Tyr Glu Lys
            450                 455                 460

Val Lys Ser Gln Leu Lys Asn Asn Ala Lys Glu Ile Gly Asn Gly Cys
465                 470                 475                 480

Phe Glu Phe Tyr His Lys Cys Asp Asn Glu Cys Met Glu Ser Val Arg
                    485                 490                 495

Asn Gly Thr Tyr Asp Tyr Pro Lys Tyr Ser Glu Glu Ser Lys Leu Asn
                500                 505                 510
```

-continued

```
Arg Glu Lys Val Asp Gly Val Lys Leu Glu Ser Met Gly Ile Tyr Gln
        515                 520                 525

Ile Leu Ala Ile Tyr Ser Thr Val Ala Ser Ser Leu Val Leu Leu Val
    530                 535                 540

Ser Leu Gly Ala Ile Ser Phe Trp Met Cys Ser Asn Gly Ser Leu Gln
545                 550                 555                 560

Cys Arg Ile Cys Ile
                565

<210> SEQ ID NO 4
<211> LENGTH: 1698
<212> TYPE: DNA
<213> ORGANISM: Influenza virus
<400> SEQUENCE: 4
atgaaggcaa acctactggt cctgttaagt gcacttgcag ctgcagatgc agacacaata     60
tgtataggct accatgcgaa caattcaacc gacactgttg acacagtact cgagaagaat    120
gtgacagtga cacactctgt taacctgctc gaagacagcc acaacggaaa actatgtaga    180
ttaaaaggaa tagccccact acaattgggg aaatgtaaca tcgccggatg gctcttggga    240
aacccagaat gcgacccact gcttccagtg agatcatggt cctacattgt agaaacacca    300
aactctgaga atggaatatg ttatccagga gatttcatcg actatgagga gctgagggag    360
caattgagct cagtgtcatc attcgaaaga ttcgaaatat ttcccaaaga aagctcatgg    420
cccaaccaca acacaaacgg agtaacggca gcatgctccc atgaggggaa aagcagtttt    480
tacagaaatt tgctatggct gacggagaag gagggctcat acccaaagct gaaaaattct    540
tatgtgaaca aaaaagggaa agaagtcctt gtactgtggg gtattcatca cccgcctaac    600
agtaaggaac aacagaatct ctatcagaat gaaaatgctt atgtctctgt agtgacttca    660
aattataaca ggagatttac cccggaaata gcagaaagac ccaaagtaag agatcaagct    720
gggaggatga actattactg gaccttgcta aaacccggag acacaataat atttgaggca    780
aatggaaatc taatagcacc aatgtatgct ttcgcactga gtagaggctt tgggtccggc    840
atcatcacct caaacgcatc aatgcatgag tgtaacacga agtgtcaaac acccctggga    900
gctataaaca gcagtctccc ttaccagaat atacacccag tcacaatagg agagtgccca    960
aaatacgtca ggagtgccaa attgaggatg gttacaggac taaggaacac tccgtccatt   1020
caatccagag gtctatttgg agccattgcc ggttttattg aagggggatg gactggaatg   1080
atagatggat ggtatggtta tcatcatcag aatgaacagg gatcaggcta tgcagcggat   1140
caaaaaagca cacaaaatgc cattaacggg attacaaaca aggtgaacac tgttatcgag   1200
aaaatgaaca ttcaattcac agctgtgggt aaagaattca acaaattaga aaaaaggatg   1260
gaaaatttaa ataaaaaagt tgatgatgga tttctggaca tttggacata taatgcagaa   1320
ttgttagttc tactggaaaa tgaaaggact ctggatttcc atgactcaaa tgtgaagaat   1380
ctgtatgaga aagtaaaaag ccaattaaag aataatgcca aagaaatcgg aaatggatgt   1440
tttgagttct accacaagtg tgacaatgaa tgcatggaaa gtgtaagaaa tgggacttat   1500
gattatccca aatattcaga agagtcaaag ttgaacaggg aaaaggtaga tggagtgaaa   1560
ttggaatcaa tggggatcta tcagattctg gcgatctact caactgtcgc cagttcactg   1620
gtgcttttgg tctccctggg ggcaatcagt ttctggatgt gttctaatgg atctttgcag   1680
tgcagaatat gcatctga                                                1698
```

<210> SEQ ID NO 5
<211> LENGTH: 1698
<212> TYPE: DNA
<213> ORGANISM: Artificial Sequence
<220> FEATURE:
<223> OTHER INFORMATION: Chemically synthesized

<400> SEQUENCE: 5

```
atgaaggcga acctgctggt cctgctgagc gcgctggcgg cggcggacgc ggacacgatc     60
tgcatcggct accacgcgaa caacagcacc gacacggtcg acacggtcct cgagaagaac    120
gtgaccgtga cccacagcgt caacctgctc gaggacagcc acaacgggaa gctgtgcagg    180
ctcaagggca tcgccccgct gcagctgggg aagtgcaaca tcgccggctg gctcttgggg    240
aaccccgagt gcgacccgct gctcccggtg aggagctggt cctacatcgt ggagaccccg    300
aactcggaga cgggatctg ctacccgggg gacttcatcg actacgagga gctgagggag    360
cagttgagct cggtgtcgtc cttcgagagg ttcgagatct cccccaagga gagctcgtgg    420
cccaaccaca caccaacgg ggtcacggcc gcgtgctccc acgagggga agagcagcttc    480
tacaggaact tgctgtggct gacggagaag gagggctcgt acccgaagct gaagaactcg    540
tacgtgaaca agaagggga aggaggtcctc gtactgtggg gcatccacca cccgccgaac    600
agcaaggagc agcagaacct ctaccagaac gagaacgcgt acgtctccgt ggtgacctcg    660
aactacaaca ggaggttcac cccggagatc gcggagaggc ccaaggtcag ggaccaggcc    720
gggaggatga actactactg gaccttgctg aagcccggcg acaccatcat cttcgaggcg    780
aacgggaacc tgatcgcacc gatgtacgcg ttcgcgctga gcaggggctt cgggtccggc    840
atcatcacct cgaacgcgtc catgcacgag tgcaacacga agtgccagac gcccctgggc    900
gcgatcaaca gcagcctccc gtaccagaac atccacccgg tcacgatcgg ggagtgcccc    960
aagtacgtca ggagcgccaa gttgaggatg gtgaccgggc tcaggaacac gccgtccatc   1020
cagtccaggg gcctgttcgg ggccatcgcc gggttcatcg agggggggctg gaccggcatg   1080
atcgacgggt ggtacggata ccaccaccag aacgagcagg ggtcgggcta cgcggcggac   1140
cagaagagca cgcagaacgc catcaacggg atcacgaaca aggtgaacac ggtcatcgag   1200
aagatgaaca tccagttcac ggccgtgggg aaggagttca caagttggaa gaagaggatg   1260
gagaacttga caagaaggt cgacgacggg ttcctggaca tctggacgta caacgcggag   1320
ttgttggtgc tgctggagaa cgagaggacg ctggacttcc acgactcgaa cgtgaagaac   1380
ctgtacgaga aggtgaagag ccagttgaag aacaacgcca aggagatcgg caacgggtgc   1440
ttcgagttct accacaagtg cgacaacgag tgcatggaga gcgtgaggaa cgggacgtac   1500
gactacccca gtactccga gagtcgaag ttgaacaggg agaaggtgga cggggtgaag   1560
ttggagtcga tggggatcta ccagatcctg gcgatctact cgacggtcgc cagctccctg   1620
gtgctgttgg tctccctggg ggcgatcagc ttctggatgt gctccaacgg gtcgttgcag   1680
tgcaggatct gcatctga                                                 1698
```

<210> SEQ ID NO 6
<211> LENGTH: 566
<212> TYPE: PRT
<213> ORGANISM: Influenza virus

<400> SEQUENCE: 6

```
Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
```

```
                20                  25                  30
Val Asp Thr Val Leu Glu Lys Asn Val Thr Val Thr His Ser Val Asn
            35                  40                  45
Leu Leu Glu Asp Lys His Asn Gly Lys Leu Cys Lys Leu Arg Gly Val
        50                  55                  60
Ala Pro Leu His Leu Gly Lys Cys Asn Ile Ala Gly Trp Ile Leu Gly
65                  70                  75                  80
Asn Pro Glu Cys Glu Ser Leu Ser Thr Ala Ser Ser Trp Ser Tyr Ile
                85                  90                  95
Val Glu Thr Pro Ser Ser Asp Asn Gly Thr Cys Tyr Pro Gly Asp Phe
            100                 105                 110
Ile Asp Tyr Glu Glu Leu Arg Glu Gln Leu Ser Ser Val Ser Ser Phe
        115                 120                 125
Glu Arg Phe Glu Ile Phe Pro Lys Thr Ser Ser Trp Pro Asn His Asp
    130                 135                 140
Ser Asn Lys Gly Val Thr Ala Ala Cys Pro His Ala Gly Ala Lys Ser
145                 150                 155                 160
Phe Tyr Lys Asn Leu Ile Trp Leu Val Lys Lys Gly Asn Ser Tyr Pro
                165                 170                 175
Lys Leu Ser Lys Ser Tyr Ile Asn Asp Lys Gly Lys Glu Val Leu Val
            180                 185                 190
Leu Trp Gly Ile His His Pro Ser Thr Ser Ala Asp Gln Gln Ser Leu
        195                 200                 205
Tyr Gln Asn Ala Asp Ala Tyr Val Phe Val Gly Ser Ser Arg Tyr Ser
    210                 215                 220
Lys Lys Phe Lys Pro Glu Ile Ala Ile Arg Pro Lys Val Arg Gly Gln
225                 230                 235                 240
Glu Gly Arg Met Asn Tyr Tyr Trp Thr Leu Val Glu Pro Gly Asp Lys
                245                 250                 255
Ile Thr Phe Glu Ala Thr Gly Asn Leu Val Val Pro Arg Tyr Ala Phe
            260                 265                 270
Ala Met Glu Arg Asn Ala Gly Ser Gly Ile Ile Ile Ser Asp Thr Pro
        275                 280                 285
Val His Asp Cys Asn Thr Thr Cys Gln Thr Pro Lys Gly Ala Ile Asn
    290                 295                 300
Thr Ser Leu Pro Phe Gln Asn Ile His Pro Ile Thr Ile Gly Lys Cys
305                 310                 315                 320
Pro Lys Tyr Val Lys Ser Thr Lys Leu Arg Leu Ala Thr Gly Leu Arg
                325                 330                 335
Asn Ile Pro Ser Ile Gln Ser Arg Gly Leu Phe Gly Ala Ile Ala Gly
            340                 345                 350
Phe Ile Glu Gly Gly Trp Thr Gly Met Val Asp Gly Trp Tyr Gly Tyr
        355                 360                 365
His His Gln Asn Glu Gln Gly Ser Gly Tyr Ala Ala Asp Leu Lys Ser
    370                 375                 380
Thr Gln Asn Ala Ile Asp Glu Ile Thr Asn Lys Val Asn Ser Val Ile
385                 390                 395                 400
Glu Lys Met Asn Thr Gln Phe Thr Ala Val Gly Lys Glu Phe Asn His
                405                 410                 415
Leu Glu Lys Arg Ile Glu Asn Leu Asn Lys Lys Val Asp Asp Gly Phe
            420                 425                 430
Leu Asp Ile Trp Thr Tyr Asn Ala Glu Leu Leu Val Leu Leu Glu Asn
        435                 440                 445
```

```
Glu Arg Thr Leu Asp Tyr His Asp Ser Asn Val Lys Asn Leu Tyr Glu
        450                 455                 460
Lys Val Arg Ser Gln Leu Lys Asn Asn Ala Lys Glu Ile Gly Asn Gly
465                 470                 475                 480
Cys Phe Glu Phe Tyr His Lys Cys Asp Asn Thr Cys Met Glu Ser Val
            485                 490                 495
Lys Asn Gly Thr Tyr Asp Tyr Pro Lys Tyr Ser Glu Glu Ala Lys Leu
            500                 505                 510
Asn Arg Glu Glu Ile Asp Gly Val Lys Leu Glu Ser Thr Arg Ile Tyr
            515                 520                 525
Gln Ile Leu Ala Ile Tyr Ser Thr Val Ala Ser Leu Val Leu Val
        530                 535                 540
Val Ser Leu Gly Ala Ile Ser Phe Trp Met Cys Ser Asn Gly Ser Leu
545                 550                 555                 560
Gln Cys Arg Ile Cys Ile
                565

<210> SEQ ID NO 7
<211> LENGTH: 1701
<212> TYPE: DNA
<213> ORGANISM: Influenza virus

<400> SEQUENCE: 7
atgaaagcaa tactagtagt tctgctatat acatttgcaa ccgcaaatgc agacacatta      60
tgtataggtt atcatgcgaa caattcaaca gacactgtag acacagtact agaaaagaat     120
gtaacagtaa cacactctgt taaccttcta agacaagc ataacgggaa actatgcaaa      180
ctaagagggg tagccccatt gcatttgggt aaatgtaaca ttgctggctg gatcctggga     240
aatccagagt gtgaatcact ctccacagca agctcatggt cctacattgt ggaaacacct     300
agttcagaca tggaacgtg ttacccagga gatttcatcg attatgagga gctaagagag     360
caattgagct cagtgtcatc atttgaaagg tttgagatat tccccaagac aagttcatgg     420
cccaatcatg actcgaacaa aggtgtaacg cagcatgtc ctcatgctgg agcaaaaagc     480
ttctacaaaa atttaatatg gctagttaaa aaaggaaatt catacccaaa gctcagcaaa     540
tcctacatta tgataaagg gaaagaagtc ctcgtgctat ggggcattca ccatccatct     600
actagtgctg accaacaaag tctctatcag aatgcagatg catatgtttt tgtggggtca     660
tcaagataca gcaagaagtt caagccggaa atagcaataa gacccaaagt gaggggtcaa     720
gaagggagaa tgaactatta ctggacacta gtagagccgg gagacaaaat aacattcgaa     780
gcaactggaa atctagtggt accgagatat gcattcgcaa tggaaagaaa tgctggatct     840
ggtattatca tttcagatac accagtccac gattgcaata acttgtca acacccaag     900 ggtgctataa acaccagcct cccatttcag aatatacatc cgatcacaat ggaaaatgt     960 ccaaaatatg taaaagcac aaaattgaga ctggccacag gattgaggaa tatcccgtct    1020
attcaatcta gaggcctatt tggggccatt gccggtttca ttgaagggg gtggacaggg    1080 atggtagatg gatggtacgg ttatcaccat caaaatgagc aggggtcagg atatgcagcc    1140
gacctgaaga gcacacagaa tgccattgac gagattacta caaagtaaa ttctgttatt    1200 gaaagatga atacacagtt cacagcagta ggtaaagagt tcaaccacct ggaaaaaaga    1260
atagagaatt taaataaaaa agttgatgat ggtttcctgg acatttggac ttacaatgcc    1320
gaactgttgg ttctattgga aaatgaaaga actttggact accacgattc aaatgtgaag    1380
```

| aacttatatg aaaaggtaag aagccagcta aaaaacaatg ccaaggaaat tggaaacggc | 1440 |
| tgctttgaat tttaccacaa atgcgataac acgtgcatgg aaagtgtcaa aaatgggact | 1500 |
| tatgactacc caaaatactc agaggaagca aaattaaaca gagaagaaat agatggggta | 1560 |
| aagctggaat caacaaggat ttaccagatt ttggcgatct attcaactgt cgccagttca | 1620 |
| ttggtactgg tagtctccct gggggcaatc agtttctgga tgtgctctaa tgggtctcta | 1680 |
| cagtgtagaa tatgtattta a | 1701 |

<210> SEQ ID NO 8
<211> LENGTH: 1701
<212> TYPE: DNA
<213> ORGANISM: Artificial Sequence
<220> FEATURE:
<223> OTHER INFORMATION: Chemically synthisized

<400> SEQUENCE: 8

| atgaaagcaa tactagtagt actgctatac acattcgcaa ccgcaaacgc agacacatta | 60 |
| tgcataggct accacgcgaa caactcaaca gacaccgtag acacagtact agaaaagaac | 120 |
| gtaacagtaa cacactccgt caacctccta gaagacaagc acaacgggaa actatgcaaa | 180 |
| ctaagagggg tagccccatt gcacttgggc aaatgcaaca tcgctggctg gatcctggga | 240 |
| aacccagagt gcgaatcact ctccacagca agctcatggt cctacatcgt ggaaacaccg | 300 |
| agctcagaca acggaacgtg ctacccagga gacttcatcg actacgagga gctaagagag | 360 |
| caattgagct cagtgtcatc attcgaaagg ttcgagatat tccccaagac aagctcatgg | 420 |
| cccaaccacg actcgaacaa aggcgtaacg gcagcatgcc cgcacgccgg agcaaaaagc | 480 |
| ttctacaaaa acttaatatg gctagtgaaa aaggaaact catacccaaa gctcagcaaa | 540 |
| tcctacatca acgacaaagg gaagaagtc ctcgtgctat ggggcatcca ccacccatcg | 600 |
| accagcgccg accaacaaag cctctaccag aacgcagacg catacgtgtt cgtggggtca | 660 |
| tcaagataca gcaagaagtt caagccggaa atagcaataa gacccaaagt gaggggccaa | 720 |
| gaagggagaa tgaactacta ctggacacta gtagagccgg gagacaaaat aacattcgaa | 780 |
| gcaaccggaa acctagtggt accgagatac gcattcgcaa tggaaagaaa cgccggatcc | 840 |
| ggcatcatca tatcagacac accagtccac gactgcaaca aacctgcca acacccaag | 900 |
| ggcgcgataa acaccagcct cccattccag aacatacacc cgatcacaat cggaaaatgc | 960 |
| ccaaaatacg taaaaagcac aaaattgaga ctggccacag gattgaggaa tatcccgtcc | 1020 |
| atccaatcca gaggcctatt cggggccatc gccggcttca tcgaaggggg gtggacaggg | 1080 |
| atggtagatg gatggtacgg ttaccaccac caaaacgagc aggggtcagg atacgcagcc | 1140 |
| gacctgaaga gcacacagaa cgccatcgac gagatcacga caaagtaaaa ctccgtcatc | 1200 |
| gaaaagatga acacacagtt cacagcagta ggcaaagagt tcaaccacct ggaaaaaaga | 1260 |
| atagagaact aaacaaaaaa agtcgacgac ggcttcctgg acatctggac ctacaacgcc | 1320 |
| gaactgttgg tcctattgga aaacgaaaga accttggact accacgactc aaacgtgaag | 1380 |
| aacttatacg aaaaggtaag aagccagcta aaaacaacg ccaaggaaat cggaaacggc | 1440 |
| tgcttcgaat tctaccacaa atgcgacaac acgtgcatgg aaagcgtcaa aaacgggacg | 1500 |
| tacgactacc caaaatactc agaggaagca aaattaaaca gagaagaaat agacggggta | 1560 |
| aagctggaat caacaaggat ctaccagatc ttggcgatct actcaaccgt cgccagctca | 1620 |

```
ttggtactgg tagtctccct gggggcaatc agtttctgga tgtgctccaa cgggtcccta    1680
cagtgcagaa tatgcatcta a                                              1701
```

NUCLEOSIDE-MODIFIED RNA FOR INDUCING AN ADAPTIVE IMMUNE RESPONSE

CROSS-REFERENCES TO RELATED APPLICATIONS

This application is a continuation of U.S. patent application Ser. No. 15/569,546, filed Oct. 26, 2017, which is a U.S. national phase application filed under 35 U.S.C. § 371 claiming benefit to International Patent Application No. PCT/US2016/029572, filed Apr. 27, 2016, which is entitled to priority under 35 U.S.C. § 119(e) to U.S. Provisional Patent Application No. 62/153,143, filed Apr. 27, 2015, each of which application is hereby incorporated herein by reference in its entirety.

STATEMENT REGARDING FEDERALLY SPONSORED RESEARCH OR DEVELOPMENT

This invention was made with government support under RO1-AI-090788 awarded by the National Institute of Health. The government has certain rights in the invention.

BACKGROUND OF THE INVENTION

Nucleic acid vaccines (NAV) have been under development for more than two decades. While significant advances have been made in terms of the use of DNA vaccine strategies, much less progress has been made with RNA vaccination strategies. Messenger RNA (mRNA) vaccines have the potential to be developed quickly and may provide a potent response. mRNA vaccines have the advantage of providing a response when delivered to the cytoplasm, as compared to DNA vaccines, which must be delivered to the nucleus.

However, mRNA vaccine development has been hampered due to problems with mRNA stability, delivery and immunogenicity directed against the mRNA itself via the innate immune system. While optimization of RNA vaccines has proven somewhat effective in recent years in an ex vivo setting, current methods of producing mRNA vaccines provide poor antibody and CD8+ T-cell responses when directly administered in vivo.

Thus, there is a need in the art for improved compositions and methods of using RNA encoding an antigen for induction of an adaptive immune response. The present invention satisfies this unmet need.

SUMMARY OF THE INVENTION

In one aspect, the present invention provides a composition for inducing an adaptive immune response in a subject, where the composition comprises at least one nucleoside-modified RNA encoding at least one antigen. In one embodiment, the at least one isolated nucleoside-modified RNA comprises pseudouridine. In one embodiment, the at least one isolated nucleoside-modified RNA comprises 1-methyl-pseudouridine. In one embodiment, the at least one antigen encoded by the nucleoside-modified RNA is a viral antigen, a bacterial antigen, a fungal antigen, a parasitic antigen, a tumor-associated antigen, or a tumor-specific antigen. In one embodiment, the at least one antigen comprises an HIV antigen. In one embodiment, the HIV antigen comprises Envelope (Env). In one embodiment, the at least one antigen comprises an influenza antigen. In one embodiment, the influenza antigen comprises hemagglutinin (HA).

In one embodiment, the composition further comprises an adjuvant. In one embodiment, the at least one nucleoside-modified RNA further encodes at least one adjuvant. In one embodiment, the composition is a vaccine.

In one embodiment, the composition further comprises a lipid nanoparticle (LNP). In one embodiment, the at least one nucleoside-modified RNA is encapsulated within the LNP. In one embodiment, the LNP comprises a compound having a structure of Formula (I):

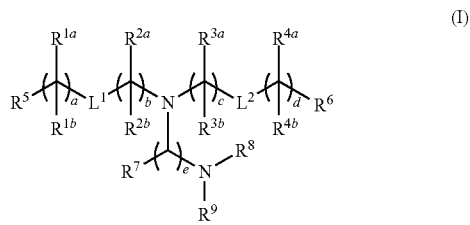

or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In one embodiment, the LNP comprises a compound having a structure of Formula (II):

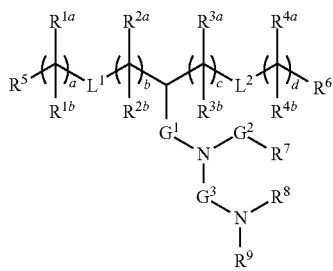

(II)

or a pharmaceutically acceptable salt, tautomer, prodrug or stereoisomer thereof, wherein:
$L^1$ and $L^2$ are each independently —O(C=O)—, —(C=O)O—, —C(=O)—, —O—, —S—S—, —C(=O)S—, —SC(=O)—, —NR$^a$C(=O)—, —C(=O)NR$^a$—, —NR$^a$C(=O)NR$^a$—, —OC(=O)NR$^a$—, —NR$^a$C(=O)O—, or a direct bond;
$G^1$ is $C_1$-$C_2$ alkylene, —(C=O)—, —O(C=O)—, —SC(=O)—, —NR$^a$C(=O)— or a direct bond;
$G^2$ is —C(=O)—, —(C=O)O—, —C(=O)S—, —C(=O)NR$^a$ or a direct bond;
$G^3$ is $C_1$-$C_6$ alkylene;
$R^a$ is H or $C_1$-$C_{12}$ alkyl;
$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;
$R^{2a}$ and $R^{2b}$ are, at each occurrence, independently either: (a) H or $C_1$-$C_{12}$ alkyl; or (b) $R^e$a is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;
$R^{3a}$ and $R^{3b}$ are, at each occurrence, independently either: (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;
$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;
$R^5$ and $R^6$ are each independently H or methyl;
$R^7$ is $C_4$-$C_{20}$ alkyl;
$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;
a, b, c and d are each independently an integer from 1 to 24; and
x is 0, 1 or 2.

In one embodiment, the LNP comprises a compound having a structure of Formula (III):

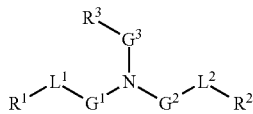

(III)

or a pharmaceutically acceptable salt, tautomer, prodrug or stereoisomer thereof, wherein:
one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;
$G^1$ and $G^2$ are each independently unsubstituted $C_1$-$C_{12}$ alkylene or $C_1$-$C_{12}$ alkenylene;
$G^3$ is $C_1$-$C_{24}$ alkylene, $C_1$-$C_{24}$ alkenylene, $C_3$-$C_8$ cycloalkylene, $C_3$-$C_8$ cycloalkenylene;
$R^a$ is H or $C_1$-$C_{12}$ alkyl;
$R^1$ and $R^2$ are each independently $C_6$-$C_{24}$ alkyl or $C_6$-$C_{24}$ alkenyl;
$R^3$ is H, OR$^5$, CN, —C(=O)OR$^4$, —OC(=O)R$^4$ or —NR$^5$C(=O)R$^4$;
$R^4$ is $C_1$-$C_{12}$ alkyl;
$R^5$ is H or $C_1$-$C_6$ alkyl; and
x is 0, 1 or 2.

In one embodiment, the LNP comprises a compound having one of the following structures:

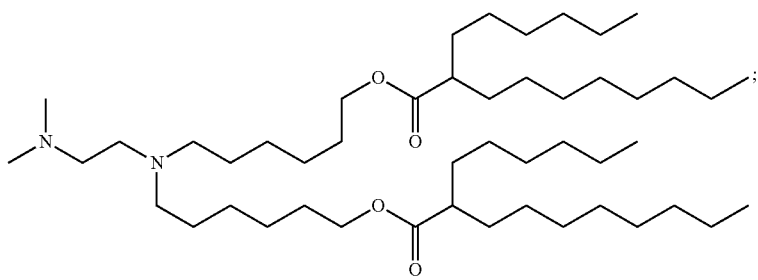

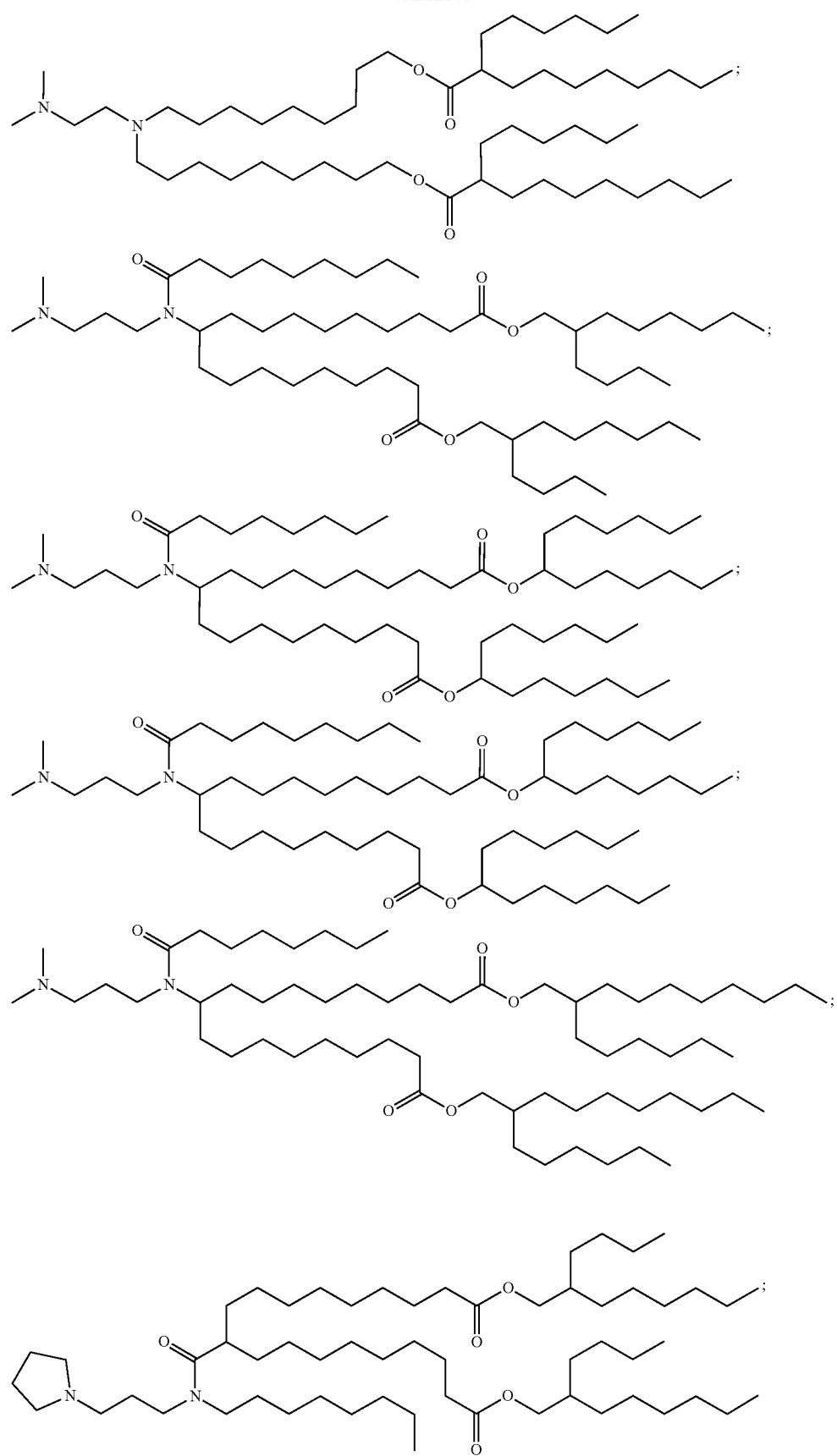

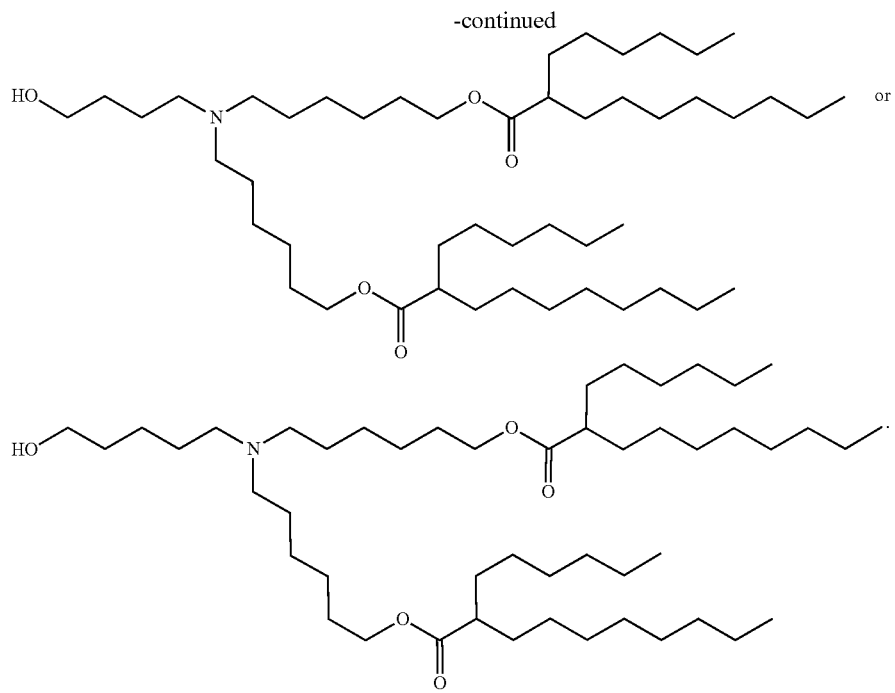

In one embodiment, the LNP comprises a pegylated lipid having the following structure (IV):

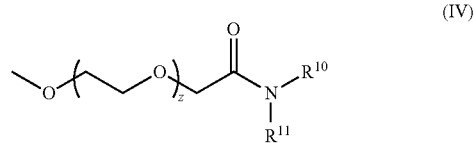

or a pharmaceutically acceptable salt, tautomer or stereoisomer thereof, wherein:
$R^{10}$ and $R^{11}$ are each independently a straight or branched, saturated or unsaturated alkyl chain containing from 10 to 30 carbon atoms, wherein the alkyl chain is optionally interrupted by one or more ester bonds; and
z has a mean value ranging from 30 to 60.

In one embodiment, the pegylated lipid has the following structure (IVa):

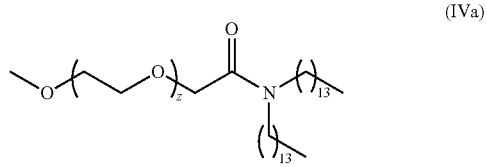

wherein n is an integer selected such that the average molecular weight of the pegylated lipid is about 2500 g/mol.

In one aspect, the present invention provides a method of inducing an adaptive immune response in a subject. The method comprises administering to the subject an effective amount of a composition comprising at least one nucleoside-modified RNA encoding at least one antigen. In one embodiment, the at least one isolated nucleoside-modified RNA comprises pseudouridine. In one embodiment, the at least one isolated nucleoside-modified RNA comprises 1-methyl-pseudouridine.

In one embodiment, the at least one antigen encoded by the nucleoside-modified RNA is a viral antigen, a bacterial antigen, a fungal antigen, a parasitic antigen, a tumor-associated antigen, or a tumor-specific antigen. In one embodiment, the at least one antigen comprises an HIV antigen. In one embodiment, the HIV antigen comprises Envelope (Env). In one embodiment, the at least one antigen comprises an influenza antigen. In one embodiment, the influenza antigen comprises hemagglutinin (HA).

In one embodiment, the composition further comprises an adjuvant. In one embodiment, the at least one nucleoside-modified RNA further encodes at least one adjuvant. In one embodiment, the composition is a vaccine.

In one embodiment, the composition further comprises a lipid nanoparticle (LNP). In one embodiment, the at least one nucleoside-modified RNA is encapsulated within the LNP. In one embodiment, the LNP comprises a compound having a structure of Formula (I):

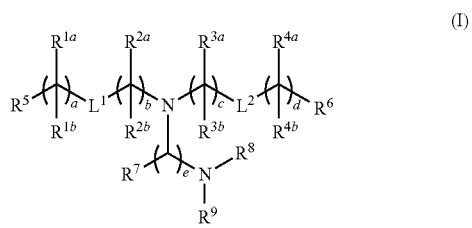

or a pharmaceutically acceptable salt, tautomer, prodrug or stereoisomer thereof, wherein:
$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;
b and c are each independently an integer from 1 to 24; and
e is 1 or 2.

In one embodiment, the LNP comprises a compound having a structure of Formula (II):

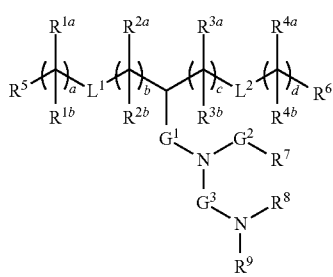

(II)

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S—S—, —C(=O)S—, —SC(=O)—, —NR$^a$C(=O)—, —C(=O)NR$^a$—, —NR$^a$C(=O)NR$^a$, —OC(=O) NR$^a$—, —NR$^a$C(=O)O—, or a direct bond;

$G^1$ is $C_1$-$C_2$ alkylene, —(C=O)—, —O(C=O)—, —SC (=O)—, —NR$^a$C(=O)— or a direct bond;

$G^2$ is —C(=O)—, —(C=O)O—, —C(=O)S—, —C(=O)NR$^a$ or a direct bond;

$G^3$ is C1-C6 alkylene;

$R^a$ is H or $C_1$-$C_{12}$ alkyl;

$R^{1a}$ and $R^{1b}$ are, at each occurrence, independently either: (a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either: (a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either: (a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either: (a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In one embodiment, the LNP comprises a compound having a structure of Formula (III):

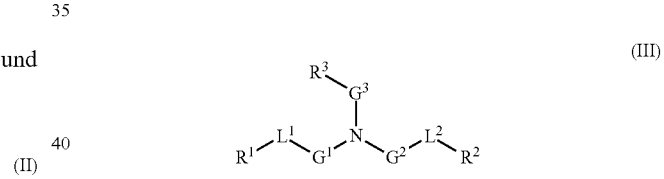

(III)

or a pharmaceutically acceptable salt, tautomer, prodrug or stereoisomer thereof, wherein:

one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O) NR$^a$—, —OC(=O)NR$^a$— or —NR$^a$C(=O)O— or a direct bond;

$G^1$ and $G^2$ are each independently unsubstituted $C_1$-$C_{12}$ alkylene or $C_1$-$C_{12}$ alkenylene;

$G^3$ is $C_1$-$C_{24}$ alkylene, $C_1$-$C_{24}$ alkenylene, $C_3$-$C_8$ cycloalkylene, $C_3$-$C_8$ cycloalkenylene;

$R^a$ is H or $C_1$-$C_{12}$ alkyl;

$R^1$ and $R^2$ are each independently $C_6$-$C_{24}$ alkyl or $C_6$-$C_{24}$ alkenyl;

$R^3$ is H, OR$^5$, CN, —C(=O)OR$^4$, —OC(=O)R$^4$ or —NR$^5$C(=O)R$^4$;

$R^4$ is $C_1$-$C_{12}$ alkyl;

$R^5$ is H or $C_1$-$C_6$ alkyl; and x is 0, 1 or 2.

In one embodiment, the LNP comprises a compound having one of the following structures:
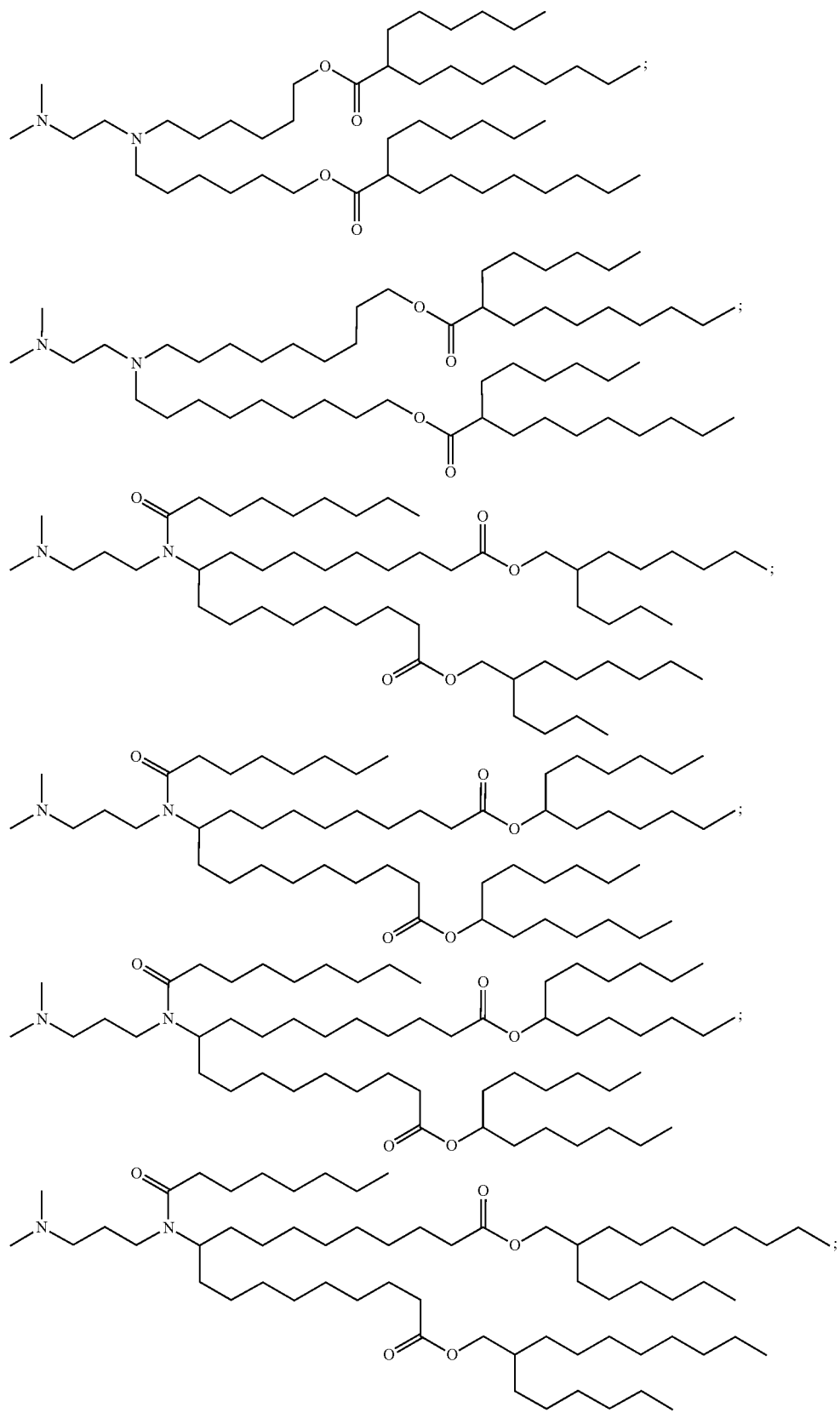

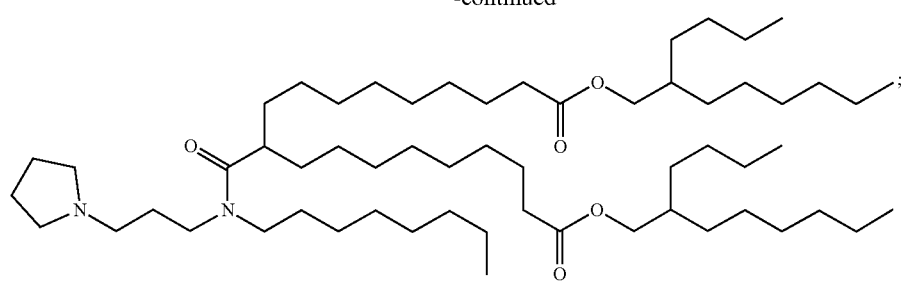

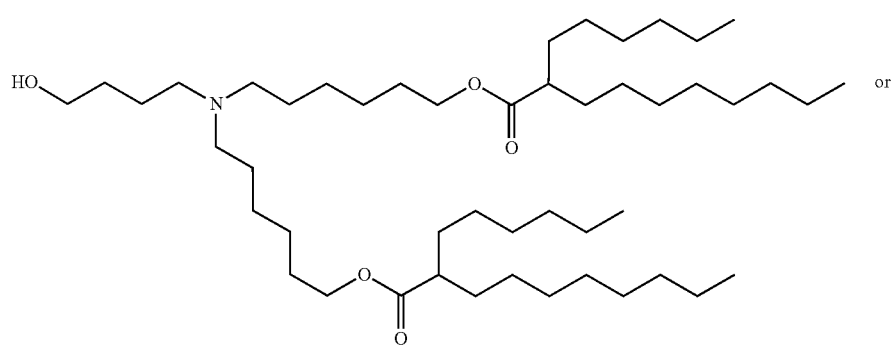

or

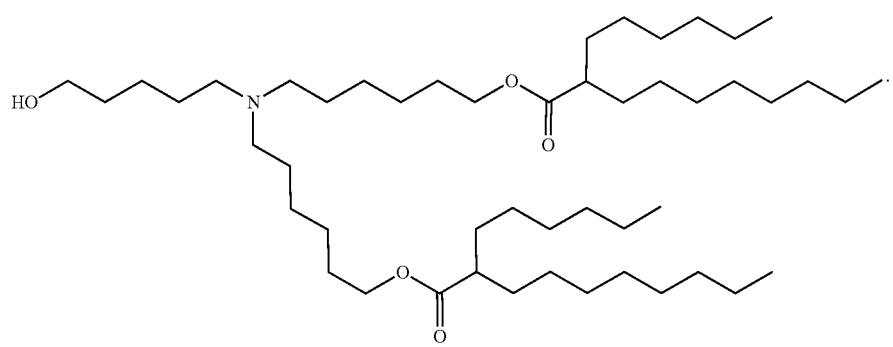

In one embodiment, the LNP comprises a pegylated lipid having the following structure (IV):

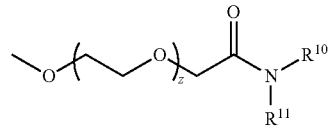

(IV)

or a pharmaceutically acceptable salt, tautomer or stereoisomer thereof, wherein:
$R^{10}$ and $R^{11}$ are each independently a straight or branched, saturated or unsaturated alkyl chain containing from 10 to 30 carbon atoms, wherein the alkyl chain is optionally interrupted by one or more ester bonds; and
z has a mean value ranging from 30 to 60.

In one embodiment, the pegylated lipid has the following structure (IVa):

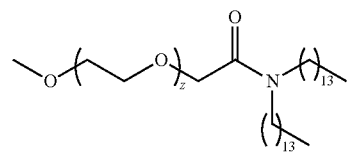

(IVa)

wherein n is an integer selected such that the average molecular weight of the pegylated lipid is about 2500 g/mol.

In one embodiment, the composition is administered by intradermal, subcutaneous, or intramuscualar delivery. In one embodiment, the method comprises a single administration of the composition. In one embodiment, the method comprises a multiple administrations of the composition.

In one embodiment, the method treats or prevents at least one selected from the group consisting of a viral infection, a bacterial infections, a fungal infection, a parasitic infection, and cancer. In one embodiment, the method treats or prevents HIV infection. In one embodiment, the method treats or prevents influenza infection.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 8 is a set of graphs illustrating that two intradermal immunizations with ENV-LNPs elicit robust multifunctional CD8+ T cell responses. The graphs depict the distribution of mono-, bi-, and trifunctional antigen specific CD8+ T cells in vaccinated animals. Pie charts show the distribution of antigen specific CD8+ T cells producing one, two or three cytokines. The bar graph shows the frequency of antigen specific CD8+ T cells producing one, two or three cytokines. ENV10=10 µg of iR3A envelope encoding mRNA injected ID. ENV30=30 µg of iR3A envelope encoding mRNA injected ID. Luc=30 µg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated on bars. G=INF-γ, T=TNF-α, 107=CD107a.

FIG. 9A depicts antigen-specific antibody responses as measured by ELISA assays. Experiments were conducted to measure HIV-1 gp120 specific IgG titers after two intradermal injections of mRNA-LNPs. Titers were measured by a gp120 specific ELISA assay where gp120 coated the plate and gp120-specific IgG was measured with a peroxidase labeled goat andi-mouse IgG. Standard error of the mean is indicated on bars. FIG. 9B depicts a set of graphs demonstrating that similar amounts of Env-specific IgG1 and IgG2 are produced two weeks after two immunizations with mRNA-LNP.

DETAILED DESCRIPTION

Figure 1:
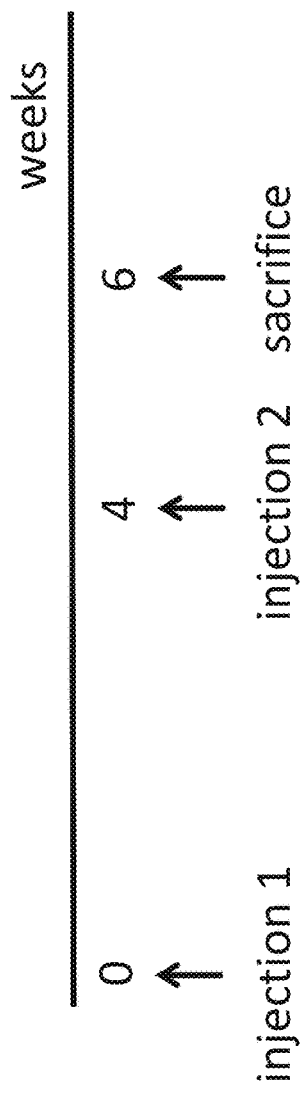
FIG. 1 is a schematic illustrating the experimental setup for ENV-LNP immunization that applies to FIG. 2-FIG. 11. Animals received two intradermal injections of either 3 µg, 10 µg or 30 µg of HIV-1 CD4-independent R3A envelope encoding mRNA encapsulated into lipid nanoparticles (LNP). Control mice were injected with 30 µg firefly luciferase (LUC) encoding mRNA complexed into LNP. There was a 4-week interval between mRNA-LNP injections and animals were sacrificed 14 days after the second injection.
Figure 2:
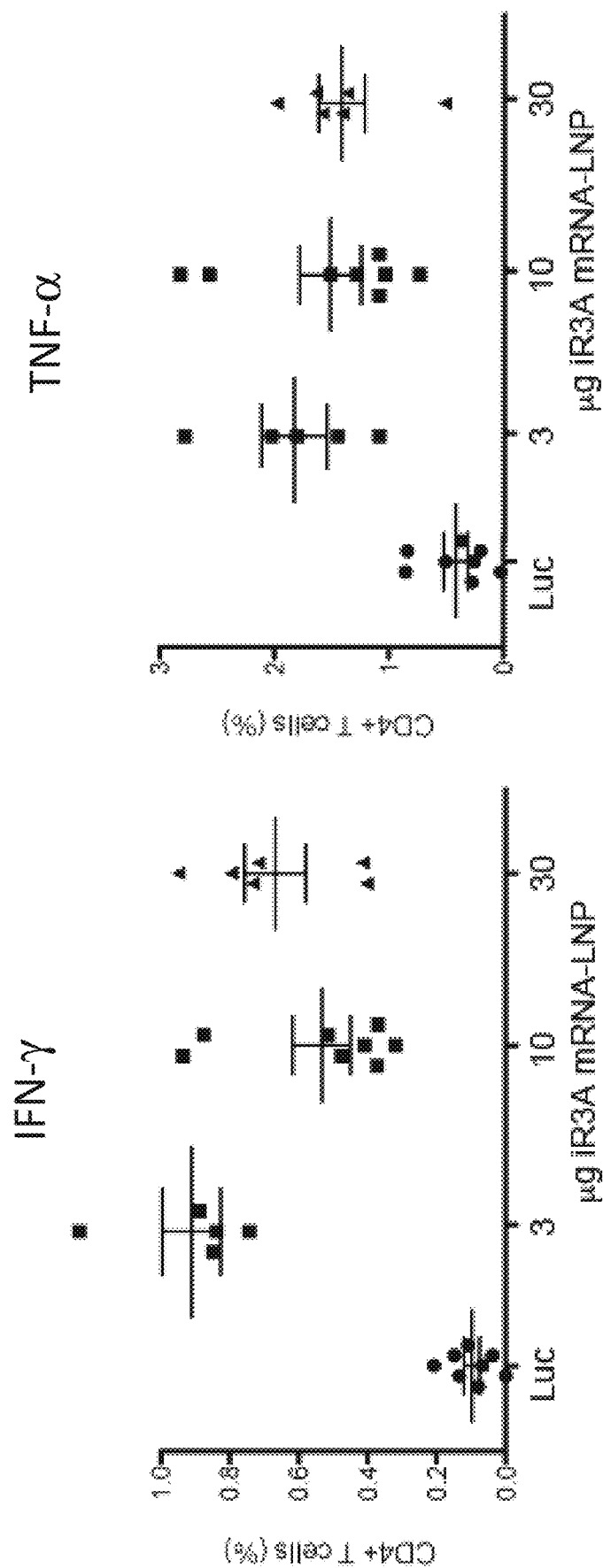
FIG. 2 is a set of graphs illustrating that two immunizations with ENV-LNPs elicit robust CD4+ T cell responses. The graphs depict IFN-γ (left) and TNF-α (right), production by antigen specific CD4+ T cells. Cytokine production of individual animals is displayed as the percent of total CD4+ T cells in the spleen. IFN=interferon, TNF=tumor necrosis factor. Luc=control mice injected with 30 µg of control luciferase encoding mRNA-LNPs injected intradermally (ID). All intracellular cytokine measurements were performed using multicolor flow cytometry after stimulation with peptide pools of 15-mers overlapping by 11 amino acids of the complete envelope sequence. Standard error of the mean is indicated.
Figure 3:
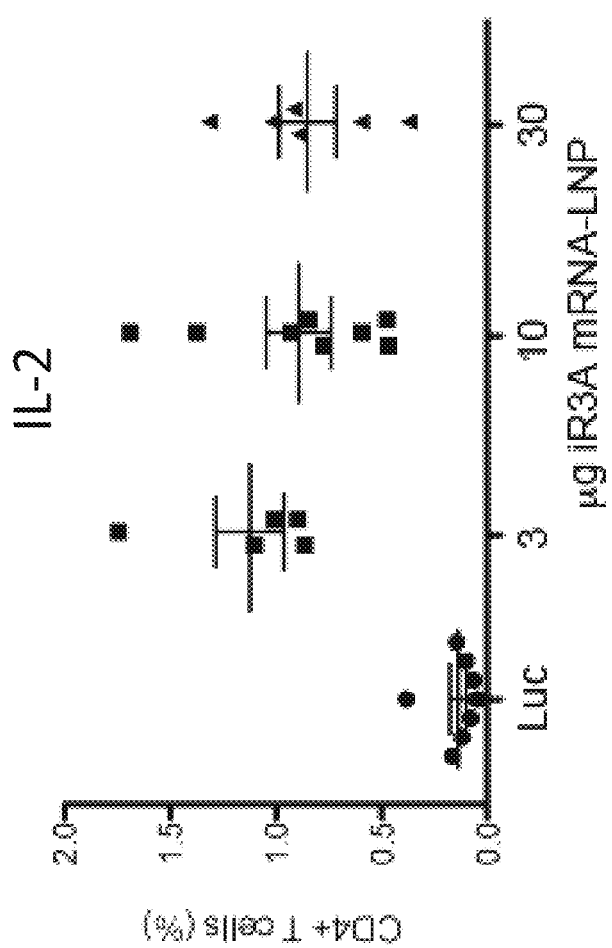
FIG. 3 is a graph illustrating that two immunizations with ENV-LNPs elicit robust CD4+ T cell responses. The graphs depict IL-2 production by antigen specific CD4+ T cells. Cytokine production of individual animals is displayed as the percent of total CD4+ T cells in the spleen. IL-2=interleukin 2. Luc=control mice injected with 30 µg of control luciferase encoding mRNA-LNPs injected intradermally (ID). All intracellular cytokine measurements were performed using multicolor flow cytometry after stimulation with peptide pools of 15-mers overlapping by 11 amino acids of the complete envelope sequence. Standard error of the mean is indicated.
Figure 4:
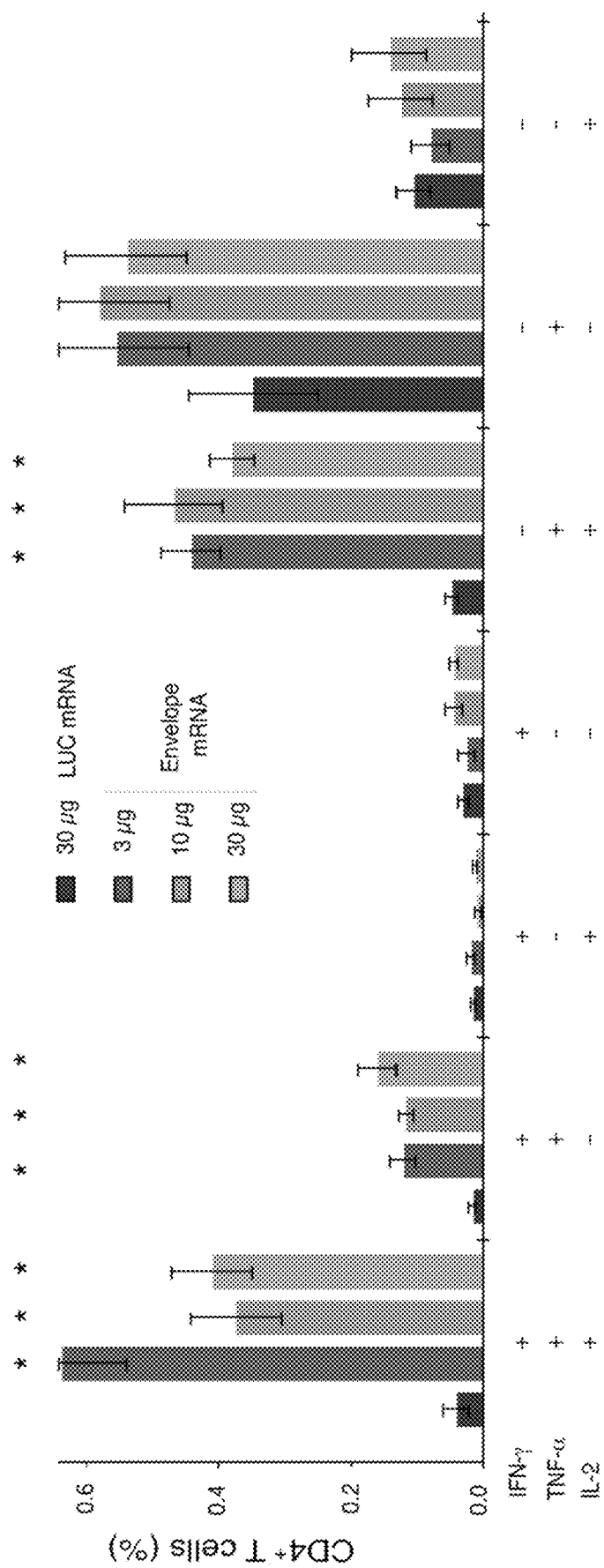
FIG. 4 is a graph illustrating that two immunizations with ENV-LNPs elicit robust multifunctional CD4+ T cell responses. The graphs depict the distribution of mono-, - bi,- and trifunctional antigen specific CD4+ T cells in vaccinated animals 14 days after the second intradermal immunization. The bar graph shows the percentage of antigen specific CD4+ T cells producing one, two or three cytokines, as indicated. All intracellular cytokine measurements were performed using multicolor flow cytometry after stimulation with peptide pools of 15-mers overlapping by 11 amino acids of the complete envelope sequence. Standard error of the mean is indicated on bars.
Figure 5:
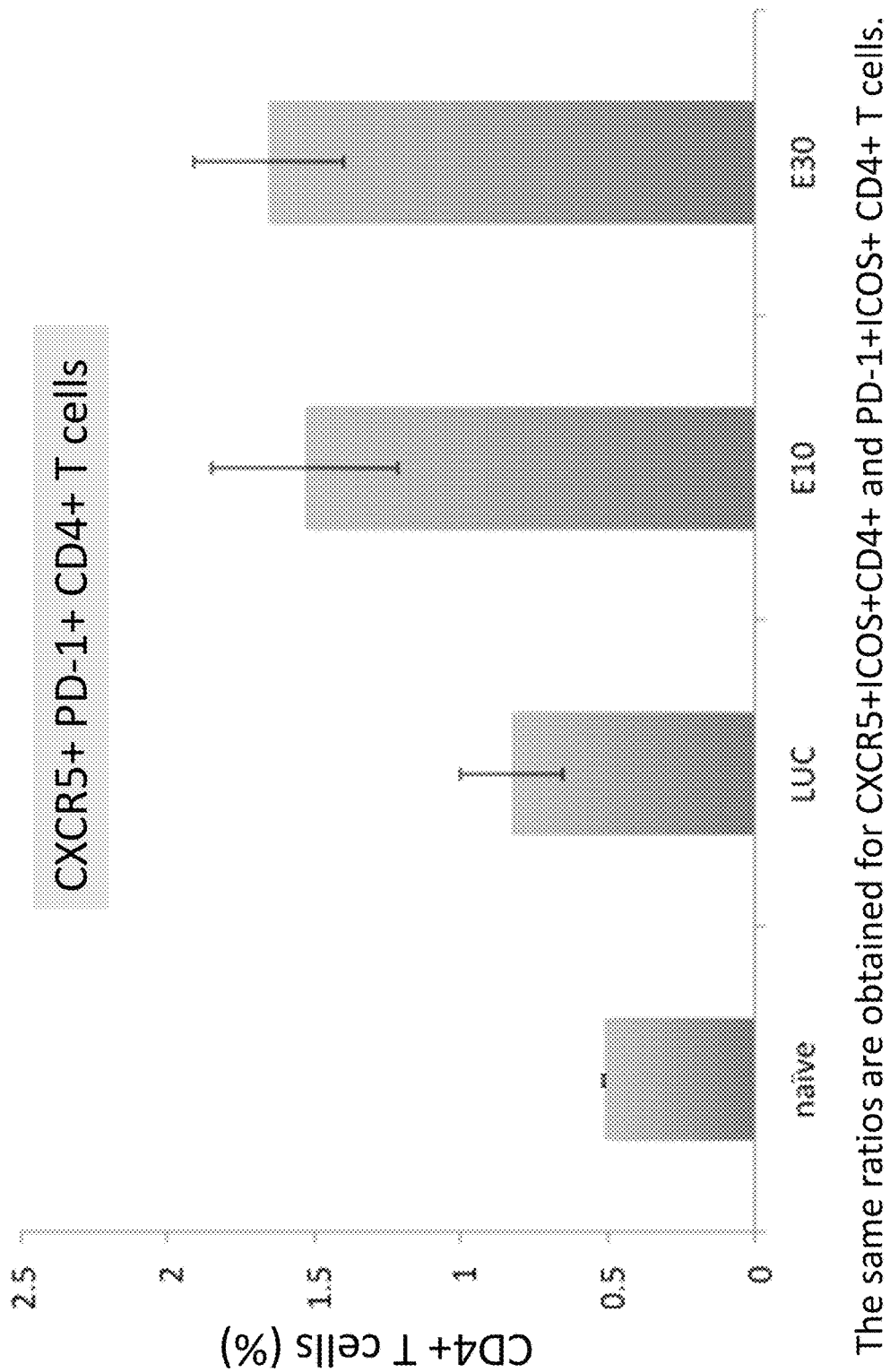
FIG. 5 is a graph illustrating that two immunizations with ENV-LNP results in a significant increase in total T follicular helper (Tfh) cell numbers. The graph depicts the frequency of splenic Tfh cells in vaccinated animals. CD4, CXCR5 and PD-1 markers were used to determine Tfh cells. E10=10 µg of iR3A envelope encoding mRNA injected ID. E30=30 µg of iR3A envelope encoding mRNA injected ID. Luc=30 µg of control luciferase encoding mRNA injected ID. Naïve: uninjected animal.
Figure 6:
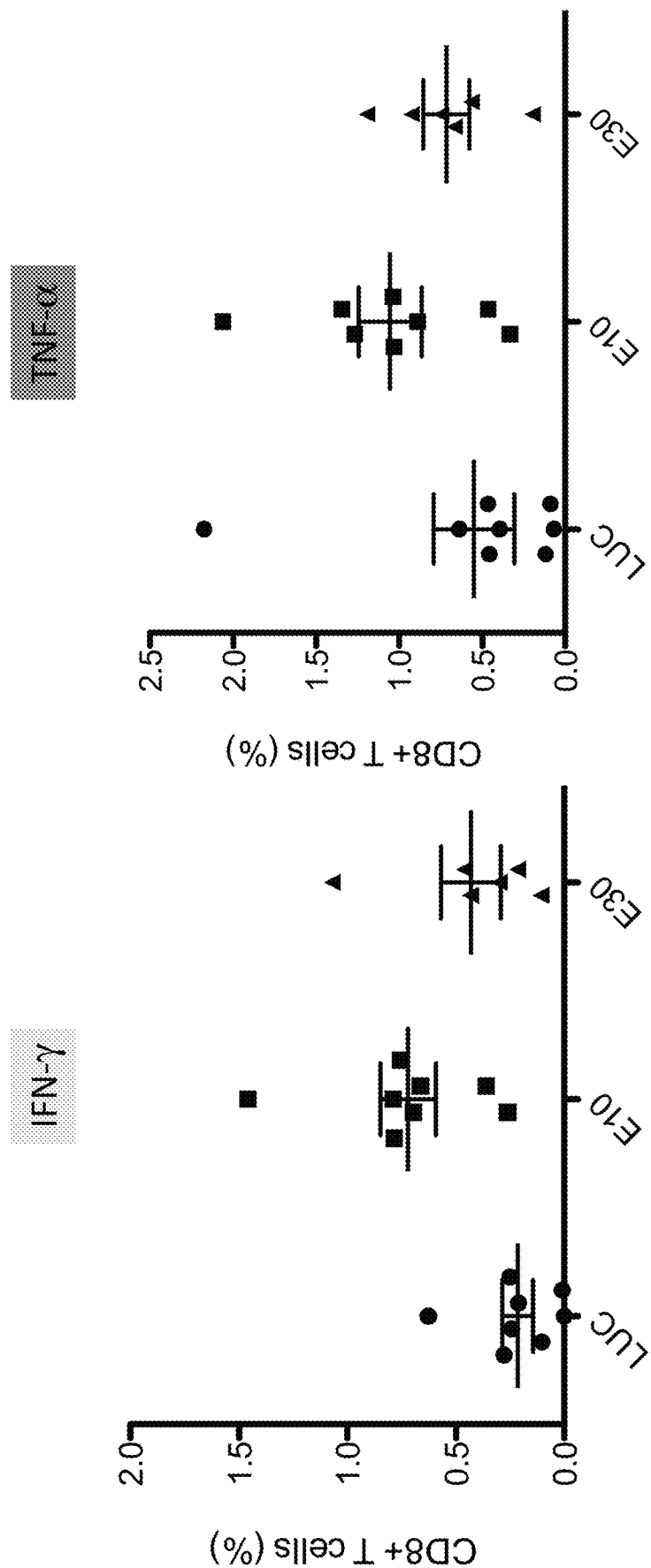
FIG. 6 is a set of graphs illustrating that two intradermal immunizations with ENV-LNPs elicits robust CD8+ T cell responses. The graphs depict IFN-γ (left) and TNF-α (right) production by antigen specific CD8+ T cells. Cytokine production of individual animals is displayed. E10=10 µg of iR3A envelope encoding mRNA injected ID. E30=30 µg of iR3A envelope encoding mRNA injected ID. Luc=30 µg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated.
Figure 7:
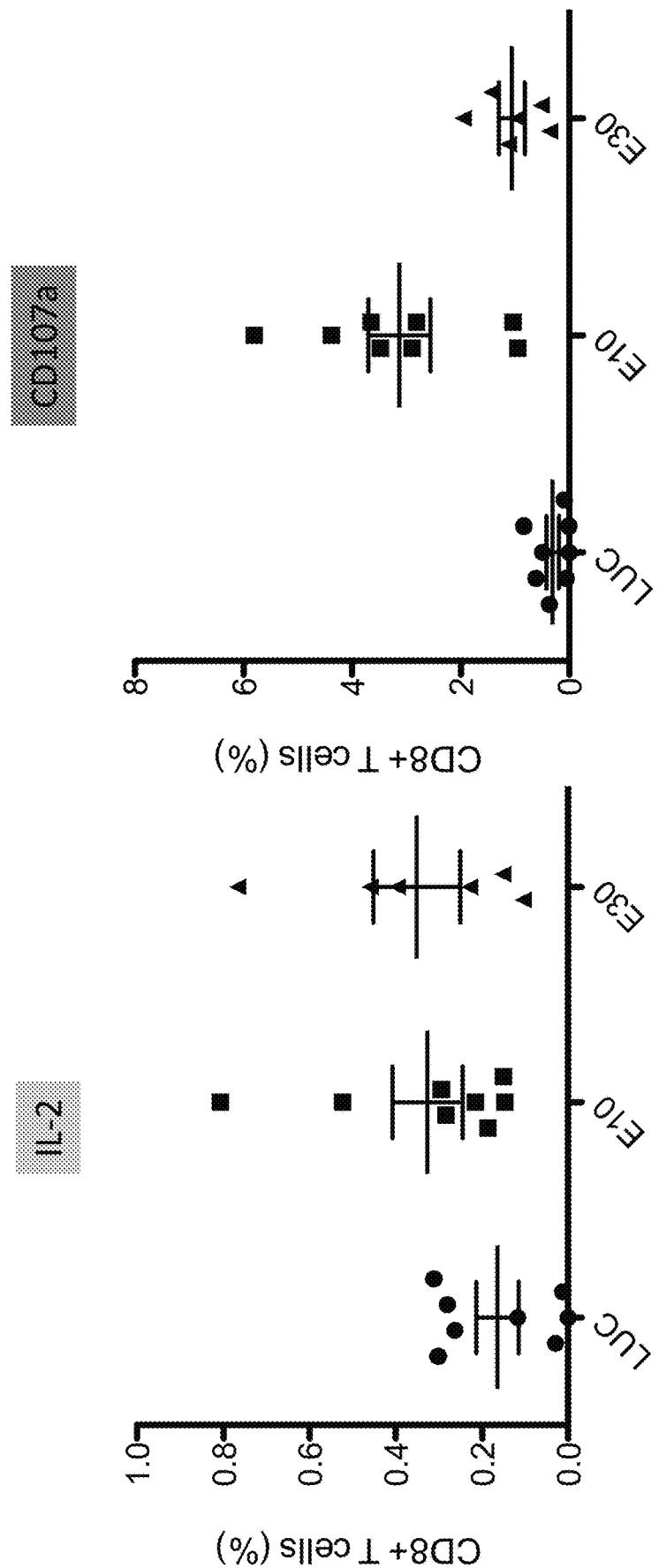
FIG. 7 is a set of graphs illustrating that two intradermal immunizations with ENV-LNPs elicit robust CD8+ T cell responses. The graphs depict IL-2 (left) and CD107a (right) production of antigen specific CD8+ T cells. IL-2 and CD107a production of individual animals is displayed. E10=10 µg of iR3A envelope encoding mRNA injected ID. E30=30 µg of iR3A envelope encoding mRNA injected ID. Luc=30 µg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated.
Figure 8:
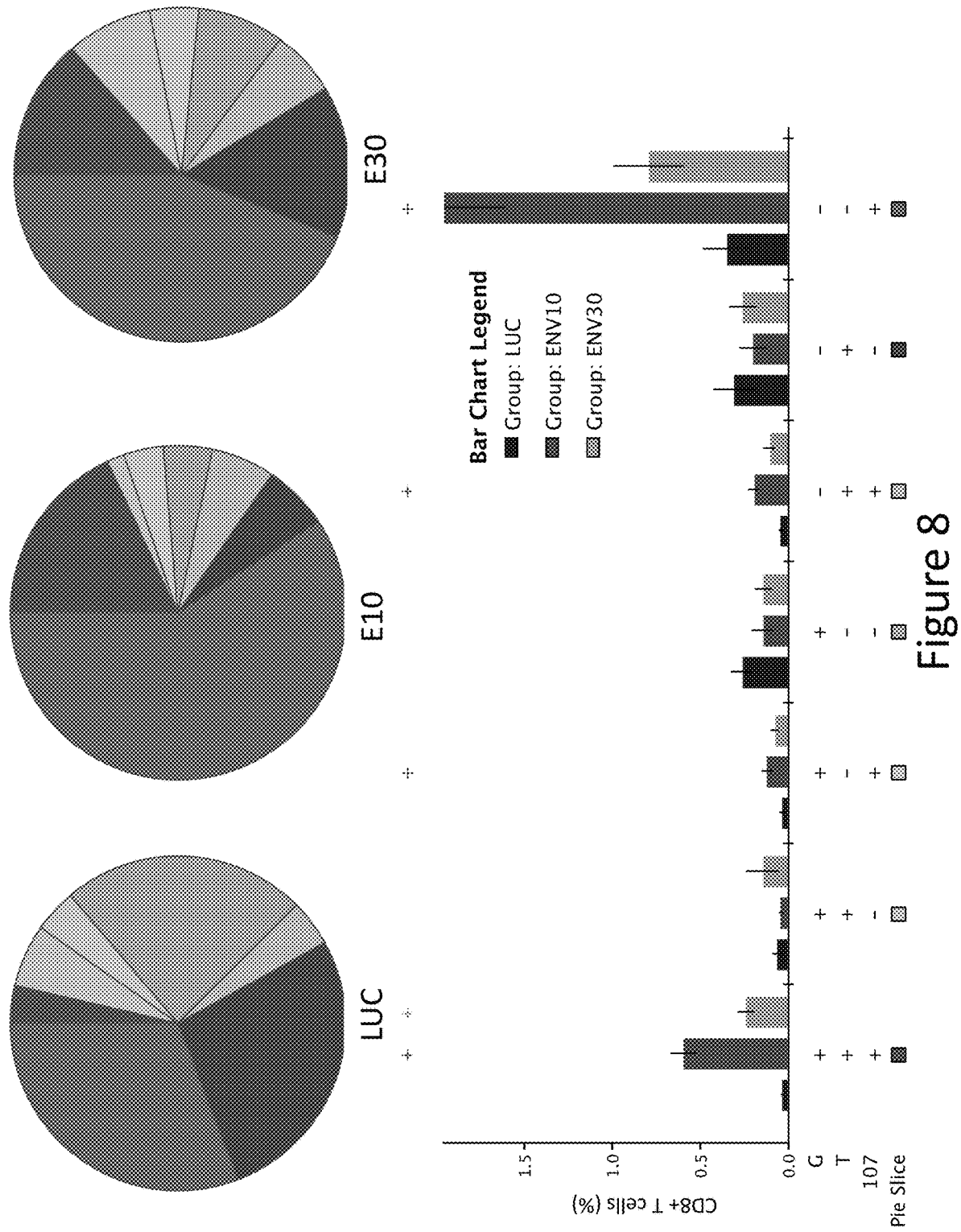
Figure 9A:
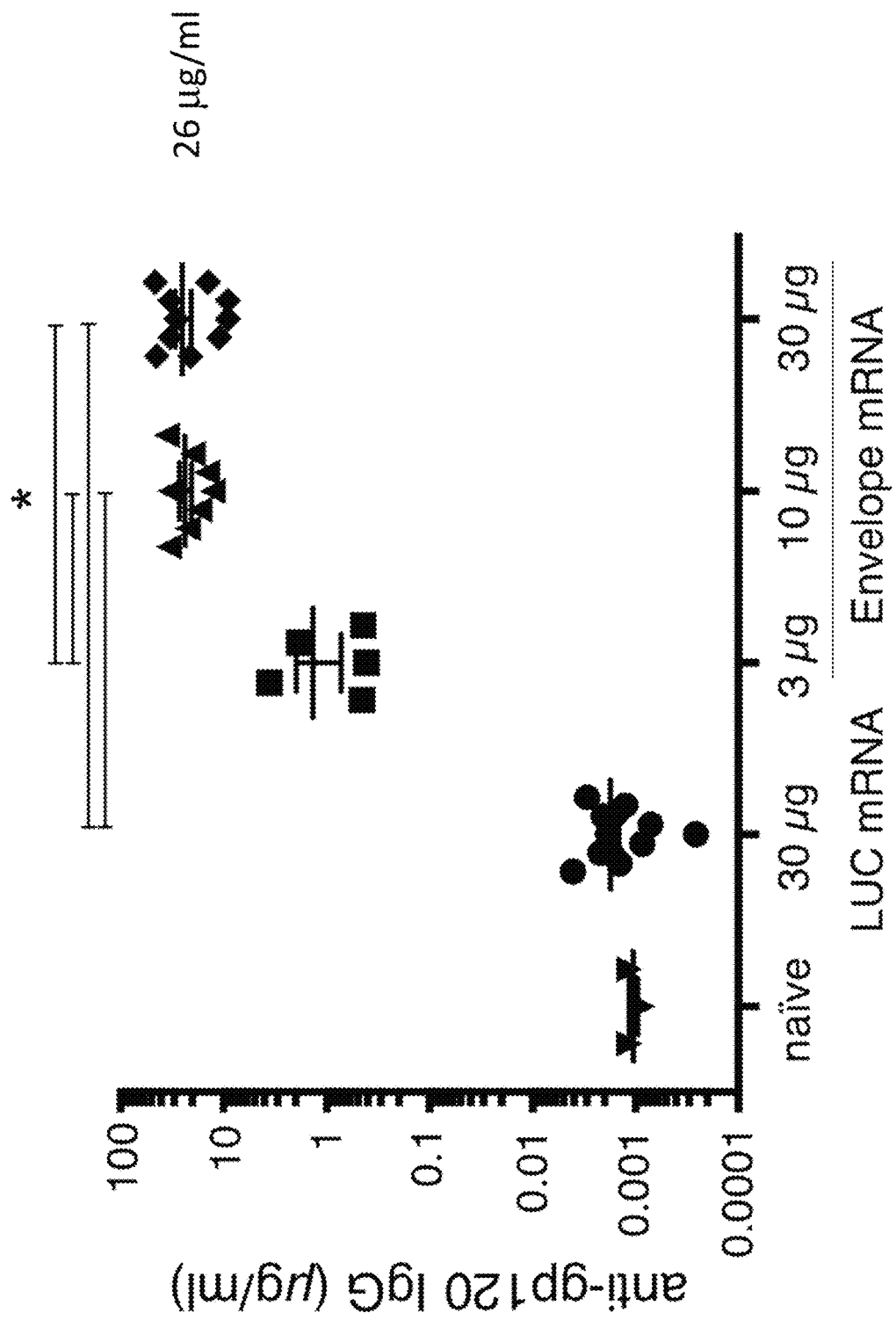
FIG. 9A and FIG. 9B are a set of graphs illustrating that immunization with ENV-LNPs elicit robust B cell responses.
Figure 9B:
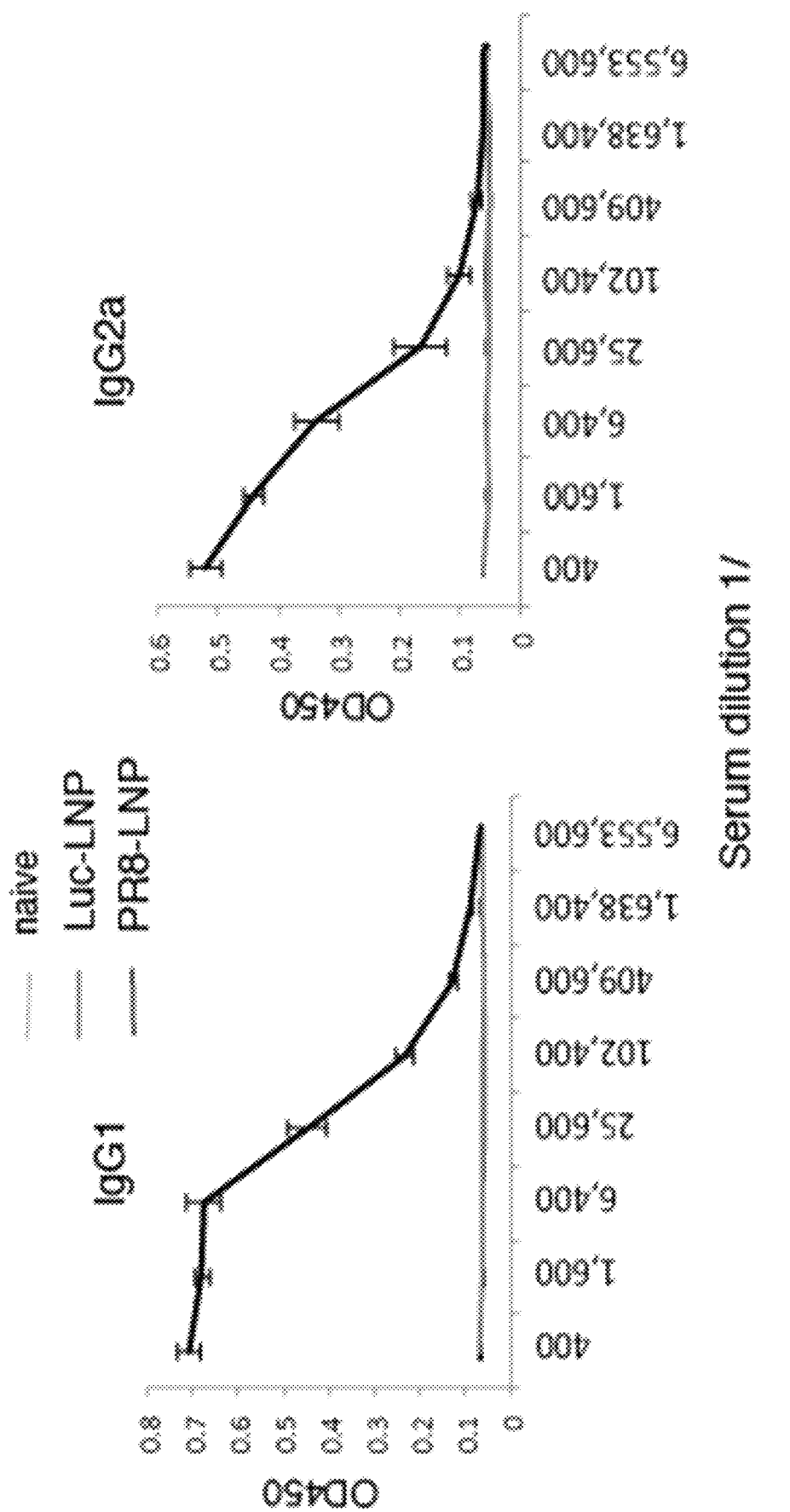
Figure 10:
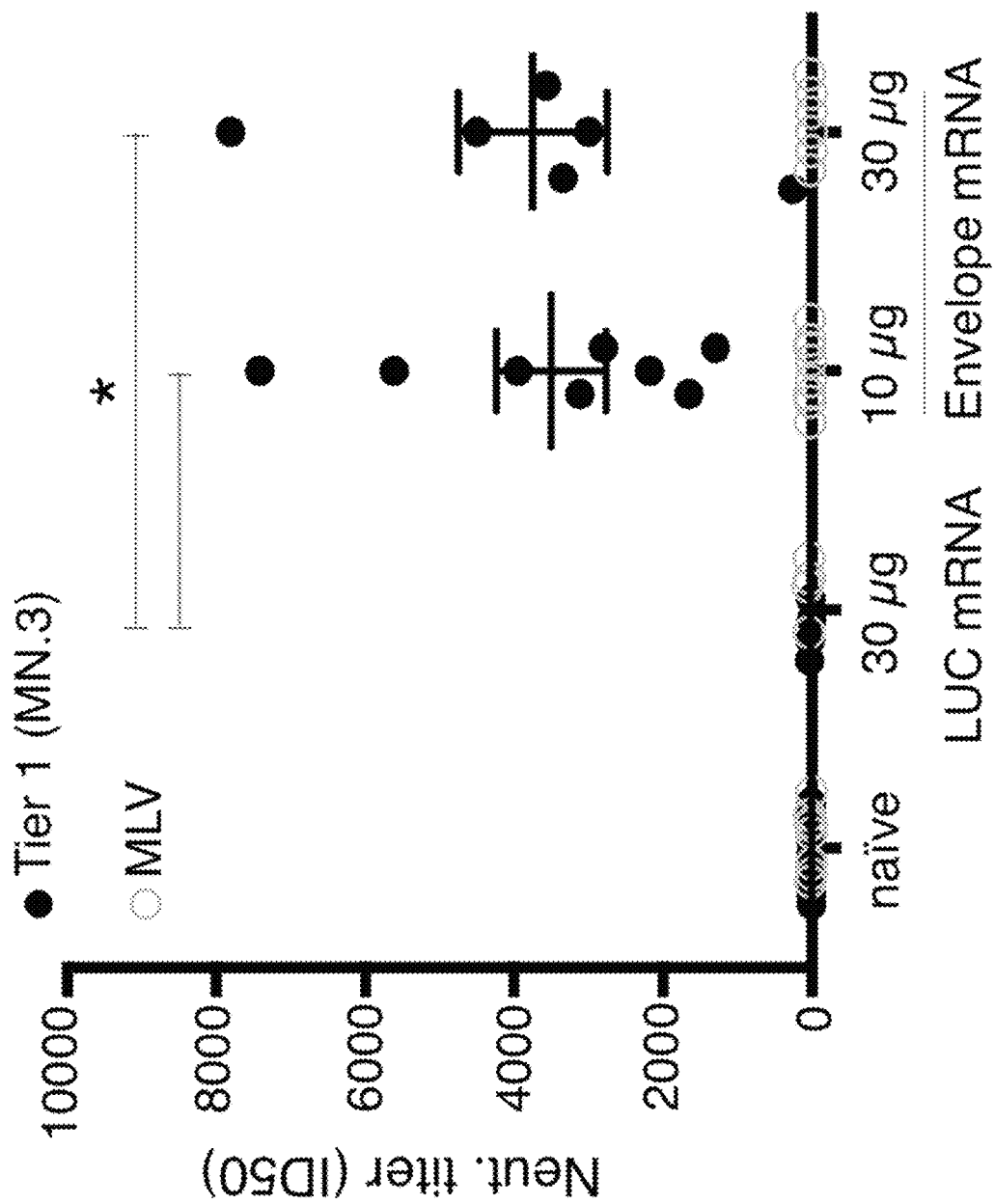
FIG. 10 is a graph depicting the results of example experiments. Mice were immunized 2 times with 30 µg of LNP complexed 1-methyl-pseudouridine-mRNA encoding luciferase (luc), or 10 or 30 µg of 1-methyl-pseudouridine modified mRNA encoding HIV envelope iR3A complexed by the intradermal route at 1 month intervals. Serum was analyzed for the ability to neutralize HIV infection by the tier 1 MN.3 strain and the control MLV. Serum was sequentially diluted and the dilution for 50% inhibition is shown. Each symbol represents an individual mouse.
Figure 11:
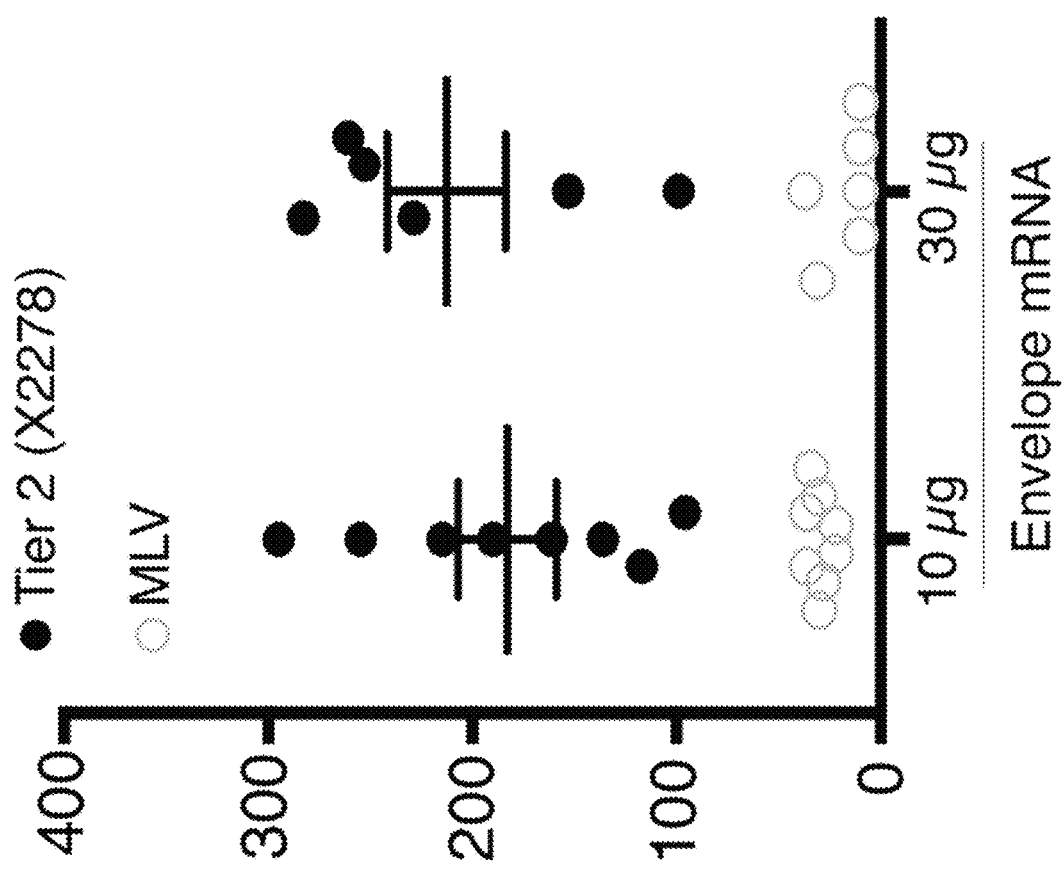
FIG. 11 is a graph depicting the results of example experiments. Mice were immunized 2 times with 10 or 30 μg of 1-methyl-pseudouridine modified mRNA encoding HIV envelope iR3A complexed to LNPs by the intradermal route at 1 month intervals. Serum was analyzed for the ability to neutralize HIV infection by the tier 2 X2278_C2_B6 strain and the control MLV. Serum was sequentially diluted and the dilution for 50% inhibition is shown.
Figure 12:
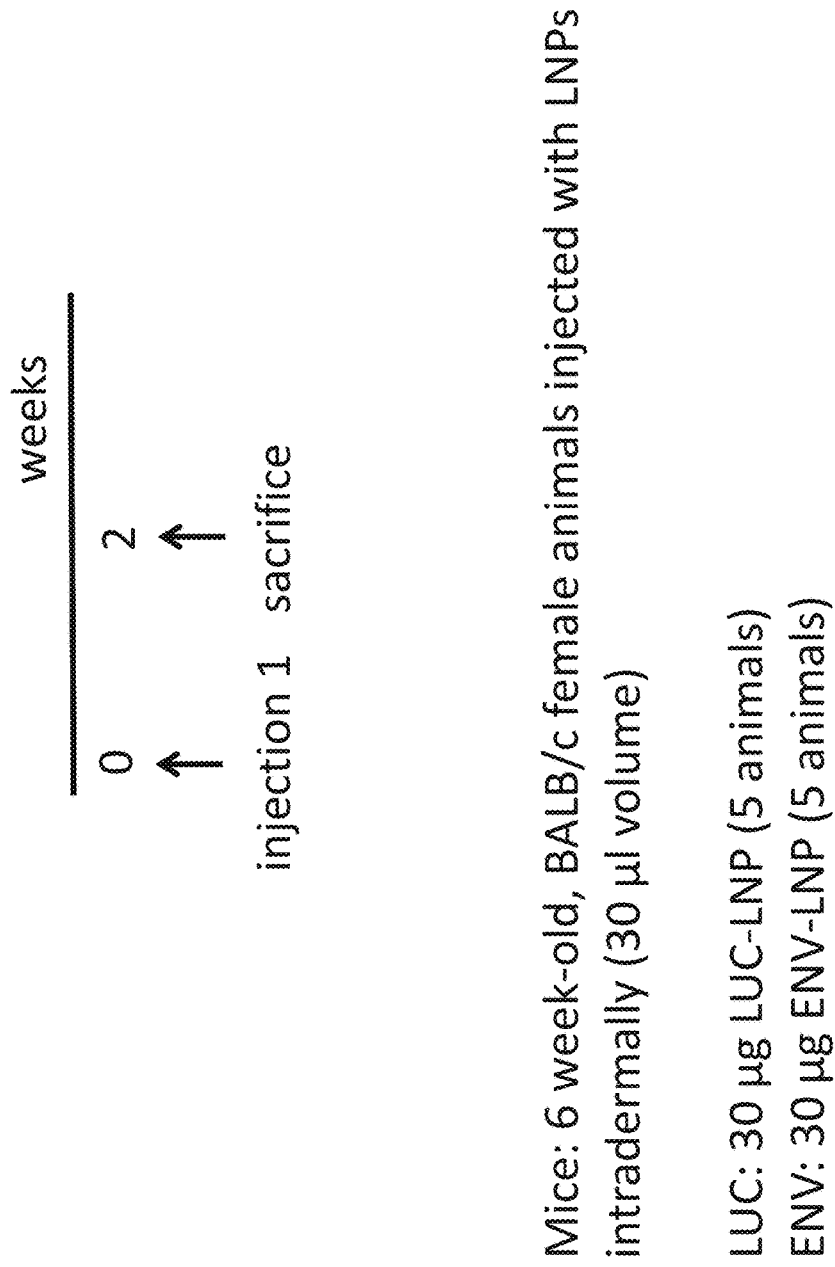
FIG. 12 is a schematic illustrating the experimental setup for ENV mRNA-LNP immunization. Animals received a single intradermal injection of 30 μg HIV-1 CD4-independent R3A envelope encoding mRNA encapsulated into lipid nanoparticles (ENV). Control mice were injected with 30 μg firefly luciferase encoding mRNA complexed into LNP. Animals were sacrificed 14 days after mRNA administration.
Figure 13:
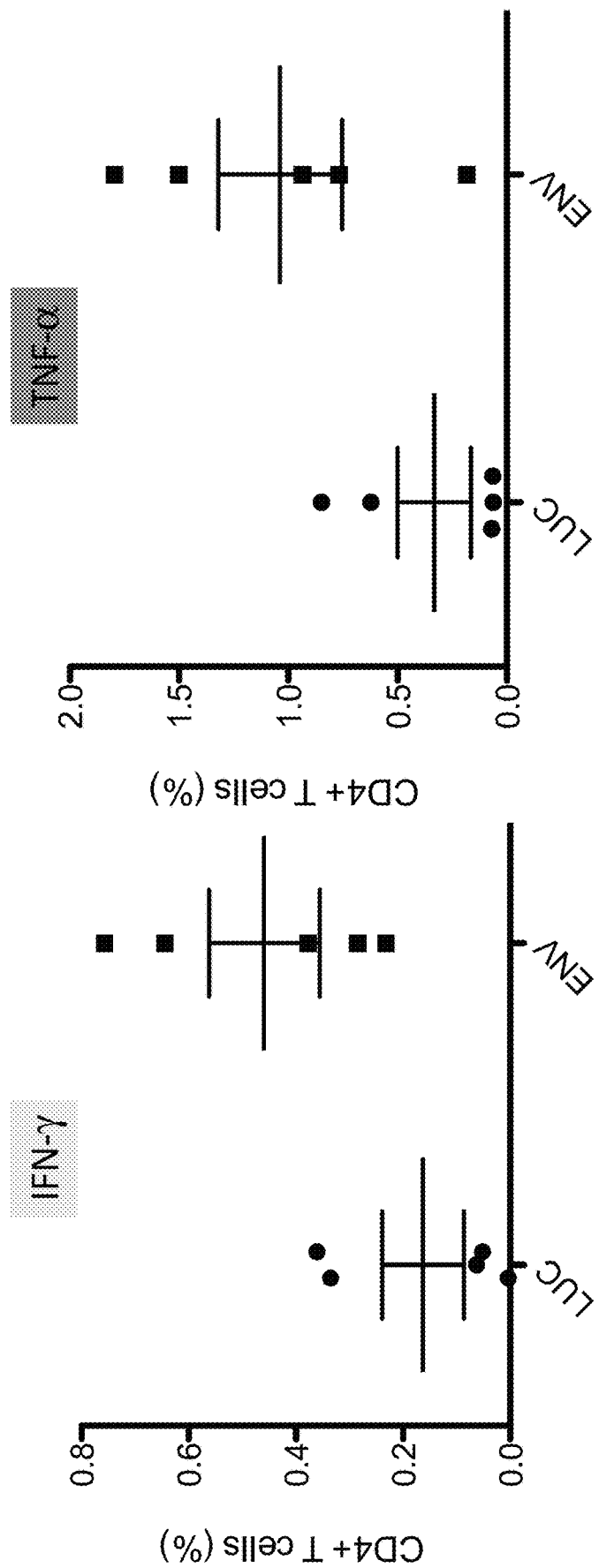
FIG. 13 is a set of graphs illustrating that a single injection with 30 μg ENV mRNA-LNPs elicits robust CD4+ T cell responses. The graphs depict IFN-γ (left) and TNF-α (right) production of antigen specific CD4+ T cells. Cytokine production of individual animals is displayed. ENV=30 μg of iR3A envelope encoding mRNA injected ID. Luc=30 ug of control luciferase encoding mRNA injected ID. All intracellular cytokine measurements were performed using multicolor flow cytometry after stimulation with peptide pools of 15-mers overlapping by 11 amino acids of the complete envelope sequence. The percent of total spleen cells expressing cytokine after peptide stimulation is expressed. Standard error of the mean is indicated.
Figure 14:
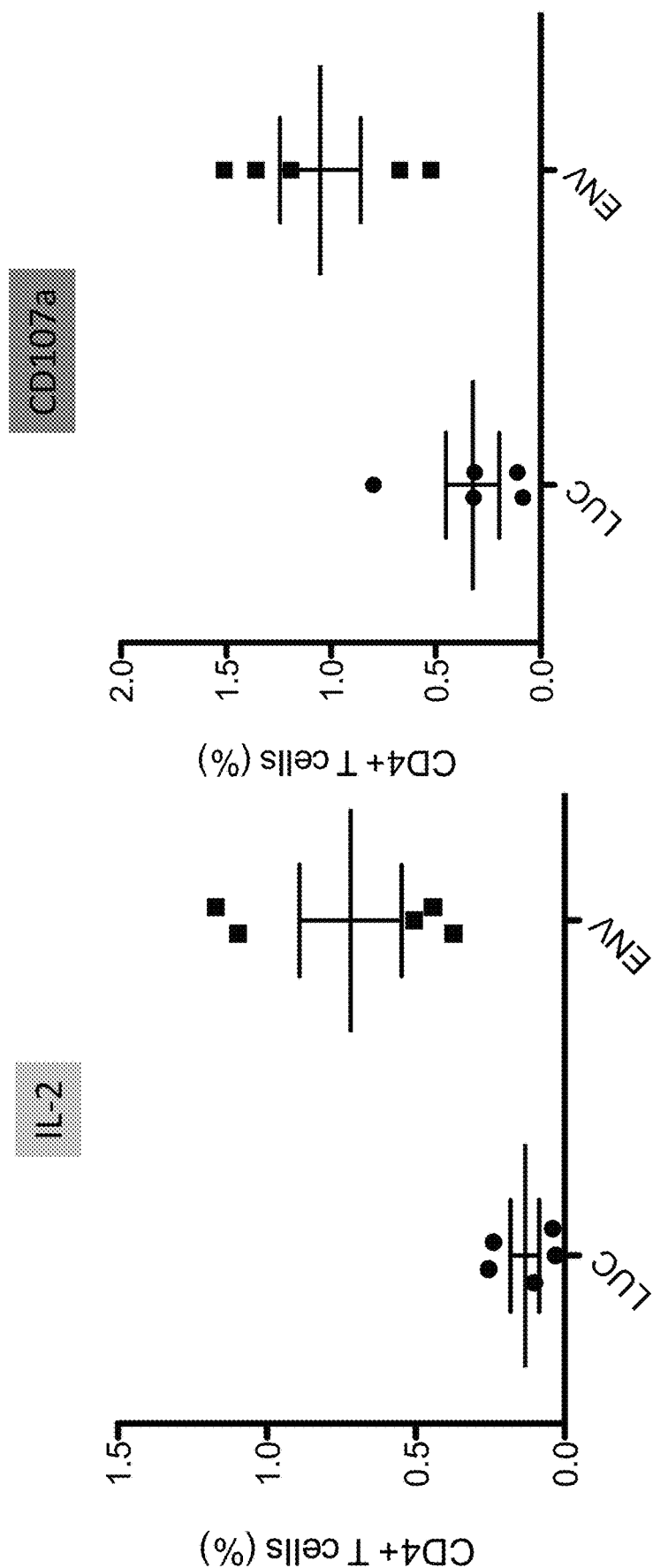
FIG. 14 is a set of graphs illustrating that a single injection with 30 μg ENV mRNA-LNPs elicits robust CD4+ T cell responses. The graphs depict IL-2 (left) and CD107a production (right) of antigen specific CD4+ T cells. IL-2 and CD107a production of individual animals is displayed. ENV=30 μg of iR3A envelope encoding mRNA injected ID. Luc=30 μg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated.
Figure 15:
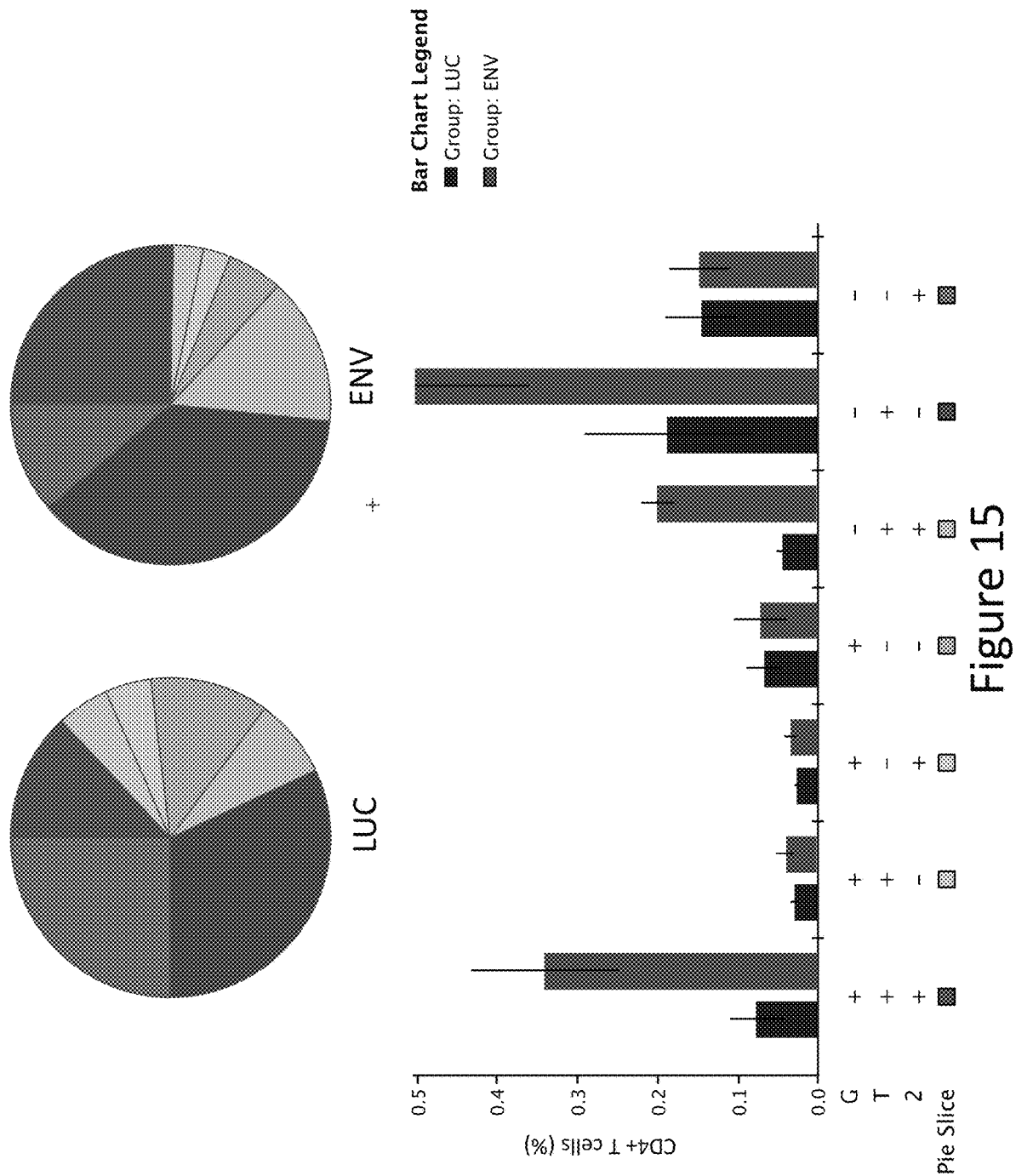
FIG. 15 is a set of graphs illustrating that a single injection with 30 μg ENV mRNA-LNPs elicit robust polyfunctional CD4+ T cell responses. The graphs depict the distribution of mono-, bi- and trifunctional antigen specific CD4+ T cells in vaccinated animals. Pie charts show the distribution of antigen specific CD4+ T cells producing one, two or three cytokines. The bar graph shows the frequency of antigen specific CD4+ T cells producing one, two or three cytokines. ENV=30 μg of iR3A envelope encoding mRNA injected ID. Luc=30 μg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated on bars. G=INF-γ, T=TNF-α, 2=IL-2
Figure 16:
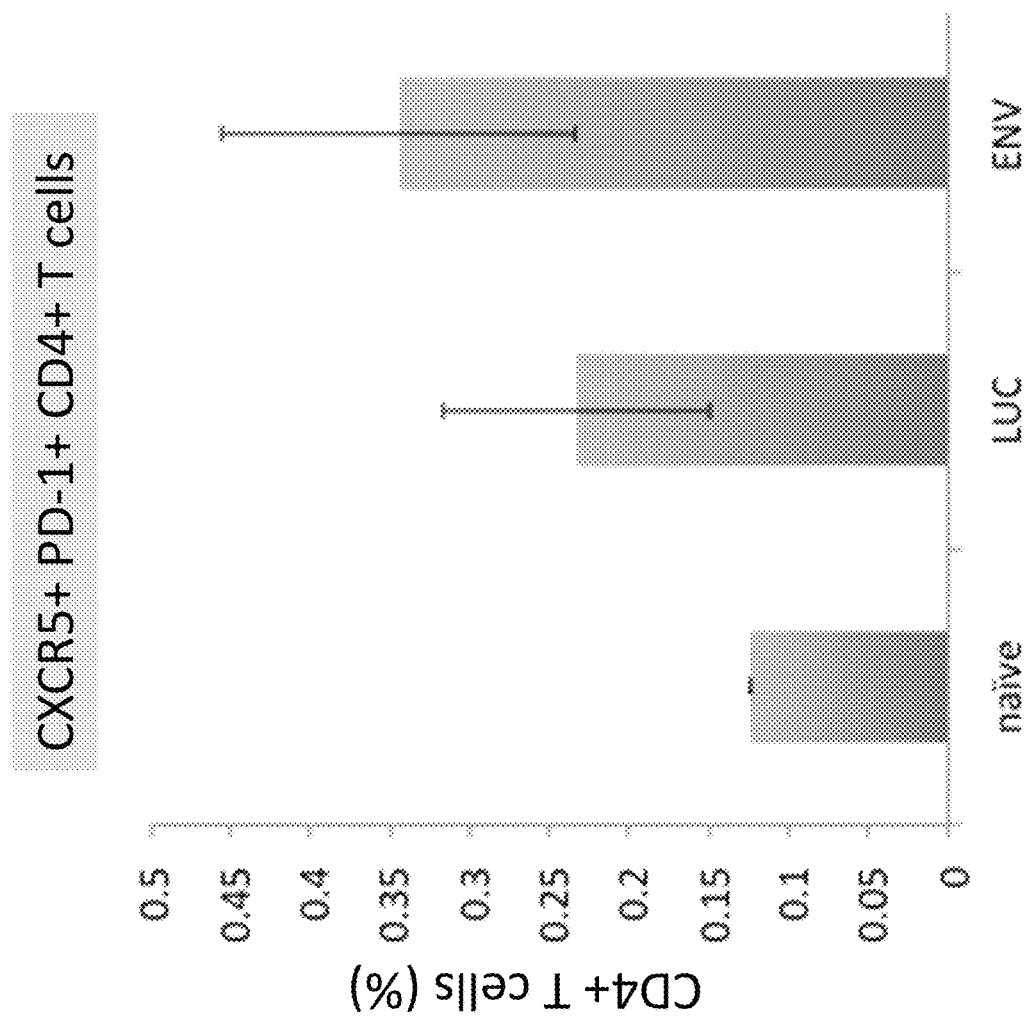
FIG. 16 is a graph illustrating that a single injection with 30 μg ENV mRNA-LNPs results in a significant increase in total Tfh cell numbers in the spleen. The graph depicts the frequency of Tfh cells in vaccinated animals. CD4, CXCR5 and PD-1 markers were used to determine Tfh cells. ENV=30 μg of iR3A envelope encoding mRNA injected ID. Luc=30 μg of control luciferase encoding mRNA injected ID. Standard error of the mean is indicated on the bars. Naïve: uninjected animals
Figure 17:
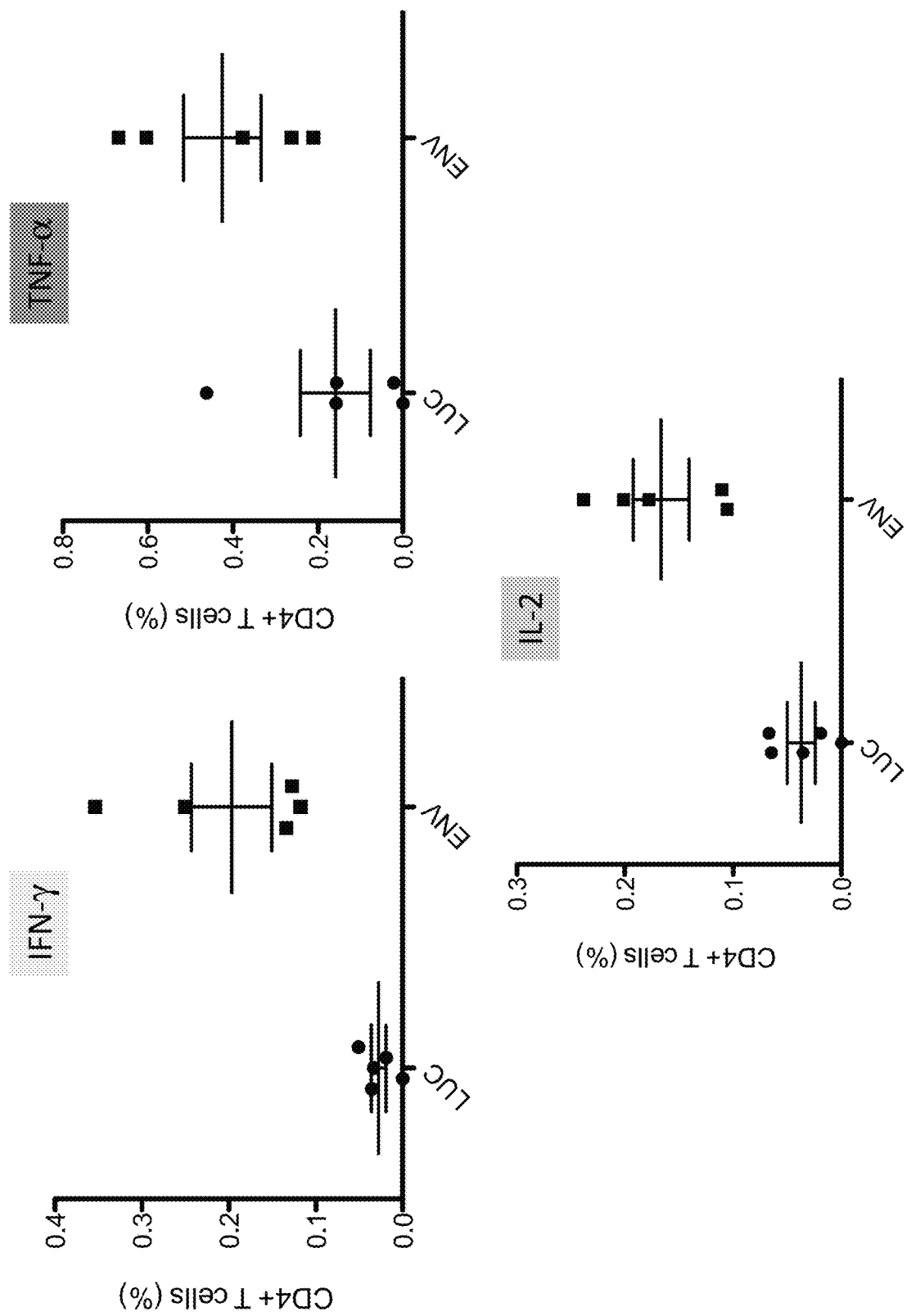
FIG. 17 is a set of graphs illustrating that a single injection with 30 ENV-LNPs elicit robust antigen specific Tfh cell immune responses. The graphs depict IFN-γ (top left), TNF-α (top right), and IL-2 (bottom) production of antigen specific Tfh CD4+ T cells. Tfh cells were identified by expression of nuclear Bcl6. Cytokine production of individual animals is displayed. ENV=30 μg of iR3A envelope encoding mRNA injected ID. Luc=30 μg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated.

The present invention relates to compositions and methods for inducing an adaptive immune response in a subject. In certain embodiments, the invention provides a composition comprising at least one nucleoside-modified RNA encoding at least one antigen, adjuvant, or a combination thereof. For example, in one embodiment, the composition is a vaccine comprising at least one nucleoside-modified RNA encoding at least one antigen, adjuvant, or a combination thereof, where the vaccine induces immunity in the subject to the at least one antigen, and therefore induces immunity in the subject to a pathogen or pathology associated with the at least one antigen. In certain embodiments, the at least one nucleoside-modified RNA is encapsulated in a lipid nanoparticle (LNP).

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

The term "antibody," as used herein, refers to an immunoglobulin molecule, which specifically binds with an antigen. Antibodies can be intact immunoglobulins derived from natural sources or from recombinant sources and can be immunoreactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. κ and λ light chains refer to the two major antibody light chain isotypes.

By the term "synthetic antibody" as used herein, is meant an antibody, which is generated using recombinant DNA technology, such as, for example, an antibody expressed by a bacteriophage. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art. The term should also be construed to mean an antibody, which has been generated by the synthesis of an RNA molecule encoding the antibody. The RNA molecule expresses an antibody protein, or an amino acid sequence specifying the antibody, wherein the RNA has been obtained by transcribing DNA (synthetic or cloned) or other technology, which is available and well known in the art.

The term "antigen" or "Ag" as used herein is defined as a molecule that provokes an adaptive immune response. This immune response may involve either antibody production, or the activation of specific immunogenically-competent cells, or both. The skilled artisan will understand that any macromolecule, including virtually all proteins or peptides, can serve as an antigen. Furthermore, antigens can be derived from recombinant or genomic DNA or RNA. A skilled artisan will understand that any DNA or RNA, which comprises a nucleotide sequences or a partial nucleotide sequence encoding a protein that elicits an adaptive immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "adjuvant" as used herein is defined as any molecule to enhance an antigen-specific adaptive immune response.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) RNA, and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"Immunogen" refers to any substance introduced into the body in order to generate an immune response. That substance can a physical molecule, such as a protein, or can be encoded by a vector, such as DNA, mRNA, or a virus.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleosides (nucleobase bound to ribose or deoxyribose sugar via N-glycosidic linkage) are used. "A" refers to adenosine, "C" refers to cytidine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns. In addition, the nucleotide sequence may contain modified nucleosides that are capable of being translation by translational machinery in a cell. For example, an mRNA where all of the uridines have been replaced with pseudouridine, 1-methyl psuedouridien, or another modified nucleoside.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA or RNA sequences are contiguous and, where necessary to join two protein coding regions, in the same reading frame.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

In certain instances, the polynucleotide or nucleic acid of the invention is a "nucleoside-modified nucleic acid," which refers to a nucleic acid comprising at least one modified nucleoside. A "modified nucleoside" refers to a nucleoside with a modification. For example, over one hundred different nucleoside modifications have been identified in RNA (Rozenski, et al., 1999, The RNA Modification Database: 1999 update. Nucl Acids Res 27: 196-197).

In certain embodiments, "pseudouridine" refers, in another embodiment, to $m^1acp^3\Psi$ (1-methyl-3-(3-amino-3-carboxypropyl) pseudouridine. In another embodiment, the term refers to $m^1\Psi$ (1-methylpseudouridine). In another embodiment, the term refers to $\Psi m$ (2'-O-methylpseudouridine). In another embodiment, the term refers to $m^5D$ (5-methyldihydrouridine). In another embodiment, the term refers to $m^3\Psi$ (3-methylpseudouridine). In another embodiment, the term refers to a pseudouridine moiety that is not further modified. In another embodiment, the term refers to a monophosphate, diphosphate, or triphosphate of any of the above pseudouridines. In another embodiment, the term refers to any other pseudouridine known in the art. Each possibility represents a separate embodiment of the present invention.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence. For example, the promoter that is recognized by bacteriophage RNA polymerase and is used to generate the mRNA by in vitro transcription.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more other species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "therapeutic" as used herein means a treatment and/or prophylaxis. A therapeutic effect is obtained by suppression, diminution, remission, or eradication of at least one sign or symptom of a disease or disorder state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Alkyl" refers to a straight or branched hydrocarbon chain radical consisting solely of carbon and hydrogen atoms, which is saturated or unsaturated (i.e., contains one or more double and/or triple bonds), having from one to twenty-four carbon atoms ($C_1$-$C_{24}$ alkyl), one to twelve carbon atoms ($C_1$-$C_{12}$ alkyl), one to eight carbon atoms ($C_1$-$C_8$ alkyl) or one to six carbon atoms ($C_1$-$C_6$ alkyl) and which is attached to the rest of the molecule by a single bond, e.g., methyl, ethyl, n propyl, 1-methylethyl (iso propyl), n butyl, n pentyl, 1,1 dimethylethyl (t butyl), 3 methylhexyl, 2 methylhexyl, ethenyl, prop 1 enyl, but-1-enyl, pent-1-enyl, penta-1,4-dienyl, ethynyl, propynyl, butynyl, pentynyl, hexynyl, and the like. Unless specifically stated otherwise, an alkyl group is optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double (alkenylene) and/or triple bonds (alkynylene)), and having, for example, from one to twenty-four carbon atoms ($C_1$-$C_{24}$ alkylene), one to fifteen carbon atoms ($C_1$-$C_{15}$ alkylene), one to twelve carbon atoms ($C_1$-$C_{12}$ alkylene), one to eight carbon atoms ($C_1$-$C_8$ alkylene), one to six carbon atoms ($C_1$-$C_6$ alkylene), two to four carbon atoms ($C_2$-$C_4$ alkylene), one to two carbon atoms ($C_1$-$C_2$ alkylene), e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Cycloalkyl" or "carbocyclic ring" refers to a stable non aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7 dimethyl bicyclo[2.2.1] heptanyl, and the like. Unless specifically stated otherwise, a cycloalkyl group is optionally substituted.

"Cycloalkylene" is a divalent cycloalkyl group. Unless otherwise stated specifically in the specification, a cycloalkylene group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxothiomorpholinyl. Unless specifically stated otherwise, a heterocyclyl group may be optionally substituted.

The term "substituted" used herein means any of the above groups (e.g., alkyl, cycloalkyl or heterocyclyl) wherein at least one hydrogen atom is replaced by a bond to a non-hydrogen atoms such as, but not limited to: a halogen atom such as F, $C_1$, Br, and I; oxo groups (=O); hydroxyl groups (—OH); alkoxy groups (—OR$^a$, where R$^a$ is $C_1$-$C_{12}$ alkyl or cycloalkyl); carboxyl groups (—OC(=O)R$^a$ or —C(=O)OR$^a$, where R$^a$ is H, $C_1$-$C_{12}$ alkyl or cycloalkyl); amine groups (—NR$^a$R$^b$, where R$^a$ and R$^b$ are each independently H, $C_1$-$C_{12}$ alkyl or cycloalkyl); $C_1$-$C_{12}$ alkyl groups; and cycloalkyl groups. In some embodiments the substituent is a $C_1$-$C_{12}$ alkyl group. In other embodiments, the substituent is a cycloalkyl group. In other embodiments, the substituent is a halo group, such as fluoro. In other embodiments, the substituent is a oxo group. In other embodiments, the substituent is a hydroxyl group. In other embodiments, the substituent is an alkoxy group. In other embodiments, the substituent is a carboxyl group. In other embodiments, the substituent is an amine group.

"Optional" or "optionally" (e.g., optionally substituted) means that the subsequently described event of circumstances may or may not occur, and that the description includes instances where said event or circumstance occurs and instances in which it does not. For example, "optionally substituted alkyl" means that the alkyl radical may or may not be substituted and that the description includes both substituted alkyl radicals and alkyl radicals having no substitution.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to compositions and methods for inducing an adaptive immune response in a subject. In certain embodiments, the present invention provides a composition comprising a nucleic acid molecule encoding an antigen, where the antigen induces an adaptive immune response in the subject. For example, in certain embodiments, the composition comprises a vaccine comprising a nucleic acid molecule encoding an antigen.

In one embodiment, the composition of the invention comprises in vitro transcribed (IVT) RNA. For example, in certain embodiments, the composition of the invention comprises IVT RNA which encodes an antigen, where the antigen induces an adaptive immune response. In certain embodiments, the antigen is at least one of a viral antigen, bacterial antigen, fungal antigen, parasitic antigen, tumor-specific antigen, or tumor-associated antigen. However, the present invention is not limited to any particular antigen or combination of antigens.

In certain embodiments, the antigen-encoding nucleic acid of the present composition is a nucleoside-modified RNA. The present invention is based in part on the finding that nucleoside-modified RNA encoding an antigen induces robust CD4+ T-cell, CD8+ T-cell, or Tfh cell antigen-specific immune responses. Further, the antigen-encoding nucleoside-modified RNA was observed to induce antigen-specific antibody production. The nucleoside-modified RNA is demonstrated to induce adaptive immune responses that are comparable or superior to current prime-boost vaccine regimens and viral vector based regimens.

In certain embodiments, the composition comprises a lipid nanoparticle (LNP). For example, in one embodiment, the composition comprises an antigen-encoding nucleic acid molecule encapsulated within a LNP. In certain instances the LNP enhances cellular uptake of the nucleic acid molecule.

In certain embodiments, the composition comprises an adjuvant. In certain embodiments, the composition comprises a nucleic acid molecule encoding an adjuvant. For example, in one embodiment, the composition comprises a nucleoside-modified RNA encoding an adjuvant. In one embodiment, the composition comprises a nucleoside-modified RNA encoding an antigen and an adjuvant. In one embodiment, the composition comprises a first nucleoside-modified RNA, which encodes an antigen, and a second nucleoside-modified RNA, which encodes an adjuvant.

In one embodiment, the present invention provides a method for inducing an adaptive immune response in a subject. For example, the method can be used to provide immunity in the subject against a virus, bacteria, fungus, parasite, cancer, or the like. In some embodiments, the method comprises administering to the subject a composition comprising one or more nucleoside-modified RNA encoding an antigen, adjuvant, or a combination thereof.

In one embodiment, the method comprises the systemic administration of the composition into the subject, including for example intradermal administration. In certain embodiments, the method comprises administering a plurality of doses to the subject. In another embodiment, the method comprises administering a single dose of the composition, where the single dose is effective in inducing an adaptive immune response.

Vaccine

In one embodiment, the present invention provides an immunogenic composition for inducing an adaptive immune response in a subject. For example, in one embodiment, the immunogenic composition is a vaccine. For a composition to be useful as a vaccine, the composition must induce an adaptive immune response to the antigen in a cell, tissue or mammal (e.g., a human). In certain instances, the vaccine induces a protective immune response in the mammal. As used herein, an "immunogenic composition" may comprise an antigen (e.g., a peptide or polypeptide), a nucleic acid encoding an antigen, a cell expressing or presenting an antigen or cellular component, or a combination thereof. In particular embodiments the composition comprises or encodes all or part of any peptide antigen described herein, or an immunogenically functional equivalent thereof. In other embodiments, the composition is in a mixture that comprises an additional immunostimulatory agent or nucleic acids encoding such an agent. Immunostimulatory agents include but are not limited to an additional antigen, an immunomodulator, an antigen presenting cell or an adjuvant. In other embodiments, one or more of the additional agent(s) is covalently bonded to the antigen or an immunostimulatory agent, in any combination. In certain embodiments, the antigenic composition is conjugated to or comprises an HLA anchor motif amino acids.

In the context of the present invention, the term "vaccine" refers to a substance that induces immunity upon inoculation into animals.

A vaccine of the present invention may vary in its composition of nucleic acid and/or cellular components. In a non-limiting example, a nucleic acid encoding an antigen might also be formulated with an adjuvant. Of course, it will be understood that various compositions described herein may further comprise additional components. For example, one or more vaccine components may be comprised in a lipid, liposome, or lipid nanoparticle. In another non-limiting example, a vaccine may comprise one or more adjuvants. A vaccine of the present invention, and its various components, may be prepared and/or administered by any method disclosed herein or as would be known to one of ordinary skill in the art, in light of the present disclosure.

The induction of the immunity by the expression of the antigen can be detected by observing in vivo or in vitro the response of all or any part of the immune system in the host against the antigen.

For example, a method for detecting the induction of cytotoxic T lymphocytes is well known. A foreign substance that enters the living body is presented to T cells and B cells by the action of APCs. T cells that respond to the antigen presented by APC in an antigen specific manner differentiate into cytotoxic T cells (also referred to as cytotoxic T lymphocytes or CTLs) due to stimulation by the antigen. These antigen stimulated cells then proliferate. This process is referred to herein as "activation" of T cells. Therefore, CTL induction by an epitope of a polypeptide or peptide or combinations thereof can be evaluated by presenting an epitope of a polypeptide or peptide or combinations thereof to a T cell by APC, and detecting the induction of CTL. Furthermore, APCs have the effect of activating B cells, CD4+ T cells, CD8+ T cells, macrophages, eosinophils and NK cells.

A method for evaluating the inducing action of CTL using dendritic cells (DCs) as APC is well known in the art. DC is a representative APC having a robust CTL inducing action among APCs. In the methods of the invention, the epitope of a polypeptide or peptide or combinations thereof is initially expressed by the DC and then this DC is contacted with T cells. Detection of T cells having cytotoxic effects against the cells of interest after the contact with DC shows that the epitope of a polypeptide or peptide or combinations thereof has an activity of inducing the cytotoxic T cells. Furthermore, the induced immune response can be also examined by measuring IFN-gamma produced and released by CTL in the presence of antigen-presenting cells that carry immobilized peptide or combination of peptides by visualizing using anti-IFN-gamma antibodies, such as an ELISPOT assay.

Apart from DC, peripheral blood mononuclear cells (PBMCs) may also be used as the APC. The induction of CTL is reported to be enhanced by culturing PBMC in the presence of GM-CSF and IL-4. Similarly, CTL has been shown to be induced by culturing PBMC in the presence of keyhole limpet hemocyanin (KLH) and IL-7.

The antigens confirmed to possess CTL-inducing activity by these methods are antigens having DC activation effect and subsequent CTL-inducing activity. Furthermore, CTLs that have acquired cytotoxicity due to presentation of the antigen by APC can be also used as vaccines against antigen-associated disorders.

The induction of immunity by expression of the antigen can be further confirmed by observing the induction of antibody production against the antigen. For example, when antibodies against an antigen are induced in a laboratory animal immunized with the composition encoding the antigen, and when antigen-associated pathology is suppressed by those antibodies, the composition is determined to induce immunity.

The induction of immunity by expression of the antigen can be further confirmed by observing the induction of CD4+ T cells. CD4+ T cells can also lyse target cells, but mainly supply help in the induction of other types of immune responses, including CTL and antibody generation. The type of CD4+ T cell help can be characterized, as Th1, Th2, Th9, Th17, Tregulatory, or T follicular helper ($T_{fh}$) cells. Each subtype of CD4+ T cell supplies help to certain types of immune responses. Of particular interest to this invention, the Tfh subtype provides help in the generation of high affinity antibodies.

The therapeutic compounds or compositions of the invention may be administered prophylactically (i.e., to prevent disease or disorder) or therapeutically (i.e., to treat disease or disorder) to subjects suffering from or at risk of (or susceptible to) developing the disease or disorder. Such subjects may be identified using standard clinical methods. In the context of the present invention, prophylactic administration occurs prior to the manifestation of overt clinical symptoms of disease, such that a disease or disorder is prevented or alternatively delayed in its progression. In the context of the field of medicine, the term "prevent" encompasses any activity which reduces the burden of mortality or morbidity from disease. Prevention can occur at primary, secondary and tertiary prevention levels. While primary prevention avoids the development of a disease, secondary and tertiary levels of prevention encompass activities aimed at preventing the progression of a disease and the emergence of symptoms as well as reducing the negative impact of an already established disease by restoring function and reducing disease-related complications.

Nucleic Acids

In one embodiment, the invention includes a nucleoside-modified nucleic acid molecule. In one embodiment, the nucleoside-modified nucleic acid molecule encodes an antigen. In one embodiment, the nucleoside-modified nucleic acid molecule encodes a plurality of antigens. In certain embodiments, the nucleoside-modified nucleic acid molecule encodes an antigen that induces an adaptive immune response against the antigen. In one embodiment, the invention includes a nucleoside-modified nucleic acid molecule encoding an adjuvant.

The nucleotide sequences encoding an antigen or adjuvant, as described herein, can alternatively comprise sequence variations with respect to the original nucleotide sequences, for example, substitutions, insertions and/or deletions of one or more nucleotides, with the condition that the resulting polynucleotide encodes a polypeptide according to the invention. Therefore, the scope of the present invention includes nucleotide sequences that are substantially homologous to the nucleotide sequences recited herein and encode an antigen or adjuvant of interest.

In certain embodiments, the nucleotide sequence encodes an HIV Env antigen. For example, in certain embodiments, the nucleotide sequence encodes an HIV Env encoded by the nucleotide sequences of SEQ ID NO: or SEQ ID NO: 2. In one embodiment, the nucleotide sequence encodes influenza hemagglutinin (HA). For example, in certain embodiments, the nucleotide sequence encodes HA from PR8. For example, in one embodiment, the nucleotide sequence encodes PR8 HA having an amino acid sequence of SEQ ID NO: 3. In certain embodiments, the nucleotide sequence encodes PR8 HA encoded by the nucleotide sequences of SEQ ID NO: 4 or SEQ ID NO: 5. For example, in certain embodiments, the nucleotide sequence encodes HA from Cal/7/2009. For example, in one embodiment, the nucleotide sequence encodes Cal/7/2009 HA having an amino acid sequence of SEQ ID NO: 6. In certain embodiments, the nucleotide sequence encodes Cal/7/2009/HA encoded by the nucleotide sequences of SEQ ID NO: 7 or SEQ ID NO: 8.

As used herein, a nucleotide sequence is "substantially homologous" to any of the nucleotide sequences described herein when its nucleotide sequence has a degree of identity with respect to the nucleotide sequence of at least 60%, advantageously of at least 70%, preferably of at least 85%, and more preferably of at least 95%. A nucleotide sequence that is substantially homologous to a nucleotide sequence encoding an antigen can typically be isolated from a producer organism of the antigen based on the information contained in the nucleotide sequence by means of introducing conservative or non-conservative substitutions, for example. Other examples of possible modifications include the insertion of one or more nucleotides in the sequence, the addition of one or more nucleotides in any of the ends of the sequence, or the deletion of one or more nucleotides in any end or inside the sequence. The degree of identity between two polynucleotides is determined using computer algorithms and methods that are widely known for the persons skilled in the art.

Further, the scope of the invention includes nucleotide sequences that encode amino acid sequences that are substantially homologous to the amino acid sequences recited herein and preserve the immunogenic function of the original amino acid sequence.

As used herein, an amino acid sequence is "substantially homologous" to any of the amino acid sequences described herein when its amino acid sequence has a degree of identity with respect to the amino acid sequence of at least 60%, advantageously of at least 70%, preferably of at least 85%, and more preferably of at least 95%. The identity between two amino acid sequences is preferably determined by using the BLASTN algorithm (BLAST Manual, Altschul, S., et al., NCBI NLM NIH Bethesda, Md. 20894, Altschul, S., et al., J. Mol. Biol. 215: 403-410 (1990)).

In one embodiment, the invention relates to a construct, comprising a nucleotide sequence encoding an antigen. In one embodiment, the construct comprises a plurality of nucleotide sequences encoding a plurality of antigens. For example, in certain embodiments, the construct encodes 1 or more, 2 or more, 5 or more, 10 or more, 15 or more, or 20 or more antigens. In one embodiment, the invention relates to a construct, comprising a nucleotide sequence encoding an adjuvant. In one embodiment, the construct comprises a first nucleotide sequence encoding an antigen and a second nucleotide sequence encoding an adjuvant.

In one embodiment, the composition comprises a plurality of constructs, each construct encoding one or more antigens. In certain embodiments, the composition comprises 1 or more, 2 or more, 5 or more, 10 or more, 15 or more, or 20 or more constructs. In one embodiment, the composition comprises a first construct, comprising a nucleotide sequence encoding an antigen; and a second construct, comprising a nucleotide sequence encoding an adjuvant.

In another particular embodiment, the construct is operatively bound to a translational control element. The construct can incorporate an operatively bound regulatory sequence for the expression of the nucleotide sequence of the invention, thus forming an expression cassette.

Vectors

The nucleic acid sequences coding for the antigen or adjuvant can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, sequencing vectors and vectors optimized for in vitro transcription.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/RNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the mRNA sequence in the host cell, a variety of assays may be performed. Such assays include, for example, "molecular biological" assays well known to those of skill in the art, such as Northern blotting and RT-PCR; "biochemical" assays, such as detecting the presence or absence of a particular peptide, e.g., by immunogenic means (ELISAs and Western blots) or by assays described herein to identify agents falling within the scope of the invention.

In Vitro Transcribed RNA

In one embodiment, the composition of the invention comprises in vitro transcribed (IVT) RNA encoding an antigen. In one embodiment, the composition of the invention comprises IVT RNA encoding a plurality of antigens. In one embodiment, the composition of the invention comprises IVT RNA encoding an adjuvant. In one embodiment, the composition of the invention comprises IVT RNA encoding one or more antigens and one or more adjuvants.

In one embodiment, an IVT RNA can be introduced to a cell as a form of transient transfection. The RNA is produced by in vitro transcription using a plasmid DNA template generated synthetically. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. In one embodiment, the desired template for in vitro transcription is an antigen capable of inducing an adaptive immune response, including for example an antigen associated with a pathogen or tumor, as described elsewhere herein. In one embodiment, the desired template for in vitro transcription is an adjuvant capable of enhancing an adaptive immune response.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. In another embodiment, the DNA to be used for PCR is a gene from a pathogenic or commensal organism, including bacteria, viruses, parasites, and fungi. In another embodiment, the DNA to be used for PCR is from a pathogenic or commensal organism, including bacteria, viruses, parasites, and fungi, including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

Genes that can be used as sources of DNA for PCR include genes that encode polypeptides that induce or enhance an adaptive immune response in an organism. Preferred genes are genes which are useful for a short term treatment, or where there are safety concerns regarding dosage or the expressed gene.

In various embodiments, a plasmid is used to generate a template for in vitro transcription of mRNA which is used for transfection.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 RNA polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is effective in eukaryotic transfection when it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which can be ameliorated through the use of recombination incompetent bacterial cells for plasmid propagation.

Poly(A) tails of RNAs can be further extended following in vitro transcription with the use of a poly(A) polymerase, such as E. coli polyA polymerase (E-PAP) or yeast polyA polymerase. In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to mRNA molecules. In a preferred embodiment, RNAs produced by the methods to include a 5' cap1 structure. Such cap1 structure can be generated using Vaccinia capping enzyme and 2'-O-methyltransferase enzymes (CellScript, Madison, WI). Alternatively, 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001). In certain embodiments RNA of the invention is introduced to a cell with a method comprising the use of TransIT®-mRNA transfection Kit (Mirus, Madison WI), which, in some instances, provides high efficiency, low toxicity, transfection.

Nucleoside-Modified RNA

In one embodiment, the composition of the present invention comprises a nucleoside-modified nucleic acid encoding an antigen as described herein. In one embodiment, the composition of the present invention comprises a nucleoside-modified nucleic acid encoding a plurality of antigens. In one embodiment, the composition of the present invention comprises a nucleoside-modified nucleic acid encoding an adjuvant as described herein. In one embodiment, the composition of the present invention comprises a nucleoside-modified nucleic acid encoding one or more antigens and one or more adjuvants.

For example, in one embodiment, the composition comprises a nucleoside-modified RNA. In one embodiment, the composition comprises a nucleoside-modified mRNA. Nucleoside-modified mRNA have particular advantages over non-modified mRNA, including for example, increased stability, low or absent innate immunogenicity, and enhanced translation. Nucleoside-modified mRNA useful in the present invention is further described in U.S. Pat. No. 8,278,036, which is incorporated by reference herein in its entirety.

In certain embodiments, nucleoside-modified mRNA does not activate any pathophysiologic pathways, translates very efficiently and almost immediately following delivery, and serve as templates for continuous protein production in vivo lasting for several days (Karikó et al., 2008, Mol Ther 16:1833-1840; Karikó et al., 2012, Mol Ther 20:948-953). The amount of mRNA required to exert a physiological effect is small and that makes it applicable for human therapy. For example, as described herein, nucleoside-modified mRNA encoding an antigen has demonstrated the ability to induce CD4+ and CD8+ T-cell and antigen-specific antibody production. For example, in certain instances, antigen encoded by nucleoside-modified mRNA induces greater production of antigen-specific antibody production as compared to antigen encoded by non-modified mRNA.

In certain instances, expressing a protein by delivering the encoding mRNA has many benefits over methods that use protein, plasmid DNA or viral vectors. During mRNA transfection, the coding sequence of the desired protein is the only substance delivered to cells, thus avoiding all the side effects associated with plasmid backbones, viral genes, and viral proteins. More importantly, unlike DNA- and viral-based vectors, the mRNA does not carry the risk of being incorporated into the genome and protein production starts immediately after mRNA delivery. For example, high levels of circulating proteins have been measured within 15 to 30 minutes of in vivo injection of the encoding mRNA. In certain embodiments, using mRNA rather than the protein also has many advantages. Half-lives of proteins in the circulation are often short, thus protein treatment would need frequent dosing, while mRNA provides a template for continuous protein production for several days. Purification of proteins is problematic and they can contain aggregates and other impurities that cause adverse effects (Kromminga and Schellekens, 2005, Ann NY Acad Sci 1050:257-265).

In certain embodiments, the nucleoside-modified RNA comprises the naturally occurring modified-nucleoside pseudouridine. In certain embodiments, inclusion of pseudouridine makes the mRNA more stable, non-immunogenic, and highly translatable (Karikó et al., 2008, Mol Ther 16:1833-1840; Anderson et al., 2010, Nucleic Acids Res 38:5884-5892; Anderson et al., 2011, Nucleic Acids Research 39:9329-9338; Karikó et al., 2011, Nucleic Acids Research 39:e142; Karikó et al., 2012, Mol Ther 20:948-953; Karikó et al., 2005, Immunity 23:165-175).

It has been demonstrated that the presence of modified nucleosides, including pseudouridines in RNA suppress their innate immunogenicity (Karikó et al., 2005, Immunity 23:165-175). Further, protein-encoding, in vitro-transcribed RNA containing pseudouridine can be translated more efficiently than RNA containing no or other modified nucleosides (Karikó et al., 2008, Mol Ther 16:1833-1840). Subsequently, it is shown that the presence of pseudouridine improves the stability of RNA (Anderson et al., 2011, Nucleic Acids Research 39:9329-9338) and abates both activation of PKR and inhibition of translation (Anderson et al., 2010, Nucleic Acids Res 38:5884-5892). A preparative HPLC purification procedure has been established that was critical to obtain pseudouridine-containing RNA that has superior translational potential and no innate immunogenicity (Karikó et al., 2011, Nucleic Acids Research 39:e142). Administering HPLC-purified, pseudourine-containing RNA coding for erythropoietin into mice and macaques resulted in a significant increase of serum EPO levels (Karikó et al., 2012, Mol Ther 20:948-953), thus confirming that pseudouridine-containing mRNA is suitable for in vivo protein therapy.

The present invention encompasses RNA, oligoribonucleotide, and polyribonucleotide molecules comprising pseudouridine or a modified nucleoside. In certain embodiments, the composition comprises an isolated nucleic acid encoding an antigen, wherein the nucleic acid comprises a pseudouridine or a modified nucleoside. In certain embodiments, the composition comprises a vector, comprising an isolated nucleic acid encoding an antigen, adjuvant, or combination thereof, wherein the nucleic acid comprises a pseudouridine or a modified nucleoside.

In one embodiment, the nucleoside-modified RNA of the invention is IVT RNA, as described elsewhere herein. For example, in certain embodiments, the nucleoside-modified RNA is synthesized by T7 phage RNA polymerase. In another embodiment, the nucleoside-modified mRNA is synthesized by SP6 phage RNA polymerase. In another embodiment, the nucleoside-modified RNA is synthesized by T3 phage RNA polymerase.

In one embodiment, the modified nucleoside is $m^1acp^3\Psi$ (1-methyl-3-(3-amino-3-carboxypropyl) pseudouridine. In another embodiment, the modified nucleoside is $m^1\Psi$ (1-methylpseudouridine). In another embodiment, the modified nucleoside is $\Psi m$ (2'-O-methylpseudouridine. In another embodiment, the modified nucleoside is $m^5D$ (5-methyldihydrouridine). In another embodiment, the modified nucleoside is $m^3\Psi$ (3-methylpseudouridine). In another embodiment, the modified nucleoside is a pseudouridine moiety that is not further modified. In another embodiment, the modified nucleoside is a monophosphate, diphosphate, or triphosphate of any of the above pseudouridines. In another embodiment, the modified nucleoside is any other pseudouridine-like nucleoside known in the art.

In another embodiment, the nucleoside that is modified in the nucleoside-modified RNA the present invention is uridine (U). In another embodiment, the modified nucleoside is cytidine (C). In another embodiment, the modified nucleoside is adenosine (A). In another embodiment the modified nucleoside is guanosine (G).

In another embodiment, the modified nucleoside of the present invention is $m^5C$ (5-methylcytidine). In another embodiment, the modified nucleoside is $m^5U$ (5-methyluridine). In another embodiment, the modified nucleoside is $m^6A$ ($N^6$-methyladenosine). In another embodiment, the modified nucleoside is $s^2U$ (2-thiouridine). In another embodiment, the modified nucleoside is 4' (pseudouridine). In another embodiment, the modified nucleoside is Um (2'-O-methyluridine).

In other embodiments, the modified nucleoside is m'A (1-methyladenosine); $m^2A$ (2-methyladenosine); Am (2'-O-methyladenosine); $ms^2$ $m^6A$ (2-methylthio-$N^6$-methyladenosine); $i^6A$ ($N^6$-isopentenyladenosine); $ms^2i6A$ (2-methylthio-$N^6$isopentenyladenosine); $io^6A$ ($N^6$-(cis-hydroxyisopentenyl)adenosine); $ms^2io^6A$ (2-methylthio-$N^6$-(cis-hydroxyisopentenyl) adenosine); $g^6A$ ($N^6$-glycinylcarbamoyladenosine); $t^6A$ ($N^6$-threonylcarbamoyladenosine); $ms^2t^6A$ (2-methylthio-$N^6$-threonyl carbamoyladenosine); m6t6A methyl-$N^6$-threonylcarbamoyladenosine); $hn^6A$($N^6$-hydroxynorvalylcarbamoyladenosine); $ms^2hn^6A$ (2-methylthio-$N^6$-hydroxynorvalyl carbamoyladenosine); Ar(p) (2'-O-ribosyladenosine (phosphate)); I (inosine); $m^1I$ (1-methylinosine); $m^1Im$ (1,2'-O-dimethylinosine); $m^3C$ (3-methylcytidine); Cm (2'-O-methylcytidine); $s^2C$ (2-thiocytidine); $ac^4C$ ($N^4$-acetylcytidine); $f^5C$ (5-formylcytidine); $m^5Cm$ (5,2'-O-dimethylcytidine); $ac^4Cm$ ($N^4$-acetyl-2'-O-methylcytidine); $k^2C$ (lysidine); $m^1G$ (1-methylguanosine); $m^2G$ ($N^2$-methylguanosine); $m^7G$ (7-methylguanosine); Gm (2'-O-methylguanosine); $m^2_2$ G ($N^2,N^2$-dimethylguanosine); $m^2Gm$ ($N^2$2'-O-dimethylguanosine); $m^2$2 Gm ($N^2,N^2$,2'-O-trimethylguanosine); Gr(p) (2'-O-ribosylguanosine (phosphate)); yW (wybutosine); $o_2yW$ (peroxywybutosine); OHyW (hydroxywybutosine); OHyW* (undermodified hydroxywybutosine); imG (wyosine); mimG (methylwyosine); Q (queuosine); oQ (epoxyqueuosine); galQ (galactosyl-queuosine); manQ (mannosyl-queuosine); preQo (7-cyano-7-deazaguanosine); $preQ_1$ (7-aminomethyl-7-deazaguanosine); (archaeosine); D (dihydrouridine); $m^5Um$ (5,2'-O-dimethyluridine); $s^4U$ (4-thiouridine); $m^5s^2U$ (5-methyl-2-thiouridine); $s^2Um$ (2-thio-2'-O-methyluridine); $acp^3U$ (3-(3-amino-3-carboxypropyl)uridine); $ho^5U$ (5-hydroxyuridine); $mo^5U$ (5-methoxyuridine); $cmo^5U$ (uridine 5-oxyacetic acid); $mcmo^5U$ (uridine 5-oxyacetic acid methyl ester); $chm^5U$ (5-(carboxyhydroxymethyl)uridine)); $mchm^5U$ (5-(carboxyhydroxymethyl)uridine methyl ester); $mcm^5U$ (5-methoxycarbonylmethyluridine); $mcm^5Um$ (5-methoxycarbonylmethyl-2'-O-methyluridine); $mcm^5s^2U$ (5-methoxycarbonylmethyl-2-thiouridine); $nm^5s^2U$ (5-aminomethyl-2-thiouridine); $mnm^5U$ (5-methylaminomethyluridine); $mnm^5s^2U$ (5-methylaminomethyl-2-thiouridine); $mnm^5se^2U$ (5-methylaminomethyl-2-selenouridine); $ncm^5U$ (5-carbamoylmethyluridine); $ncm^5Um$ (5-carbamoylmethyl-2'-O-methyluridine); $cmnm^5U$ (5-carboxymethylaminomethyluridine); $cmnm^5Um$ (5-carboxymethylaminomethyl-2'-O-methyluridine); $cmnm^5s^2U$ (5-carboxymethylaminomethyl-2-thiouridine); $m^6_2A$ ($N^6,N^6$-dimethyladenosine); Im (2'-O-methylinosine); $m^4C$ ($N^4$-methylcytidine); $m^4Cm$ ($N^4$,2'-O-dimethylcytidine); $hm^5C$ (5-hydroxymethylcytidine); $m^3U$ (3-methyluridine); $cm^5U$ (5-carboxymethyluridine); $m^6Am$ ($N^6$,2'-O-dimethyladenosine); $m^6_2$ Am ($N^6,N^6$,O-2'-trimethyladenosine); $m^{2,7}G$ ($N^2$,7-dimethylguanosine); $m^{2,2,7}G$ ($N^2,N^2$,7-trimethylguanosine); $m^3Um$ (3,2'-O-dimethyluridine); $m^5D$ (5-methyldihydrouridine); $f^5Cm$ (5-formyl-2'-O-methylcytidine); $m^1Gm$ (1,2'-O-dimethylguanosine); $m^1Am$ (1,2'-O-dimethyladenosine); $\tau m^5U$ (5-taurinomethyluridine); $\tau m^5s^2U$ (5-taurinomethyl-2-thiouridine)); imG-14 (4-demethylwyosine); imG2 (isowyosine); or $ac^6A$ ($N^6$-acetyladenosine).

In another embodiment, a nucleoside-modified RNA of the present invention comprises a combination of 2 or more of the above modifications. In another embodiment, the nucleoside-modified RNA comprises a combination of 3 or more of the above modifications. In another embodiment, the nucleoside-modified RNA comprises a combination of more than 3 of the above modifications.

In another embodiment, between 0.1% and 100% of the residues in the nucleoside-modified of the present invention are modified (e.g. either by the presence of pseudouridine or a modified nucleoside base). In another embodiment, 0.1% of the residues are modified. In another embodiment, the fraction of modified residues is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 8%. In another embodiment, the fraction is less than 10%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, 0.1% of the residues of a given nucleoside (i.e., uridine, cytidine, guanosine, or adenosine) are modified. In another embodiment, the fraction of the given nucleotide that is modified is 0.2%. In another embodiment, the fraction is 0.3%. In another embodiment, the fraction is 0.4%. In another embodiment, the fraction is 0.5%. In another embodiment, the fraction is 0.6%. In another embodiment, the fraction is 0.8%. In another embodiment, the fraction is 1%. In another embodiment, the fraction is 1.5%. In another embodiment, the fraction is 2%. In another embodiment, the fraction is 2.5%. In another embodiment, the fraction is 3%. In another embodiment, the fraction is 4%. In another embodiment, the fraction is 5%. In another embodiment, the fraction is 6%. In another embodiment, the fraction is 8%. In another embodiment, the fraction is 10%. In another embodiment, the fraction is 12%. In another embodiment, the fraction is 14%. In another embodiment, the fraction is 16%. In another embodiment, the fraction is 18%. In another embodiment, the fraction is 20%. In another embodiment, the fraction is 25%. In another embodiment, the fraction is 30%. In another embodiment, the fraction is 35%. In another embodiment, the fraction is 40%. In another embodiment, the fraction is 45%. In another embodiment, the fraction is 50%. In another embodiment, the fraction is 60%. In another embodiment, the fraction is 70%. In another embodiment, the fraction is 80%. In another embodiment, the fraction is 90%. In another embodiment, the fraction is 100%.

In another embodiment, the fraction of the given nucleotide that is modified is less than 8%. In another embodiment, the fraction is less than 10%. In another embodiment, the fraction is less than 5%. In another embodiment, the fraction is less than 3%. In another embodiment, the fraction is less than 1%. In another embodiment, the fraction is less than 2%. In another embodiment, the fraction is less than 4%. In another embodiment, the fraction is less than 6%. In another embodiment, the fraction is less than 12%. In another embodiment, the fraction is less than 15%. In another embodiment, the fraction is less than 20%. In another embodiment, the fraction is less than 30%. In another embodiment, the fraction is less than 40%. In another embodiment, the fraction is less than 50%. In another embodiment, the fraction is less than 60%. In another embodiment, the fraction is less than 70%.

In another embodiment, a nucleoside-modified RNA of the present invention is translated in the cell more efficiently than an unmodified RNA molecule with the same sequence. In another embodiment, the nucleoside-modified RNA exhibits enhanced ability to be translated by a target cell. In another embodiment, translation is enhanced by a factor of 2-fold relative to its unmodified counterpart. In another embodiment, translation is enhanced by a 3-fold factor. In another embodiment, translation is enhanced by a 5-fold factor. In another embodiment, translation is enhanced by a 7-fold factor. In another embodiment, translation is enhanced by a 10-fold factor. In another embodiment, translation is enhanced by a 15-fold factor. In another embodiment, translation is enhanced by a 20-fold factor. In another embodiment, translation is enhanced by a 50-fold factor. In another embodiment, translation is enhanced by a 100-fold factor. In another embodiment, translation is enhanced by a 200-fold factor. In another embodiment, translation is enhanced by a 500-fold factor. In another embodiment, translation is enhanced by a 1000-fold factor. In another embodiment, translation is enhanced by a 2000-fold factor. In another embodiment, the factor is 10-1000-fold. In another embodiment, the factor is 10-100-fold. In another embodiment, the factor is 10-200-fold. In another embodiment, the factor is 10-300-fold. In another embodiment, the factor is 10-500-fold. In another embodiment, the factor is 20-1000-fold. In another embodiment, the factor is 30-1000-fold. In another embodiment, the factor is 50-1000-fold. In another embodiment, the factor is 100-1000-fold. In another embodiment, the factor is 200-1000-fold. In another embodiment, translation is enhanced by any other significant amount or range of amounts.

In another embodiment, the nucleoside-modified antigen-encoding RNA of the present invention induces significantly more adaptive immune response than an unmodified in vitro-synthesized RNA molecule with the same sequence. In another embodiment, the modified RNA molecule exhibits an adaptive immune response that is 2-fold greater than its unmodified counterpart. In another embodiment, the adaptive immune response is increased by a 3-fold factor. In another embodiment the adaptive immune response is increased by a 5-fold factor. In another embodiment, the adaptive immune response is increased by a 7-fold factor. In another embodiment, the adaptive immune response is increased by a 10-fold factor. In another embodiment, the adaptive immune response is increased by a 15-fold factor. In another embodiment the adaptive immune response is increased by a 20-fold factor. In another embodiment, the adaptive immune response is increased by a 50-fold factor. In another embodiment, the adaptive immune response is increased by a 100-fold factor. In another embodiment, the adaptive immune response is increased by a 200-fold factor. In another embodiment, the adaptive immune response is increased by a 500-fold factor. In another embodiment, the adaptive immune response is increased by a 1000-fold factor. In another embodiment, the adaptive immune response is increased by a 2000-fold factor. In another embodiment, the adaptive immune response is increased by another fold difference.

In another embodiment, "induces significantly more adaptive immune response" refers to a detectable increase in an adaptive immune response. In another embodiment, the term refers to a fold increase in the adaptive immune response (e.g., 1 of the fold increases enumerated above). In another embodiment, the term refers to an increase such that the nucleoside-modified RNA can be administered at a lower dose or frequency than an unmodified RNA molecule with the same species while still inducing an effective adaptive immune response. In another embodiment, the increase is such that the nucleoside-modified RNA can be administered using a single dose to induce an effective adaptive immune response.

In another embodiment, the nucleoside-modified RNA of the present invention exhibits significantly less innate immunogenicity than an unmodified in vitro-synthesized RNA molecule with the same sequence. In another embodiment, the modified RNA molecule exhibits an innate immune response that is 2-fold less than its unmodified counterpart. In another embodiment, innate immunogenicity is reduced by a 3-fold factor. In another embodiment, innate immunogenicity is reduced by a 5-fold factor. In another embodiment, innate immunogenicity is reduced by a 7-fold factor. In another embodiment, innate immunogenicity is reduced by a 10-fold factor. In another embodiment, innate immunogenicity is reduced by a 15-fold factor. In another embodiment, innate immunogenicity is reduced by a 20-fold factor. In another embodiment, innate immunogenicity is reduced by a 50-fold factor. In another embodiment, innate immunogenicity is reduced by a 100-fold factor. In another embodiment, innate immunogenicity is reduced by a 200-fold factor. In another embodiment, innate immunogenicity is reduced by a 500-fold factor. In another embodiment, innate immunogenicity is reduced by a 1000-fold factor. In another embodiment, innate immunogenicity is reduced by a 2000-fold factor. In another embodiment, innate immunogenicity is reduced by another fold difference.

In another embodiment, "exhibits significantly less innate immunogenicity" refers to a detectable decrease in innate immunogenicity. In another embodiment, the term refers to a fold decrease in innate immunogenicity (e.g., 1 of the fold decreases enumerated above). In another embodiment, the term refers to a decrease such that an effective amount of the nucleoside-modified RNA can be administered without triggering a detectable innate immune response. In another embodiment, the term refers to a decrease such that the nucleoside-modified RNA can be repeatedly administered without eliciting an innate immune response sufficient to detectably reduce production of the recombinant protein. In another embodiment, the decrease is such that the nucleoside-modified RNA can be repeatedly administered without eliciting an innate immune response sufficient to eliminate detectable production of the recombinant protein.

Lipid Nanoparticle

In one embodiment, delivery of nucleoside-modified RNA comprises any suitable delivery method, including exemplary RNA transfection methods described elsewhere herein. In certain embodiments, delivery of a nucleoside-modified RNA to a subject comprises mixing the nucleoside-modified RNA with a transfection reagent prior to the step of contacting. In another embodiment, a method of present invention further comprises administering nucleoside-modified RNA together with the transfection reagent. In another embodiment, the transfection reagent is a cationic lipid reagent.

In another embodiment, the transfection reagent is a lipid-based transfection reagent. In another embodiment, the transfection reagent is a protein-based transfection reagent. In another embodiment, the transfection reagent is a polyethyleneimine based transfection reagent. In another embodiment, the transfection reagent is calcium phosphate. In another embodiment, the transfection reagent is Lipofectin®, Lipofectamine®, or TransIT®. In another embodiment, the transfection reagent is any other transfection reagent known in the art.

In another embodiment, the transfection reagent forms a liposome. Liposomes, in another embodiment, increase intracellular stability, increase uptake efficiency and improve biological activity. In another embodiment, liposomes are hollow spherical vesicles composed of lipids arranged in a similar fashion as those lipids which make up the cell membrane. They have, in another embodiment, an internal aqueous space for entrapping water-soluble compounds and range in size from 0.05 to several microns in diameter. In another embodiment, liposomes can deliver RNA to cells in a biologically active form.

In one embodiment, the composition comprises a lipid nanoparticle (LNP) and one or more nucleic acid molecules described herein. For example, in one embodiment, the composition comprises an LNP and one or more nucleoside-modified RNA molecules encoding one or more antigens, adjuvants, or a combination thereof.

The term "lipid nanoparticle" refers to a particle having at least one dimension on the order of nanometers (e.g., 1-1,000 nm) which includes one or more lipids, for example a lipid of Formula (I), (II) or (III). In some embodiments, lipid nanoparticles are included in a formulation comprising a nucleoside-modified RNA as described herein. In some embodiments, such lipid nanoparticles comprise a cationic lipid (e.g., a lipid of Formula (I), (II) or (III)) and one or more excipient selected from neutral lipids, charged lipids, steroids and polymer conjugated lipids (e.g., a pegylated lipid such as a pegylated lipid of structure (IV), such as compound IVa). In some embodiments, the nucleoside-modified RNA is encapsulated in the lipid portion of the lipid nanoparticle or an aqueous space enveloped by some or all of the lipid portion of the lipid nanoparticle, thereby protecting it from enzymatic degradation or other undesirable effects induced by the mechanisms of the host organism or cells e.g. an adverse immune response.

In various embodiments, the lipid nanoparticles have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, 35 nm, 40 nm, 45 nm, 50 nm, 55 nm, 60 nm, 65 nm, 70 nm, 75 nm, 80 nm, 85 nm, 90 nm, 95 nm, 100 nm, 105 nm, 110 nm, 115 nm, 120 nm, 125 nm, 130 nm, 135 nm, 140 nm, 145 nm, or 150 nm, and are substantially non-toxic. In certain embodiments, the nucleoside-modified RNA, when present in the lipid nanoparticles, is resistant in aqueous solution to degradation with a nuclease.

The LNP may comprise any lipid capable of forming a particle to which the one or more nucleic acid molecules are attached, or in which the one or more nucleic acid molecules are encapsulated. The term "lipid" refers to a group of organic compounds that are derivatives of fatty acids (e.g., esters) and are generally characterized by being insoluble in water but soluble in many organic solvents. Lipids are usually divided in at least three classes: (1) "simple lipids" which include fats and oils as well as waxes; (2) "compound lipids" which include phospholipids and glycolipids; and (3) "derived lipids" such as steroids.

In one embodiment, the LNP comprises one or more cationic lipids, and one or more stabilizing lipids. Stabilizing lipids include neutral lipids and pegylated lipids.

In one embodiment, the LNP comprises a cationic lipid. As used herein, the term "cationic lipid" refers to a lipid that is cationic or becomes cationic (protonated) as the pH is lowered below the pK of the ionizable group of the lipid, but is progressively more neutral at higher pH values. At pH values below the pK, the lipid is then able to associate with negatively charged nucleic acids. In certain embodiments, the cationic lipid comprises a zwitterionic lipid that assumes a positive charge on pH decrease.

In certain embodiments, the cationic lipid comprises any of a number of lipid species which carry a net positive charge at a selective pH, such as physiological pH. Such lipids include, but are not limited to, N,N-dioleyl-N,N-dimethylammonium chloride (DODAC); N-(2,3-dioleyloxy)propyl)-N,N,N-trimethylammonium chloride (DOTMA); N,N-distearyl-N,N-dimethylammonium bromide (DDAB); N-(2,3-dioleoyloxy)propyl)-N,N,N-trimethylammonium chloride (DOTAP); 3-(N—(N',N'-dimethylaminoethane)-carbamoyl)cholesterol (DC-Chol), N-(1-(2,3-dioleoyloxy)propyl)-N-2-(sperminecarboxamido)ethyl)-N,N-dimethylammonium trifluoracetate (DOSPA), dioctadecylamidoglycyl carboxyspermine (DOGS), 1,2-dioleoyl-3-dimethylammonium propane (DODAP), N,N-dimethyl-2,3-dioleoyloxy)propylamine (DODMA), and N-(1,2-dimyristyloxyprop-3-yl)-N,N-dimethyl-N-hydroxyethyl ammonium bromide (DMRIE). Additionally, a number of commercial preparations of cationic lipids are available which can be used in the present invention. These include, for example, LIPOFECTIN® (commercially available cationic liposomes comprising DOTMA and 1,2-dioleoyl-sn-3-phosphoethanolamine (DOPE), from GIBCO/BRL, Grand Island, N.Y.); LIPOFECTAMINE® (commercially available cationic liposomes comprising N-(1-(2,3-dioleyloxy)propyl)-N-(2-(sperminecarboxamido)ethyl)-N,N-dimethylammonium trifluoroacetate (DOSPA) and (DOPE), from GIBCO/BRL); and TRANSFECTAM® (commercially available cationic lipids comprising dioctadecylamidoglycyl carboxyspermine (DOGS) in ethanol from Promega Corp., Madison, Wis.). The following lipids are cationic and have a positive charge at below physiological pH: DODAP, DODMA, DMDMA, 1,2-dilinoleyloxy-N,N-dimethylaminopropane (DLinDMA), 1,2-dilinolenyloxy-N,N-dimethylaminopropane (DLenDMA).

In one embodiment, the cationic lipid is an amino lipid. Suitable amino lipids useful in the invention include those described in WO 2012/016184, incorporated herein by reference in its entirety. Representative amino lipids include, but are not limited to, 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanediol (DOAP), 1,2-dilinoleyloxo-3-(2-N,N-dimethylamino)ethoxypropane (DLin-EG-DMA), and 2,2-dilinoleyl-4-dimethylaminomethyl-[1,3]-dioxolane (DLin-K-DMA).

Suitable amino lipids include those having the formula:

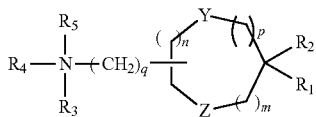

wherein $R_1$ and $R_2$ are either the same or different and independently optionally substituted $C_{10}$-$C_{24}$ alkyl, optionally substituted $C_{10}$-$C_{24}$ alkenyl, optionally substituted $C_{10}$-$C_{24}$ alkynyl, or optionally substituted $C_{10}$-$C_{24}$ acyl;

$R_3$ and $R_4$ are either the same or different and independently optionally substituted $C_1$-$C_6$ alkyl, optionally substituted $C_2$-$C_6$ alkenyl, or optionally substituted $C_2$-$C_6$ alkynyl or $R_3$ and $R_4$ may join to form an optionally substituted heterocyclic ring of 4 to 6 carbon atoms and 1 or 2 heteroatoms chosen from nitrogen and oxygen;

$R_5$ is either absent or present and when present is hydrogen or $C_1$-$C_6$ alkyl;

m, n, and p are either the same or different and independently either 0 or 1 with the proviso that m, n, and p are not simultaneously 0;

q is 0, 1, 2, 3, or 4; and

Y and Z are either the same or different and independently 0, S, or NH.

In one embodiment, $R_1$ and $R_2$ are each linoleyl, and the amino lipid is a dilinoleyl amino lipid. In one embodiment, the amino lipid is a dilinoleyl amino lipid.

A representative useful dilinoleyl amino lipid has the formula:

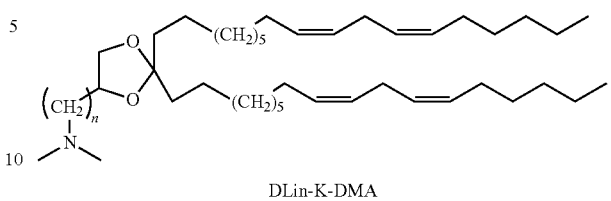

DLin-K-DMA wherein n is 0, 1, 2, 3, or 4.

In one embodiment, the cationic lipid is a DLin-K-DMA. In one embodiment, the cationic lipid is DLin-KC2-DMA (DLin-K-DMA above, wherein n is 2).

In one embodiment, the cationic lipid component of the LNPs has the structure of Formula (I):

I or a pharmaceutically acceptable salt, tautomer, prodrug or stereoisomer thereof, wherein:

$L^1$ and $L^2$ are each independently —O(C=O)—, —(C=O)O— or a carbon-carbon double bond;

$R^{1a}$ and $R^{1b}$ are, at each occurrence, independently either (a) H or $C_1$-$C_{12}$ alkyl, or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either (a) H or $C_1$-$C_{12}$ alkyl, or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either (a) H or $C_1$-$C_{12}$ alkyl, or (b) $R^{3a}$ is H or $C_1$-$C_{12}$ alkyl, and $R^{a}b$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either (a) H or $C_1$-$C_{12}$ alkyl, or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently methyl or cycloalkyl;

$R^7$ is, at each occurrence, independently H or $C_1$-$C_{12}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring comprising one nitrogen atom;

a and d are each independently an integer from 0 to 24;

b and c are each independently an integer from 1 to 24; and e is 1 or 2.

In certain embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—. In other embodiments, $R^{1a}$ and $R^{1b}$ are not isopropyl when a is 6 or n-butyl when a is 8.

In still further embodiments of Formula (I), at least one of $R^{1a}$, $R^{2a}$, $R^{3a}$ or $R^{4a}$ is $C_1$-$C_{12}$ alkyl, or at least one of $L^1$ or $L^2$ is —O(C=O)— or —(C=O)O—; and $R^{1a}$ and $R^{1b}$ are not isopropyl when a is 6 or n-butyl when a is 8.

In other embodiments of Formula (I), $R^8$ and $R^9$ are each independently unsubstituted $C_1$-$C_{12}$ alkyl; or $R^8$ and $R^9$, together with the nitrogen atom to which they are attached, form a 5, 6 or 7-membered heterocyclic ring comprising one nitrogen atom;

In certain embodiments of Formula (I), any one of $L^1$ or $L^2$ may be —O(C=O)— or a carbon-carbon double bond. $L^1$ and $L^2$ may each be —O(C=O)— or may each be a carbon-carbon double bond.

In some embodiments of Formula (I), one of $L^1$ or $L^2$ is —O(C=O)—. In other embodiments, both $L^1$ and $L^2$ are —O(C=O)—.

In some embodiments of Formula (I), one of $L^1$ or $L^2$ is —(C=O)O—. In other embodiments, both $L^1$ and $L^2$ are —(C=O)O—.

In some other embodiments of Formula (I), one of $L^1$ or $L^2$ is a carbon-carbon double bond. In other embodiments, both $L^1$ and $L^2$ are a carbon-carbon double bond.

In still other embodiments of Formula (I), one of $L^1$ or $L^2$ is —O(C=O)— and the other of $L^1$ or $L^2$ is —(C=O)O—. In more embodiments, one of $L^1$ or $L^2$ is —O(C=O)— and the other of $L^1$ or $L^2$ is a carbon-carbon double bond. In yet more embodiments, one of $L^1$ or $L^2$ is —(C=O)O— and the other of $L^1$ or $L^2$ is a carbon-carbon double bond.

It is understood that "carbon-carbon" double bond, as used throughout the specification, refers to one of the following structures:

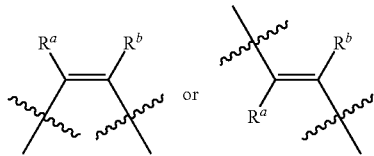

wherein $R^a$ and $R^b$ are, at each occurrence, independently H or a substituent. For example, in some embodiments $R^a$ and $R^b$ are, at each occurrence, independently H, $C_1$-$C_{12}$ alkyl or cycloalkyl, for example H or $C_1$-$C_{12}$ alkyl.

In other embodiments, the lipid compounds of Formula (I) have the following structure (Ia):

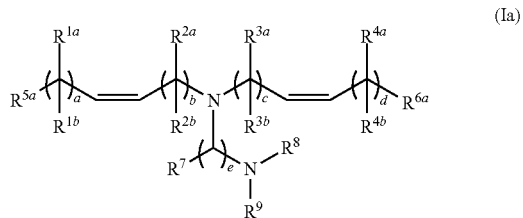

In other embodiments, the lipid compounds of Formula (I) have the following structure (Ib):

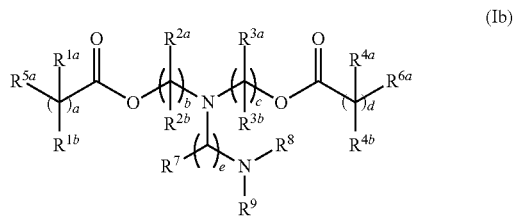

In yet other embodiments, the lipid compounds of Formula (I) have the following structure (Ic):

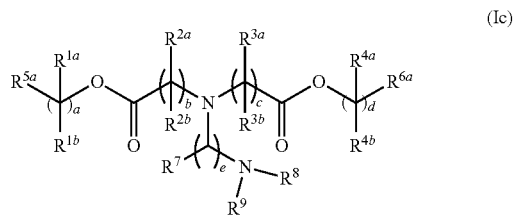

In certain embodiments of the lipid compound of Formula (I), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some other embodiments of Formula (I), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some more embodiments of Formula (I), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain other embodiments of Formula (I), d is 0. In some embodiments, d is 1. In other embodiments, d is 2. In more embodiments, d is 3. In yet other embodiments, d is 4. In some embodiments, d is 5. In other embodiments, d is 6. In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some other various embodiments of Formula (I), a and d are the same. In some other embodiments, b and c are the same. In some other specific embodiments, a and d are the same and b and c are the same.

The sum of a and b and the sum of c and d in Formula (I) are factors which may be varied to obtain a lipid of Formula (I) having the desired properties. In one embodiment, a and b are chosen such that their sum is an integer ranging from 14 to 24. In other embodiments, c and d are chosen such that their sum is an integer ranging from 14 to 24. In further embodiment, the sum of a and b and the sum of c and d are the same. For example, in some embodiments the sum of a and b and the sum of c and d are both the same integer which may range from 14 to 24. In still more embodiments, a, b, c and d are selected such the sum of a and b and the sum of c and d is 12 or greater.

In some embodiments of Formula (I), e is 1. In other embodiments, e is 2.

The substituents at $R^{1a}$, $R^{2a}$, $R^{3a}$ and $R^{4a}$ of Formula (I) are not particularly limited. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (I), $R^{1a}$, $R^{1b}$, $R^{4a}$ and $R^{4b}$ are $C_1$-$C_{12}$, alkyl at each occurrence.

In further embodiments of Formula (I), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (I), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (I) are not particularly limited in the foregoing embodiments. In certain embodiments one or both of $R^5$ or $R^6$ is methyl. In certain other embodiments one or both of $R^5$ or $R^6$ is cycloalkyl for example cyclohexyl. In these embodiments the cycloalkyl may be substituted or not substituted. In certain other embodiments the cycloalkyl is substituted with $C_1$-$C_{12}$ alkyl, for example tert-butyl.

The substituents at $R^7$ are not particularly limited in the foregoing embodiments of Formula (I). In certain embodiments at least one $R^7$ is H. In some other embodiments, $R^7$ is H at each occurrence. In certain other embodiments $R^7$ is $C_1$-$C_{12}$ alkyl.

In certain other of the foregoing embodiments of Formula (I), one of $R^8$ or $R^9$ is methyl. In other embodiments, both $R^8$ and $R^9$ are methyl.

In some different embodiments of Formula (I), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring.

In various different embodiments, the lipid of Formula (I) has one of the structures set forth in Table 1 below.

TABLE 1

Representative Lipids of Formula (I)

| No. | Structure | Prep. Method |
|---|---|---|
| I-1 | 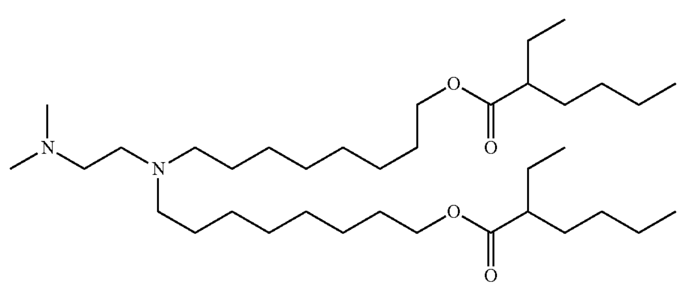 [SMILES: CCCCC(CC)C(=O)OCCCCCCCCN(CCCCCCCCOC(=O)C(CC)CCCC)CCN(C)C] | B |
| I-2 | 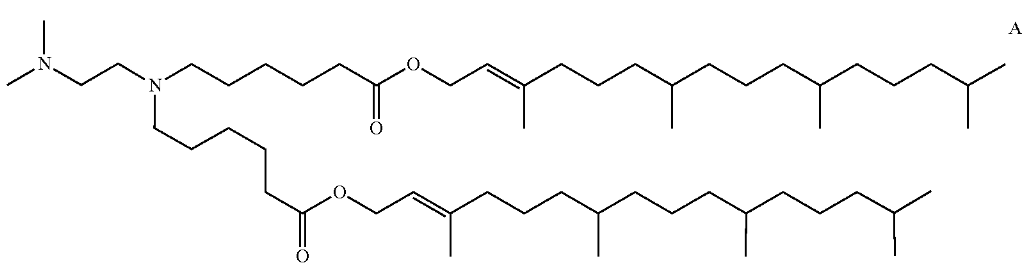 | A |

TABLE 1-continued
Representative Lipids of Formula (I)
| No. | Structure | Prep. Method |
|---|---|---|
| I-3 | 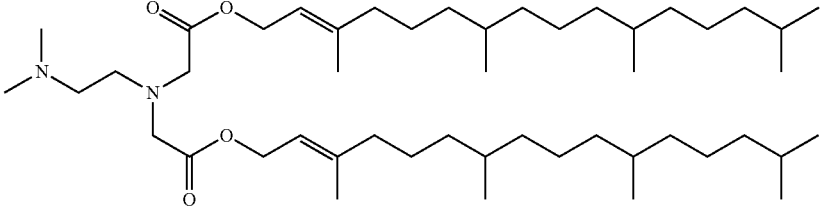 [SMILES: C/C(=C\COC(=O)CN(CCN(C)C)CC(=O)OC/C=C(\C)CCCC(C)CCCC(C)CCCC(C)C)CCCC(C)CCCC(C)CCCC(C)C] | A |
| I-4 | 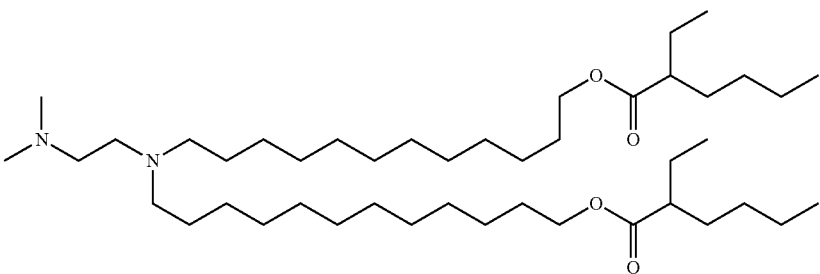 [SMILES: CCCCC(CC)C(=O)OCCCCCCCCCCCCN(CCCCCCCCCCCCOC(=O)C(CC)CCCC)CCN(C)C] | B |
| I-5 | 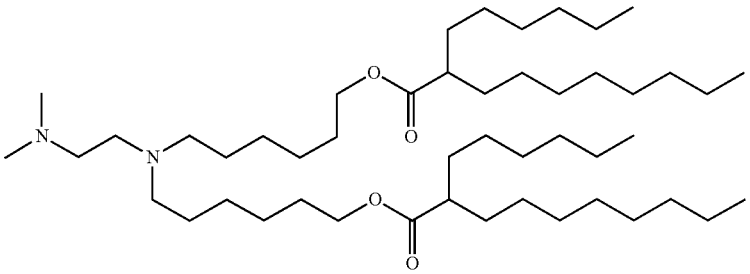 [SMILES: CCCCCCCCC(CCCCCC)C(=O)OCCCCCCN(CCCCCCOC(=O)C(CCCCCC)CCCCCCCC)CCN(C)C] | B |
| I-6 | 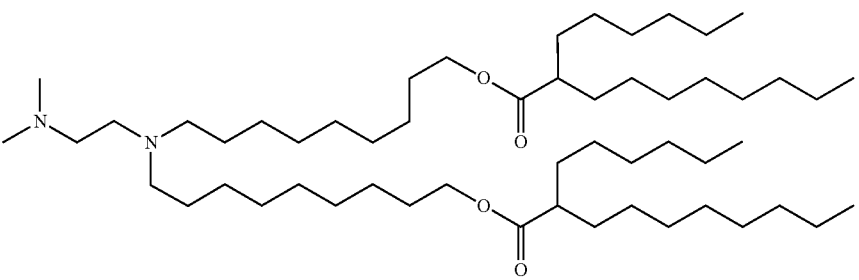 [SMILES: CCCCCCCCC(CCCCCC)C(=O)OCCCCCCCCCN(CCCCCCCCCOC(=O)C(CCCCCC)CCCCCCCC)CCN(C)C] | B |
| I-7 | 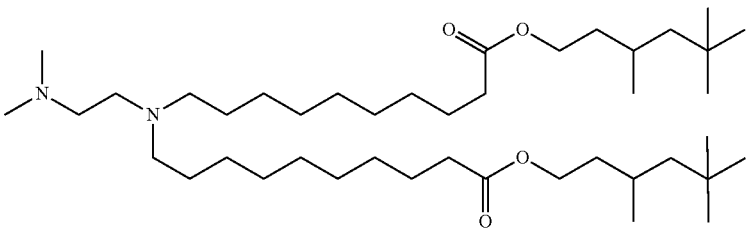 [SMILES: CC(CCOC(=O)CCCCCCCCCN(CCCCCCCCCC(=O)OCCC(C)CC(C)(C)C)CCN(C)C)CC(C)(C)C] | A |

TABLE 1-continued

Representative Lipids of Formula (I)

| No. | Structure | Prep. Method |
|---|---|---|
| I-8 | 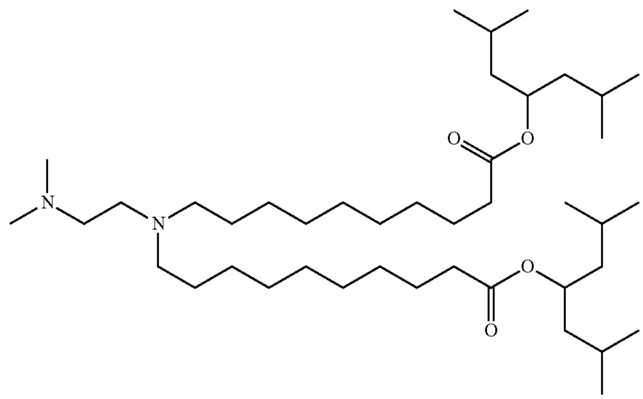 [SMILES: CC(C)CC(CC(C)C)OC(=O)CCCCCCCCCN(CCCCCCCCCC(=O)OC(CC(C)C)CC(C)C)CCN(C)C] | A |
| I-9 | 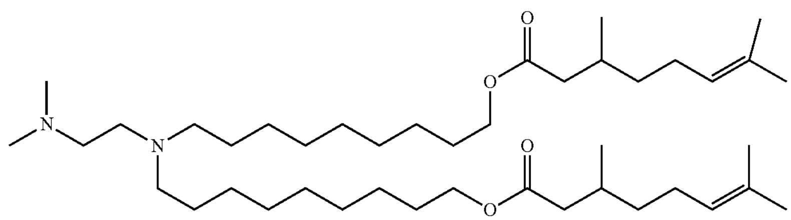 [SMILES: CC(C)=CCCC(C)CC(=O)OCCCCCCCCCN(CCCCCCCCCOC(=O)CC(C)CCC=C(C)C)CCN(C)C] | B |
| I-10 | 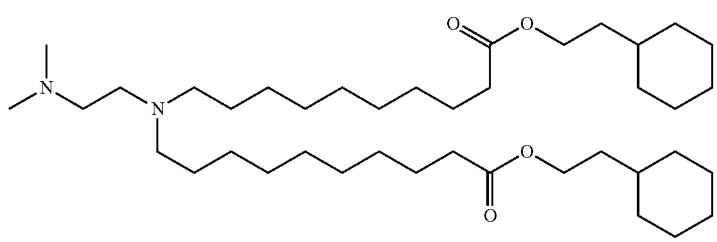 [SMILES: CN(C)CCN(CCCCCCCCCC(=O)OCCC1CCCCC1)CCCCCCCCCC(=O)OCCC1CCCCC1] | A |
| I-11 | 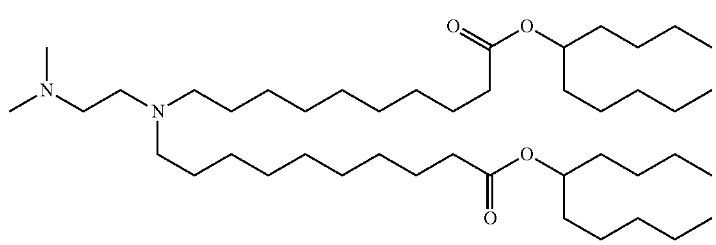 [SMILES: CCCCCC(CCCC)OC(=O)CCCCCCCCCN(CCCCCCCCCC(=O)OC(CCCC)CCCCC)CCN(C)C] | A |
| I-12 | 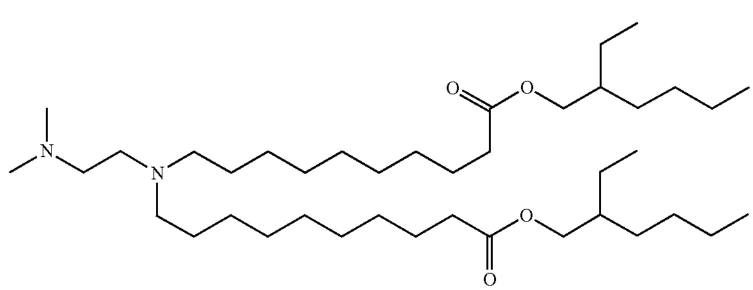 [SMILES: CCCCC(CC)COC(=O)CCCCCCCCCN(CCCCCCCCCC(=O)OCC(CC)CCCC)CCN(C)C] | A |

TABLE 1-continued

Representative Lipids of Formula (I)

| No. | Structure | Prep. Method |
|---|---|---|
| I-13 | 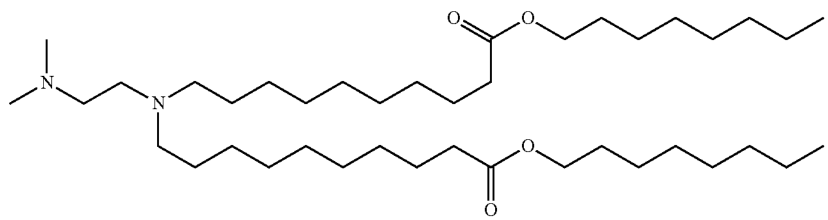 [SMILES: CCCCCCCCOC(=O)CCCCCCCCCN(CCCCCCCCCC(=O)OCCCCCCCC)CCN(C)C] | A |
| I-14 | 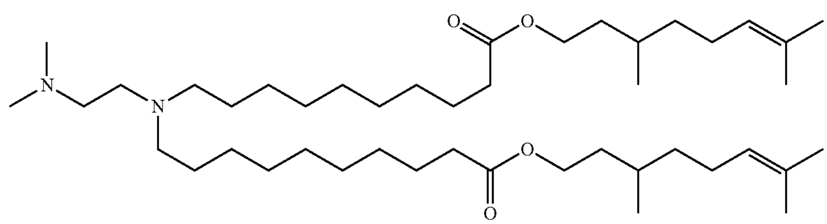 [SMILES: CC(C)=CCCC(C)CCOC(=O)CCCCCCCCCN(CCCCCCCCCC(=O)OCCC(C)CCC=C(C)C)CCN(C)C] | A |
| I-15 | 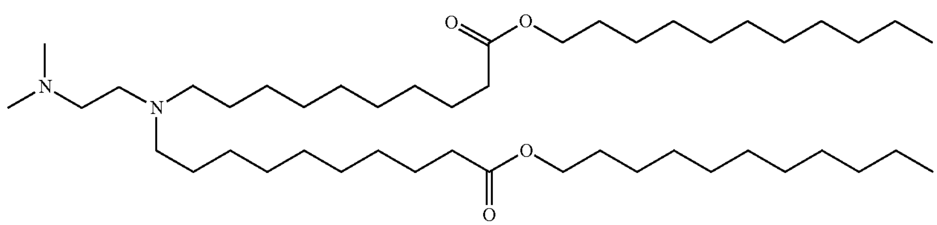 [SMILES: CCCCCCCCCCCOC(=O)CCCCCCCCCN(CCCCCCCCCC(=O)OCCCCCCCCCCC)CCN(C)C] | A |
| I-16 | 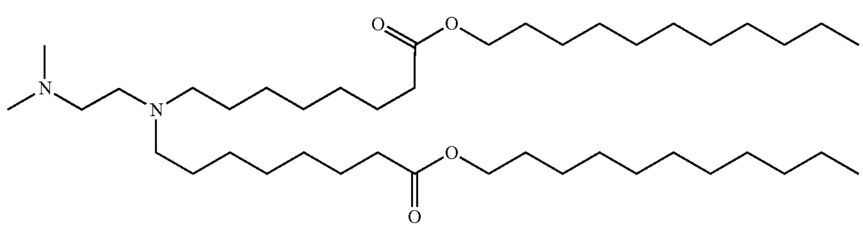 [SMILES: CCCCCCCCCCCOC(=O)CCCCCCCN(CCCCCCCC(=O)OCCCCCCCCCCC)CCN(C)C] | A |
| I-17 | 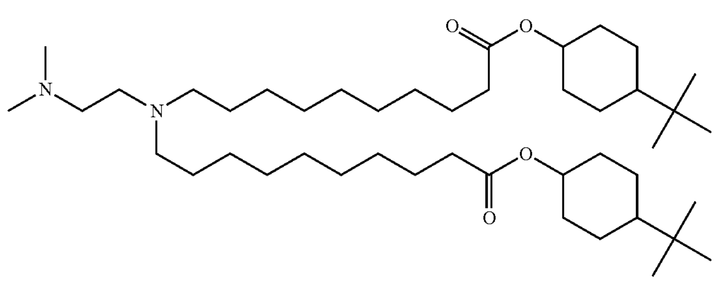 [SMILES: CN(C)CCN(CCCCCCCCCC(=O)OC1CCC(C(C)(C)C)CC1)CCCCCCCCCC(=O)OC1CCC(C(C)(C)C)CC1] | A |
| I-18 | 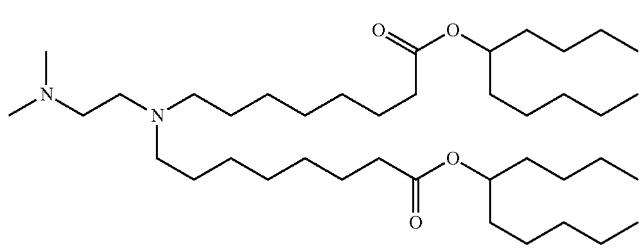 [SMILES: CCCCCC(CCCC)OC(=O)CCCCCCCN(CCCCCCCC(=O)OC(CCCC)CCCCC)CCN(C)C] | A |

TABLE 1-continued

Representative Lipids of Formula (I)

| No. | Structure | Prep. Method |
|---|---|---|
| I-19 | 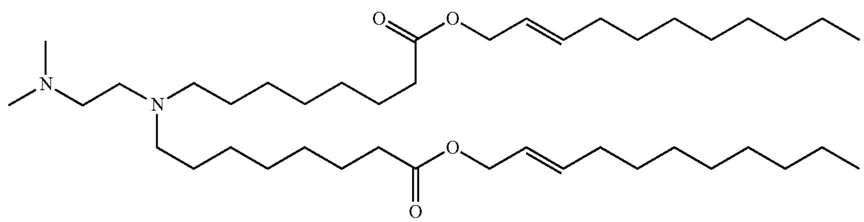 [SMILES: CCCCCCCC/C=C/COC(=O)CCCCCCCN(CCCCCCCC(=O)OC/C=C/CCCCCCCC)CCN(C)C] | A |
| I-20 | 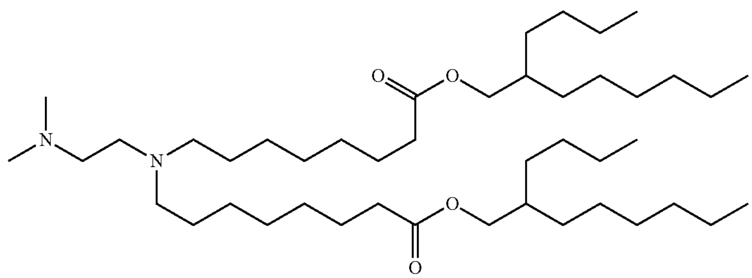 [SMILES: CCCCCCC(CCCC)COC(=O)CCCCCCCN(CCCCCCCC(=O)OCC(CCCC)CCCCCC)CCN(C)C] | A |
| I-21 | 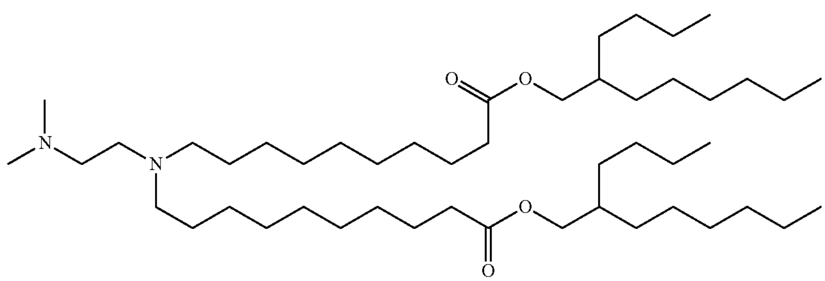 [SMILES: CCCCCCC(CCCC)COC(=O)CCCCCCCCCN(CCCCCCCCCC(=O)OCC(CCCC)CCCCCC)CCN(C)C] | A |
| I-22 | 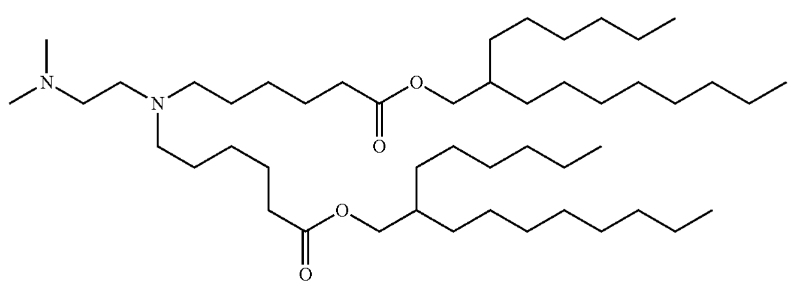 [SMILES: CCCCCCCCC(CCCCCC)COC(=O)CCCCCN(CCCCCC(=O)OCC(CCCCCC)CCCCCCCC)CCN(C)C] | A |
| I-23 | 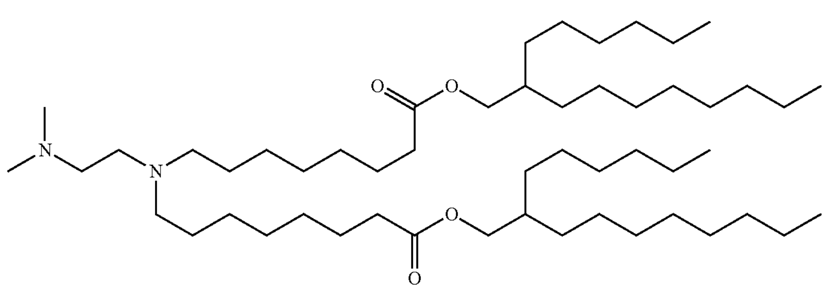 [SMILES: CCCCCCCCC(CCCCCC)COC(=O)CCCCCCCN(CCCCCCCC(=O)OCC(CCCCCC)CCCCCCCC)CCN(C)C] | A |

TABLE 1-continued

Representative Lipids of Formula (I)

| No. | Structure | Prep. Method |
|---|---|---|
| I-24 | 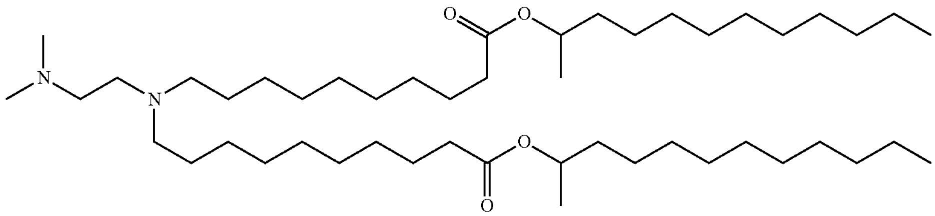 [SMILES: CCCCCCCCCCC(C)OC(=O)CCCCCCCCCN(CCCCCCCCCC(=O)OC(C)CCCCCCCCCC)CCN(C)C] | A |
| I-25 | 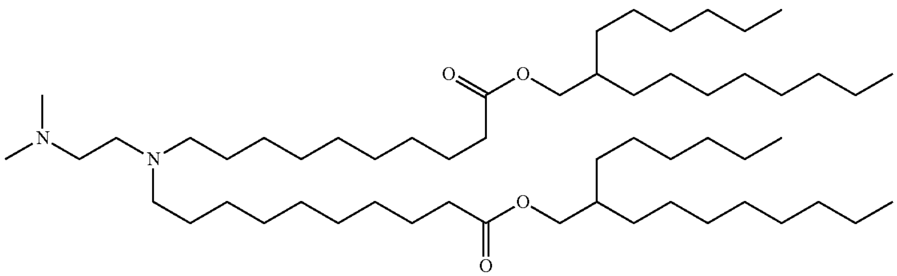 [SMILES: CCCCCCCCC(CCCCCC)COC(=O)CCCCCCCCCN(CCCCCCCCCC(=O)OCC(CCCCCC)CCCCCCCC)CCN(C)C] | A |
| I-26 | 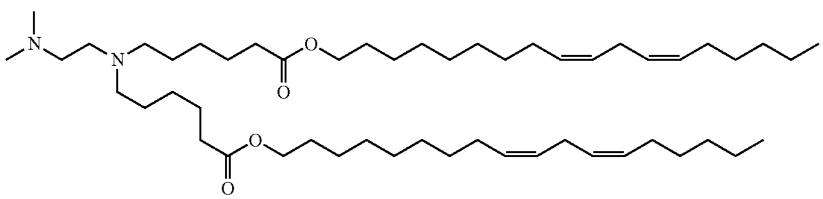 [SMILES: CCCCC/C=C\C/C=C\CCCCCCCCOC(=O)CCCCCN(CCCCCC(=O)OCCCCCCCC/C=C\C/C=C\CCCCC)CCN(C)C] | A |
| I-27 | 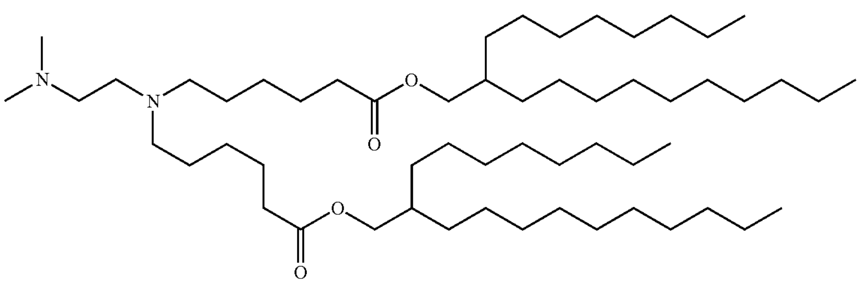 [SMILES: CCCCCCCCCCC(CCCCCCCC)COC(=O)CCCCCN(CCCCCC(=O)OCC(CCCCCCCC)CCCCCCCCCC)CCN(C)C] | A |
| I-28 | 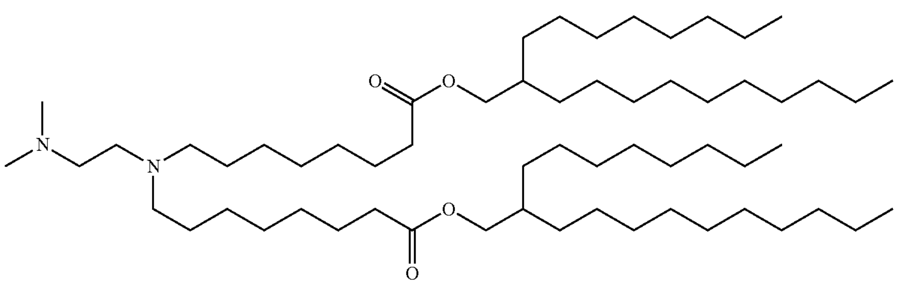 [SMILES: CCCCCCCCCCC(CCCCCCCC)COC(=O)CCCCCCCN(CCCCCCCC(=O)OCC(CCCCCCCC)CCCCCCCCCC)CCN(C)C] | A |
| I-29 | 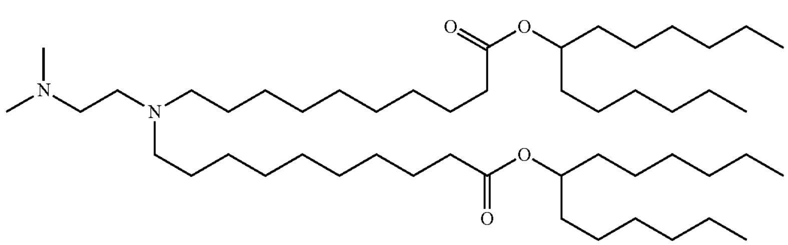 [SMILES: CCCCCCC(CCCCCC)OC(=O)CCCCCCCCCN(CCCCCCCCCC(=O)OC(CCCCCC)CCCCCC)CCN(C)C] | A |

TABLE 1-continued

Representative Lipids of Formula (I)

| No. | Structure | Prep. Method |
|---|---|---|
| I-30 | 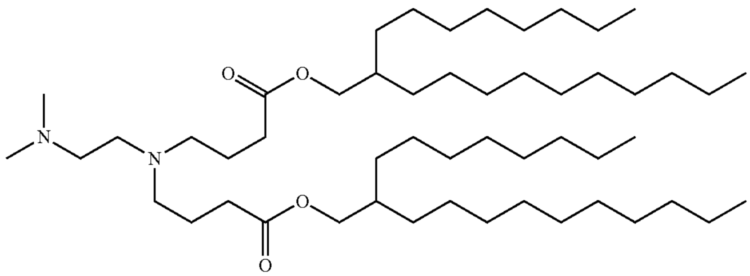 [SMILES: CCCCCCCCCCC(CCCCCCCC)COC(=O)CCCN(CCCC(=O)OCC(CCCCCCCC)CCCCCCCCCC)CCN(C)C] | A |
| I-31 | 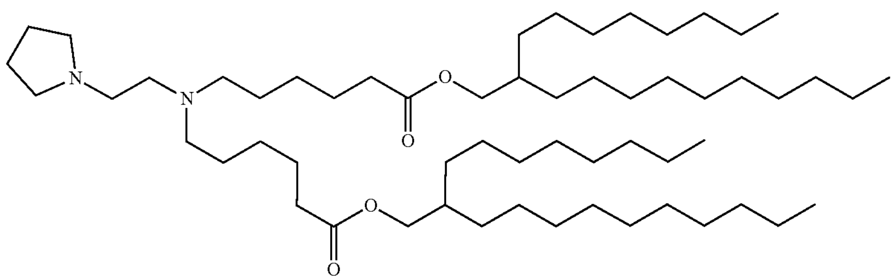 [SMILES: CCCCCCCCCCC(CCCCCCCC)COC(=O)CCCCCN(CCCCCC(=O)OCC(CCCCCCCC)CCCCCCCCCC)CCN1CCCC1] | C |
| I-32 | 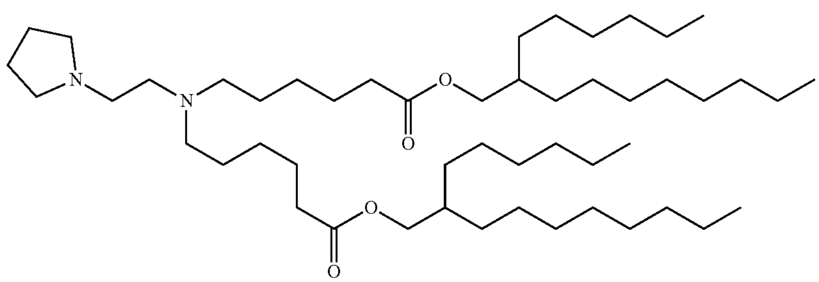 [SMILES: CCCCCCCCC(CCCCCC)COC(=O)CCCCCN(CCCCCC(=O)OCC(CCCCCC)CCCCCCCC)CCN1CCCC1] | C |
| I-33 | 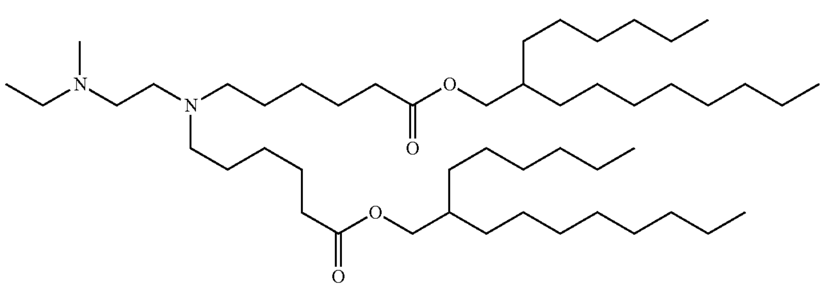 [SMILES: CCCCCCCCC(CCCCCC)COC(=O)CCCCCN(CCCCCC(=O)OCC(CCCCCC)CCCCCCCC)CCN(C)CC] | C |
| I-34 | 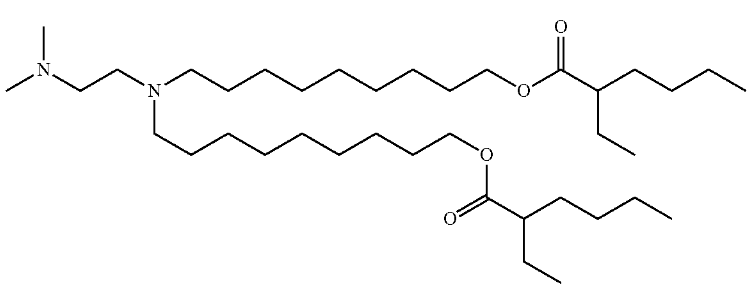 [SMILES: CCCCC(CC)C(=O)OCCCCCCCCCN(CCCCCCCCCOC(=O)C(CC)CCCC)CCN(C)C] | B |

TABLE 1-continued

Representative Lipids of Formula (I)

| No. | Structure | Prep. Method |
|---|---|---|
| I-35 | 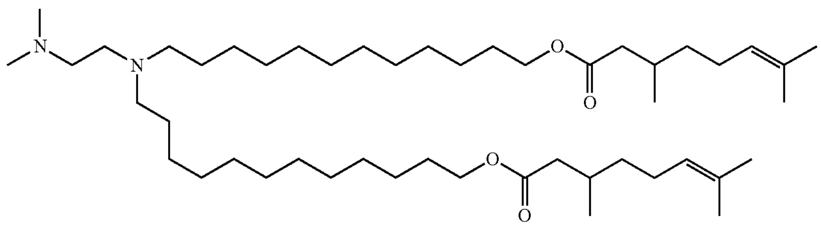 [SMILES: CC(C)=CCCC(C)CC(=O)OCCCCCCCCCCCCN(CCCCCCCCCCCCOC(=O)CC(C)CCC=C(C)C)CCN(C)C] | B |
| I-36 | 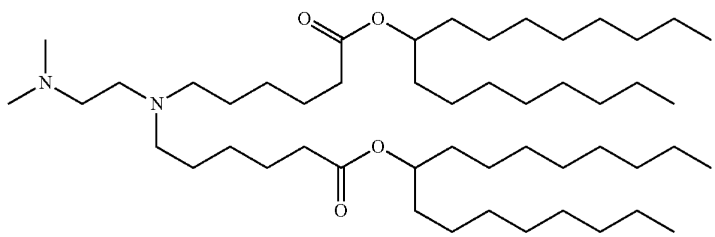 [SMILES: CCCCCCCCC(CCCCCCCC)OC(=O)CCCCCN(CCCCCC(=O)OC(CCCCCCCC)CCCCCCCC)CCN(C)C] | C |
| I-37 | 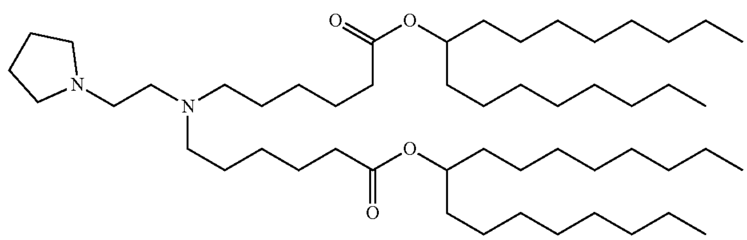 [SMILES: CCCCCCCCC(CCCCCCCC)OC(=O)CCCCCN(CCCCCC(=O)OC(CCCCCCCC)CCCCCCCC)CCN1CCCC1] | C |
| I-38 | 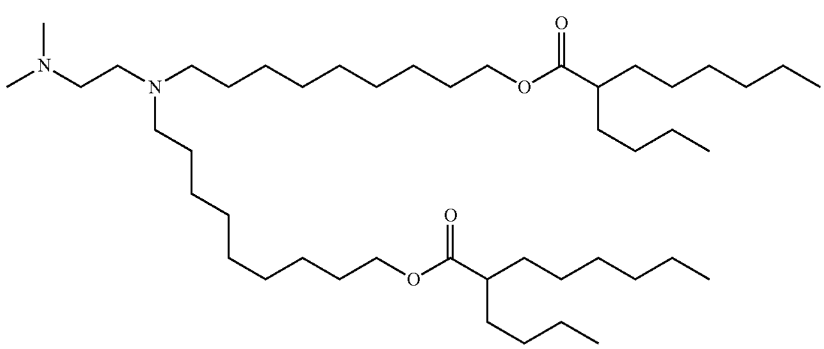 [SMILES: CCCCCCC(CCCC)C(=O)OCCCCCCCCCN(CCCCCCCCCOC(=O)C(CCCC)CCCCCC)CCN(C)C] | B |
| I-39 | 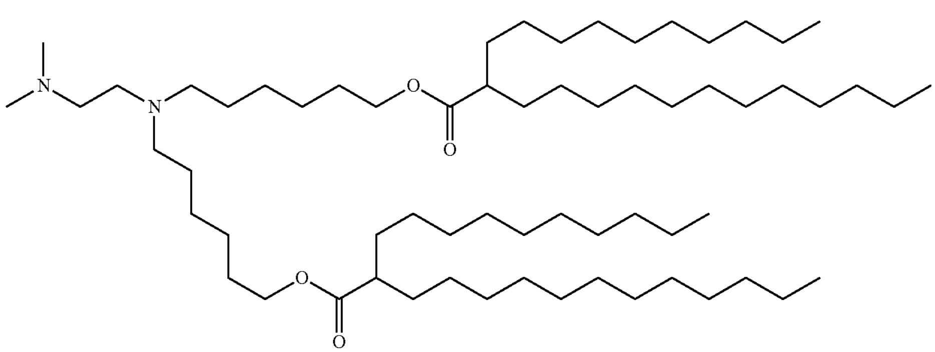 [SMILES: CCCCCCCCCCCCC(CCCCCCCCCC)C(=O)OCCCCCCN(CCCCCCOC(=O)C(CCCCCCCCCC)CCCCCCCCCCCC)CCN(C)C] | B |

TABLE 1-continued

Representative Lipids of Formula (I)

| No. | Structure | Prep. Method |
|---|---|---|
| I-40 | 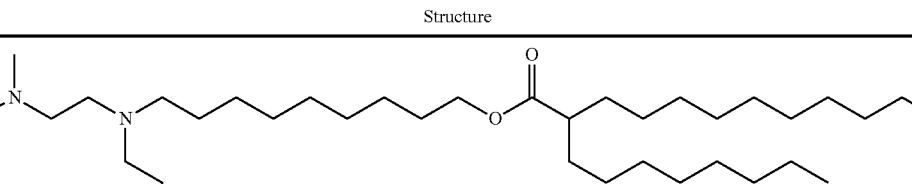 | B |
| I-41 | 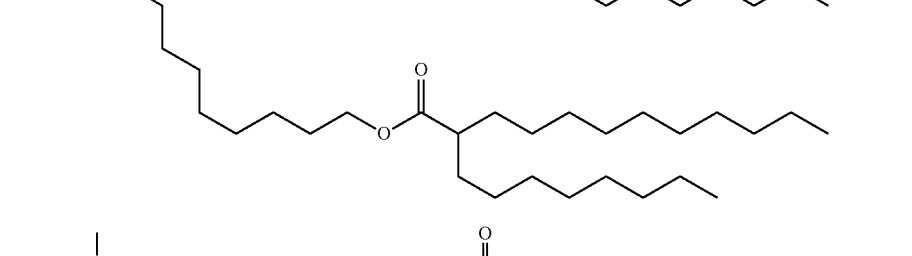 | B |

In some embodiments, the LNPs comprise a lipid of Formula (I), a nucleoside-modified RNA and one or more excipients selected from neutral lipids, steroids and pegylated lipids. In some embodiments the lipid of Formula (I) is compound 1-5. In some embodiments the lipid of Formula (I) is compound 1-6.

In some other embodiments, the cationic lipid component of the LNPs has the structure of Formula (II):

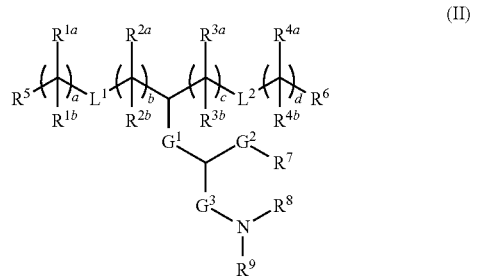

or a pharmaceutically acceptable salt, tautomer, prodrug or stereoisomer thereof, wherein:

$L^1$ and $L^2$ are each independently —O(C=O)—, —(C=O)O—, —C(=O)—, —O—, —S(O)$_x$—, —S—S—, —C(=O)S—, —SC(=O)—, —NR$^a$C(=O)—, —C(=O)NR$^a$—, —NR$^a$C(=O)NR$^a$—, —OC(=O)NR$^a$—, —NR$a$C(=O)O—, or a direct bond;

$G^1$ is $C_1$-$C_2$ alkylene, —(C=O)—, —O(C=O)—, —SC(=O)—, —NR$^a$C(=O)— or a direct bond;

$G^2$ is —C(=O)—, —(C=O)O—, —C(=O)S—, —C(=O)NR$^a$ or a direct bond;

$G^3$ is $C_1$-$C_6$ alkylene;

$R^a$ is H or $C_1$-$C_{12}$ alkyl;

$R^{1a}$ and $R^{1b}$ are, at each occurrence, independently either:
(a) H or $C_1$-$C_{12}$ alkyl; or (b) $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond;

$R^{2a}$ and $R^{2b}$ are, at each occurrence, independently either:
(a) H or $C_1$-$C_{12}$ alkyl; or (b) $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond;

$R^{3a}$ and $R^{3b}$ are, at each occurrence, independently either:
(a) H or $C_1$-$C_{12}$ alkyl; or (b) $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond;

$R^{4a}$ and $R^{4b}$ are, at each occurrence, independently either:
(a) H or $C_1$-$C_{12}$ alkyl; or (b) $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond;

$R^5$ and $R^6$ are each independently H or methyl;

$R^7$ is $C_4$-$C_{20}$ alkyl;

$R^8$ and $R^9$ are each independently $C_1$-$C_{12}$ alkyl; or $R^8$ and $R^9$, together with the nitrogen atom to which they are attached, form a 5, 6 or 7-membered heterocyclic ring;

a, b, c and d are each independently an integer from 1 to 24; and x is 0, 1 or 2.

In some embodiments of Formula (II), $L^1$ and $L^2$ are each independently —O(C=O)—, —(C=O)O— or a direct bond. In other embodiments, $G^1$ and $G^2$ are each independently —(C=O)— or a direct bond. In some different embodiments, $L^1$ and $L^2$ are each independently —O(C=O)—, —(C=O)O— or a direct bond; and $G^1$ and $G^2$ are each independently —(C=O)— or a direct bond.

In some different embodiments of Formula (II), $L^1$ and $L^2$ are each independently —C(=O)—, —O—, —S—S—, —C(=O)S—, —SC(=O)—, —NR$^a$C(=O)—, —C(=O)NR$^a$—, —NR$^a$C(=O)NR$^a$—, —OC(=O)NR$^a$—, —NR$^a$C(=O)O—, —NRaS(O)$_x$NR$^a$—, —NR$^a$S(O)$_x$— or —S(O)$_x$NR$^a$—.

In other of the foregoing embodiments of Formula (II), the lipid compound has one of the following structures (IIA) or (IIB):

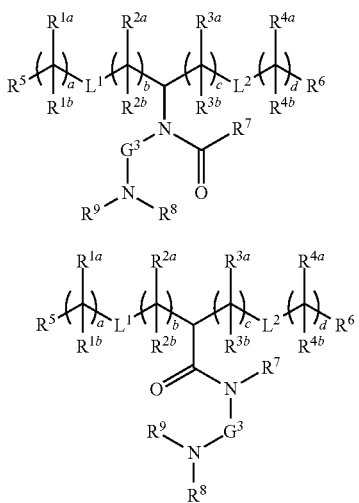

In some embodiments of Formula (II), the lipid compound has structure (IIA). In other embodiments, the lipid compound has structure (IIB).

In any of the foregoing embodiments of Formula (II), one of $L^1$ or $L^2$ is —O(C=O)—. For example, in some embodiments each of $L^1$ and $L^2$ are —O(C=O)—.

In some different embodiments of Formula (II), one of $L^1$ or $L^2$ is —(C=O)O—. For example, in some embodiments each of $L^1$ and $L^2$ is —(C=O)O—. In different embodiments of Formula (II), one of $L^1$ or $L^2$ is a direct bond.

As used herein, a "direct bond" means the group (e.g., $L^1$ or $L^2$) is absent. For example, in some embodiments each of $L^1$ and $L^2$ is a direct bond.

In other different embodiments of Formula (II), for at least one occurrence of $R^{1a}$ and $R^{1b}$, $R^{1a}$ is H or $C_1$-$C_{12}$ alkyl, and $R^{1b}$ together with the carbon atom to which it is bound is taken together with an adjacent $R^{1b}$ and the carbon atom to which it is bound to form a carbon-carbon double bond.

In still other different embodiments of Formula (II), for at least one occurrence of $R^{4a}$ and $R^{4b}$, $R^{4a}$ is H or $C_1$-$C_{12}$ alkyl, and $R^{4b}$ together with the carbon atom to which it is bound is taken together with an adjacent $R^{4b}$ and the carbon atom to which it is bound to form a carbon-carbon double bond.

In more embodiments of Formula (II), for at least one occurrence of $R^{2a}$ and $R^{2b}$, $R^{2a}$ is H or $C_1$-$C_{12}$ alkyl, and $R^{2b}$ together with the carbon atom to which it is bound is taken together with an adjacent $R^{2b}$ and the carbon atom to which it is bound to form a carbon-carbon double bond.

In other different embodiments of Formula (II), for at least one occurrence of $R^{1a}$ and $R^{3b}$, $R^{3a}$ is H or $C_1$-$C_{12}$ alkyl, and $R^{3b}$ together with the carbon atom to which it is bound is taken together with an adjacent $R^{3b}$ and the carbon atom to which it is bound to form a carbon-carbon double bond.

In various other embodiments of Formula (II), the lipid compound has one of the following structures (IIC) or (IID):

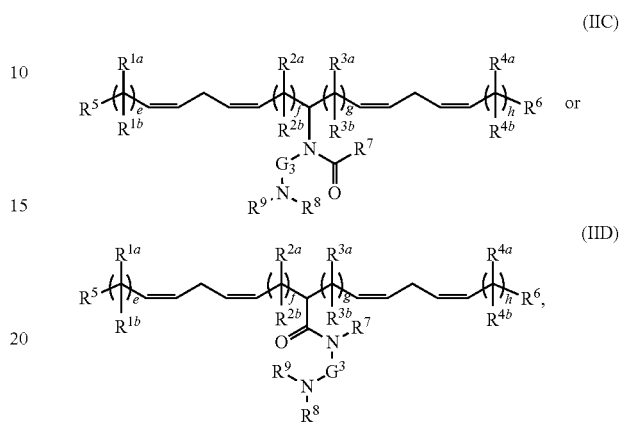

wherein e, f, g and h are each independently an integer from 1 to 12.

In some embodiments of Formula (II), the lipid compound has structure (IIC). In other embodiments, the lipid compound has structure (IID).

In various embodiments of structures (IIC) or (IID), e, f, g and h are each independently an integer from 4 to 10.

In certain embodiments of Formula (II), a, b, c and d are each independently an integer from 2 to 12 or an integer from 4 to 12. In other embodiments, a, b, c and d are each independently an integer from 8 to 12 or 5 to 9. In some certain embodiments, a is 0. In some embodiments, a is 1. In other embodiments, a is 2. In more embodiments, a is 3. In yet other embodiments, a is 4. In some embodiments, a is 5. In other embodiments, a is 6. In more embodiments, a is 7. In yet other embodiments, a is 8. In some embodiments, a is 9. In other embodiments, a is 10. In more embodiments, a is 11. In yet other embodiments, a is 12. In some embodiments, a is 13. In other embodiments, a is 14. In more embodiments, a is 15. In yet other embodiments, a is 16.

In some embodiments of Formula (II), b is 1. In other embodiments, b is 2. In more embodiments, b is 3. In yet other embodiments, b is 4. In some embodiments, b is 5. In other embodiments, b is 6. In more embodiments, b is 7. In yet other embodiments, b is 8. In some embodiments, b is 9. In other embodiments, b is 10. In more embodiments, b is 11. In yet other embodiments, b is 12. In some embodiments, b is 13. In other embodiments, b is 14. In more embodiments, b is 15. In yet other embodiments, b is 16.

In some embodiments of Formula (II), c is 1. In other embodiments, c is 2. In more embodiments, c is 3. In yet other embodiments, c is 4. In some embodiments, c is 5. In other embodiments, c is 6. In more embodiments, c is 7. In yet other embodiments, c is 8. In some embodiments, c is 9. In other embodiments, c is 10. In more embodiments, c is 11. In yet other embodiments, c is 12. In some embodiments, c is 13. In other embodiments, c is 14. In more embodiments, c is 15. In yet other embodiments, c is 16.

In some certain embodiments of Formula (II), d is 0. In some embodiments, d is 1. In other embodiments, d is 2. In more embodiments, d is 3. In yet other embodiments, d is 4. In some embodiments, d is 5. In other embodiments, d is 6.

In more embodiments, d is 7. In yet other embodiments, d is 8. In some embodiments, d is 9. In other embodiments, d is 10. In more embodiments, d is 11. In yet other embodiments, d is 12. In some embodiments, d is 13. In other embodiments, d is 14. In more embodiments, d is 15. In yet other embodiments, d is 16.

In some embodiments of Formula (II), e is 1. In other embodiments, e is 2. In more embodiments, e is 3. In yet other embodiments, e is 4. In some embodiments, e is 5. In other embodiments, e is 6. In more embodiments, e is 7. In yet other embodiments, e is 8. In some embodiments, e is 9. In other embodiments, e is 10. In more embodiments, e is 11. In yet other embodiments, e is 12.

In some embodiments of Formula (II), f is 1. In other embodiments, f is 2. In more embodiments, f is 3. In yet other embodiments, f is 4. In some embodiments, f is 5. In other embodiments, f is 6. In more embodiments, f is 7. In yet other embodiments, f is 8. In some embodiments, f is 9. In other embodiments, f is 10. In more embodiments, f is 11. In yet other embodiments, f is 12.

In some embodiments of Formula (II), g is 1. In other embodiments, g is 2. In more embodiments, g is 3. In yet other embodiments, g is 4. In some embodiments, g is 5. In other embodiments, g is 6. In more embodiments, g is 7. In yet other embodiments, g is 8. In some embodiments, g is 9. In other embodiments, g is 10. In more embodiments, g is 11. In yet other embodiments, g is 12.

In some embodiments of Formula (II), h is 1. In other embodiments, e is 2. In more embodiments, h is 3. In yet other embodiments, h is 4. In some embodiments, e is 5. In other embodiments, h is 6. In more embodiments, h is 7. In yet other embodiments, h is 8. In some embodiments, h is 9. In other embodiments, h is 10. In more embodiments, h is 11. In yet other embodiments, h is 12.

In some other various embodiments of Formula (II), a and d are the same. In some other embodiments, b and c are the same. In some other specific embodiments and a and d are the same and b and c are the same.

The sum of a and b and the sum of c and d of Formula (II) are factors which may be varied to obtain a lipid having the desired properties. In one embodiment, a and b are chosen such that their sum is an integer ranging from 14 to 24. In other embodiments, c and d are chosen such that their sum is an integer ranging from 14 to 24.

In further embodiment, the sum of a and b and the sum of c and d are the same. For example, in some embodiments the sum of a and b and the sum of c and d are both the same integer which may range from 14 to 24. In still more embodiments, a. b, c and d are selected such that the sum of a and b and the sum of c and d is 12 or greater.

The substituents at $R^{1a}$, $R^{2a}$, $R^{3a}$ and $R^{4a}$ of Formula (II) are not particularly limited. In some embodiments, at least one of $R^{1a}$, $R^{2a}$, $R^{3a}$ and $R^{4a}$ is H. In certain embodiments $R^{1a}$, $R^{2a}$, $R^{3a}$ and $R^{4a}$ are H at each occurrence. In certain other embodiments at least one of $R^{1a}$, $R^{2a}$, $R^{3a}$ and $R^{4a}$ is $C_1$-$C_{12}$ alkyl. In certain other embodiments at least one of $R^{1a}$, $R^{2a}$, $R^{3a}$ and $R^{4a}$ is $C_1$-$C_8$ alkyl. In certain other embodiments at least one of $R^{1a}$, $R^{2a}$, $R^{3a}$ and $R^{4a}$ is $C_1$-$C_6$ alkyl. In some of the foregoing embodiments, the $C_1$-$C_8$ alkyl is methyl, ethyl, n-propyl, iso-propyl, n-butyl, iso-butyl, tert-butyl, n-hexyl or n-octyl.

In certain embodiments of Formula (II), $R^{1a}$, $R^{1b}$, $R^{4a}$ and $R^{4b}$ are $C_1$-$C_{12}$ alkyl at each occurrence.

In further embodiments of Formula (II), at least one of $R^{1b}$, $R^{2b}$, $R^{3b}$ and $R^{4b}$ is H or $R^{1b}$, $R^{2b}$, $R^{3b}$ and $R^{4b}$ are H at each occurrence.

In certain embodiments of Formula (II), $R^{1b}$ together with the carbon atom to which it is bound is taken together with an adjacent $R^{1b}$ and the carbon atom to which it is bound to form a carbon-carbon double bond. In other embodiments of the foregoing $R^{4b}$ together with the carbon atom to which it is bound is taken together with an adjacent $R^{4b}$ and the carbon atom to which it is bound to form a carbon-carbon double bond.

The substituents at $R^5$ and $R^6$ of Formula (II) are not particularly limited in the foregoing embodiments. In certain embodiments one of $R^5$ or $R^6$ is methyl. In other embodiments each of $R^5$ or $R^6$ is methyl.

The substituents at $R^7$ of Formula (II) are not particularly limited in the foregoing embodiments. In certain embodiments $R^7$ is $C_6$-$C_{16}$ alkyl. In some other embodiments, $R^7$ is $C_6$-$C_9$ alkyl. In some of these embodiments, $R^7$ is substituted with —(C=O)O$R^b$, —O(C=O)$R^b$, —C(=O)$R^b$, —O$R^b$, —S(O)$_x$$R^b$, —S—S$R^b$, —C(=O)S$R^b$, —SC(=O)$R^b$, —N$R^a$$R^b$, —N$R^a$C(=O)$R^b$, —C(=O)N$R^a$$R^b$, —N$R^a$C(=O)N$R^a$$R^b$, —OC(=O)N$R^a$$R^b$, —N$R^a$C(=O)O$R^b$, —N$R^a$S(O)$_x$N$R^a$$R^b$, —N$R^a$S(O)$_x$$R^b$ or —S(O)$_x$N$R^a$$R^b$, wherein: $R^a$ is H or $C_1$-$C_{12}$ alkyl; $R^b$ is $C_1$-$C_{15}$ alkyl; and x is 0, 1 or 2. For example, in some embodiments $R^7$ is substituted with —(C=O)O$R^b$ or —O(C=O)$R^b$.

In various of the foregoing embodiments of Formula (II), $R^b$ is branched $C_1$-$C_{15}$ alkyl. For example, in some embodiments $R^b$ has one of the following structures:

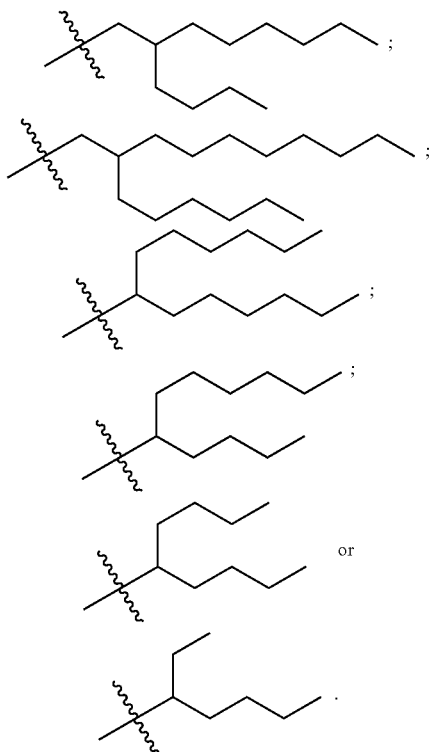

In certain other of the foregoing embodiments of Formula (II), one of $R^8$ or $R^9$ is methyl. In other embodiments, both $R^8$ and $R^9$ are methyl.

In some different embodiments of Formula (II), $R^8$ and $R^9$, together with the nitrogen atom to which they are attached, form a 5, 6 or 7-membered heterocyclic ring. In some embodiments of the foregoing, $R^8$ and $R^9$, together with the nitrogen atom to which they are attached, form a 5-membered heterocyclic ring, for example a pyrrolidinyl ring. In some different embodiments of the foregoing, $R^8$ and $R^9$, together with the nitrogen atom to which they are attached, form a 6-membered heterocyclic ring, for example a piperazinyl ring.

In still other embodiments of the foregoing lipids of Formula (II), $G^3$ is $C_2$-$C_4$ alkylene, for example $C_3$ alkylene.

In various different embodiments, the lipid compound has one of the structures set forth in Table 2 below.

TABLE 2

Representative Lipids of Formula (II)

| No. | Structure | Prep. Method |
|---|---|---|
| II-1 | 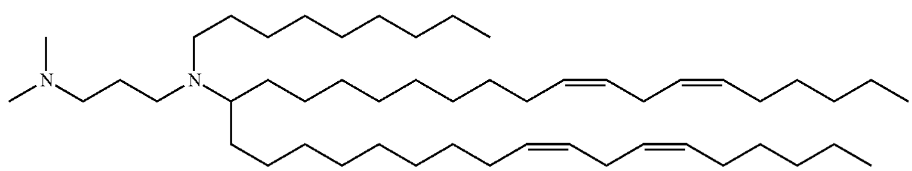 [SMILES: CCCCC/C=C\C/C=C\CCCCCCCCC(CCCCCCCC/C=C\C/C=C\CCCCC)N(CCCCCCCCC)CCCN(C)C] | D |
| II-2 | 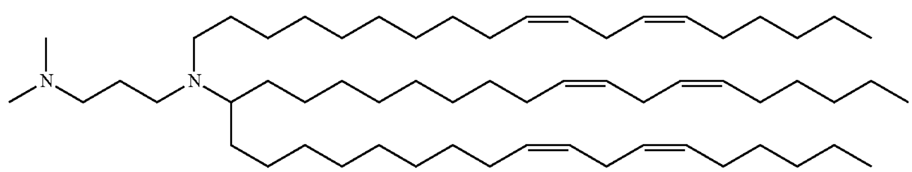 [SMILES: CCCCC/C=C\C/C=C\CCCCCCCCCN(CCCN(C)C)C(CCCCCCCC/C=C\C/C=C\CCCCC)CCCCCCCC/C=C\C/C=C\CCCCC] | D |
| II-3 | 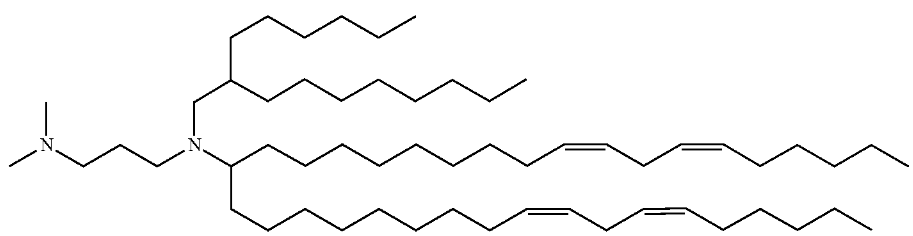 [SMILES: CCCCC/C=C\C/C=C\CCCCCCCCC(CCCCCCCC/C=C\C/C=C\CCCCC)N(CCCN(C)C)CC(CCCCCC)CCCCCCCC] | D |
| II-4 | 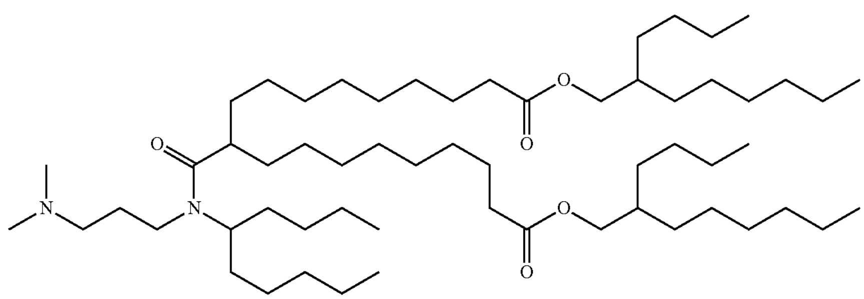 [SMILES: CCCCCCC(CCCC)COC(=O)CCCCCCCCC(CCCCCCCCC(=O)OCC(CCCC)CCCCCC)C(=O)N(CCCN(C)C)C(CCCC)CCCCC] | E |
| II-5 | 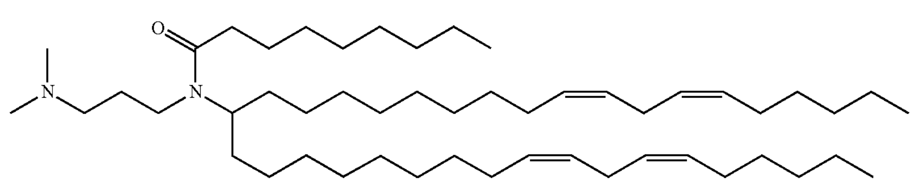 [SMILES: CCCCC/C=C\C/C=C\CCCCCCCCC(CCCCCCCC/C=C\C/C=C\CCCCC)N(CCCN(C)C)C(=O)CCCCCCCC] | D |
| II-6 | 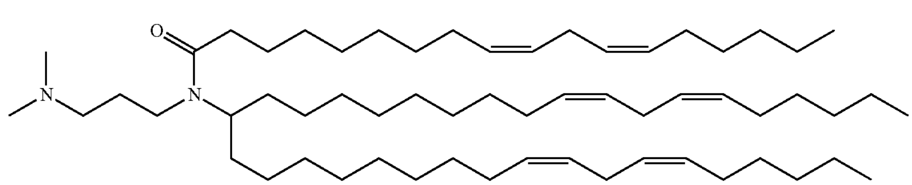 [SMILES: CCCCC/C=C\C/C=C\CCCCCCCCC(CCCCCCCC/C=C\C/C=C\CCCCC)N(CCCN(C)C)C(=O)CCCCCCC/C=C\C/C=C\CCCCC] | D |

TABLE 2-continued

Representative Lipids of Formula (II)

| No. | Structure | Prep. Method |
|---|---|---|
| II-7 | 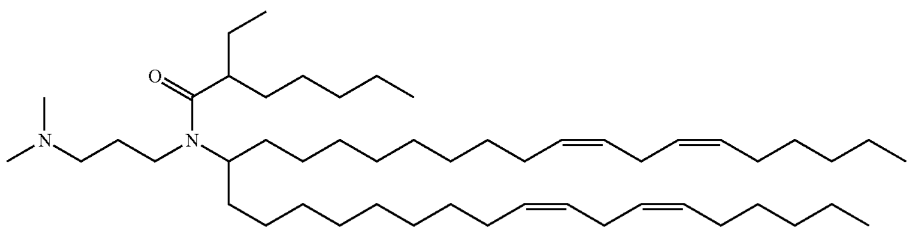 [SMILES: CCCCC/C=C\C/C=C\CCCCCCCCC(CCCCCCCC/C=C\C/C=C\CCCCC)N(CCCN(C)C)C(=O)C(CC)CCCCC] | D |
| II-8 | 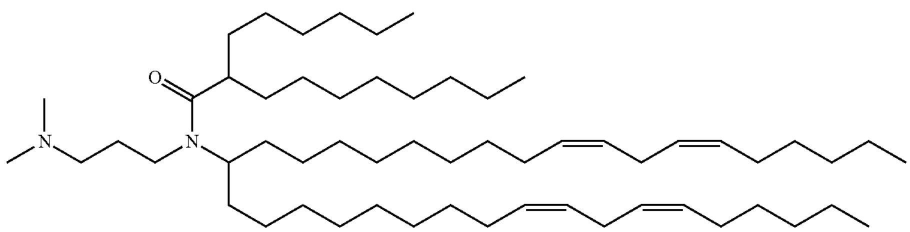 [SMILES: CCCCC/C=C\C/C=C\CCCCCCCCC(CCCCCCCC/C=C\C/C=C\CCCCC)N(CCCN(C)C)C(=O)C(CCCCCC)CCCCCCCC] | D |
| II-9 | 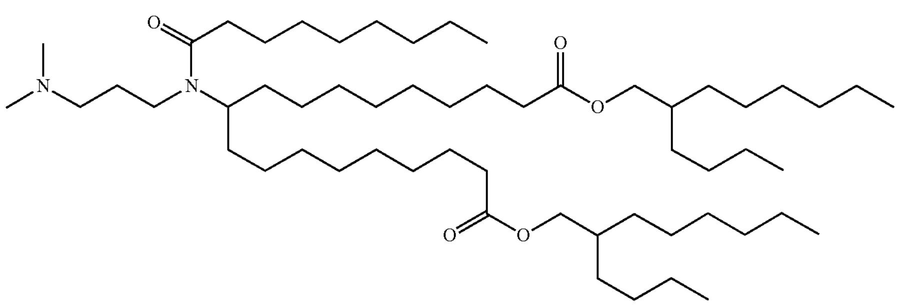 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC] | D |
| II-10 | 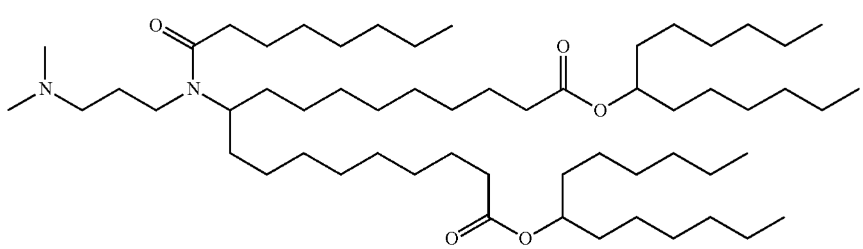 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC] | D |
| II-11 | 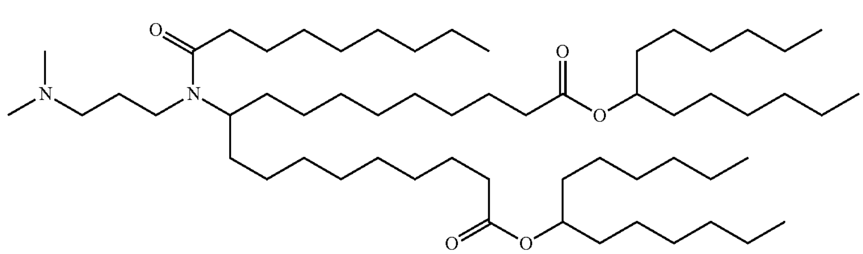 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC] | D |

TABLE 2-continued

Representative Lipids of Formula (II)

| No. | Structure | Prep. Method |
|---|---|---|
| II-12 | 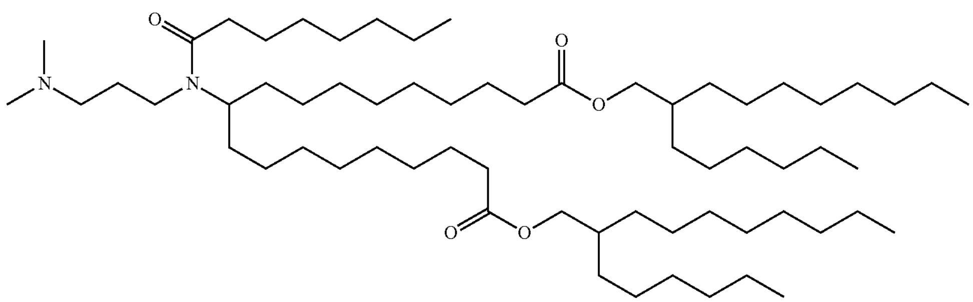 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC] | D |
| II-13 | 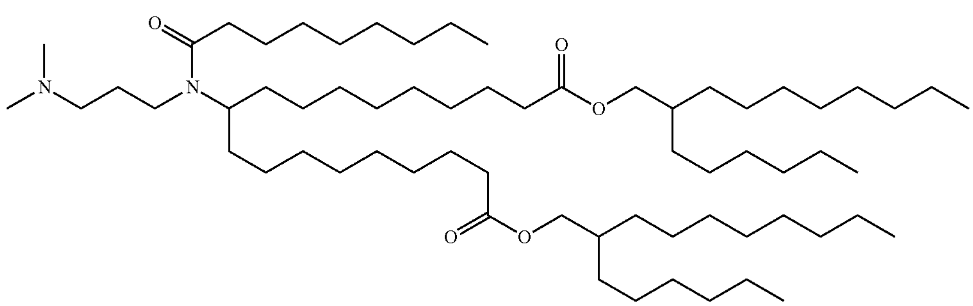 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC] | D |
| II-14 | 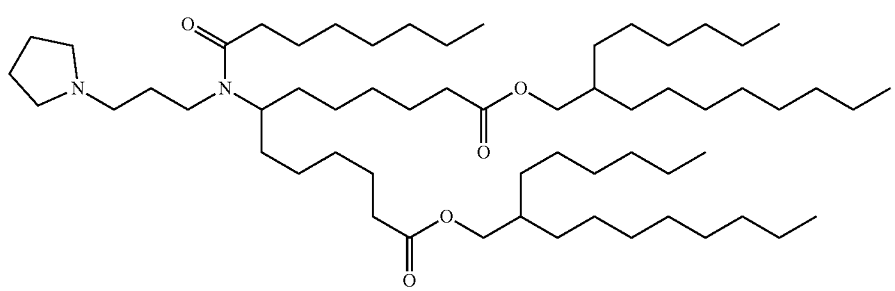 [SMILES: CCCCCCCCC(CCCCCC)COC(=O)CCCCCC(CCCCCC(=O)OCC(CCCCCC)CCCCCCCC)N(CCCN1CCCC1)C(=O)CCCCCCC] | D |
| II-15 | 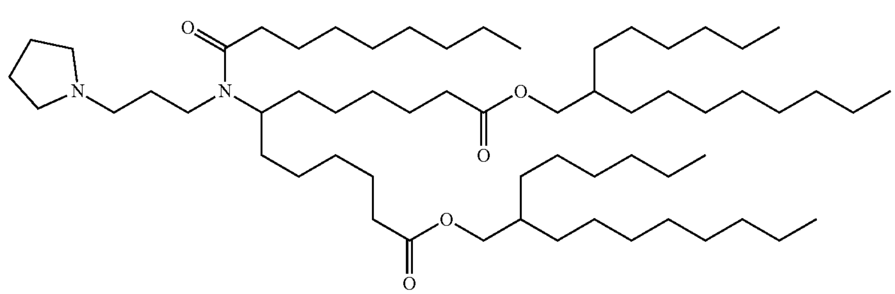 [SMILES: CCCCCCCCC(=O)N(CCCN1CCCC1)C(CCCCCC(=O)OCC(CCCCCC)CCCCCCCC)CCCCCC(=O)OCC(CCCCCC)CCCCCCCC] | D |
| II-16 | 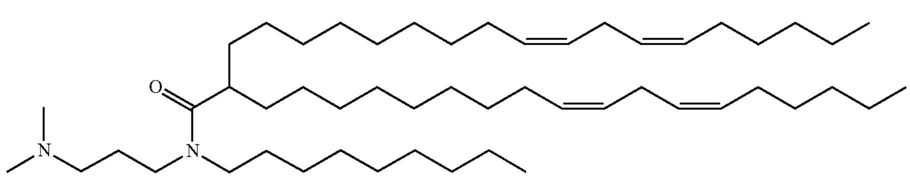 [SMILES: CCCCC/C=C\C/C=C\CCCCCCCCC(CCCCCCCC/C=C\C/C=C\CCCCC)C(=O)N(CCCCCCCCC)CCCN(C)C] | E |

TABLE 2-continued
Representative Lipids of Formula (II)
| No. | Structure | Prep. Method |
|---|---|---|
| II-17 | 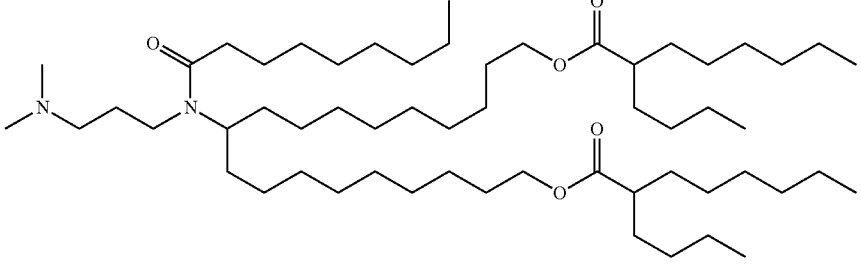 | D |
| II-18 | 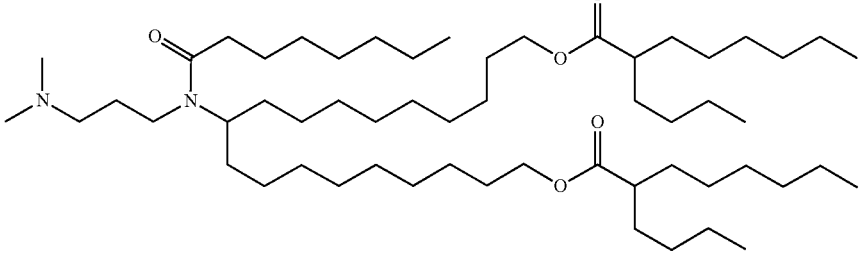 | D |
| II-19 | 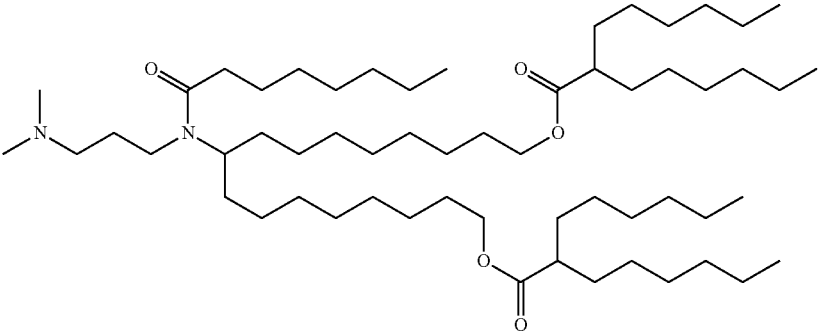 [SMILES: CCCCCCCC(=O)N(CCCN(C)C)C(CCCCCCCCOC(=O)C(CCCCCC)CCCCCC)CCCCCCCCOC(=O)C(CCCCCC)CCCCCC] | D |
| II-20 | 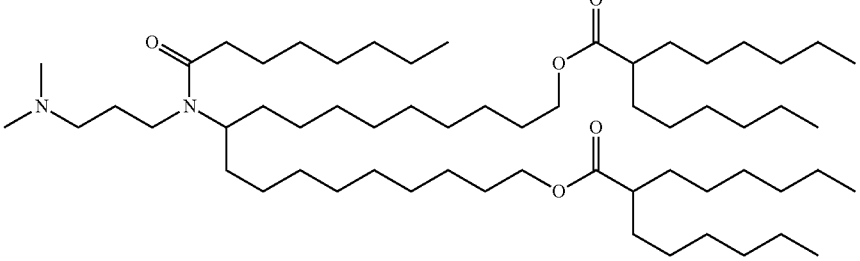 | D |
| II-21 | 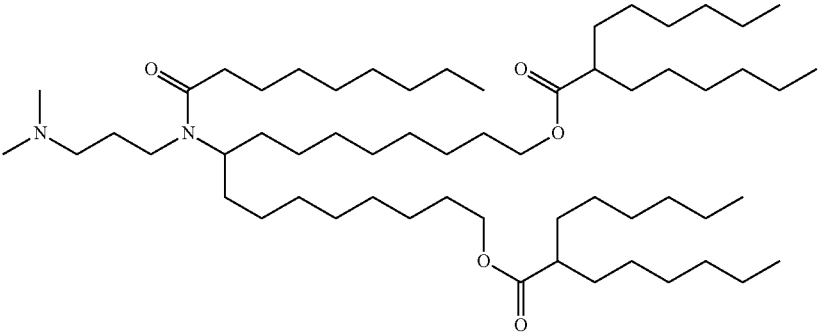 [SMILES: CCCCCCCCC(=O)N(CCCN(C)C)C(CCCCCCCCOC(=O)C(CCCCCC)CCCCCC)CCCCCCCCOC(=O)C(CCCCCC)CCCCCC] | D |

TABLE 2-continued

Representative Lipids of Formula (II)

| No. | Structure | Prep. Method |
|---|---|---|
| II-22 | 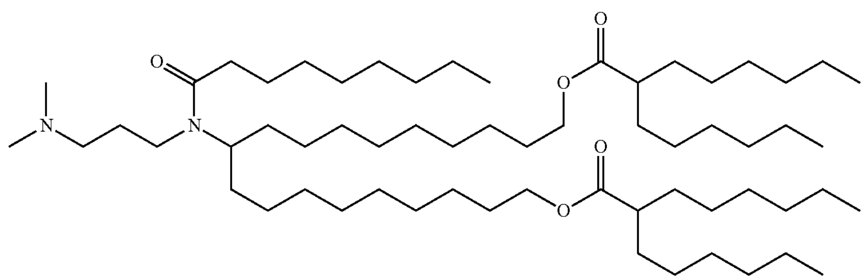 [SMILES: CCCCCCCCC(=O)N(CCCN(C)C)C(CCCCCCCCCOC(=O)C(CCCCCC)CCCCCC)CCCCCCCCCOC(=O)C(CCCCCC)CCCCCC] | D |
| II-23 | 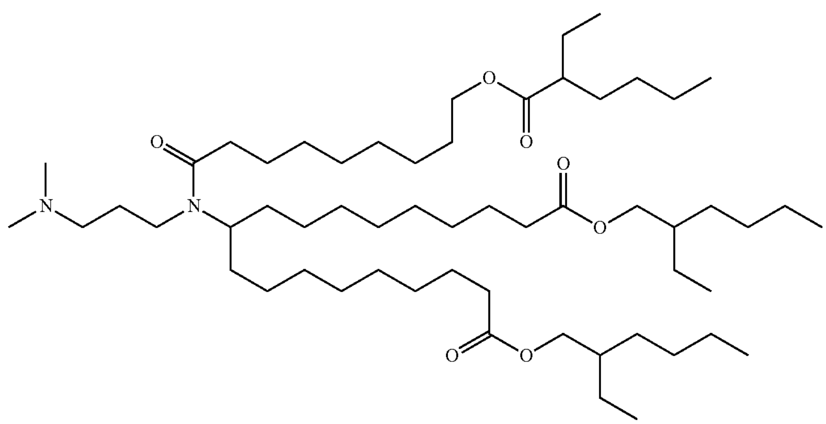 [SMILES: CCCCC(CC)COC(=O)CCCCCCCCC(CCCCCCCCC(=O)OCC(CC)CCCC)N(CCCN(C)C)C(=O)CCCCCCCCOC(=O)C(CC)CCCC] | D |
| II-24 | 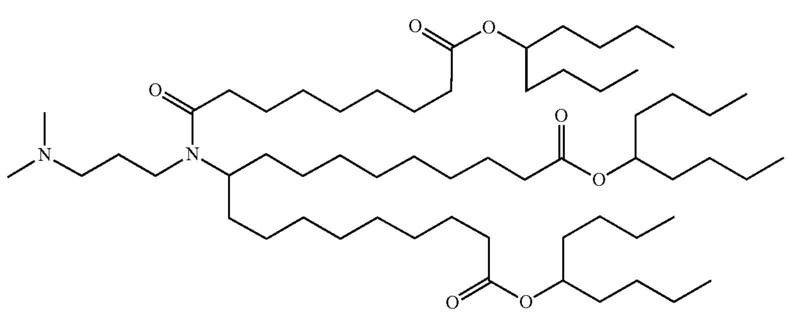 [SMILES: CCCCC(CCCC)OC(=O)CCCCCCCCC(CCCCCCCCC(=O)OC(CCCC)CCCC)N(CCCN(C)C)C(=O)CCCCCCCC(=O)OC(CCCC)CCCC] | D |
| II-25 | 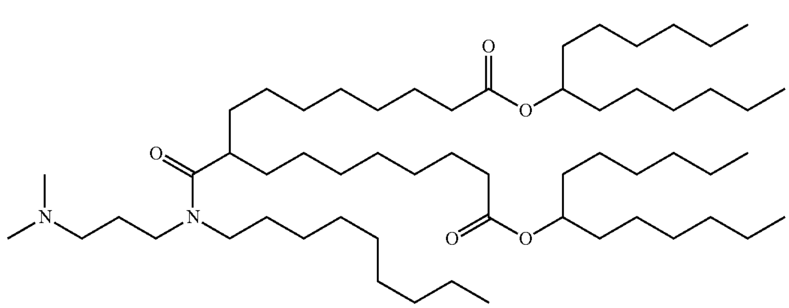 [SMILES: CCCCCCCCCN(CCCN(C)C)C(=O)C(CCCCCCCC(=O)OC(CCCCCC)CCCCCC)CCCCCCCC(=O)OC(CCCCCC)CCCCCC] | E |

TABLE 2-continued

Representative Lipids of Formula (II)

| No. | Structure | Prep. Method |
|---|---|---|
| II-26 | 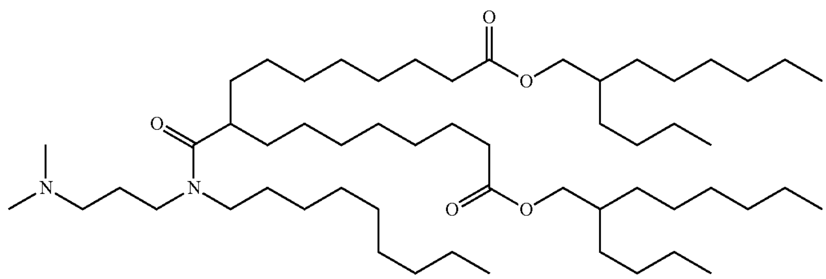 [SMILES: CCCCCCCCCN(CCCN(C)C)C(=O)C(CCCCCCCC(=O)OCC(CCCC)CCCCCC)CCCCCCCC(=O)OCC(CCCC)CCCCCC] | E |
| II-27 | 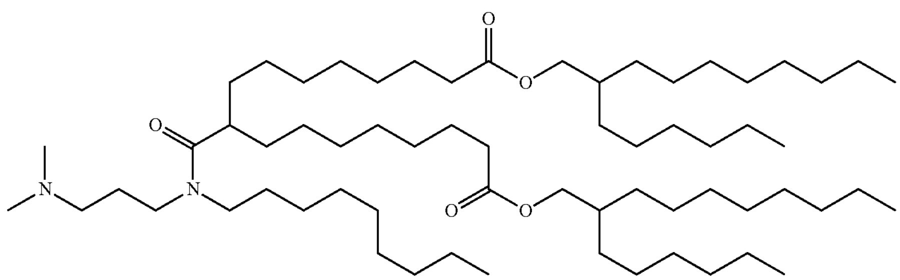 [SMILES: CCCCCCCCCN(CCCN(C)C)C(=O)C(CCCCCCCC(=O)OCC(CCCCCC)CCCCCCCC)CCCCCCCC(=O)OCC(CCCCCC)CCCCCCCC] | E |
| II-28 | 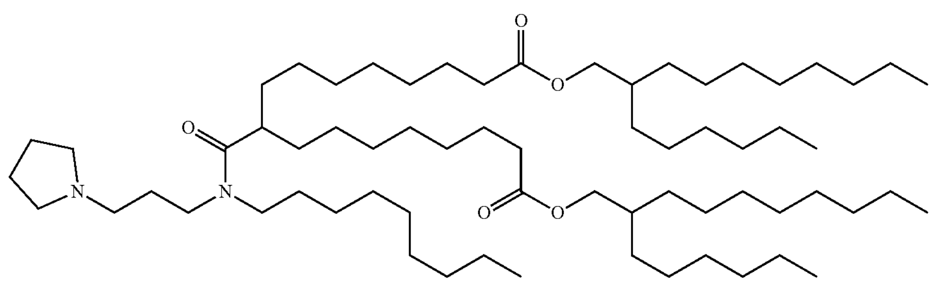 [SMILES: CCCCCCCCCN(CCCN1CCCC1)C(=O)C(CCCCCCCC(=O)OCC(CCCCCC)CCCCCCCC)CCCCCCCC(=O)OCC(CCCCCC)CCCCCCCC] | E |
| II-29 | 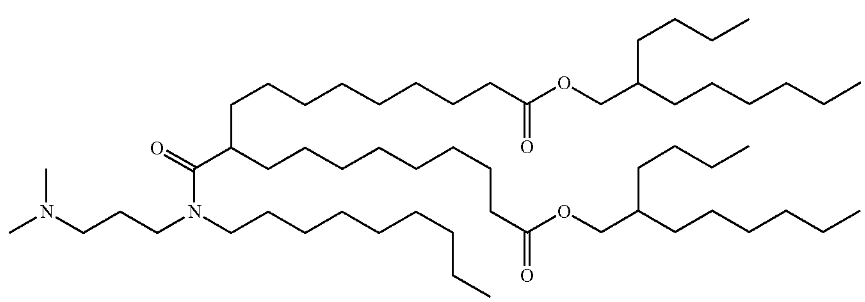 [SMILES: CCCCCCCCCN(CCCN(C)C)C(=O)C(CCCCCCCCC(=O)OCC(CCCC)CCCCCC)CCCCCCCCC(=O)OCC(CCCC)CCCCCC] | E |
| II-30 | 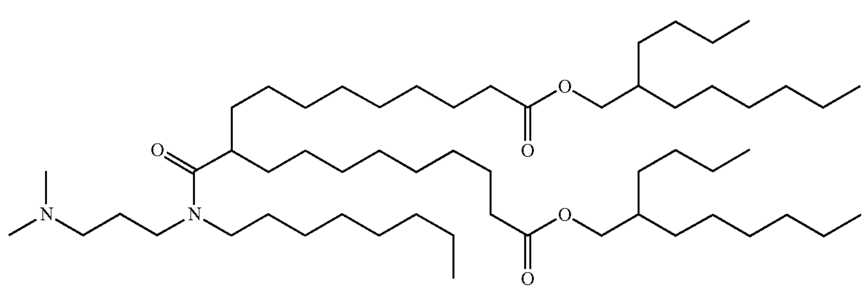 [SMILES: CCCCCCCCN(CCCN(C)C)C(=O)C(CCCCCCCCC(=O)OCC(CCCC)CCCCCC)CCCCCCCCC(=O)OCC(CCCC)CCCCCC] | E |

TABLE 2-continued

Representative Lipids of Formula (II)

| No. | Structure | Prep. Method |
|---|---|---|
| II-31 | 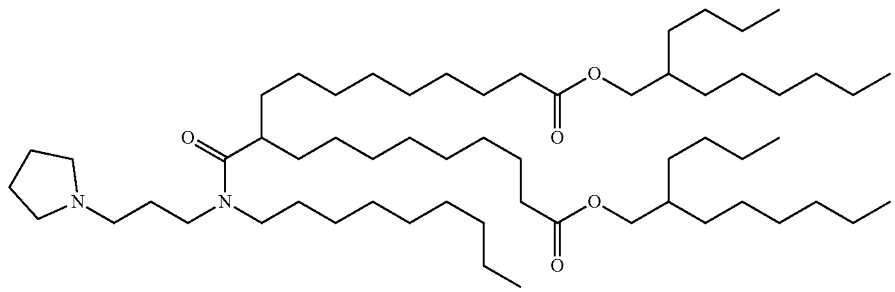 [SMILES: CCCCCCCCCN(CCCN1CCCC1)C(=O)C(CCCCCCCCC(=O)OCC(CCCC)CCCCCC)CCCCCCCCC(=O)OCC(CCCC)CCCCCC] | E |
| II-32 | 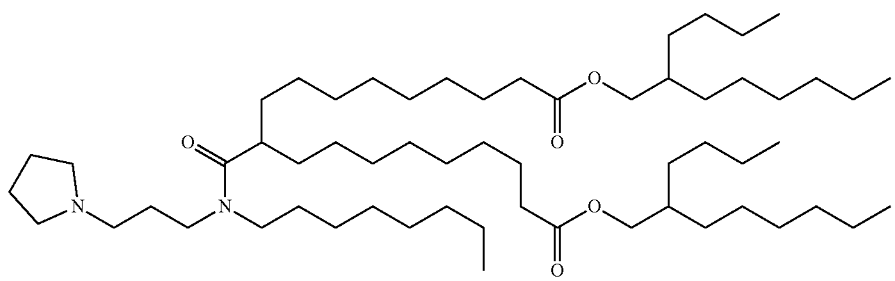 [SMILES: CCCCCCCCN(CCCN1CCCC1)C(=O)C(CCCCCCCCC(=O)OCC(CCCC)CCCCCC)CCCCCCCCC(=O)OCC(CCCC)CCCCCC] | E |
| II-33 | 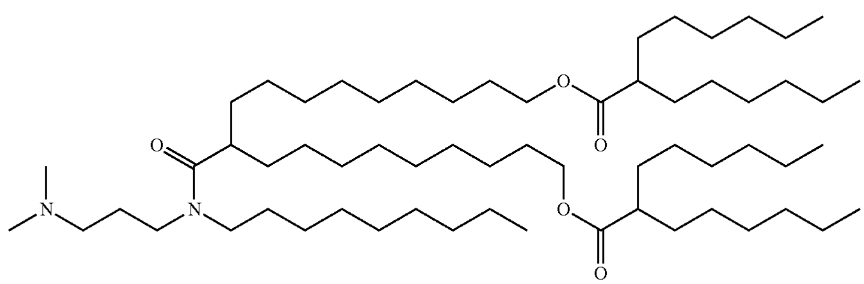 [SMILES: CCCCCCCCCN(CCCN(C)C)C(=O)C(CCCCCCCCCOC(=O)C(CCCCCC)CCCCCC)CCCCCCCCCOC(=O)C(CCCCCC)CCCCCC] | E |
| II-34 | 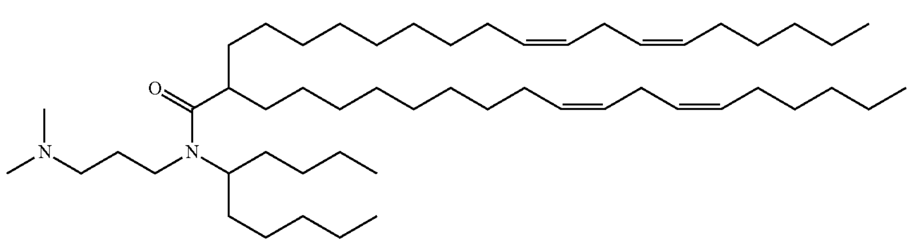 [SMILES: CCCCC/C=C\C/C=C\CCCCCCCCC(CCCCCCCC/C=C\C/C=C\CCCCC)C(=O)N(CCCN(C)C)C(CCCC)CCCCC] | E |

In some embodiments, the LNPs comprise a lipid of Formula (II), a nucleoside-modified RNA and one or more excipient selected from neutral lipids, steroids and pegylated lipids. In some embodiments the lipid of Formula (II) is compound 11-9. In some embodiments the lipid of Formula (II) is compound II-10. In some embodiments the lipid of Formula (II) is compound II-11. In some embodiments the lipid of Formula (II) is compound 11-12. In some embodiments the lipid of Formula (II) is compound 11-32.

In some other embodiments, the cationic lipid component of the LNPs has the structure of Formula (III):

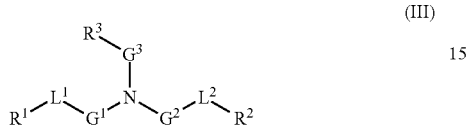

(III)

or a pharmaceutically acceptable salt, tautomer, prodrug or stereoisomer thereof, wherein:
one of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O—, and the other of $L^1$ or $L^2$ is —O(C=O)—, —(C=O)O—, —C(=O)—, —O—, —S(O)$_x$—, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond;
$G^1$ and $G^2$ are each independently unsubstituted $C_1$-$C_{12}$ alkylene or $C_1$-$C_{12}$ alkenylene;
$G^3$ is $C_1$-$C_{24}$ alkylene, $C_1$-$C_{24}$ alkenylene, $C_3$-$C_8$ cycloalkylene, $C_3$-$C_8$ cycloalkenylene;
$R^a$ is H or $C_1$-$C_{12}$ alkyl;
$R^1$ and $R^2$ are each independently $C_6$-$C_{24}$ alkyl or $C_6$-$C_{24}$ alkenyl;
$R^3$ is H, OR$^5$, CN, —C(=O)OR$^4$, —OC(=O)R$^4$ or —NR$^5$C(=O)R$^4$;
$R^4$ is $C_1$-$C_{12}$ alkyl;
$R^5$ is H or $C_1$-$C_6$ alkyl; and
x is 0, 1 or 2.

In some of the foregoing embodiments of Formula (III), the lipid has one of the following structures (IIIA) or (IIIB):

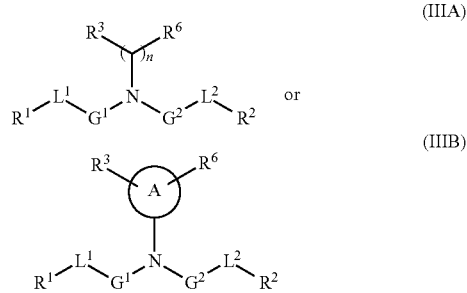

(IIIA)

or (IIIB)

wherein:
A is a 3 to 8-membered cycloalkyl or cycloalkylene ring;
$R^6$ is, at each occurrence, independently H, OH or $C_1$-$C_{24}$ alkyl;
n is an integer ranging from 1 to 15.

In some of the foregoing embodiments of Formula (III), the lipid has structure (IIIA), and in other embodiments, the lipid has structure (IIIB).

In other embodiments of Formula (III), the lipid has one of the following structures (IIIC) or (IIID):

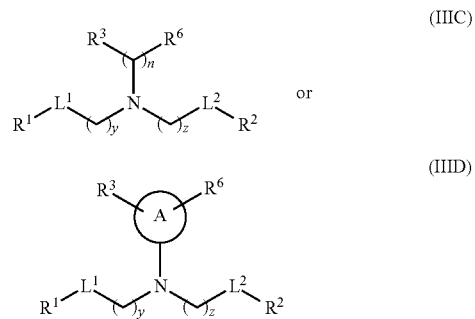

(IIIC)

or (IIID)

wherein y and z are each independently integers ranging from 1 to 12.

In any of the foregoing embodiments of Formula (III), one of $L^1$ or $L^2$ is —O(C=O)—. For example, in some embodiments each of 12 and $L^2$ are —O(C=O)—. In some different embodiments of any of the foregoing, $L^1$ and $L^2$ are each independently —(C=O)O— or —O(C=O)—. For example, in some embodiments each of $L^1$ and $L^2$ is —(C=O)O—.

In some different embodiments of Formula (III), the lipid has one of the following structures (IIIE) or (IIIF):

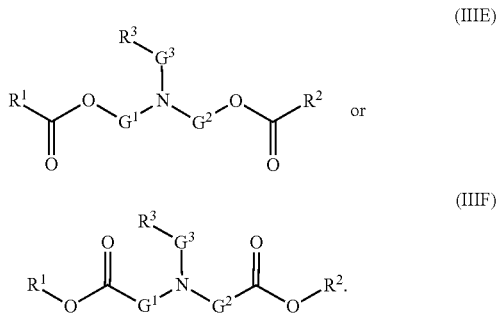

(IIIE)

or (IIIF)

In some of the foregoing embodiments of Formula (III), the lipid has one of the following structures (IIIG), (IIIH), (IIII), or (IIIJ):

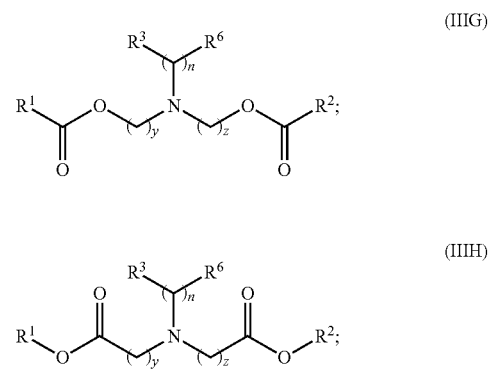

(IIIG)

(IIIH)

-continued

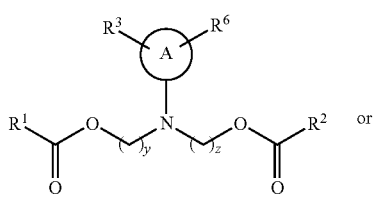

(III)

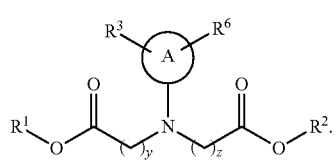

(IIIJ)

In some of the foregoing embodiments of Formula (III), n is an integer ranging from 2 to 12, for example from 2 to 8 or from 2 to 4. For example, in some embodiments, n is 3, 4, 5 or 6. In some embodiments, n is 3. In some embodiments, n is 4. In some embodiments, n is 5. In some embodiments, n is 6.

In some other of the foregoing embodiments of Formula (III), y and z are each independently an integer ranging from 2 to 10. For example, in some embodiments, y and z are each independently an integer ranging from 4 to 9 or from 4 to 6.

In some of the foregoing embodiments of Formula (III), $R^6$ is H. In other of the foregoing embodiments, $R^6$ is $C_1$-$C_{24}$ alkyl. In other embodiments, $R^6$ is OH.

In some embodiments of Formula (III), $G^3$ is unsubstituted. In other embodiments, G3 is substituted. In various different embodiments, $G^3$ is linear $C_1$-$C_{24}$ alkylene or linear $C_1$-$C_{24}$ alkenylene.

In some other foregoing embodiments of Formula (III), $R^1$ or $R^2$, or both, is $C_6$-$C_{24}$ alkenyl. For example, in some embodiments, $R^1$ and $R^2$ each, independently have the following structure:

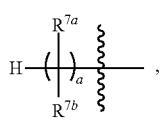

wherein:

$R^{7a}$ and $R^{7b}$ are, at each occurrence, independently H or $C_1$-$C_{12}$ alkyl; and a is an integer from 2 to 12, wherein $R^{7a}$, $R^{7b}$ and a are each selected such that $R^1$ and $R^2$ each independently comprise from 6 to 20 carbon atoms. For example, in some embodiments a is an integer ranging from 5 to 9 or from 8 to 12.

In some of the foregoing embodiments of Formula (III), at least one occurrence of $R^{7a}$ is H. For example, in some embodiments, $R^{7a}$ is H at each occurrence. In other different embodiments of the foregoing, at least one occurrence of $R^{7b}$ is $C_1$-$C_8$ alkyl. For example, in some embodiments, $C_1$-$C_8$ alkyl is methyl, ethyl, n-propyl, iso-propyl, n-butyl, iso-butyl, tert-butyl, n-hexyl or n-octyl.

In different embodiments of Formula (III), $R^1$ or $R^2$, or both, has one of the following structures.

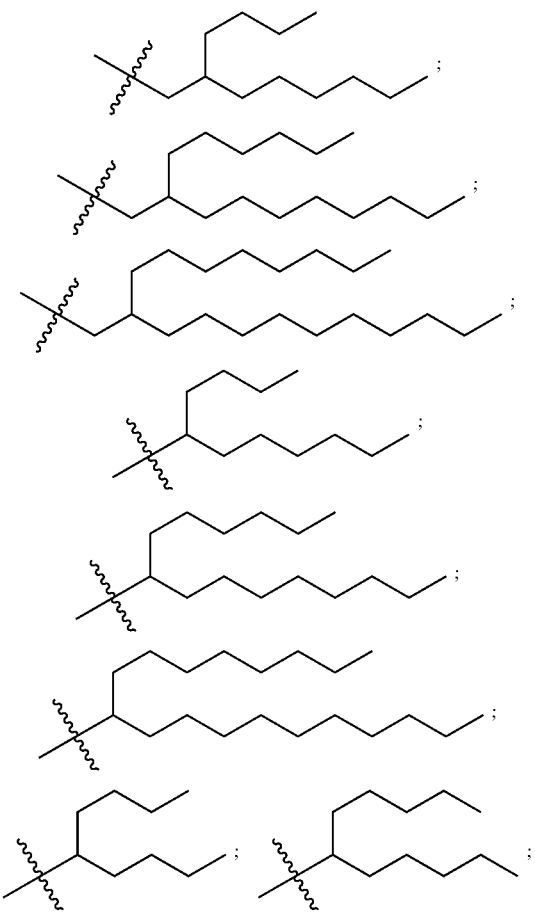

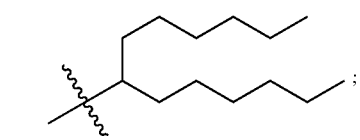

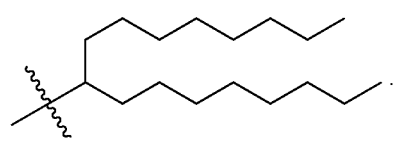

In some of the foregoing embodiments of Formula (III), $R^3$ is OH, CN, —C(=O)O$R^4$, —OC(=O)$R^4$ or —NHC(=O)$R^4$. In some embodiments, $R^4$ is methyl or ethyl.

In various different embodiments, the cationic lipid of Formula (III) has one of the structures set forth in Table 3 below.

TABLE 3

Representative Compounds of Formula (III)

| No. | Structure | Prep. Method |
|---|---|---|
| III-1 | 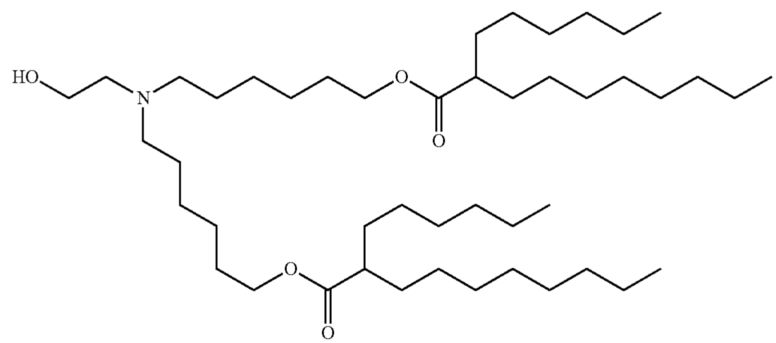 [SMILES: CCCCCCCCC(CCCCCC)C(=O)OCCCCCCN(CCO)CCCCCCOC(=O)C(CCCCCC)CCCCCCCC] | F |
| III-2 | 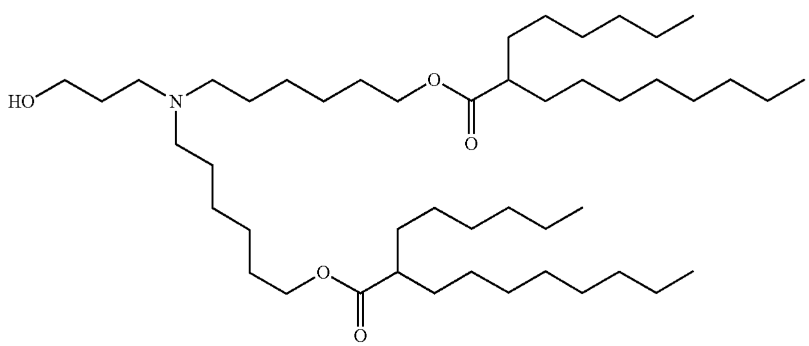 [SMILES: CCCCCCCCC(CCCCCC)C(=O)OCCCCCCN(CCCO)CCCCCCOC(=O)C(CCCCCC)CCCCCCCC] | F |
| III-3 | 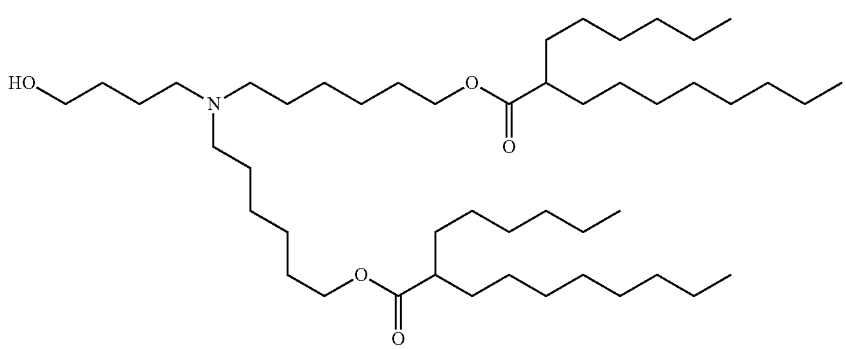 [SMILES: CCCCCCCCC(CCCCCC)C(=O)OCCCCCCN(CCCCO)CCCCCCOC(=O)C(CCCCCC)CCCCCCCC] | F |
| III-4 | 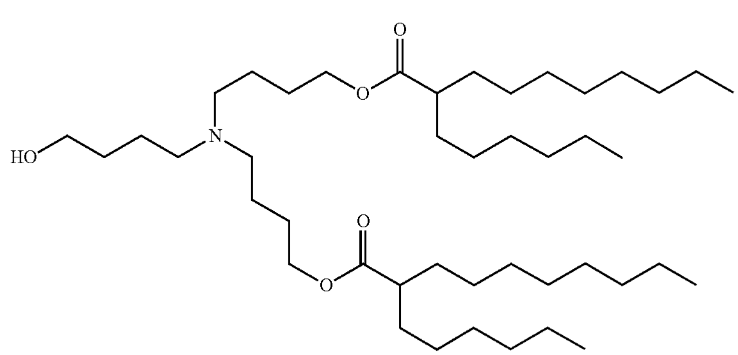 [SMILES: CCCCCCCCC(CCCCCC)C(=O)OCCCCN(CCCCO)CCCCOC(=O)C(CCCCCC)CCCCCCCC] | F |

TABLE 3-continued

Representative Compounds of Formula (III)

| No. | Structure | Prep. Method |
|---|---|---|
| III-5 | 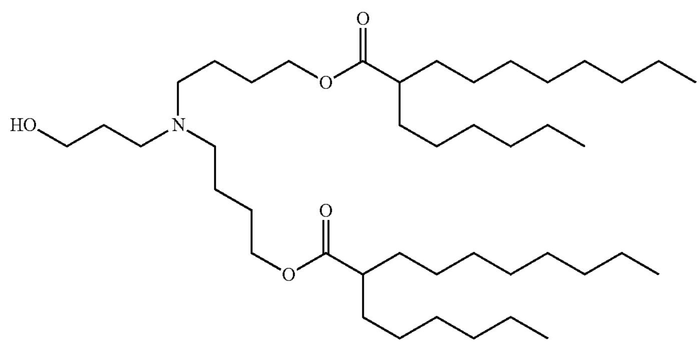 [SMILES: CCCCCCCCC(CCCCCC)C(=O)OCCCCN(CCCO)CCCCOC(=O)C(CCCCCC)CCCCCCCC] | F |
| III-6 | 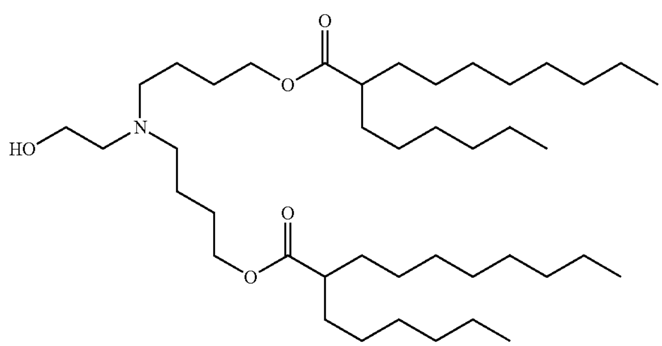 [SMILES: CCCCCCCCC(CCCCCC)C(=O)OCCCCN(CCO)CCCCOC(=O)C(CCCCCC)CCCCCCCC] | F |
| III-7 | 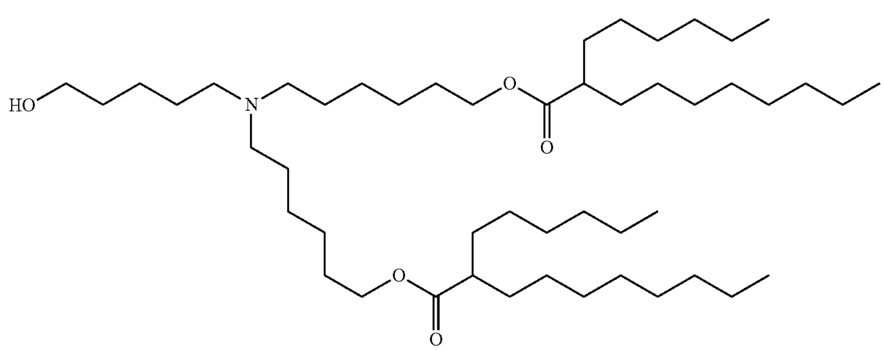 [SMILES: CCCCCCCCC(CCCCCC)C(=O)OCCCCCCN(CCCCCO)CCCCCCOC(=O)C(CCCCCC)CCCCCCCC] | F |
| III-8 | 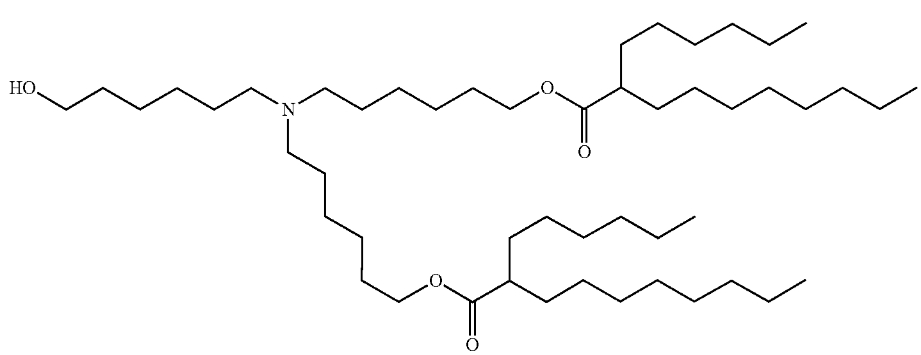 [SMILES: CCCCCCCCC(CCCCCC)C(=O)OCCCCCCN(CCCCCCO)CCCCCCOC(=O)C(CCCCCC)CCCCCCCC] | F |

TABLE 3-continued

Representative Compounds of Formula (III)

| No. | Structure | Prep. Method |
|---|---|---|
| III-9 | 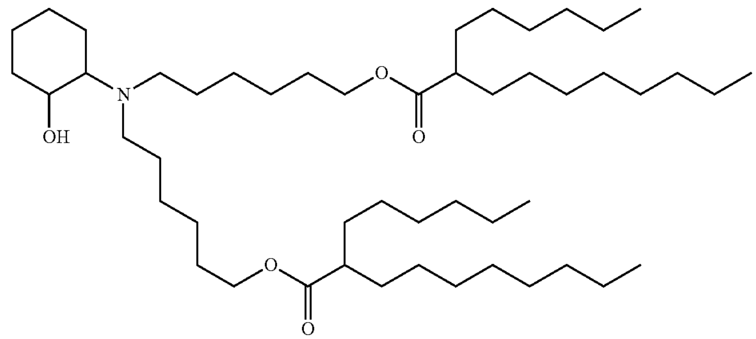 [SMILES: CCCCCCCCC(CCCCCC)C(=O)OCCCCCCN(CCCCCCOC(=O)C(CCCCCC)CCCCCCCC)C1CCCCC1O] | F |
| III-10 | 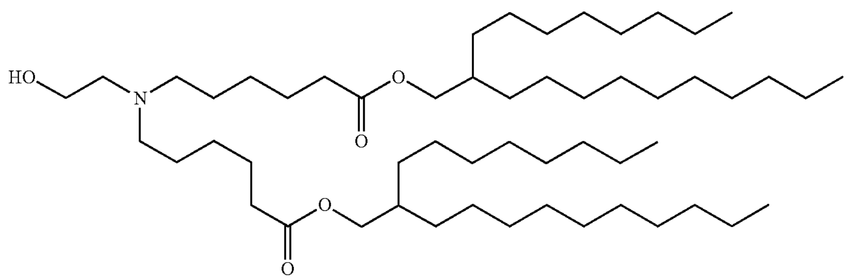 [SMILES: CCCCCCCCCCC(CCCCCCCC)COC(=O)CCCCCN(CCO)CCCCCC(=O)OCC(CCCCCCCC)CCCCCCCCCC] | F |
| III-11 | 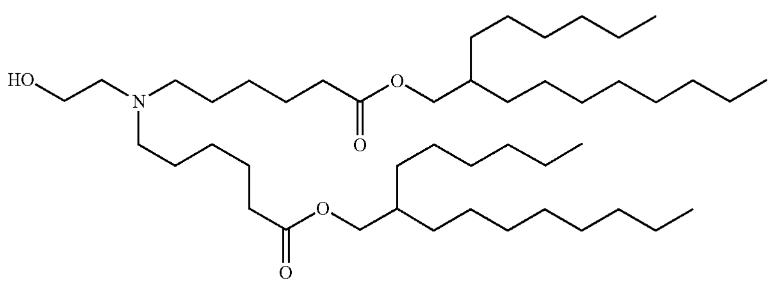 [SMILES: CCCCCCCCC(CCCCCC)COC(=O)CCCCCN(CCO)CCCCCC(=O)OCC(CCCCCC)CCCCCCCC] | F |
| III-12 | 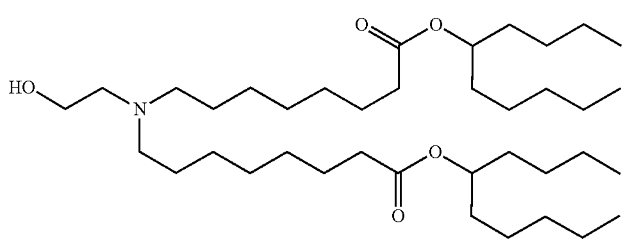 [SMILES: CCCCCC(CCCC)OC(=O)CCCCCCCN(CCO)CCCCCCCC(=O)OC(CCCC)CCCCC] | F |
| III-13 | 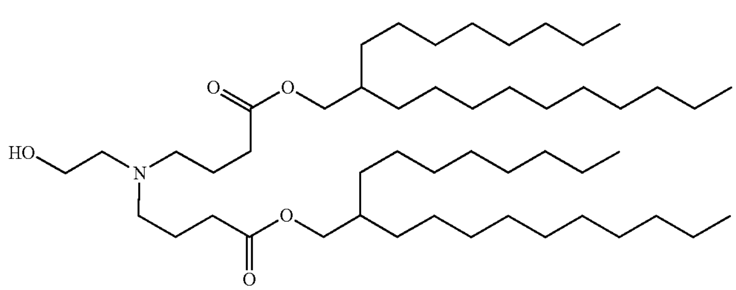 [SMILES: CCCCCCCCCCC(CCCCCCCC)COC(=O)CCCN(CCO)CCCC(=O)OCC(CCCCCCCC)CCCCCCCCCC] | F |

TABLE 3-continued
Representative Compounds of Formula (III)
| No. | Structure | Prep. Method |
|---|---|---|
| III-14 | 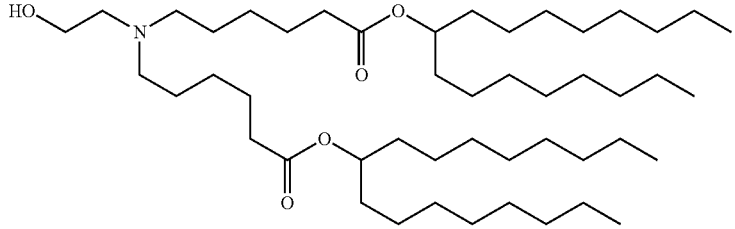 [SMILES: CCCCCCCCC(CCCCCCCC)OC(=O)CCCCCN(CCO)CCCCCC(=O)OC(CCCCCCCC)CCCCCCCC] | F |
| III-15 | 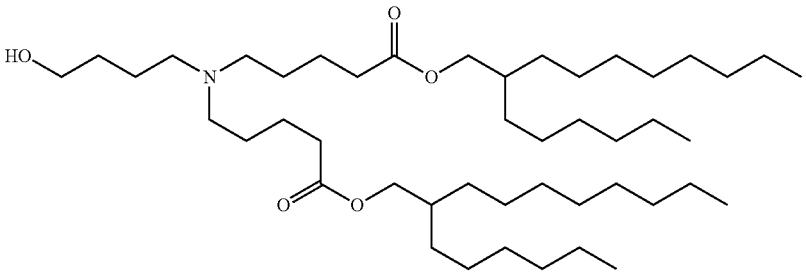 [SMILES: CCCCCCCCC(CCCCCC)COC(=O)CCCCN(CCCCO)CCCCC(=O)OCC(CCCCCC)CCCCCCCC] | F |
| III-16 | 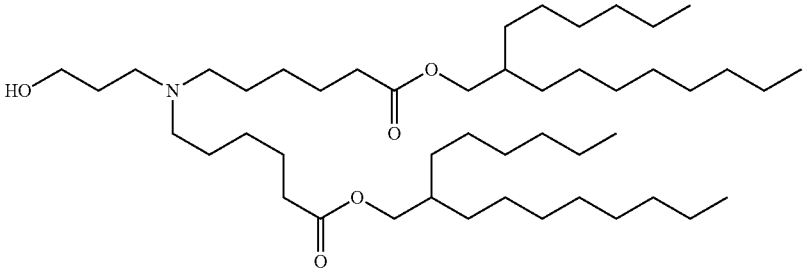 [SMILES: CCCCCCCCC(CCCCCC)COC(=O)CCCCCN(CCCO)CCCCCC(=O)OCC(CCCCCC)CCCCCCCC] | F |
| III-17 | 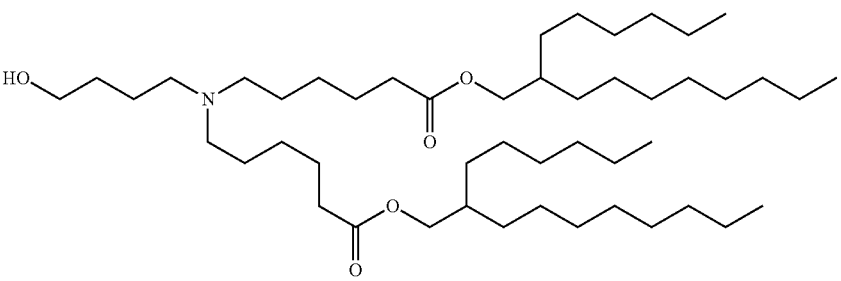 [SMILES: CCCCCCCCC(CCCCCC)COC(=O)CCCCCN(CCCCO)CCCCCC(=O)OCC(CCCCCC)CCCCCCCC] | F |
| III-18 | 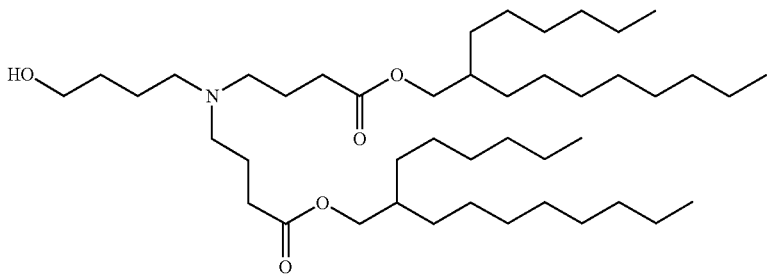 [SMILES: CCCCCCCCC(CCCCCC)COC(=O)CCCN(CCCCO)CCCC(=O)OCC(CCCCCC)CCCCCCCC] | F |

TABLE 3-continued

Representative Compounds of Formula (III)

| No. | Structure | Prep. Method |
|---|---|---|
| III-19 | 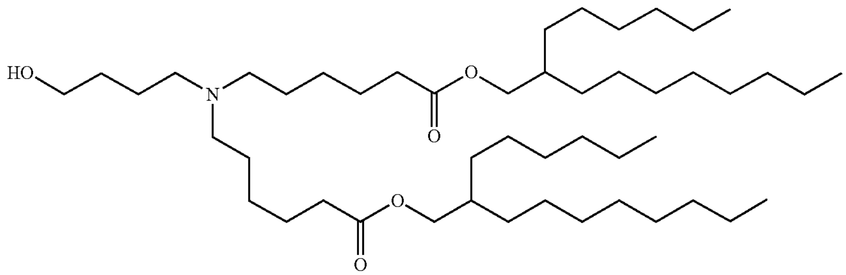 [SMILES: CCCCCCCCC(CCCCCC)COC(=O)CCCCCN(CCCCO)CCCCCC(=O)OCC(CCCCCC)CCCCCCCC] | F |
| III-20 | 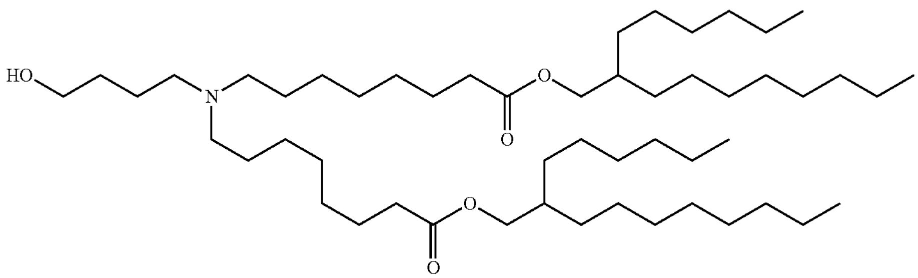 [SMILES: CCCCCCCCC(CCCCCC)COC(=O)CCCCCCCN(CCCCO)CCCCCCCC(=O)OCC(CCCCCC)CCCCCCCC] | F |
| III-21 | 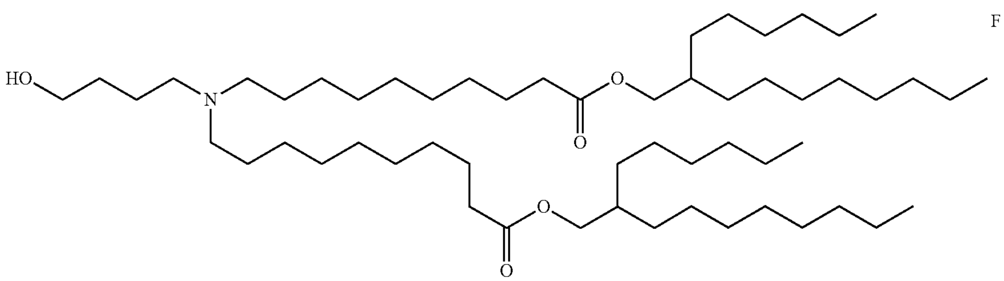 | F |
| III-22 | 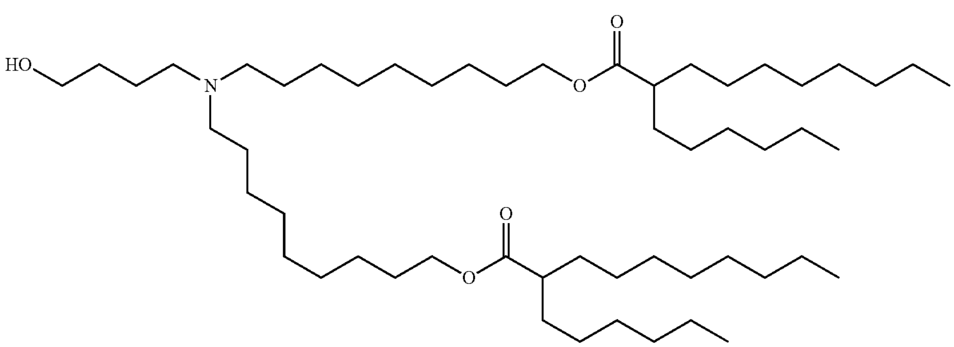 [SMILES: CCCCCCCCC(CCCCCC)C(=O)OCCCCCCCCCN(CCCCO)CCCCCCCCCOC(=O)C(CCCCCC)CCCCCCCC] | F |
| III-23 | 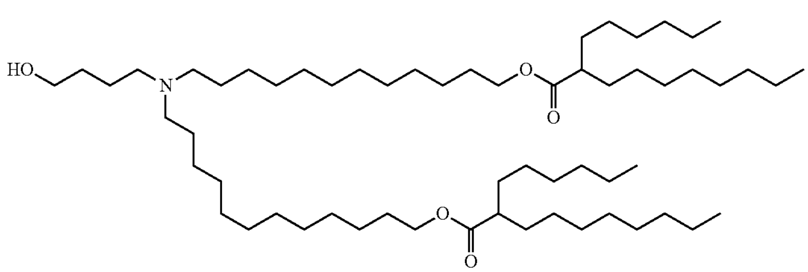 [SMILES: CCCCCCCCC(CCCCCC)C(=O)OCCCCCCCCCCCCN(CCCCO)CCCCCCCCCCCCOC(=O)C(CCCCCC)CCCCCCCC] | F |

TABLE 3-continued

Representative Compounds of Formula (III)

| No. | Structure | Prep. Method |
|---|---|---|
| III-24 | 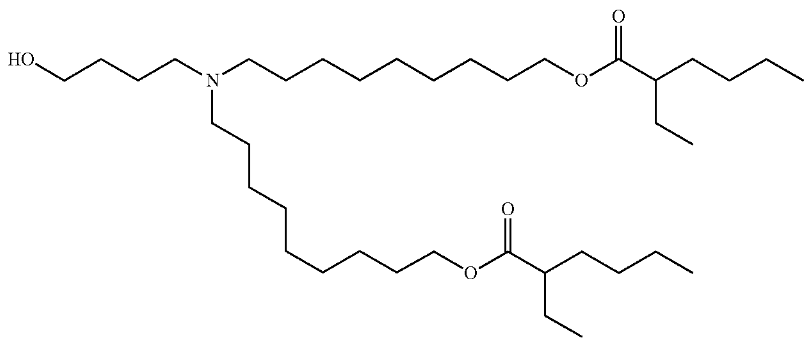 [SMILES: CCCCC(CC)C(=O)OCCCCCCCCCN(CCCCO)CCCCCCCCCOC(=O)C(CC)CCCC] | F |
| III-25 | 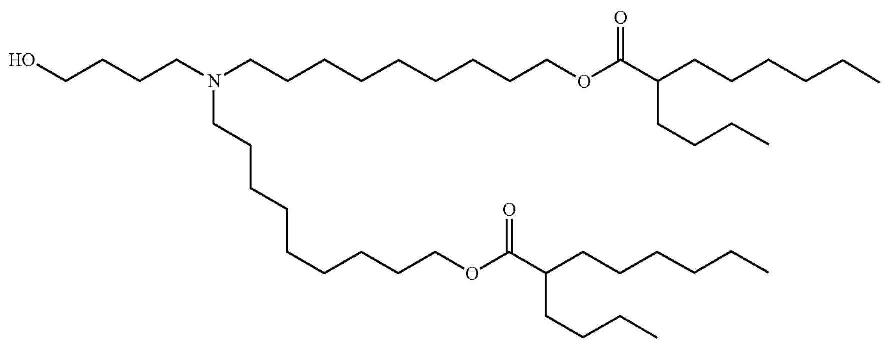 [SMILES: CCCCCCC(CCCC)C(=O)OCCCCCCCCCN(CCCCO)CCCCCCCCCOC(=O)C(CCCC)CCCCCC] | F |
| III-26 | 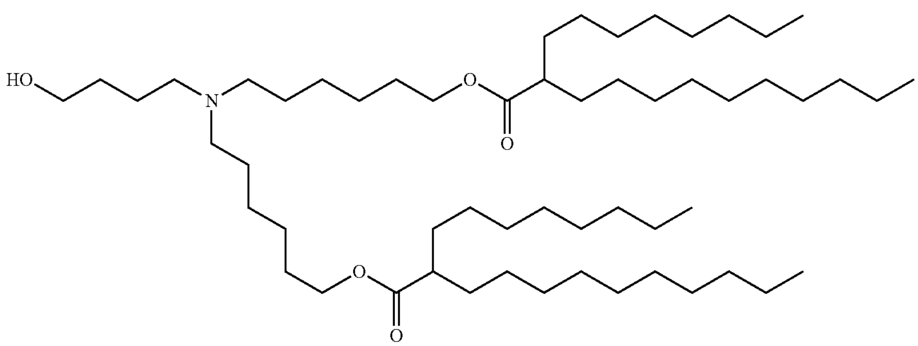 [SMILES: CCCCCCCCCCC(CCCCCCCC)C(=O)OCCCCCCN(CCCCO)CCCCCCOC(=O)C(CCCCCCCC)CCCCCCCCCC] | F |
| III-27 | 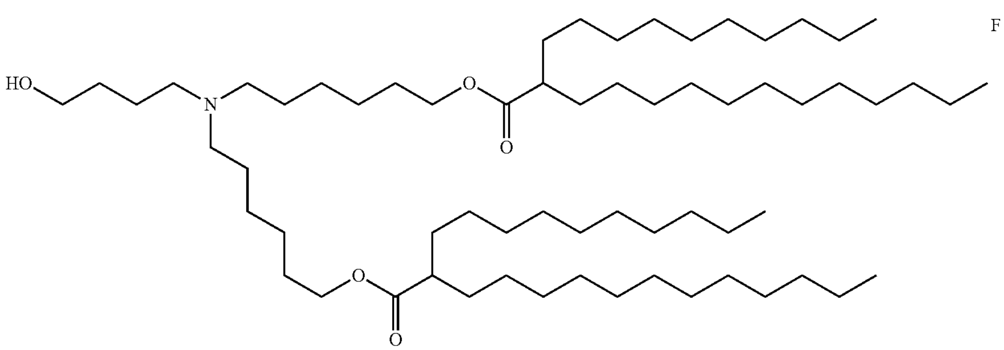 | F |

TABLE 3-continued

Representative Compounds of Formula (III)

| No. | Structure | Prep. Method |
|---|---|---|
| III-28 | 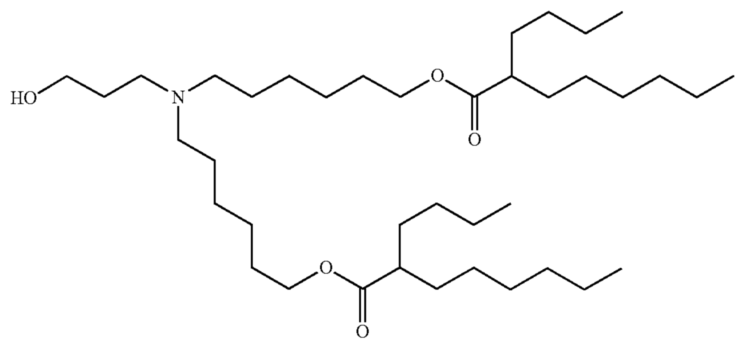 [SMILES: CCCCCCC(CCCC)C(=O)OCCCCCCN(CCCO)CCCCCCOC(=O)C(CCCC)CCCCCC] | F |
| III-29 | 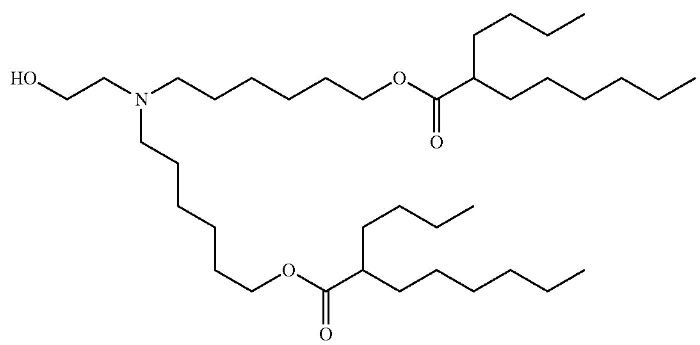 [SMILES: CCCCCCC(CCCC)C(=O)OCCCCCCN(CCO)CCCCCCOC(=O)C(CCCC)CCCCCC] | F |
| III-30 | 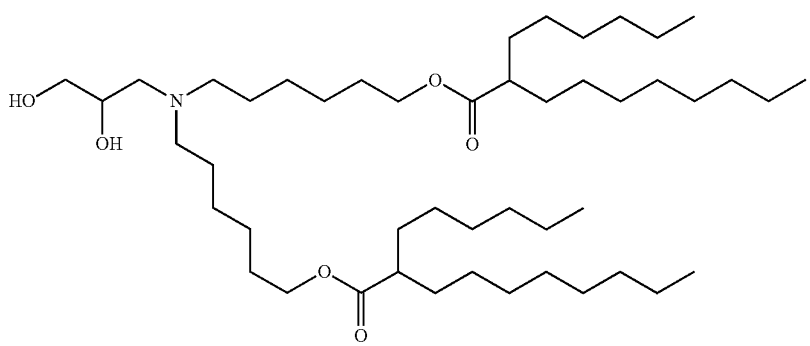 [SMILES: CCCCCCCCC(CCCCCC)C(=O)OCCCCCCN(CCCCCCOC(=O)C(CCCCCC)CCCCCCCC)CC(O)CO] | F |
| III-31 | 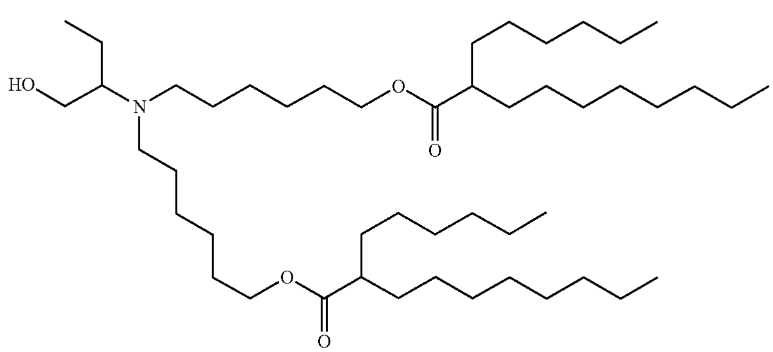 [SMILES: CCCCCCCCC(CCCCCC)C(=O)OCCCCCCN(CCCCCCOC(=O)C(CCCCCC)CCCCCCCC)C(CC)CO] | F |

TABLE 3-continued

Representative Compounds of Formula (III)

| No. | Structure | Prep. Method |
|---|---|---|
| III-32 | 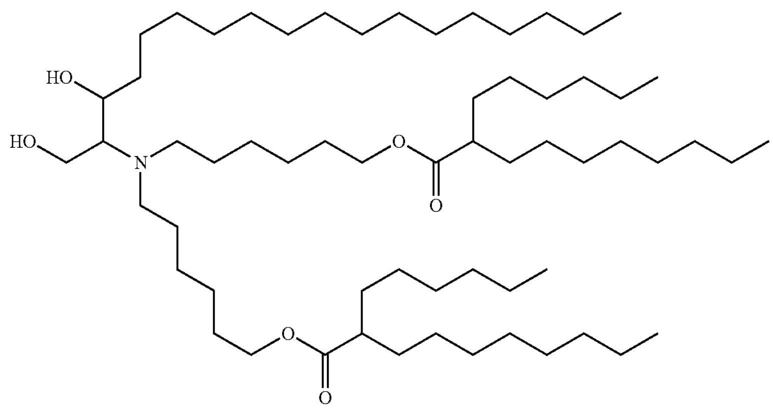 [SMILES: CCCCCCCCCCCCCCCC(O)C(CO)N(CCCCCCOC(=O)C(CCCCCC)CCCCCCCC)CCCCCCOC(=O)C(CCCCCC)CCCCCCCC] | F |
| III-33 | 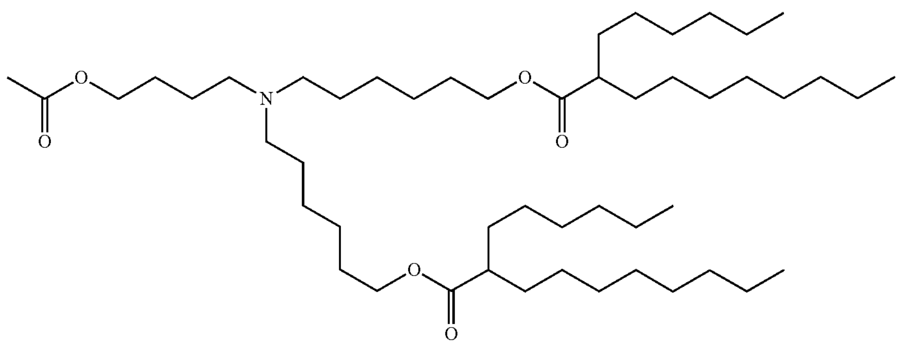 | F |
| III-34 | 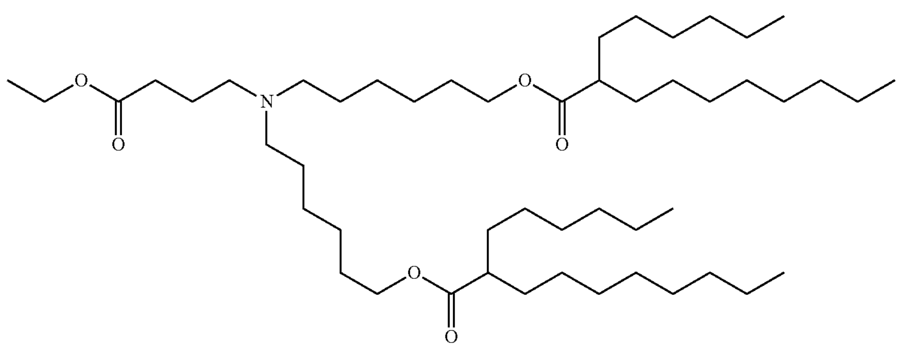 [SMILES: CCCCCCCCC(CCCCCC)C(=O)OCCCCCCN(CCCCCCOC(=O)C(CCCCCC)CCCCCCCC)CCCC(=O)OCC] | F |
| III-35 | 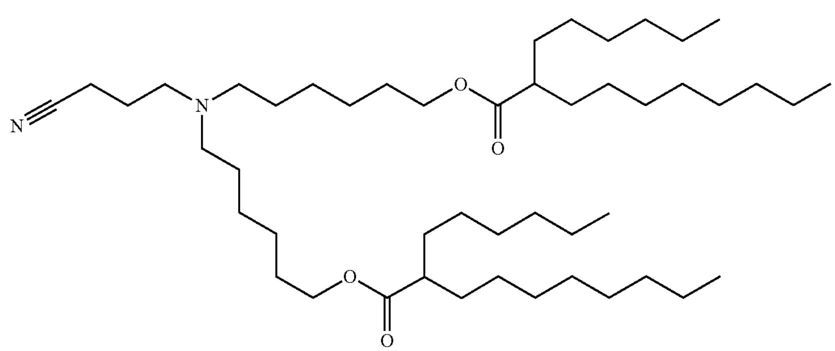 [SMILES: CCCCCCCCC(CCCCCC)C(=O)OCCCCCCN(CCCC#N)CCCCCCOC(=O)C(CCCCCC)CCCCCCCC] | F |

TABLE 3-continued

Representative Compounds of Formula (III)

| No. | Structure | Prep. Method |
|---|---|---|
| III-36 | 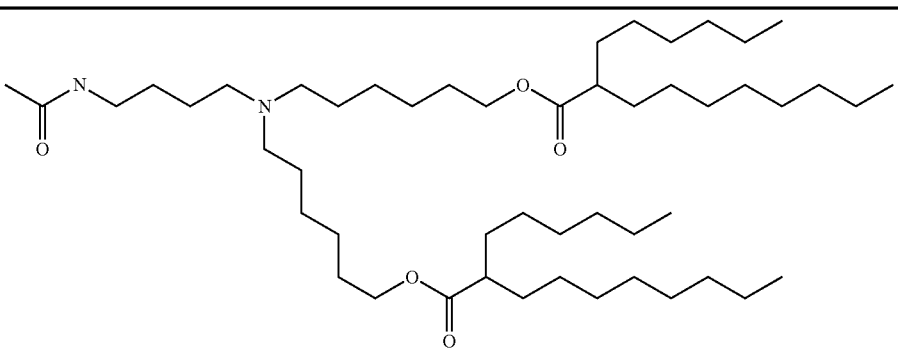 | F |

In some embodiments, the LNPs comprise a lipid of Formula (III), a nucleoside-modified RNA and one or more excipient selected from neutral lipids, steroids and pegylated lipids. In some embodiments the lipid of Formula (III) is compound 111-3. In some embodiments the lipid of Formula (III) is compound 111-7.

In certain embodiments, the cationic lipid is present in the LNP in an amount from about 30 to about 95 mole percent. In one embodiment, the cationic lipid is present in the LNP in an amount from about 30 to about 70 mole percent. In one embodiment, the cationic lipid is present in the LNP in an amount from about 40 to about 60 mole percent. In one embodiment, the cationic lipid is present in the LNP in an amount of about 50 mole percent. In one embodiment, the LNP comprises only cationic lipids.

In certain embodiments, the LNP comprises one or more additional lipids which stabilize the formation of particles during their formation.

Suitable stabilizing lipids include neutral lipids and anionic lipids.

The term "neutral lipid" refers to any one of a number of lipid species that exist in either an uncharged or neutral zwitterionic form at physiological pH.

Representative neutral lipids include diacylphosphatidylcholines, diacylphosphatidylethanolamines, ceramides, sphingomyelins, dihydro sphingomyelins, cephalins, and cerebrosides.

Exemplary neutral lipids include, for example, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoyl-phosphatidylethanolamine (POPE) and dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), 16-O-monomethyl PE, 16-O-dimethyl PE, 18-1-trans PE, 1-stearioyl-2-oleoyl-phosphatidyethanol amine (SOPE), and 1,2-dielaidoyl-sn-glycero-3-phophoethanolamine (transDOPE). In one embodiment, the neutral lipid is 1,2-distearoyl-sn-glycero-3-phosphocholine (DSPC).

In some embodiments, the LNPs comprise a neutral lipid selected from DSPC, DPPC, DMPC, DOPC, POPC, DOPE and SM. In various embodiments, the molar ratio of the cationic lipid (e.g., lipid of Formula (I)) to the neutral lipid ranges from about 2:1 to about 8:1.

In various embodiments, the LNPs further comprise a steroid or steroid analogue. A "steroid" is a compound comprising the following carbon skeleton:

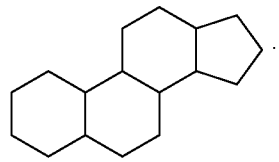 [SMILES: C1CCC2C(C1)CCC1C3CCCC3CCC21]

In certain embodiments, the steroid or steroid analogue is cholesterol. In some of these embodiments, the molar ratio of the cationic lipid (e.g., lipid of Formula (I)) to cholesterol ranges from about 2:1 to 1:1.

The term "anionic lipid" refers to any lipid that is negatively charged at physiological pH. These lipids include phosphatidylglycerol, cardiolipin, diacylphosphatidylserine, diacylphosphatidic acid, N-dodecanoylphosphatidylethanolamines, N-succinylphosphatidylethanolamines, N-glutarylphosphatidylethanolamines, lysylphosphatidylglycerols, palmitoyloleyolphosphatidylglycerol (POPG), and other anionic modifying groups joined to neutral lipids.

In certain embodiments, the LNP comprises glycolipids (e.g., monosialoganglioside $GM_1$). In certain embodiments, the LNP comprises a sterol, such as cholesterol.

In some embodiments, the LNPs comprise a polymer conjugated lipid. The term "polymer conjugated lipid" refers to a molecule comprising both a lipid portion and a polymer portion. An example of a polymer conjugated lipid is a pegylated lipid. The term "pegylated lipid" refers to a molecule comprising both a lipid portion and a polyethylene glycol portion. Pegylated lipids are known in the art and include 1-(monomethoxy-polyethyleneglycol)-2,3-dimyristoylglycerol (PEG-s-DMG) and the like.

In certain embodiments, the LNP comprises an additional, stabilizing-lipid which is a polyethylene glycol-lipid (pegylated lipid). Suitable polyethylene glycol-lipids include PEG-modified phosphatidylethanolamine, PEG-modified phosphatidic acid, PEG-modified ceramides (e.g., PEG-CerC14 or PEG-CerC20), PEG-modified dialkylamines, PEG-modified diacylglycerols, PEG-modified dialkylglycerols.

Representative polyethylene glycol-lipids include PEG-c-DOMG, PEG-c-DMA, and PEG-s-DMG. In one embodiment, the polyethylene glycol-lipid is N-[(methoxy poly(ethylene glycol)$_{2000}$)carbamyl]-1,2-dimyristyloxlpropyl-3-amine (PEG-c-DMA). In one embodiment, the polyethylene glycol-lipid is PEG-c-DOMG). In other embodiments, the LNPs comprise a pegylated diacylglycerol (PEG-DAG) such as 1-(monomethoxy-polyethyleneglycol)-2,3-dimyristoylglycerol (PEG-DMG), a pegylated phosphatidylethanoloamine (PEG-PE), a PEG succinate diacylglycerol (PEG-S-DAG) such as 4-O-(2,3'-di(tetradecanoyloxy)propyl-1-O-(ω-methoxy(polyethoxy)ethyl)butanedioate (PEG-S-DMG), a pegylated ceramide (PEG-cer), or a PEG dialkoxypropylcarbamate such as ω-methoxy(polyethoxy)ethyl-N-(2,3-di(tetradecanoxy)propyl)carbamate or 2,3-di(tetradecanoxy)propyl-N-(ω-methoxy(polyethoxy)ethyl) carbamate. In various embodiments, the molar ratio of the cationic lipid to the pegylated lipid ranges from about 100:1 to about 25:1.

In some embodiments, the LNPs comprise a pegylated lipid having the following structure (IV):

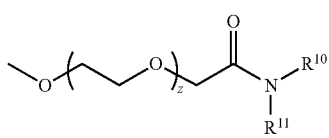

(IV)

or a pharmaceutically acceptable salt, tautomer or stereoisomer thereof, wherein:

R$^{10}$ and R$^{11}$ are each independently a straight or branched, saturated or unsaturated alkyl chain containing from 10 to 30 carbon atoms, wherein the alkyl chain is optionally interrupted by one or more ester bonds; and z has mean value ranging from 30 to 60.

In some of the foregoing embodiments of the pegylated lipid (IV), R$^{10}$ and R$^{11}$ are not both n-octadecyl when z is 42. In some other embodiments, R$^{10}$ and R$^{11}$ are each independently a straight or branched, saturated or unsaturated alkyl chain containing from 10 to 18 carbon atoms. In some embodiments, R$^{10}$ and R$^{11}$ are each independently a straight or branched, saturated or unsaturated alkyl chain containing from 12 to 16 carbon atoms. In some embodiments, R$^{10}$ and R$^{11}$ are each independently a straight or branched, saturated or unsaturated alkyl chain containing 12 carbon atoms. In some embodiments, R$^{10}$ and R$^{11}$ are each independently a straight or branched, saturated or unsaturated alkyl chain containing 14 carbon atoms. In other embodiments, R$^{10}$ and R$^{11}$ are each independently a straight or branched, saturated or unsaturated alkyl chain containing 16 carbon atoms. In still more embodiments, R$^{10}$ and R$^{11}$ are each independently a straight or branched, saturated or unsaturated alkyl chain containing 18 carbon atoms. In still other embodiments, R$^{10}$ is a straight or branched, saturated or unsaturated alkyl chain containing 12 carbon atoms and R$^{11}$ is a straight or branched, saturated or unsaturated alkyl chain containing 14 carbon atoms.

In various embodiments, z spans a range that is selected such that the PEG portion of (II) has an average molecular weight of about 400 to about 6000 g/mol. In some embodiments, the average z is about 45.

In other embodiments, the pegylated lipid has one of the following structures:

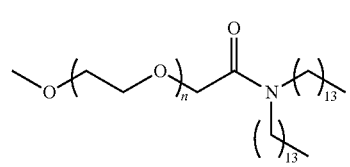

(IVa)

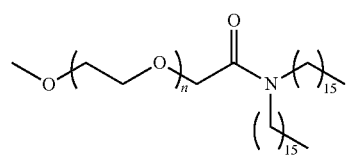

(IVb)

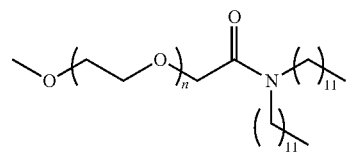

(IVc)

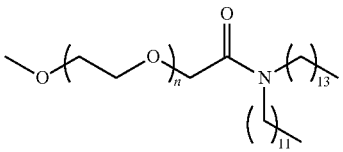

(IVd)

wherein n is an integer selected such that the average molecular weight of the pegylated lipid is about 2500 g/mol.

In certain embodiments, the additional lipid is present in the LNP in an amount from about 1 to about 10 mole percent. In one embodiment, the additional lipid is present in the LNP in an amount from about 1 to about 5 mole percent. In one embodiment, the additional lipid is present in the LNP in about 1 mole percent or about 1.5 mole percent.

In some embodiments, the LNPs comprise a lipid of Formula (I), a nucleoside-modified RNA, a neutral lipid, a steroid and a pegylated lipid. In some embodiments the lipid of Formula (I) is compound 1-6. In different embodiments, the neutral lipid is DSPC. In other embodiments, the steroid is cholesterol. In still different embodiments, the pegylated lipid is compound IVa.

In certain embodiments, the LNP comprises one or more targeting moieties which are capable of targeting the LNP to a cell or cell population. For example, in one embodiment, the targeting moiety is a ligand which directs the LNP to a receptor found on a cell surface.

In certain embodiments, the LNP comprises one or more internalization domains. For example, in one embodiment, the LNP comprises one or more domains which bind to a cell to induce the internalization of the LNP. For example, in one embodiment, the one or more internalization domains bind to a receptor found on a cell surface to induce receptor-mediated uptake of the LNP. In certain embodiments, the LNP is capable of binding a biomolecule in vivo, where the LNP-bound biomolecule can then be recognized by a cell-surface receptor to induce internalization. For example, in one embodiment, the LNP binds systemic ApoE, which leads to the uptake of the LNP and associated cargo.

Other exemplary LNPs and their manufacture are described in the art, for example in U.S. Patent Application Publication No. US20120276209, Semple et al., 2010, Nat Biotechnol., 28(2):172-176; Akinc et al., 2010, Mol Ther., 18(7): 1357-1364; Basha et al., 2011, Mol Ther, 19(12): 2186-2200; Leung et al., 2012, J Phys Chem C Nanomater Interfaces, 116(34): 18440-18450; Lee et al., 2012, Int J Cancer., 131(5): E781-90; Belliveau et al., 2012, Mol Ther nucleic Acids, 1: e37; Jayaraman et al., 2012, Angew Chem Int Ed Engl., 51(34): 8529-8533; Mui et al., 2013, Mol Ther Nucleic Acids. 2, e139; Maier et al., 2013, Mol Ther., 21(8): 1570-1578; and Tam et al., 2013, Nanomedicine, 9(5): 665-74, each of which are incorporated by reference in their entirety.

The following Reaction Schemes illustrate methods to make lipids of Formula (I), (II) or (III).

GENERAL REACTION SCHEME 1

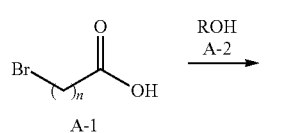

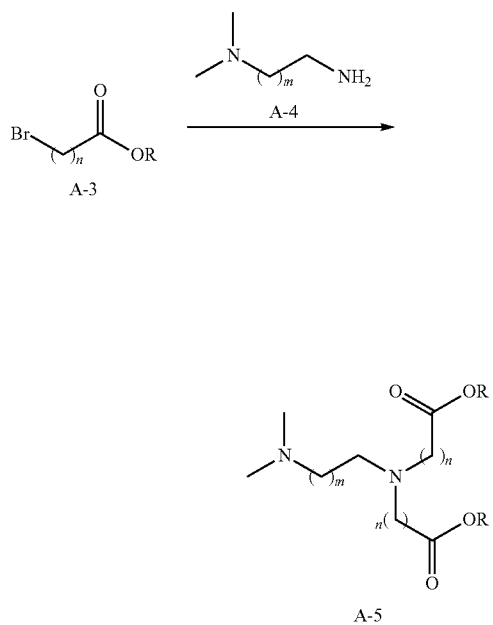

Embodiments of the lipid of Formula (I) (e.g., compound A-5) can be prepared according to General Reaction Scheme 1 ("Method A"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 1, compounds of structure A-1 can be purchased from commercial sources or prepared according to methods familiar to one of ordinary skill in the art. A mixture of A-1, A-2 and DMAP is treated with DCC to give the bromide A-3. A mixture of the bromide A-3, a base (e.g., N,N-diisopropylethylamine) and the N,N-dimethyldiamine A-4 is heated at a temperature and time sufficient to produce A-5 after any necessarily workup and or purification step.

GENERAL REACTION SCHEME 2

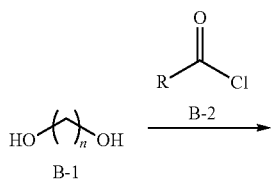

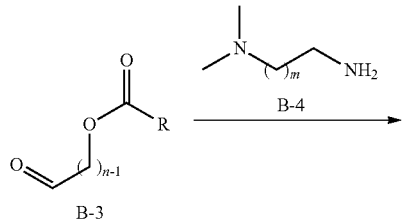

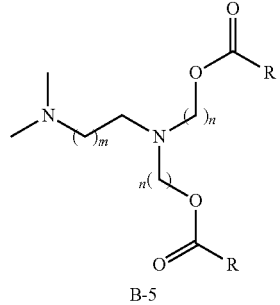

Other embodiments of the compound of Formula (I) (e.g., compound B-5) can be prepared according to General Reaction Scheme 2 ("Method B"), wherein R is a saturated or unsaturated $C_1$-$C_{24}$ alkyl or saturated or unsaturated cycloalkyl, m is 0 or 1 and n is an integer from 1 to 24. As shown in General Reaction Scheme 2, compounds of structure B-1 can be purchased from commercial sources or prepared according to methods familiar to one of ordinary skill in the art. A solution of B-1 (1 equivalent) is treated with acid chloride B-2 (1 equivalent) and a base (e.g., triethylamine). The crude product is treated with an oxidizing agent (e.g., pyridinum chlorochromate) and intermediate product B-3 is recovered. A solution of crude B-3, an acid (e.g., acetic acid), and N,N-dimethylaminoamine B-4 is then treated with a reducing agent (e.g., sodium triacetoxyborohydride) to obtain B-5 after any necessary work up and/or purification.

It should be noted that although starting materials A-1 and B-1 are depicted above as including only saturated methylene carbons, starting materials which include carbon-carbon double bonds may also be employed for preparation of compounds which include carbon-carbon double bonds.

GENERAL REACTION SCHEME 3

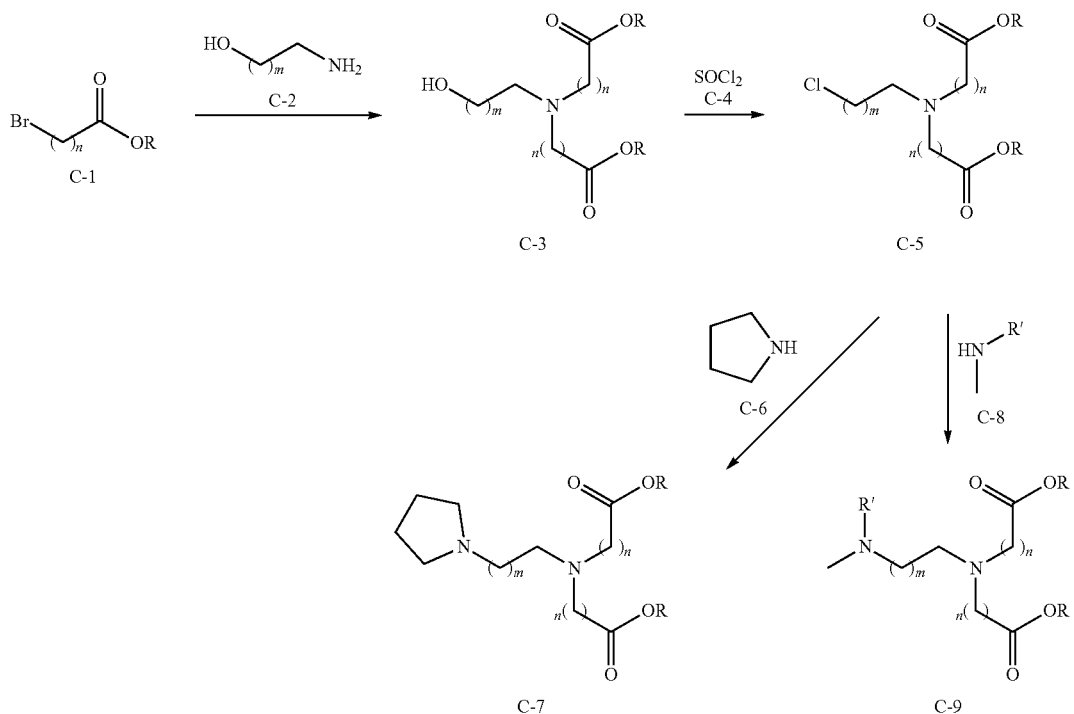

Different embodiments of the lipid of Formula (I) (e.g., compound C-7 or C-9) can be prepared according to General Reaction Scheme 3 ("Method C"), wherein R is a saturated or unsaturated $C_1$-$C_{24}$ alkyl or saturated or unsaturated cycloalkyl, m is 0 or 1 and n is an integer from 1 to 24. Referring to General Reaction Scheme 3, compounds of structure C-1 can be purchased from commercial sources or prepared according to methods familiar to one of ordinary skill in the art.

GENERAL REACTION SCHEME 4

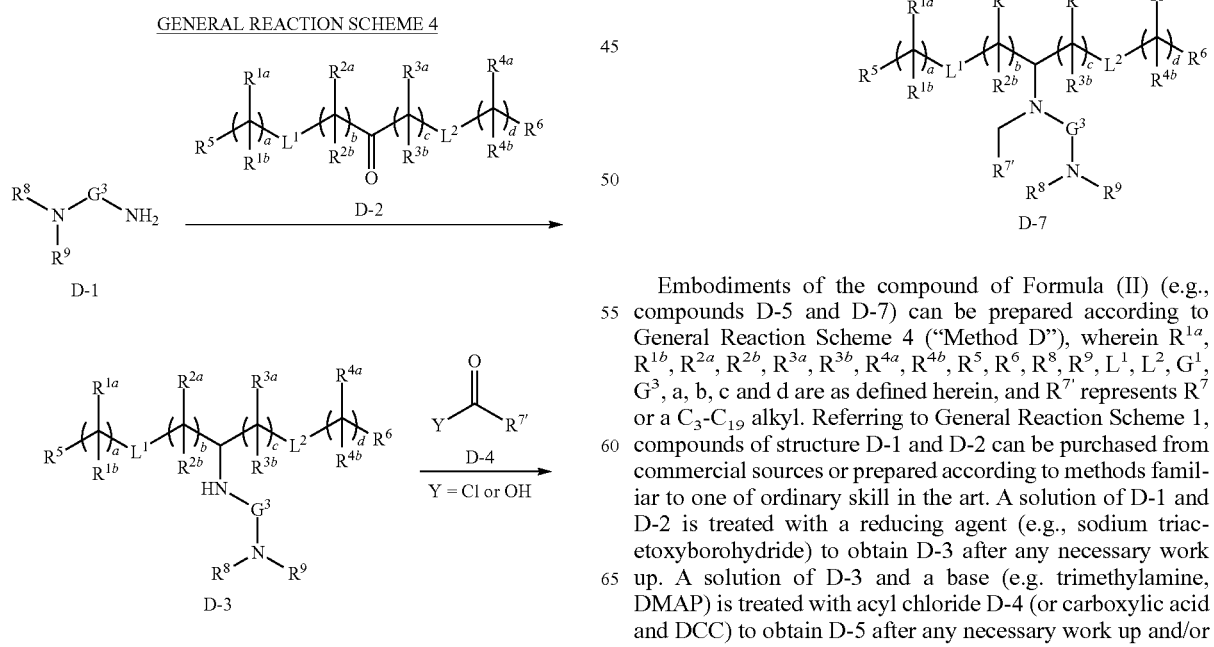

Embodiments of the compound of Formula (II) (e.g., compounds D-5 and D-7) can be prepared according to General Reaction Scheme 4 ("Method D"), wherein $R^{1a}$, $R^{1b}$, $R^{2a}$, $R^{2b}$, $R^{3a}$, $R^{3b}$, $R^{4a}$, $R^{4b}$, $R^5$, $R^6$, $R^8$, $R^9$, $L^1$, $L^2$, $G^1$, $G^3$, a, b, c and d are as defined herein, and $R^{7'}$ represents $R^7$ or a $C_3$-$C_{19}$ alkyl. Referring to General Reaction Scheme 1, compounds of structure D-1 and D-2 can be purchased from commercial sources or prepared according to methods familiar to one of ordinary skill in the art. A solution of D-1 and D-2 is treated with a reducing agent (e.g., sodium triacetoxyborohydride) to obtain D-3 after any necessary work up. A solution of D-3 and a base (e.g. trimethylamine, DMAP) is treated with acyl chloride D-4 (or carboxylic acid and DCC) to obtain D-5 after any necessary work up and/or purification. D-5 can be reduced with LiAlH4 D-6 to give D-7 after any necessary work up and/or purification.

GENERAL REACTION SCHEME 5

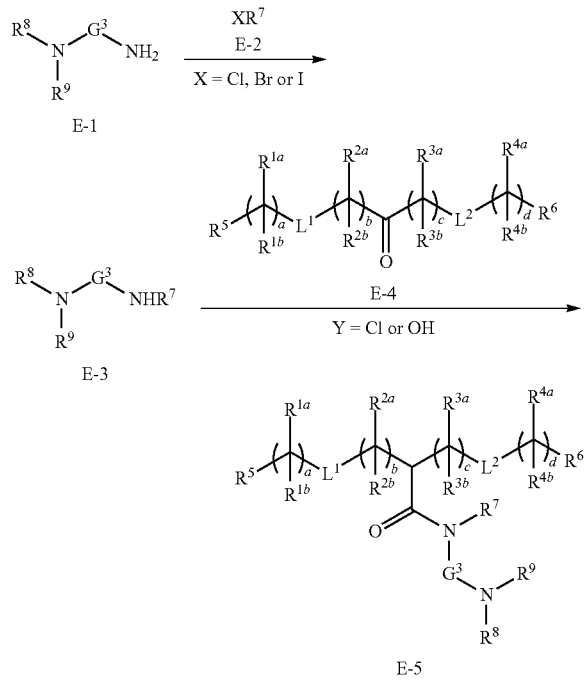

Embodiments of the lipid of Formula (II) (e.g., compound E-5) can be prepared according to General Reaction Scheme 5 ("Method E"), wherein $R^{1a}$, $R^{1b}$, $R^{2a}$, $R^{2b}$, $R^{1a}$, $R^{3b}$, $R^{4a}$, $R^{4b}$, $R^5$, $R^6$, $R^7$, $R^8$, $R^9$, $L^1$, $L^2$, $G^3$, a, b, c and d are as defined herein. Referring to General Reaction Scheme 2, compounds of structure E-1 and E-2 can be purchased from commercial sources or prepared according to methods familiar to one of ordinary skill in the art. A mixture of E-1 (in excess), E-2 and a base (e.g., potassium carbonate) is heated to obtain E-3 after any necessary work up. A solution of E-3 and a base (e.g. trimethylamine, DMAP) is treated with acyl chloride E-4 (or carboxylic acid and DCC) to obtain E-5 after any necessary work up and/or purification.

GENERAL REACTION SCHEME 6

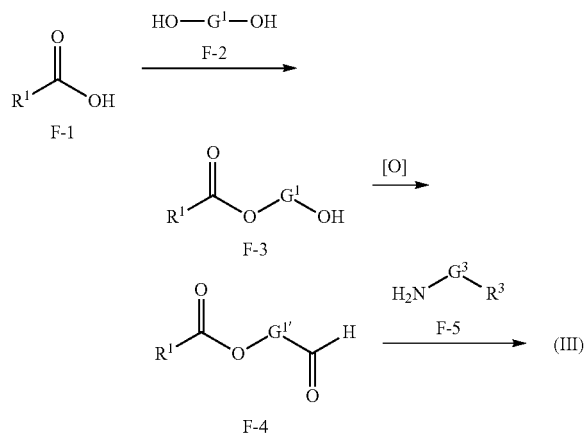

General Reaction Scheme 6 provides an exemplary method (Method F) for preparation of Lipids of Formula (III). $G^1$, $G^3$, $R^1$ and $R^3$ in General Reaction Scheme 6 are as defined herein for Formula (III), and G1' refers to a one-carbon shorter homologue of G1. Compounds of structure F-1 are purchased or prepared according to methods known in the art. Reaction of F-1 with diol F-2 under appropriate condensation conditions (e.g., DCC) yields ester/alcohol F-3, which can then be oxidized (e.g., PCC) to aldehyde F-4. Reaction of F-4 with amine F-5 under reductive amination conditions yields a lipid of Formula (III).

It should be noted that various alternative strategies for preparation of lipids of Formula (III) are available to those of ordinary skill in the art. For example, other lipids of Formula (III) wherein $L^1$ and $L^2$ are other than ester can be prepared according to analogous methods using the appropriate starting material. Further, General Reaction Scheme 6 depicts preparation of a lipids of Formula (III), wherein $G^1$ and $G^2$ are the same; however, this is not a required aspect of the invention and modifications to the above reaction scheme are possible to yield compounds wherein $G^1$ and $G^2$ are different.

It will be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

Antigen

The present invention provides a composition that induces an adaptive immune response in a subject. In one embodiment, the composition comprises an antigen. In one embodiment, the composition comprises a nucleic acid sequence which encodes an antigen. For example, in certain embodiments, the composition comprises a nucleoside-modified RNA encoding an antigen. The antigen may be any molecule or compound, including but not limited to a polypeptide, peptide or protein that induces an adaptive immune response in a subject.

In one embodiment, the antigen comprises a polypeptide or peptide associated with a pathogen, such that the antigen induces an adaptive immune response against the antigen, and therefore the pathogen. In one embodiment, the antigen comprises a fragment of a polypeptide or peptide associated with a pathogen, such that the antigen induces an adaptive immune response against the pathogen.

In certain embodiments, the antigen comprises an amino acid sequence that is substantially homologous to the amino acid sequence of an antigen described herein and retains the immunogenic function of the original amino acid sequence. For example, in certain embodiments, the amino acid sequence of the antigen has a degree of identity with respect to the original amino acid sequence of at least 60%, advantageously of at least 70%, preferably of at least 85%, and more preferably of at least 95%.

In one embodiment, the antigen is encoded by a nucleic acid sequence of a nucleic acid molecule. In certain embodiments, the nucleic acid sequence comprises DNA, RNA, cDNA, a variant thereof, a fragment thereof, or a combination thereof. In one embodiment, the nucleic acid sequence comprises a modified nucleic acid sequence. For example, in one embodiment the antigen-encoding nucleic acid sequence comprises nucleoside-modified RNA, as described in detail elsewhere herein. In certain instances, the nucleic acid sequence comprises include additional sequences that encode linker or tag sequences that are linked to the antigen by a peptide bond.

In certain embodiments, the antigen, encoded by the nucleoside-modified nucleic acid molecule, comprises a protein, peptide, a fragment thereof, or a variant thereof, or a combination thereof from any number of organisms, for example, a virus, a parasite, a bacterium, a fungus, or a mammal. For example, in certain embodiments, the antigen is associated with an autoimmune disease, allergy, or asthma. In other embodiments, the antigen is associated with cancer, herpes, influenza, hepatitis B, hepatitis C, human papilloma virus (HPV), ebola, pneumococcus, *Haemophilus influenza*, meningococcus, dengue, tuberculosis, malaria, norovirus or human immunodeficiency virus (HIV). In certain embodiments, the antigen comprises a consensus sequence based on the amino acid sequence of two or more different organisms. In certain embodiments, the nucleic acid sequence encoding the antigen is optimized for effective translation in the organism in which the composition is delivered.

In one embodiment, the antigen comprises a tumor-specific antigen or tumor-associated antigen, such that the antigen induces an adaptive immune response against the tumor. In one embodiment, the antigen comprises a fragment of a tumor-specific antigen or tumor-associated antigen, such that the antigen induces an adaptive immune response against the tumor. In certain embodiment, the tumor-specific antigen or tumor-associated antigen is a mutation variant of a host protein.

Viral Antigens

In one embodiment, the antigen comprises a viral antigen, or fragment thereof, or variant thereof. In certain embodiments, the viral antigen is from a virus from one of the following families: Adenoviridae, Arenaviridae, Bunyaviridae, Caliciviridae, Coronaviridae, Filoviridae, Hepadnaviridae, Herpesviridae, Orthomyxoviridae, Papovaviridae, Paramyxoviridae, Parvoviridae, Picornaviridae, Poxviridae, Reoviridae, Retroviridae, Rhabdoviridae, or Togaviridae. In certain embodiments, the viral antigen is from papilloma viruses, for example, human papillomoa virus (HPV), human immunodeficiency virus (HIV), polio virus, hepatitis B virus, hepatitis C virus, smallpox virus (Variola major and minor), vaccinia virus, influenza virus, rhinoviruses, dengue fever virus, equine encephalitis viruses, rubella virus, yellow fever virus, Norwalk virus, hepatitis A virus, human T-cell leukemia virus (HTLV-I), hairy cell leukemia virus (HTLV-II), California encephalitis virus, Hanta virus (hemorrhagic fever), rabies virus, Ebola fever virus, Marburg virus, measles virus, mumps virus, respiratory syncytial virus (RSV), herpes simplex 1 (oral herpes), herpes simplex 2 (genital herpes), herpes zoster (varicella-zoster, a.k.a., chickenpox), cytomegalovirus (CMV), for example human CMV, Epstein-Barr virus (EBV), flavivirus, foot and mouth disease virus, chikungunya virus, lassa virus, arenavirus, or cancer causing virus.

Hepatitis Antigen

In one embodiment, the antigen comprises a hepatitis virus antigen (i.e., hepatitis antigen), or fragment thereof, or variant thereof. In certain embodiments, the hepatitis antigen comprises an antigen or immunogen from hepatitis A virus (HAV), hepatitis B virus (HBV), hepatitis C virus (HCV), hepatitis D virus (HDV), and/or hepatitis E virus (HEV). In certain embodiments, the hepatitis antigen is full-length or immunogenic fragments of full-length proteins.

In one embodiment, the hepatitis antigen comprises an antigen from HAV. For example, in certain embodiments, the hepatitis antigen comprises a HAV capsid protein, a HAV non-structural protein, a fragment thereof, a variant thereof, or a combination thereof.

In one embodiment, the hepatitis antigen comprises an antigen from HCV. For example, in certain embodiments, the hepatitis antigen comprises a HCV nucleocapsid protein (i.e., core protein), a HCV envelope protein (e.g., E1 and E2), a HCV non-structural protein (e.g., NS1, NS2, NS3, NS4a, NS4b, NS5a, and NS5b), a fragment thereof, a variant thereof, or a combination thereof.

In one embodiment, the hepatitis antigen comprises an antigen from HDV. For example, in certain embodiments, the hepatitis antigen comprises a HDV delta antigen, fragment thereof, or variant thereof.

In one embodiment, the hepatitis antigen comprises an antigen from HEV. For example, in certain embodiments, the hepatitis antigen comprises a HEV capsid protein, fragment thereof, or variant thereof.

In one embodiment, the hepatitis antigen comprises an antigen from HBV. For example, in certain embodiments, the hepatitis antigen comprises a HBV core protein, a HBV surface protein, a HBV DNA polymerase, a HBV protein encoded by gene X, fragment thereof, variant thereof, or combination thereof. In certain embodiments, the hepatitis antigen comprises a HBV genotype A core protein, a HBV genotype B core protein, a HBV genotype C core protein, a HBV genotype D core protein, a HBV genotype E core protein, a HBV genotype F core protein, a HBV genotype G core protein, a HBV genotype H core protein, a HBV genotype A surface protein, a HBV genotype B surface protein, a HBV genotype C surface protein, a HBV genotype D surface protein, a HBV genotype E surface protein, a HBV genotype F surface protein, a HBV genotype G surface protein, a HBV genotype H surface protein, fragment thereof, variant thereof, or combination thereof.

Human Papilloma Virus (HPV) Antigen

In one embodiment, the antigen comprises a human papilloma virus (HPV) antigen, or fragment thereof, or variant thereof. For example, in certain embodiments, the antigen comprises an antigen from HPV types 16, 18, 31, 33, 35, 45, 52, and 58, which cause cervical cancer, rectal cancer, and/or other cancers. In one embodiment, the antigen comprises an antigen from HPV types 6 and 11, which cause genital warts, and are known to be causes of head and neck cancer. For example, in certain embodiments, the HPV antigen comprises a HPV E6 or E7 domain, or fragments, or variant thereof from any HPV type.

RSV Antigen

In one embodiment, the antigen comprises an RSV antigen or fragment thereof, or variant thereof. For example, in certain embodiments, the RSV antigen comprises a human RSV fusion protein (also referred to herein as "RSV F", "RSV F protein" and "F protein"), or fragment or variant thereof. In one embodiment, the human RSV fusion protein is conserved between RSV subtypes A and B. In certain embodiments, the RSV antigen comprises a RSV F protein, or fragment or variant thereof, from the RSV Long strain (GenBank AAX23994.1). In one embodiment, the RSV antigen comprises a RSV F protein from the RSV A2 strain (GenBank AAB59858.1), or a fragment or variant thereof. In certain embodiments, the RSV antigen is a monomer, a dimer or trimer of the RSV F protein, or a fragment or variant thereof. According to the invention, in certain embodiments, the RSV F protein is in a prefusion form or a postfusion form.

In one embodiment, the RSV antigen comprises a human RSV attachment glycoprotein (also referred to herein as "RSV G", "RSV G protein" and "G protein"), or fragment or variant thereof. The human RSV G protein differs between RSV subtypes A and B. In one embodiment, the antigen comprises a RSV G protein, or fragment or variant thereof, from the RSV Long strain (GenBank AAX23993). In one embodiment, the RSV antigen comprises RSV G protein from: the RSV subtype B isolate H5601, the RSV subtype B isolate H1068, the RSV subtype B isolate H5598, the RSV subtype B isolate H1123, or a fragment or variant thereof.

In other embodiments, the RSV antigen comprises a human RSV non-structural protein 1 ("NS1 protein"), or fragment or variant thereof. For example, in one embodiment, the RSV antigen comprises RSV NS1 protein, or fragment or variant thereof, from the RSV Long strain (GenBank AAX23987.1). In one embodiment, the RSV antigen comprises RSV non-structural protein 2 ("NS2 protein"), or fragment or variant thereof. For example, in one embodiment, the RSV antigen comprises RSV NS2 protein, or fragment or variant thereof, from the RSV Long strain (GenBank AAX23988.1). In one embodiment, the RSV antigen comprises human RSV nucleocapsid ("N") protein, or fragment or variant thereof. For example, in one embodiment, the RSV antigen is RSV N protein, or fragment or variant thereof, from the RSV Long strain (GenBank AAX23989.1). In one embodiment, the RSV antigen comprises human RSV Phosphoprotein ("P") protein, or fragment or variant thereof. For example, in one embodiment, the RSV antigen comprises RSV P protein, or fragment or variant thereof, from the RSV Long strain (GenBank AAX23990.1). In one embodiment, the RSV antigen comprises human RSV Matrix protein ("M") protein, or fragment or variant thereof. For example, in one embodiment, the RSV antigen comprises RSV M protein, or fragment or variant thereof, from the RSV Long strain (GenBank AAX23991.1).

In still other embodiments, the RSV antigen comprises human RSV small hydrophobic ("SH") protein, or fragment or variant thereof. For example, in one embodiment, the RSV antigen comprises RSV SH protein, or fragment or variant thereof, from the RSV Long strain (GenBank AAX23992.1). In one embodiment, the RSV antigen comprises human RSV Matrix protein2-1 ("M2-1") protein, or fragment or variant thereof. For example, in one embodiment, the RSV antigen comprises RSV M2-1 protein, or fragment or variant thereof, from the RSV Long strain (GenBank AAX23995.1). In one embodiment, the RSV antigen comprises RSV Matrix protein 2-2 ("M2-2") protein, or fragment or variant thereof. For example, in one embodiment, the RSV antigen comprises RSV M2-2 protein, or fragment or variant thereof, from the RSV Long strain (GenBank AAX23997.1). In one embodiment, the RSV antigen comprises RSV Polymerase L ("L") protein, or fragment or variant thereof. For example, in one embodiment, the RSV antigen comprises RSV L protein, or fragment or variant thereof, from the RSV Long strain (GenBank AAX23996.1).

Influenza Antigen

In one embodiment, the antigen comprises an influenza antigen or fragment thereof, or variant thereof. The influenza antigens are those capable of eliciting an adaptive immune response in a mammal against one or more influenza serotypes. In certain embodiments, the antigen comprises the full length translation product Hemagglutinin (HA)0, subunit HA1 subunit HA2, a variant thereof, a fragment thereof or a combination thereof. In certain embodiments, the influenza hemagglutinin antigen is derived from one or more strains of influenza A serotype H1, influenza A serotype H2, or influenza B.

In one embodiment, the influenza antigen contains at least one antigenic epitope that can be effective against particular influenza immunogens against which an immune response can be induced. In certain embodiments, the antigen may provide an entire repertoire of immunogenic sites and epitopes present in an intact influenza virus.

In some embodiments, the influenza antigen comprises H1 HA, H2 HA, H3 HA, H5 HA, or a BHA antigen. In certain embodiments, the influenza antigen comprises neuraminidase (NA), matrix protein, nucleoprotein, M2 ectodomain-nucleo-protein (M2e-NP), a variant thereof, a fragment thereof, or combinations thereof.

Human Immunodeficiency Virus (HIV) Antigen

In one embodiment, the antigen comprises an HIV antigen or fragment thereof, or variant thereof.

In certain embodiments, the HIV antigen comprises an envelope (Env) protein or fragment or variant thereof. For example, in certain embodiments, the HIV antigen comprises an Env protein selected from gp120, gp41, or a combination thereof.

In certain embodiments, the HIV antigen comprises at least one of nef, gag, pol, vif, vpr, vpu, tat, rev, or a fragment of variant thereof.

The HIV antigen may be derived from any strain of HIV. For example, in certain embodiments the HIV antigen comprises an antigen from HIV groups M, N, O, and P, and subtype A, HIV subtype B, HIV subtype C, HIV subtype D, subtype E, subtype F, subtype G, subtype H, subtype J, or subtype K. In one embodiment, the HIV antigen comprises Env or fragment or variant thereof, from the HIV-R3A strain (R3A-Env).

Parasite Antigens

In certain embodiments, the antigen comprises a parasite antigen or fragment or variant thereof. In certain embodiments, the parasite is a protozoa, helminth, or ectoparasite. In certain embodiments, the helminth (i.e., worm) is a flatworm (e.g., flukes and tapeworms), a thorny-headed worm, or a round worm (e.g., pinworms). In certain embodiments, the ectoparasite is lice, fleas, ticks, and mites.

In certain embodiments, the parasite is any parasite causing the following diseases: *Acanthamoeba keratitis*, Amoebiasis, Ascariasis, Babesiosis, Balantidiasis, Baylisascariasis, Chagas disease, Clonorchiasis, *Cochliomyia*, Cryptosporidiosis, Diphyllobothriasis, Dracunculiasis, Echinococcosis, Elephantiasis, Enterobiasis, Fascioliasis, Fasciolopsiasis, Filariasis, Giardiasis, Gnathostomiasis, Hymenolepiasis, Isosporiasis, Katayama fever, Leishmaniasis, Lyme disease, Malaria, Metagonimiasis, Myiasis, Onchocerciasis, Pediculosis, Scabies, Schistosomiasis, Sleeping sickness, Strongyloidiasis, Taeniasis, Toxocariasis, Toxoplasmosis, Trichinosis, and Trichuriasis.

In certain embodiments, the parasite is *Acanthamoeba, Anisakis, Ascaris lumbricoides*, Botfly, *Balantidium coli*, Bedbug, Cestoda (tapeworm), Chiggers, *Cochliomyia hominivorax, Entamoeba histolytica, Fasciola hepatica, Giardia lamblia*, Hookworm, *Leishmania, Linguatula serrata*, Liver fluke, *Loa loa, Paragonimus*—lung fluke, Pinworm, *Plasmodium falciparum, Schistosoma, Strongyloides stercoralis*, Mite, Tapeworm, *Toxoplasma gondii, Trypanosoma*, Whipworm, or *Wuchereria bancrofti*.

Malaria Antigen

In one embodiment, the antigen comprises a malaria antigen (i.e., PF antigen or PF immunogen), or fragment thereof, or variant thereof. For example, in one embodiment, the antigen comprises an antigen from a parasite causing malaria. In one embodiment, the malaria causing parasite is *Plasmodium falciparum*.

In some embodiments, the malaria antigen comprises one or more of *P. falciparum* immunogens CS; LSA1; TRAP; CelTOS; and Ama1. The immunogens may be full length or immunogenic fragments of full length proteins.

Bacterial Antigens

In one embodiment, the antigen comprises a bacterial antigen or fragment or variant thereof. In certain embodiments, the bacterium is from any one of the following phyla: Acidobacteria, Actinobacteria, Aquificae, Bacteroidetes, Caldiserica, Chlamydiae, Chlorobi, Chloroflexi, Chrysiogenetes, Cyanobacteria, Deferribacteres, *Deinococcus-Thermus*, Dictyoglomi, Elusimicrobia, Fibrobacteres, Firmicutes, Fusobacteria, Gemmatimonadetes, Lentisphaerae, Nitrospira, Planctomycetes, Proteobacteria, Spirochaetes, Synergistetes, Tenericutes, Thermodesulfobacteria, Thermotogae, and Verrucomicrobia.

In certain embodiments, the bacterium is a gram positive bacterium or a gram negative bacterium. In certain embodiments, the bacterium is an aerobic bacterium or an anaerobic bacterium. In certain embodiments, the bacterium is an autotrophic bacterium or a heterotrophic bacterium. In certain embodiments, the bacterium is a mesophile, a neutrophile, an extremophile, an acidophile, an alkaliphile, a thermophile, psychrophile, *halophile*, or an osmophile.

In certain embodiments, the bacterium is an anthrax bacterium, an antibiotic resistant bacterium, a disease causing bacterium, a food poisoning bacterium, an infectious bacterium, *Salmonella* bacterium, *Staphylococcus* bacterium, *Streptococcus* bacterium, or tetanus bacterium. In certain embodiments, bacterium is a mycobacteria, *Clostridium tetani, Yersinia pestis, Bacillus* anthracia, methicillin-resistant *Staphylococcus aureus* (MRSA), or *Clostridium difficile*.

*Mycobacterium tuberculosis* Antigens

In one embodiment, the antigen comprises a *Mycobacterium tuberculosis* antigen (i.e., TB antigen or TB immunogen), or fragment thereof, or variant thereof. The TB antigen can be from the Ag85 family of TB antigens, for example, Ag85A and Ag85B. The TB antigen can be from the Esx family of TB antigens, for example, EsxA, EsxB, EsxC, EsxD, EsxE, EsxF, EsxH, EsxO, EsxQ, EsxR, EsxS, EsxT, EsxU, EsxV, and EsxW.

Fungal Antigens

In one embodiment, the antigen comprises a fungal antigen or fragment or variant thereof. In certain embodiments, the fungus is *Aspergillus* species, *Blastomyces dermatitidis, Candida* yeasts (e.g., *Candida albicans*), *Coccidioides, Cryptococcus neoformans, Cryptococcus gattii*, dermatophyte, *Fusarium* species, *Histoplasma capsulatum*, Mucoromycotina, *Pneumocystis jirovecii, Sporothrix schenckii, Exserohilum*, or *Cladosporium*.

Tumor Antigens

In certain embodiments, the antigen comprises a tumor antigen, including for example a tumor-associated antigen or a tumor-specific antigen. In the context of the present invention, "tumor antigen" or "hyperporoliferative disorder antigen" or "antigen associated with a hyperproliferative disorder" refer to antigens that are common to specific hyperproliferative disorders. In certain aspects, the hyperproliferative disorder antigens of the present invention are derived from cancers including, but not limited to, primary or metastatic melanoma, mesothelioma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

Tumor antigens are proteins that are produced by tumor cells that elicit an immune response, particularly T-cell mediated immune responses. In one embodiment, the tumor antigen of the present invention comprises one or more antigenic cancer epitopes immunogenically recognized by tumor infiltrating lymphocytes (TIL) derived from a cancer tumor of a mammal. The selection of the antigen will depend on the particular type of cancer to be treated or prevented by way of the composition of the invention.

Tumor antigens are well known in the art and include, for example, a glioma-associated antigen, carcinoembryonic antigen (CEA), (3-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor and mesothelin.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/ MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen includes but is not limited to CD19, CD20, CD22, ROR1, Mesothelin, CD33/ IL3Ra, c-Met, PSMA, Glycolipid F77, EGFRvIII, GD-2, MY-ESO-1 TCR, MAGE A3 TCR, and the like.

Adjuvant

In one embodiment, the composition comprises an adjuvant. In one embodiment, the composition comprises a nucleic acid molecule encoding an adjuvant. In one embodiment, the adjuvant-encoding nucleic acid molecule is IVT RNA. In one embodiment, the adjuvant-encoding nucleic acid molecule is nucleoside-modified RNA. Exemplary adjuvants include, but is not limited to, alpha-interferon, gamma-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15, MHC, CD80, CD86 including IL-15 having the signal sequence deleted and optionally including the signal peptide from IgE. Other genes which may be useful adjuvants include those encoding: MCP-I, MIP-Ia, MIP-Ip, IL-8, RANTES, L-selectin, P-selectin, E-selectin, CD34, GlyCAM-1, MadCAM-1, LFA-I, VLA-I, Mac-1, p150.95, PECAM, ICAM-I, ICAM-2, ICAM-3, CD2, LFA-3, M-CSF, G-CSF, IL-4, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-I, DR3, TRAMP, Apo-3, AIR, LARD, NGRF, DR4, DR5, KILLER, TRAIL-R2, TRICK2, DR6, Caspase ICE, Fos, c-jun, Sp-I, Ap-I, Ap-2, p38, p65Rel, MyD88, IRAK, TRAF6, IkB, Inactive NIK, SAP K, SAP-I, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP 1, TAP2, anti-CTLA4-sc, anti-LAG3-Ig, anti-TIM3-Ig and functional fragments thereof.

Pharmaceutical Compositions

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desired single- or multi-dose unit.

Although the description of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, mammals including commercially relevant mammals such as non-human primates, cattle, pigs, horses, sheep, cats, and dogs.

Pharmaceutical compositions that are useful in the methods of the invention may be prepared, packaged, or sold in formulations suitable for ophthalmic, oral, rectal, vaginal, parenteral, topical, pulmonary, intranasal, buccal, intravenous, intracerebroventricular, intradermal, intramuscular, or another route of administration. Other contemplated formulations include projected nanoparticles, liposomal preparations, resealed erythrocytes containing the active ingredient, and immunogenic-based formulations.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

The relative amounts of the active ingredient, the pharmaceutically acceptable carrier, and any additional ingredients in a pharmaceutical composition of the invention will vary, depending upon the identity, size, and condition of the subject treated and further depending upon the route by which the composition is to be administered. By way of example, the composition may comprise between 0.1% and 100% (w/w) active ingredient.

In addition to the active ingredient, a pharmaceutical composition of the invention may further comprise one or more additional pharmaceutically active agents.

Controlled- or sustained-release formulations of a pharmaceutical composition of the invention may be made using conventional technology.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, intraocular, intravitreal, subcutaneous, intraperitoneal, intramuscular, intradermal, intrasternal injection, intratumoral, intravenous, intracerebroventricular and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations that are useful include those that comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Remington's Pharmaceutical Sciences (1985, Genaro, ed., Mack Publishing Co., Easton, PA), which is incorporated herein by reference.

Treatment Methods

The present invention provides methods of inducing an adaptive immune response in a subject comprising administering an effective amount of a composition comprising one or more isolated nucleic acids encoding one or more antigens, one or more adjuvants, or a combination thereof.

In one embodiment, the method provides immunity in the subject to an infection, disease, or disorder associated with an antigen. The present invention thus provides a method of treating or preventing the infection, disease, or disorder associated with the antigen. For example, the method may be used to treat or prevent a viral infection, bacterial infection, fungal infection, parasitic infection, or cancer, depending upon the type of antigen of the administered composition. Exemplary antigens and associated infections, diseases, and tumors are described elsewhere herein.

In one embodiment, the composition is administered to a subject having an infection, disease, or cancer associated with the antigen. In one embodiment, the composition is administered to a subject at risk for developing the infection, disease, or cancer associated with the antigen. For example, the composition may be administered to a subject who is at risk for being in contact with a virus, bacteria, fungus, parasite, or the like. In one embodiment, the composition is administered to a subject who has increased likelihood, though genetic factors, environmental factors, or the like, of developing cancer.

In one embodiment, the method comprises administering a composition comprising one or more nucleoside-modified nucleic acid molecules encoding one or more antigens and one or more adjuvant. In one embodiment, the method comprises administering a composition comprising a first nucleoside-modified nucleic acid molecule encoding one or more antigens and a second nucleoside-modified nucleic acid molecule encoding one or more adjuvants. In one embodiment, the method comprises administering a first composition comprising one or more nucleoside-modified nucleic acid molecules encoding one or more antigens and administering a second composition comprising one or more nucleoside-modified nucleic acid molecules encoding one or more adjuvants.

In certain embodiments, the method comprises administering to subject a plurality of nucleoside-modified nucleic acid molecules encoding a plurality of antigens, adjuvants, or a combination thereof.

In certain embodiments, the method of the invention allows for sustained expression of the antigen or adjuvant, described herein, for at least several days following administration. However, the method, in certain embodiments, also provides for transient expression, as in certain embodiments, the nucleic acid is not integrated into the subject genome.

In certain embodiments, the method comprises administering nucleoside-modified RNA which provides stable expression of the antigen or adjuvant described herein. In some embodiments, administration of nucleoside-modified RNA results in little to no innate immune response, while inducing an effective adaptive immune response.

Administration of the compositions of the invention in a method of treatment can be achieved in a number of different ways, using methods known in the art. In one embodiment, the method of the invention comprises systemic administration of the subject, including for example enteral or parenteral administration. In certain embodiments, the method comprises intradermal delivery of the composition. In another embodiment, the method comprises intravenous delivery of the composition. In some embodiments, the method comprises intramuscular delivery of the composition. In one embodiment, the method comprises subcutaneous delivery of the composition. In one embodiment, the method comprises inhalation of the composition. In one embodiment, the method comprises intranasal delivery of the composition.

It will be appreciated that the composition of the invention may be administered to a subject either alone, or in conjunction with another agent.

The therapeutic and prophylactic methods of the invention thus encompass the use of pharmaceutical compositions encoding an antigen, adjuvant, or a combination thereof, described herein to practice the methods of the invention. The pharmaceutical compositions useful for practicing the invention may be administered to deliver a dose of from ng/kg/day and 100 mg/kg/day. In one embodiment, the invention envisions administration of a dose which results in a concentration of the compound of the present invention from 10 nM and 10 µM in a mammal.

Typically, dosages which may be administered in a method of the invention to a mammal, preferably a human, range in amount from 0.01 µg to about 50 mg per kilogram of body weight of the mammal, while the precise dosage administered will vary depending upon any number of factors, including but not limited to, the type of mammal and type of disease state being treated, the age of the mammal and the route of administration. Preferably, the dosage of the compound will vary from about 0.1 µg to about 10 mg per kilogram of body weight of the mammal. More preferably, the dosage will vary from about 1 µg to about 1 mg per kilogram of body weight of the mammal.

The composition may be administered to a mammal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the mammal, etc.

In certain embodiments, administration of an immunogenic composition or vaccine of the present invention may be performed by single administration or boosted by multiple administrations.

In one embodiment, the invention includes a method comprising administering one or more compositions encoding one or more antigens or adjuvants described herein. In certain embodiments, the method has an additive effect, wherein the overall effect of the administering the combination is approximately equal to the sum of the effects of administering each antigen or adjuvant. In other embodiments, the method has a synergistic effect, wherein the overall effect of administering the combination is greater than the sum of the effects of administering each antigen or adjuvant.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the present invention and practice the claimed methods. The following working examples therefore, specifically point out the preferred embodiments of the present invention, and are not to be construed as limiting in any way the remainder of the disclosure.

Figure 18:
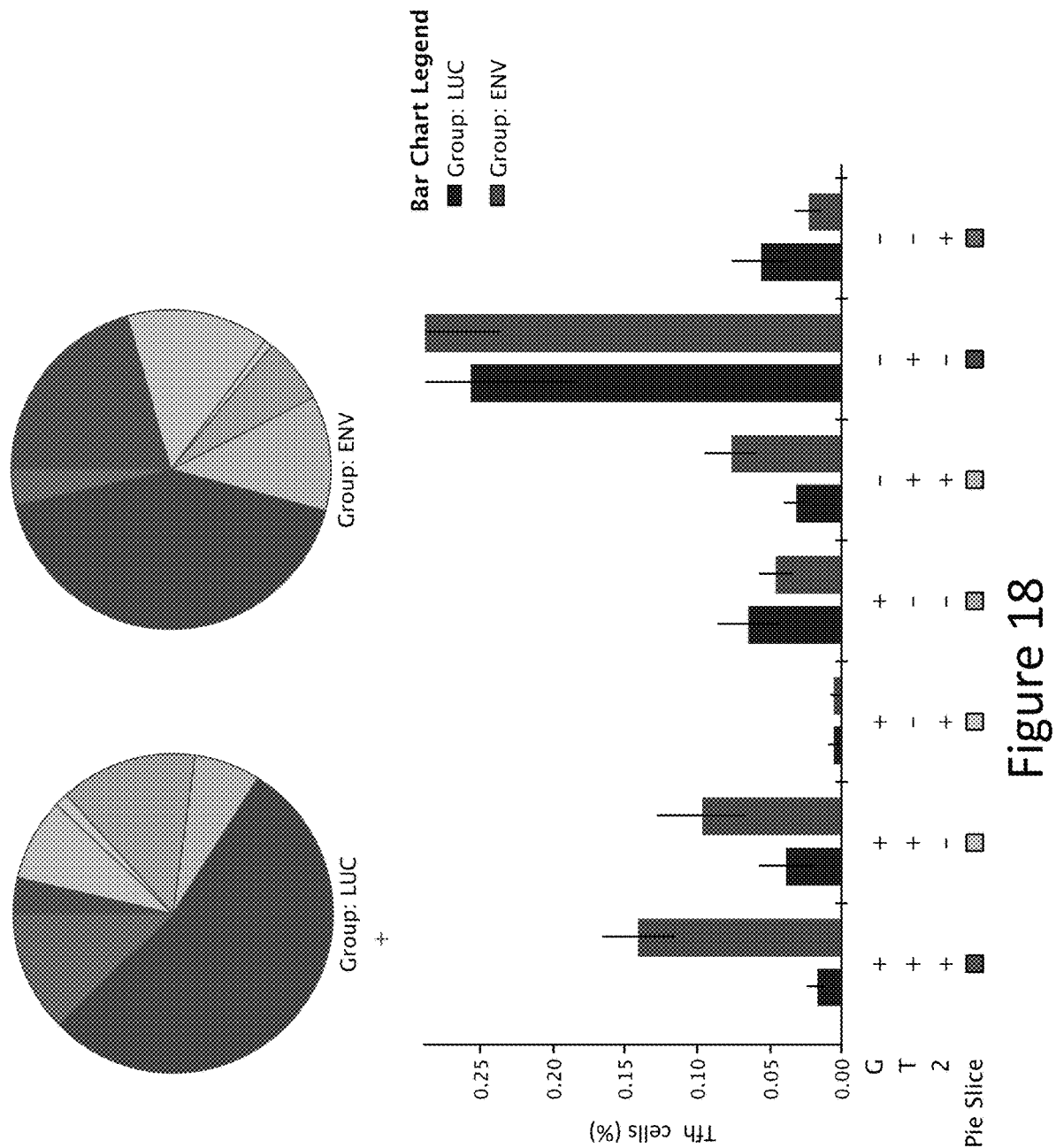
FIG. 18 is a set of graphs illustrating that a single injection with 30 ENV-LNPs elicit robust polyfunctional Tfh cell immune responses. The graphs depict the distribution of mono-, bi,- and trifunctional antigen specific Tfh cells in vaccinated animals. Pie charts show the distribution of antigen specific Tfh cells producing one, two or three cytokines. Tfh cells were identified by expression of nuclear Bcl6. The bar graph shows the frequency of antigen specific Tfh cells producing one, two or three cytokines. ENV=30 μg of iR3A envelope encoding mRNA injected ID. Luc=30 μg of control luciferase encoding mRNA injected ID. All intracellular cytokine measurements were performed using multicolor flow cytometry after stimulation with peptide pools of 15-mers overlapping by 11 amino acids of the complete envelope sequence. Standard error of the mean is indicated on bars. G=INF-γ, T=TNF-α, 2=IL-2.

Example 1: Induction of Adaptive Immune Response by Modified RNA Encoding HIV Env Protein Experiments were conducted to investigate the ability of modified RNA encoding HIV Env protein to induce adaptive immunity in a mouse model. In a first set of experiments animals received two intradermal injections of 30, 10 μg (E10) or 30 μg (E30) HIV-1 CD4-independent R3A envelope encoding mRNA encapsulated into lipid nanoparticles (ENV-LNP). The lipid nanoparticles of Examples 1~4 comprised mRNA, cationic lipid (compound 1-6), DSPC, cholesterol and pegylated lipid (compound 14-6), and were prepared according to Example 15. The lipid nanoparticles of Example 5 comprised mRNA, the indicated cationic lipid, DSPC, cholesterol and pegylated lipid (compound 14-6), and were also prepared according to Example 15. The resulting ENV-LNP had a mean diameter of 76 nm and polydispersity index of 0.007. Encapsulation efficiency was determined to be 95% using Quant-IT Ribogreen (Thermo-Fisher) to assay free mRNA in an LNP sample vs. total mRNA in a corresponding sample containing 2% v/v Triton TX100 surfactant to disrupt the LNPs and expose the total mRNA. Control mice were injected with 30 μg firefly luciferase encoding mRNA complexed into lipid nanoparticles (LUC). These control LNPs had a mean diameter of 74 nm with polydispersity index of 0.007 and encapsulation efficiency of 92%. There was a 4-week interval between mRNA-LNP injections and animals were sacrificed 14 days after the second injection (FIG. 1). Cells and serum were analyzed from the immunized animals.

Multicolor flow cytometry was used to measure intracellular cytokine production in cells after stimulation with peptide pools of 15-mers overlapping by 11 amino acids of the complete envelope sequence.

It was observed that the immunization with ENV-LNPs induces IFN-γ, TNF-α, and IL-2 production (FIG. 2 and FIG. 3) by antigen specific CD4+ T cells. Further analysis was conducted to evaluate the distribution of mono,- bi,- and trifunctional antigen specific CD4+ T cells in vaccinated animals. It was observed that Env-treated animals produced a higher percentage of CD4+ cells producing all three of IFN-γ, TNF-α, IL-2; both IFN-γ and TNF-α; and both TNF-α and IL-2 (FIG. 4). Collectively, this data demonstrates that immunization with ENV-LNPs elicit robust and high quality CD4+ T cell responses.

It was also observed that immunization with ENV-LNP results in significant increase in T follicular helper (Tfh) cell numbers that are critical for the generation of high affinity antibody responses. CD4, CXCR5 and PD-1 markers were used to determine Tfh cells (FIG. 5). The same ratios of $T_{fh}$ cells are obtained for CXCR5+ICOS+CD4+ and PD-1+ ICOS+CD4+ T cells.

Cytokine production of antigen specific CD8+ T cells was also examined. It was observed that the immunization with ENV-LNPs induces IFN-γ, TNF-α, IL-2 and CD107a production (FIG. 6 and FIG. 7) by antigen specific CD8+ T cells. Further analysis was conducted to evaluate the distribution of mono,- bi,- and trifunctional antigen specific CD8+ T cells in vaccinated animals. It was observed that E10 treated animals produced a higher percentage of CD8+ cells producing all three of IFN-γ, TNF-α, and CD107a; both IFN-γ and CD107a; both TNF-α and CD107a, and CD107a alone (FIG. 8). Further, E30 treated animals produced a higher percentage of CD8+ cells producing all three of IFN-γ, TNF-α, and CD107a. Collectively, this data demonstrates that immunization with ENV-LNPs elicits robust CD8+ T cell responses.

ELISA assays were performed to investigate antigen specific B cell responses to the HIV envelope immunogen in mice immunized with 3 μg, 10 μg, or 30 μg of HIV-1 CD4-independent R3A envelope encoding mRNA encapsulated into lipid nanoparticles. Specifically, HIV-1g120 specific 1 gG titers were measured after two injections of mRNA-LNP. Titers were measured by a gp120 specific ELISA assay. It was observed that ENV-LNP treated mice exhibited an antigen specific B cell response, as measured by the increased level of gp120-specific IgG compared to control (FIG. 9A). Further, it was observed that similar amounts of Env-specific IgG1 and IgG2a are produced 2 weeks after 2 immunizations.

Experiments were conducted to examine the functional activity of anti-ENV antibodies produced after 2 immunizations with HIV envelope iR3A encoding modified mRNA-LNP complexes. Neutralization titers to an easy to neutralize tier 1 strain of HIV called MN and a difficult to neutralize tier 2 strain of HIV called X2278_C2_B6 were determined and control neutralization titers to moloney leukemia virus (MLV) were subtracted. It was observed that high levels of tier 1 neutralization (FIG. 10) and tier 2 neutralization (FIG. 11) was induced by immunization with intradermal iR3A modified mRNA-LNPs.

Another set of experiments were conducted where mice received a single intradermal injection of 30 μg HIV-1 CD4-independent R3A envelope encoding mRNA encapsulated into lipid nanoparticles (ENV). Control mice were injected with 30 firefly luciferase encoding mRNA complexed into lipid nanoparticles (LUC). Animals were sacrificed 14 days after mRNA administration (FIG. 12).

Cytokine production of antigen specific CD4+ cells was measured in the animals treated with a single intradermal dose of 30 μg ENV-LNP. It was observed that the immunization with a single injection of ENV-LNPs induces IFN-γ, TNF-α, IL-2 and CD107a production (FIG. 13 and FIG. 14) by antigen specific CD4+ T cells. Further analysis was conducted to evaluate the distribution of mono,- bi,- and trifunctional antigen specific CD4+ T cells in vaccinated animals. It was observed ENV-LNP treated animals produced a higher percentage of CD4+ cells producing both TNF-α and IL-2 (FIG. 15). Collectively, this data demonstrates that immunization with a single dose of ENV-LNPs elicit robust CD4+ T cell responses.

It was also observed that immunization with ENV-LNP results in significant increase in Tfh cell numbers. CD4, CXCR5 and PD-1 markers were used to determine total Tfh cells (FIG. 16).

Cytokine production by antigen specific Tfh cells was then examined. It was observed that immunization with a single injection of ENV-LNPs induces IFN-γ, TNF-α, and IL-2 production (FIG. 17) by antigen specific Tfh cells.

Further analysis was conducted to evaluate the distribution of mono,- bi,- and trifunctional antigen specific Tfh cells in vaccinated animals. It was observed that animals treated with a single dose of ENV-LNP produced a higher percentage of Tfh cells producing all three of IFN-γ, TNF-α, IL2 (FIG. 18). Collectively, this data demonstrates that immunization with a single dose of ENV-LNPs elicits robust Tfh cell immune response.

Figure 19:
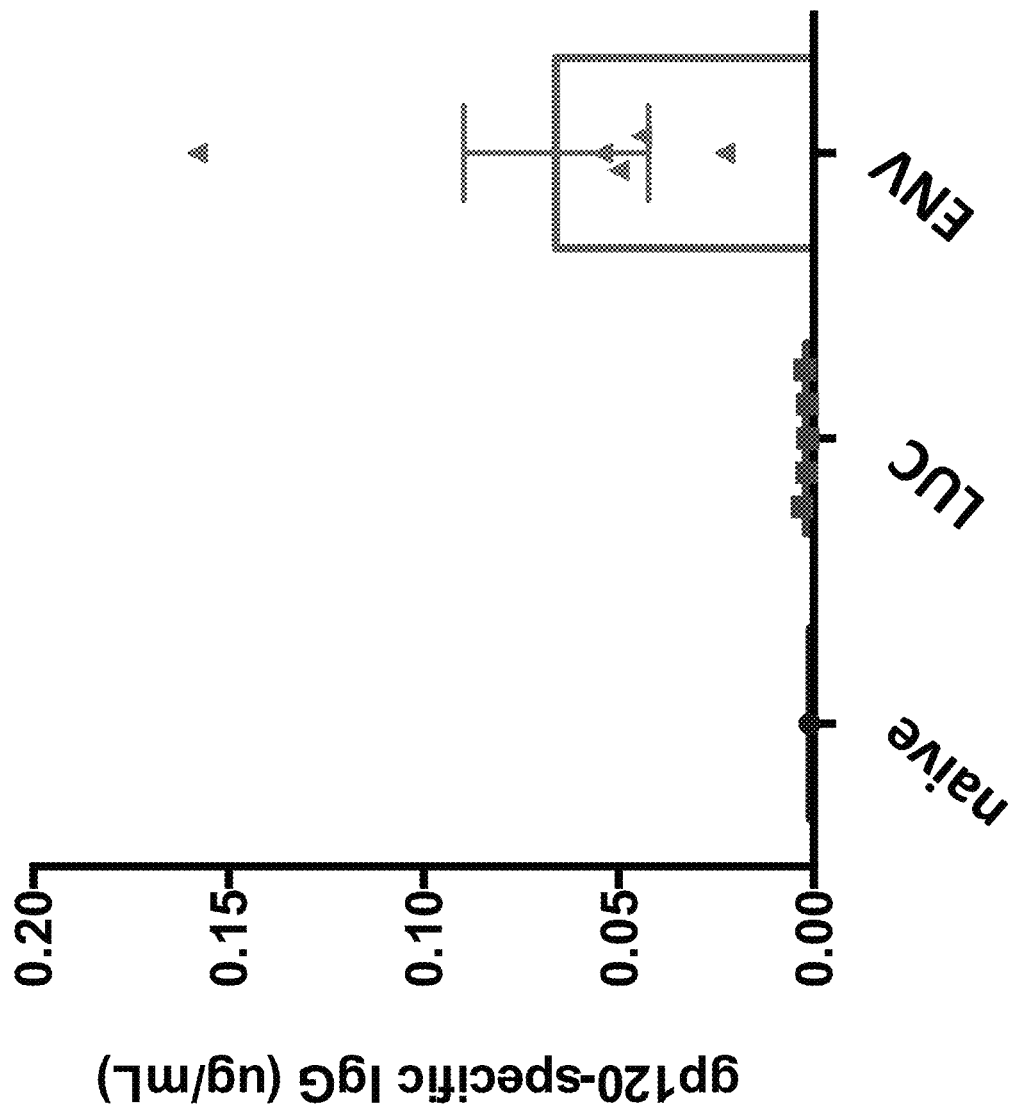
FIG. 19 is a graph illustrating that a single injection with 30 μg ENV mRNA-LNPs elicits IgG producing B cell responses. The graph depicts antigen specific antibody responses measured by ELISA assays. Experiments were conducted to measure HIV-1 gp120 specific IgG titers after a single injection with mRNA-LNPs. ENV=30 μg of iR3A envelope encoding mRNA injected ID. Luc=30 μg of control luciferase encoding mRNA injected ID. Naïve=uninjected animals. Standard error of the mean is indicated on bars.

ELISA assays were performed to investigate antigen specific B cell responses in mice immunized with a single dose of ENV-LNP. Specifically, HIV-1g120 specific IgG titers were measured after a single injection of mRNA-LNP. Titers were measured by a gp120 specific ELISA assay. It was observed that the single dose of ENV-LNP induced a robust antigen specific B cell response, as measured by the increased level of gp120-specific IgG compared to control and naïve animals (FIG. 19).

Experiments were conducted to compare the adaptive immune response induced by LNP-complexed nucleoside-modified RNA versus nucleoside-modified RNA delivered alone. Mice were immunized 2 times with 10 μg of unmodified, 1-methyl-pseudouridine modified, or 1-methyl-pseudouridine modified and LNP complexed mRNA (all encoding iR3A antigen) by the intradermal route at 1 month intervals.

Figure 20:
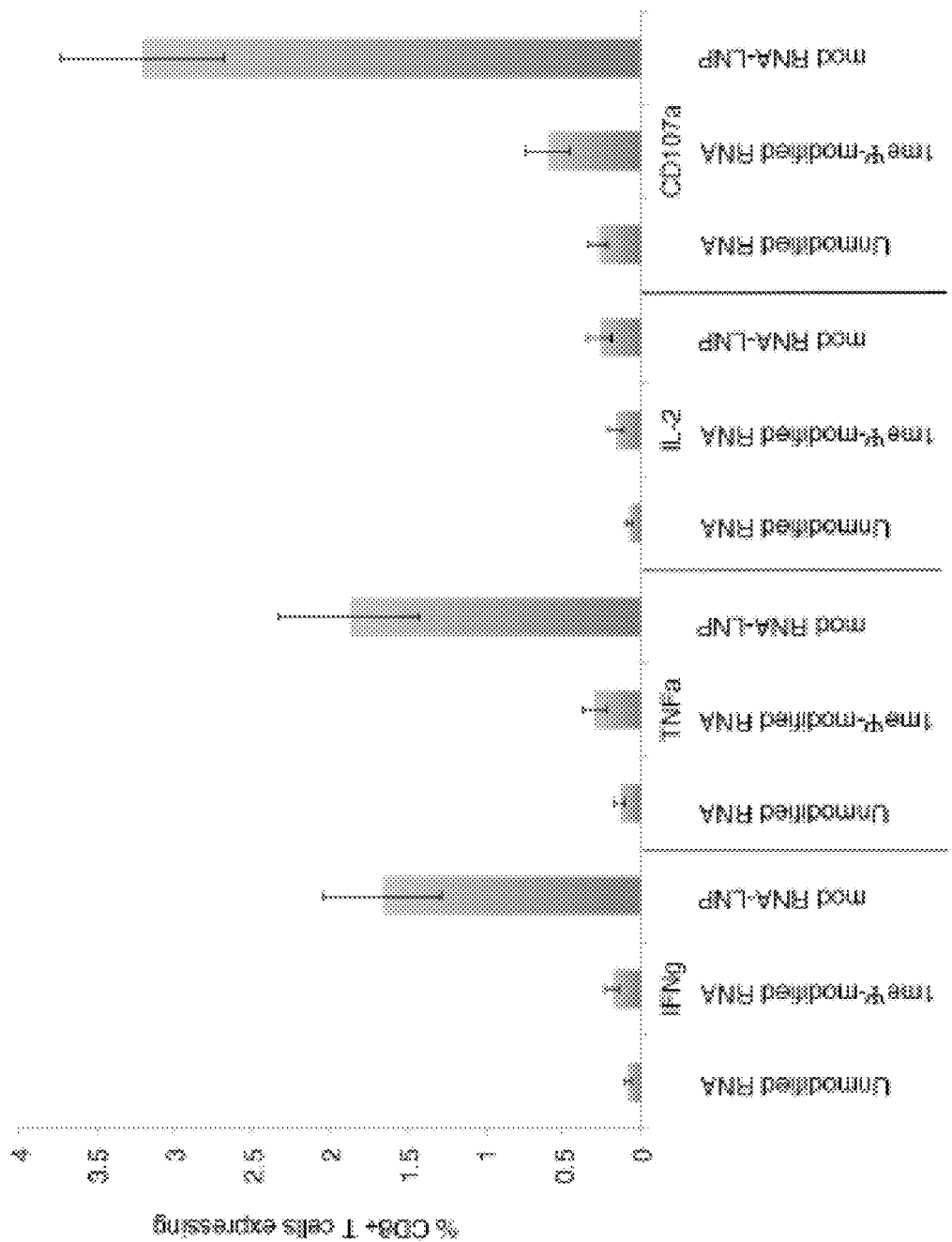
FIG. 20 is a graph depicting the results of example experiments demonstrating the benefits of nucleoside modification and LNP complexing. Mice were immunized 2 times with 10 μg of unmodified, 1-methyl-pseudouridine, or 1-methyl-pseudouridine-LNP complexed mRNA encoding iR3A HIV envelope by the intradermal route at 1 month intervals. Spleen cells obtained 14 days after the second immunization were analyzed by a 6 hour stimulation with envelope overlapping peptides and analyzed for expression of CD107A or intracellular IFN-γ, TNF-α, and IL-2 by CD3+, CD8+ T cells. Control (medium) stimulated responses were subtracted for each mouse. Groups of 6 mice were averaged. Modified mRNA-LNP responses were significantly greater (p<0.01) than uncomplexed modified or unmodified mRNA or control (luciferase modified mRNA) treated mice.
Figure 21:
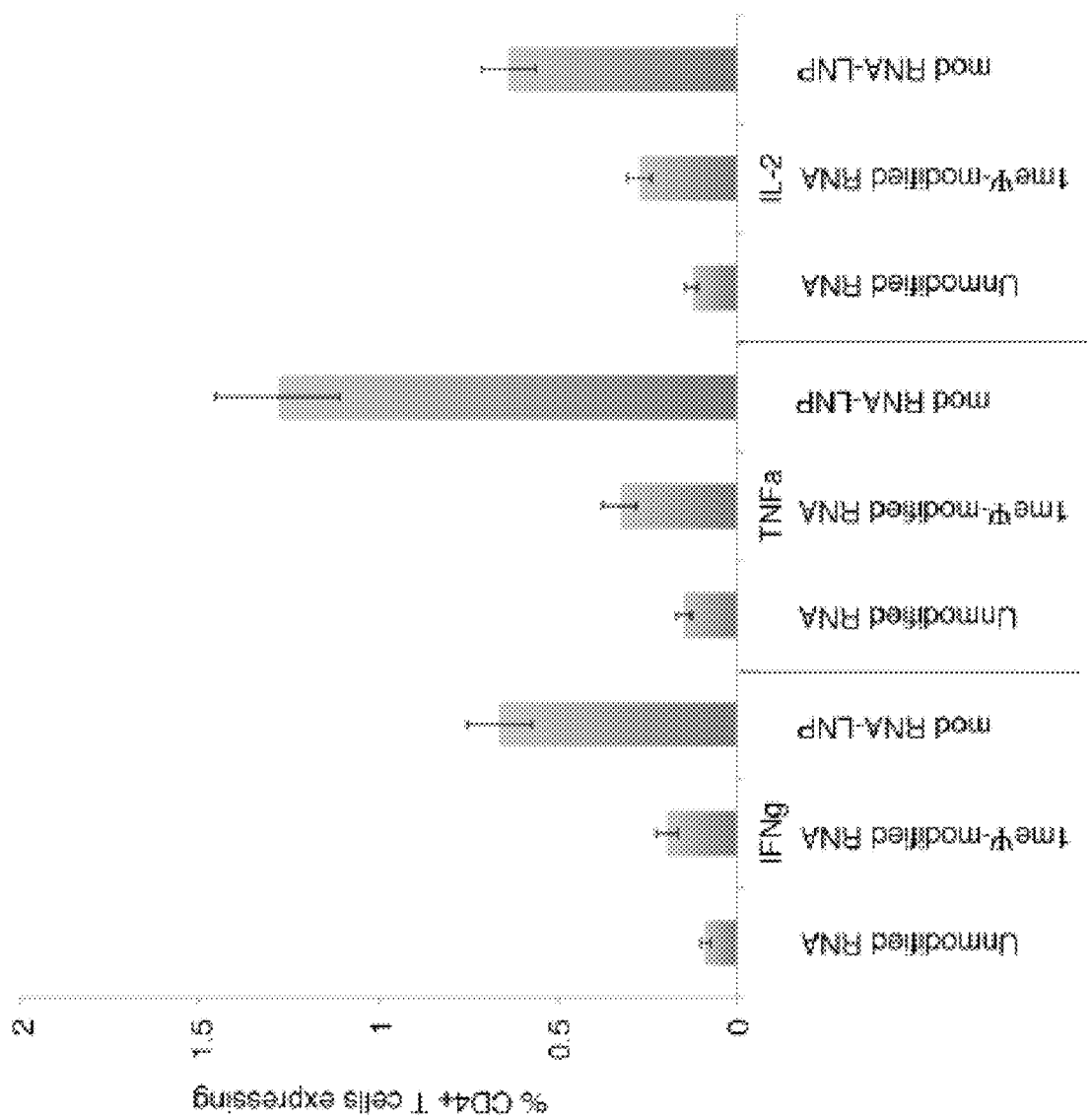
FIG. 21 is a graph depicting the results of example experiments that demonstrate the benefits of nucleoside modification and LNP complexing. Mice were immunized 2 times with 10 μg of unmodified mRNA, 1-methyl-pseudouridine mRNA, or 1-methyl-pseudouridine-mRNA-LNP complexed all encoding iR3A HIV envelope by the intradermal route at 1 month intervals. Spleen cells were analyzed by a 6 hour stimulation with envelope overlapping peptides and analyzed for expression of intracellular IFN-γ, TNF-α, and IL-2 by CD3+, CD4+ T cells. Control (medium) stimulated responses were subtracted for each mouse. Groups of 6 mice were averaged. Modified mRNA-LNP responses were significantly greater (p<0.01) than uncomplexed modified or unmodified mRNA or control (luciferase modified mRNA) treated mice.
Figure 22:
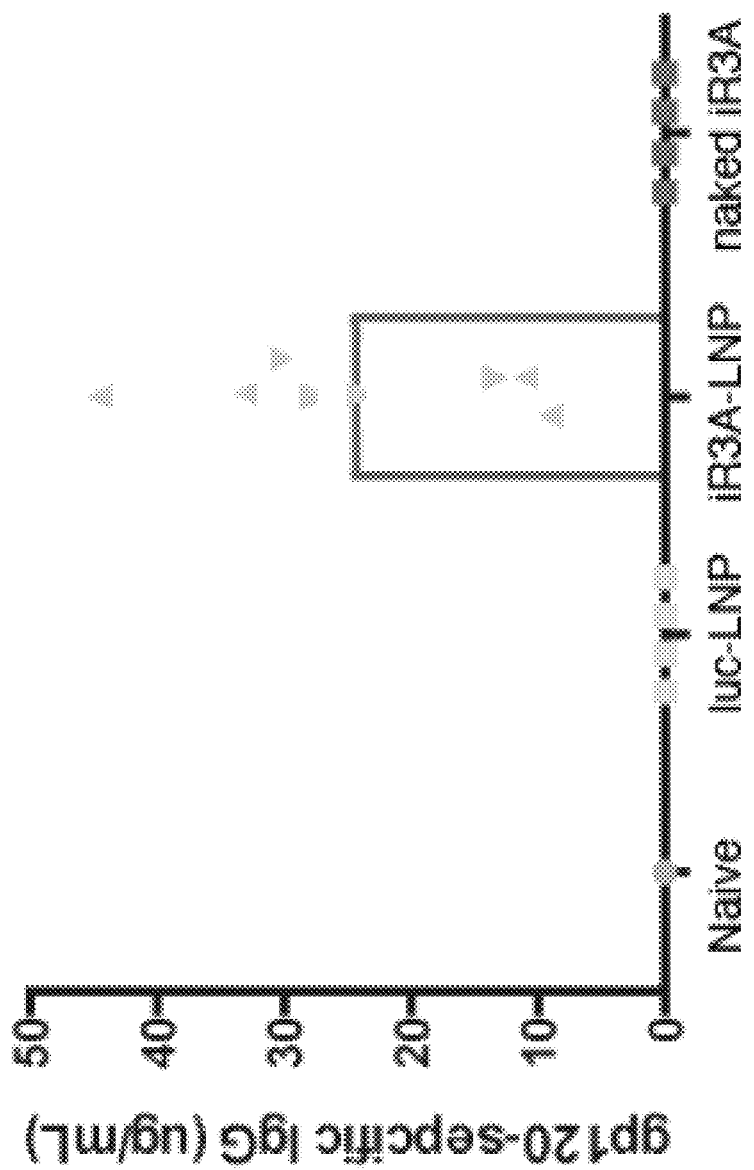
FIG. 22 is a graph depicting the results of example experiments that demonstrate the benefits of nucleoside modification and LNP complexing. Mice were immunized 2 times with 10 µg of uncomplexed 1-methyl-pseudouridine modified mRNA encoding HIV envelope iR3A (naked iR3A), 1-methyl-pseudouridine mRNA-LNPs encoding luciferase (luc-LNP), or iR3A mRNA complexed LNPs by the intradermal route at 1 month intervals. Serum was analyzed for envelope (gp120) specific responses by ELISA. Serum was diluted 1:1000 and analyzed. A monoclonal antibody specific for gp120 was used to determine concentration in serum.

Spleen cells were analyzed by a 6 hour stimulation with envelope overlapping peptides and analyzed for expression of CD107A or intracellular IFN-γ, TNF-α, and IL-2 versus CD3+, CD8+ T cells (FIG. 20) or for expression of intracellular IFN-γ, TNF-α, and IL-2 versus CD3+, CD4+ T cells (FIG. 21). Nucleoside-modified RNA-LNP responses in CD8+ and CD4+ T-cells were significantly greater (p<0.01) than uncomplexed modified or unmodified mRNA or control (luciferase modified mRNA) treated mice (FIG. 20 and FIG. 21) demonstrating the superiority of LNP complexing.

Experiments were also conducted to examine envelope-specific antibody responses induced by immunization with uncomplexed or complexed nucleoside-modified RNA. Mice were immunized 2 times with 10 μg of uncomplexed 1-methyl-pseudouridine modified mRNA encoding HIV envelope iR3A (naked iR3A), 1-methyl-pseudouridine-LNP complexed mRNA encoding luciferase (luc-LNP), or 1-methyl-pseudouridine-LNP complexed iR3A encoding mRNA (iR3A-LNP) by the intradermal route at 1 month intervals. Serum was analyzed for envelope (gp120) specific responses by ELISA. Serum was diluted 1:1000 and analyzed. A monoclonal antibody specific for gp120 was used to determine concentration in serum. It was observed that immunization with iR3A-LNP resulted in increased gp120-specific antibody response.

Figure 23:
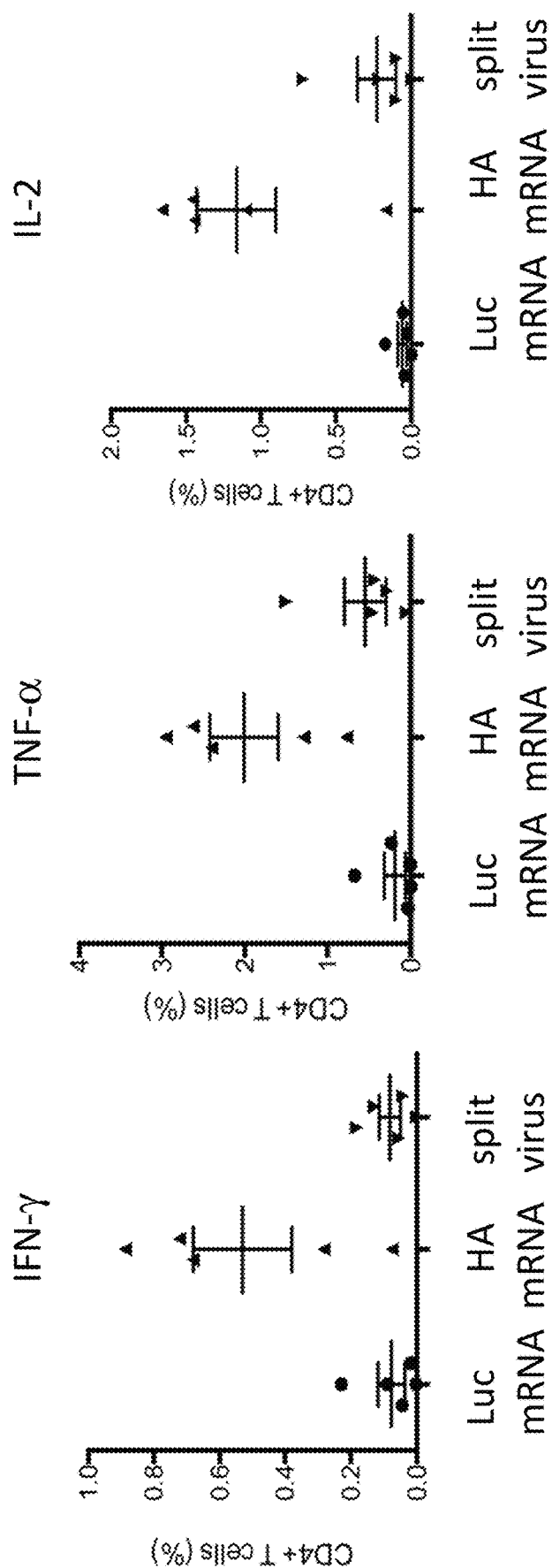
FIG. 23 is a graph depicting the results of example experiments measuring CD4+ T cell responses, as measured by IFN-γ (left), TNF-α (center), and IL-2 (right) positive CD4+ T cells detected 10 days after a single administration of 30 µg of PR8 HA encoding mRNA-LNP. All intracellular cytokine measurements were performed using multicolor flow cytometry after stimulation with peptide pools of 15-mers overlapping by 11 amino acids of the complete hemagglutinin sequence. Standard error of the mean is indicated on bars.

Example 2: Induction of Adaptive Immune Response by Modified RNA Encoding Influenza Antigen Experiments presented herein demonstrate that nucleoside-modified RNA which encodes an influenza antigen (i.e. hemagglutinin (HA)) induces an influenza-specific adaptive immune response in a subject. In these studies HA from PR8 and A/Ca1/7/2009 influenza strains were used. The amino acid sequence, nucleotide sequence, and codon optimized sequences for the PR8 and A/Ca1/7/2009 HA are provided below Experiments were conducted using m1ψ-modified mRNA. Initial experiments were conducted to examine cytokine production in CD4+ T cells, 10 days after a single administration of PR8 HA-encoding modified mRNA-LNP (30 μg). It was observed that a single intradermal administration of 30 μg PR8 HA-encoding modified mRNA-LNP induced increased production of IFN-γ, TNF-α, and IL-2, as compared to luciferase-encoding mRNA and split virus (FIG. 23). Split virus is used in standard intramuscular flu vaccines. The virus is initially grown in chick-embryo allantoic fluid. The fluid is harvested, clarified, concentrated and purified to eliminate almost all the egg protein. The virus is then disrupted with chemicals that inactivate it and break it into components to generate split virus.

Figure 24:
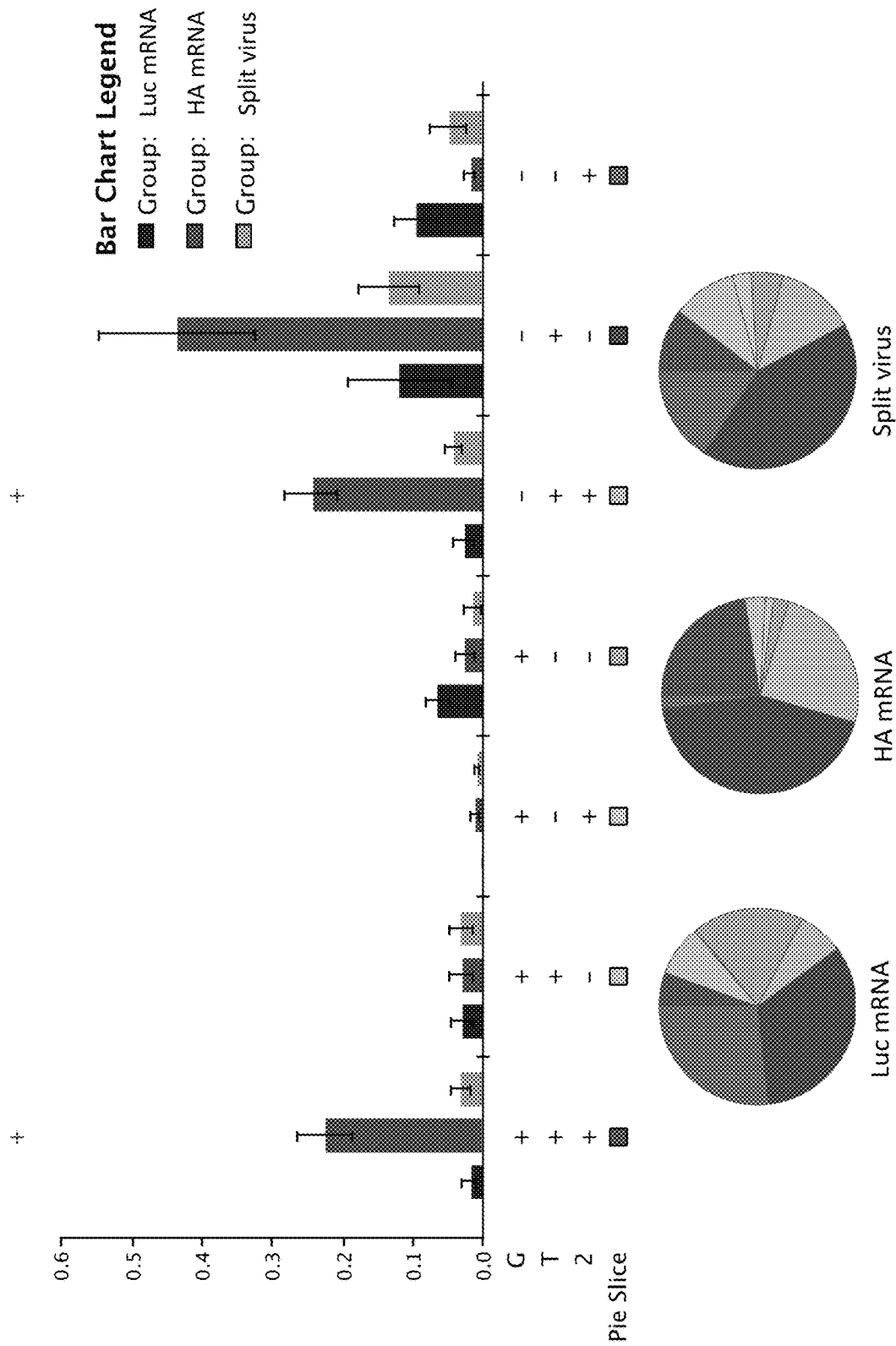
FIG. 24 is a set of graphs depicting the results of example experiments examining polyfunctional CD4+ T cell responses after single immunization of PR8 HA encoding mRNA-LNP. Pie charts show the distribution of antigen specific CD4+ T cells producing one, two or three cytokines. The bar graph shows the ratio of antigen specific CD4+ T cells producing one, two or three cytokines. G=INF-γ, T=TNF-α, 2=IL-2. All intracellular cytokine measurements were performed using multicolor flow cytometry after stimulation with peptide pools of 15-mers overlapping by 11 amino acids of the complete hemagglutinin sequence. Standard error of the mean is indicated on bars.

Further, a polyfunctional CD4+ T cell response after the single intradermal administration of 30 μg PR8 HA-encoding modified mRNA-LNP was observed, where PR8 HA-encoding modified mRNA-LNP induced the expression of all 3 measured cytokines in a significantly greater percentage of cells, as compared to control luciferase-encoding RNA and intramuscular injection with 1000 HAU of inactivated PR8 virus (FIG. 24).

Figure 25:
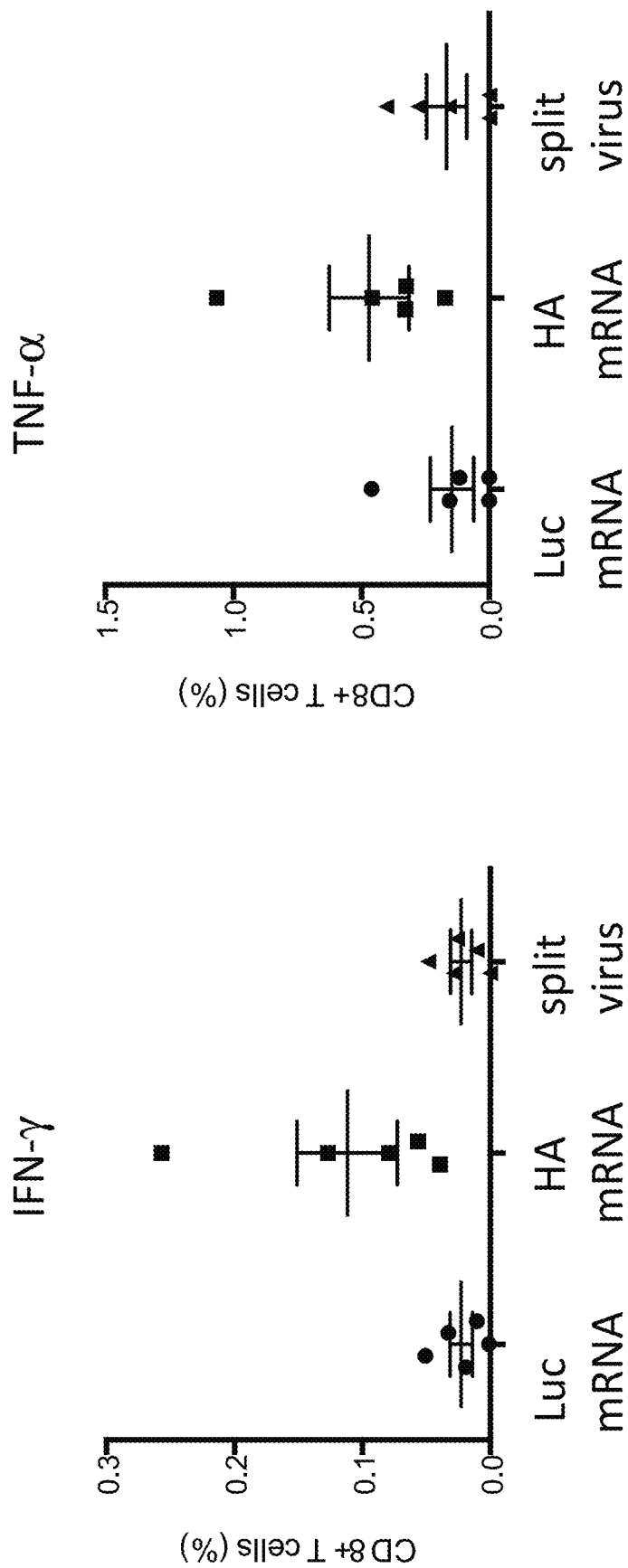
FIG. 25 is a graph depicting the results of example experiments measuring CD8+ T cell responses, as measured by IFN-γ (left) and TNF-α (right) positive CD8+ T cells detected 14 days after a single administration of 30 µg of PR8 HA encoding mRNA-LNP. All intracellular cytokine measurements were performed using multicolor flow cytometry after stimulation with peptide pools of 15-mers overlapping by 11 amino acids of the complete hemagglutinin sequence. Standard error of the mean is indicated on bars.

Experiments were conducted to examine cytokine production in CD8+ T cells, 10 days after a single intradermal administration of PR8 HA-encoding modified mRNA-LNP (30 μg). It was observed that a single administration of 30 μg PR8 HA-encoding modified mRNA-LNP induced increased production of IFN-γ and TNF-α as compared to luciferase-encoding mRNA and split virus (FIG. 25).

Figure 26:
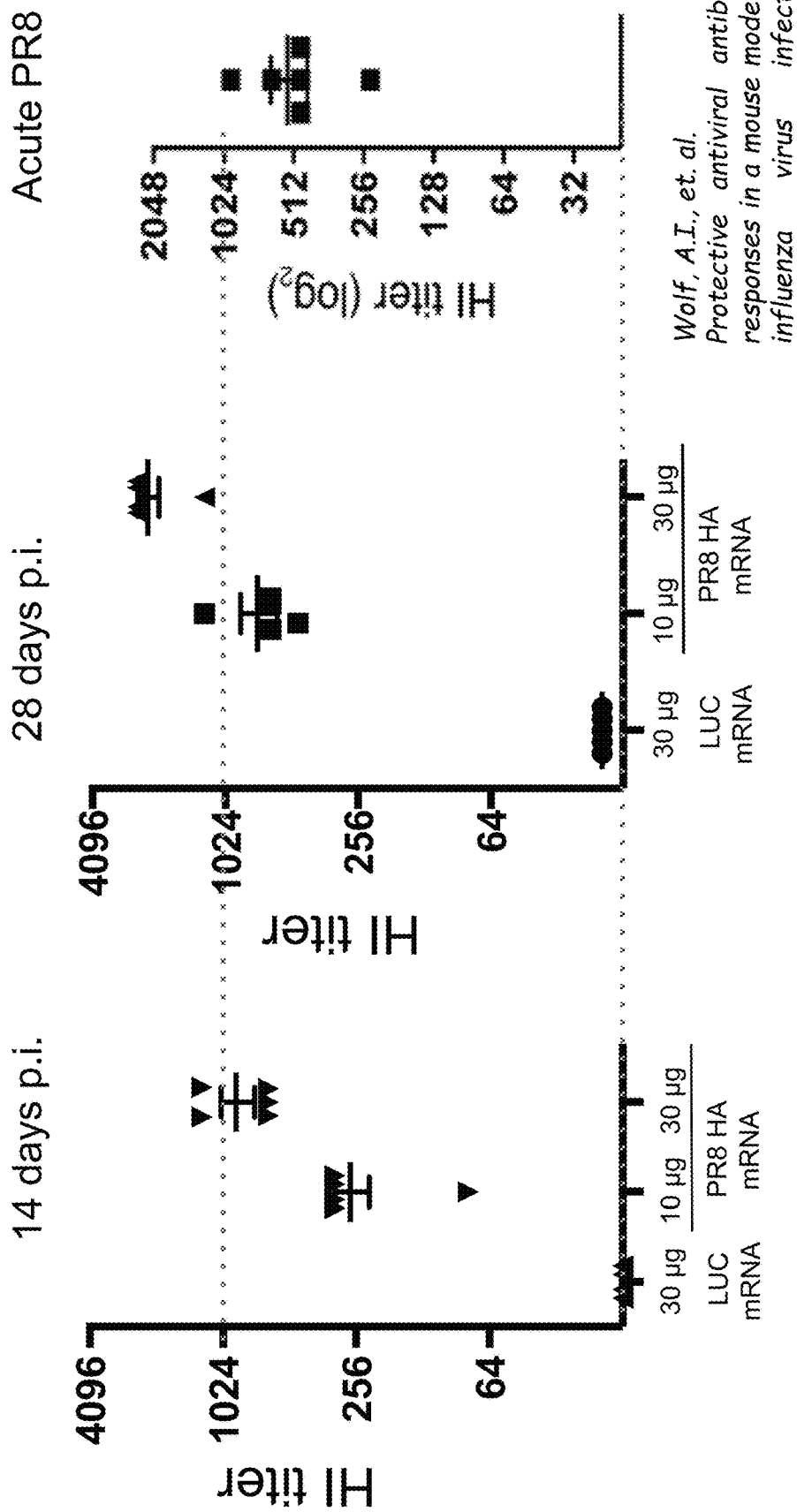
FIG. 26 is a set of graphs depicting the results of example experiments depicting HI titer 14 days and 28 days after administration of either 10 µg or 30 µg of PR8 HA mRNA-LNP. Titers were measured by the standard hemaglutinin inhibition assay, where turkey red blood cells were coated with PR8 hemagglutinin. Serum at 2-fold increasing dilutions was added to the RBCs and the titer where hemaglutination was lost was measured.

Further experiments were conducted to detect the level of neutralization, as measured by HI titer, induced 14 days or 28 days post-intradermal injection of either 10 μg or 30 μg of PR8 HA-encoding modified mRNA-LNP. Neutralization titers were measured by the standard hemaglutinin inhibition assay, where turkey red blood cells were coated with PR8 hemagglutinin. Serum at 2-fold increasing dilutions was added to the RBCs and the titer where hemaglutination was lost was measured. It was observed that both administration of 10 μg and 30 μg of PR8 HA-encoding modified mRNA-LNP resulted in increased titer as compared to luciferase encoding mRNA (FIG. 26). Further, the level of neutralization induced by acute infection with PR8 influenza was lower than that induced by modified mRNA-LNP (Wolf et al., 2011, J Clin Invest, 121: 3954-3964).

Figure 27:
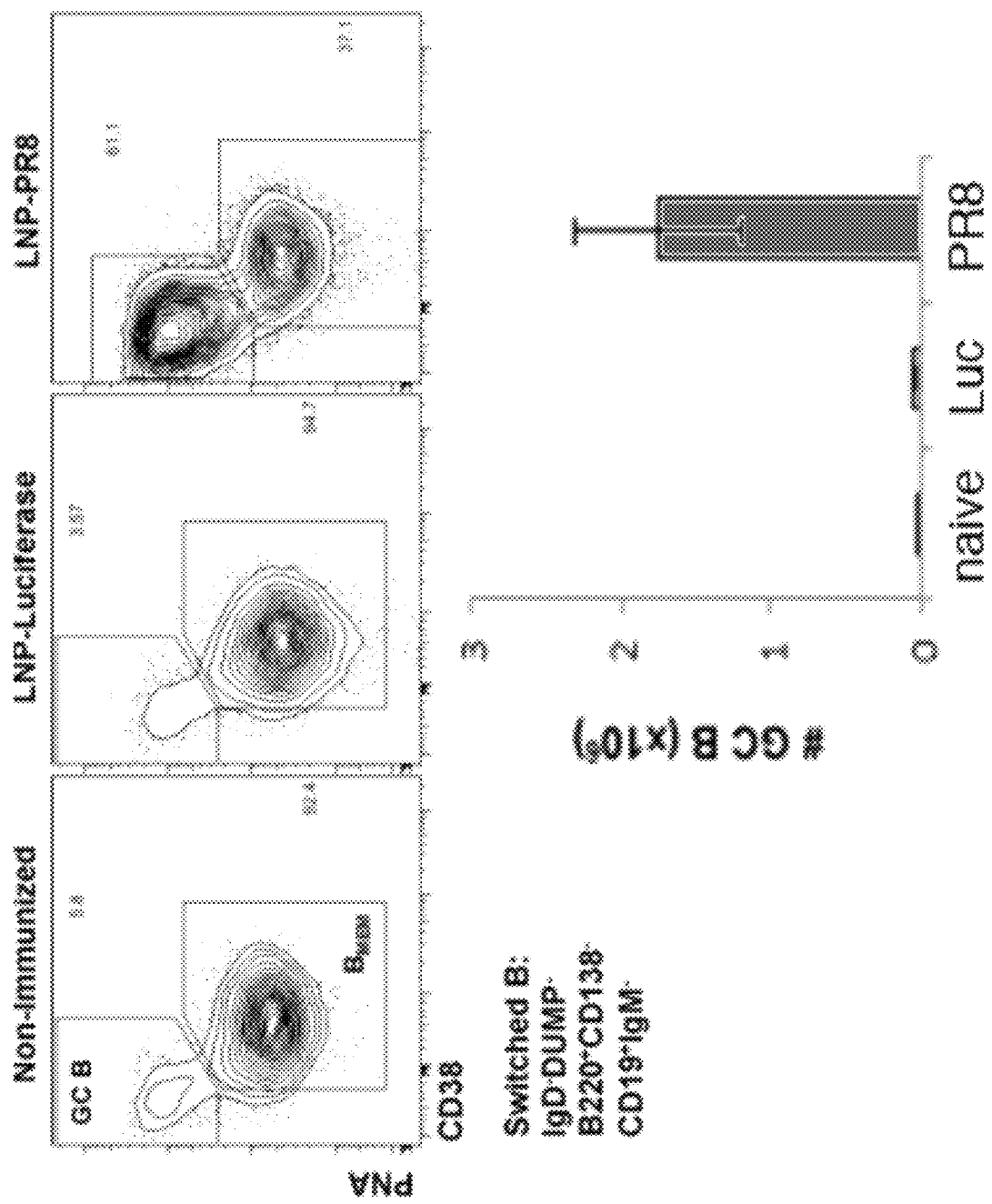
FIG. 27 is a set of graphs depicting the results of example experiments demonstrating that a single administration of PR8 HA encoding mRNA-LNP results in increased germinal center (GC) B cells. GC B cells were defined as IgD⁻, B220⁺, CD138⁻, CD19⁺, IgM⁻], CD3- and CD14-. The total number of cells in the spleen was calculated by counting the number of spleen cells and multiplying that by the % GC B cells.
Figure 28:
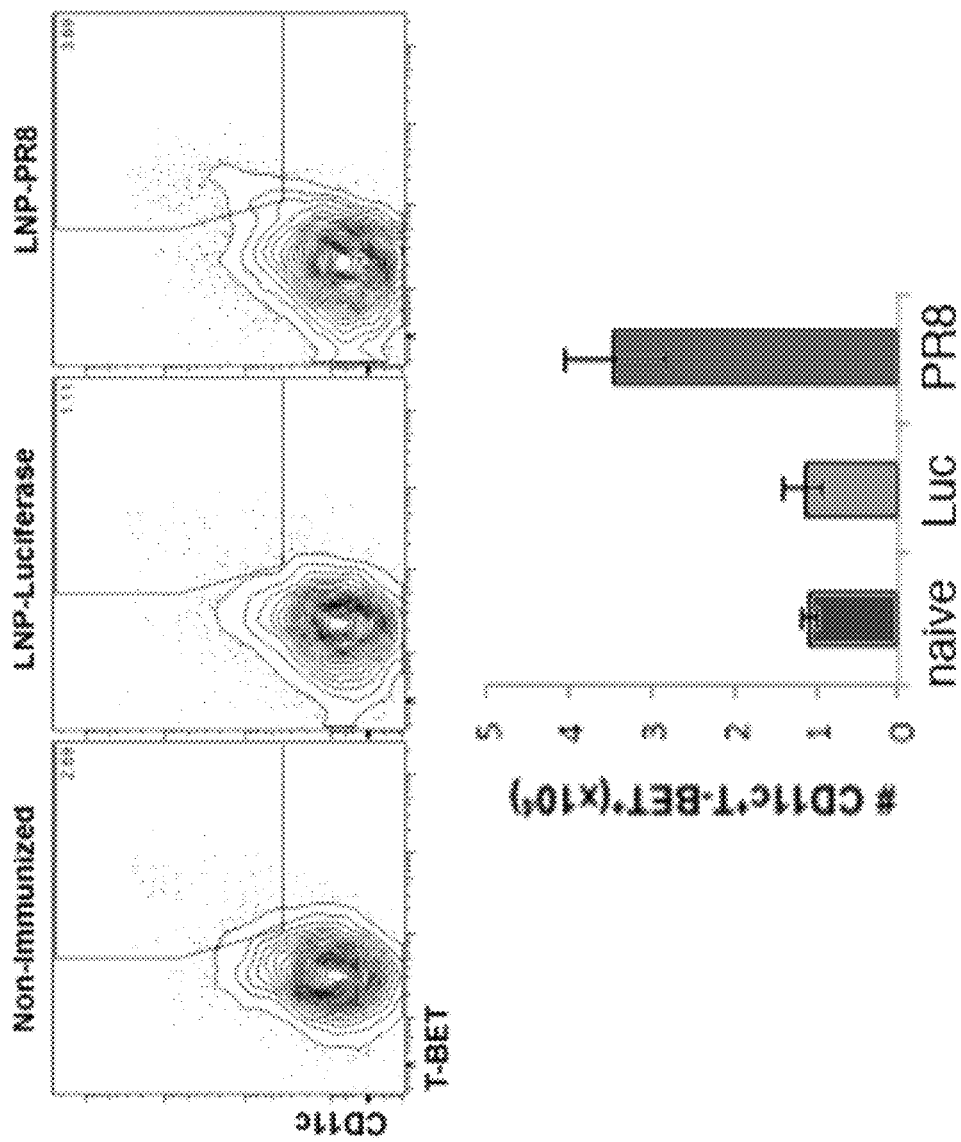
FIG. 28 is a set of graphs depicting the results of example experiments demonstrating that a single administration of PR8 HA encoding mRNA-LNP results in increased total memory B cells in the spleen. Memory B cells were defined as CD3-, CD14-, CD11c+, T-bet+. The total number of cells in the spleen was calculated by counting the number of spleen cells and multiplying that by the % memory B cells.

It was further observed that a single administration of PR8 HA-encoding modified mRNA-LNP induces the production of germinal center B cells (FIG. 27) as measured by being IgD−, B220+, CD138−, CD19+, IgM−, CD3− and CD14− Additionally, a single intradermal administration of PR8 HA-encoding modified mRNA-LNP induces an increase in total memory B cells in the spleen, as measured by the number of CD11c+ T-BET+ cells (FIG. 28).

Figure 29:
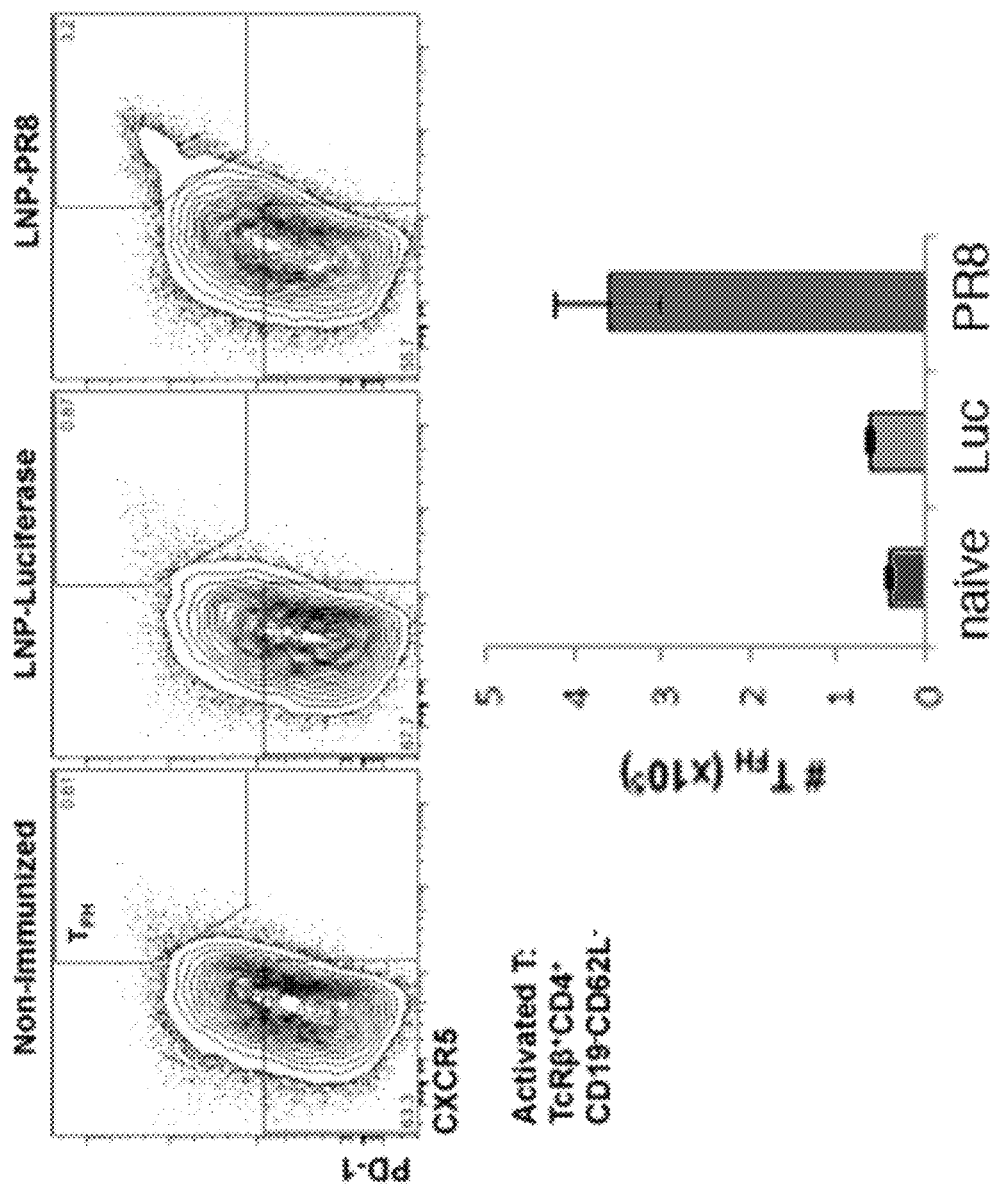
FIG. 29 is a set of graphs depicting the results of example experiments demonstrating that a single administration of PR8 HA encoding mRNA-LNP results in increased total Tfh cells in the spleen. Tfh cells were defined as CD4+, memory+, CXCR5+, PD-1+ cells. The total number of cells in the spleen was calculated by counting the number of spleen cells and multiplying that by the % Tfh cells.
Figure 30:
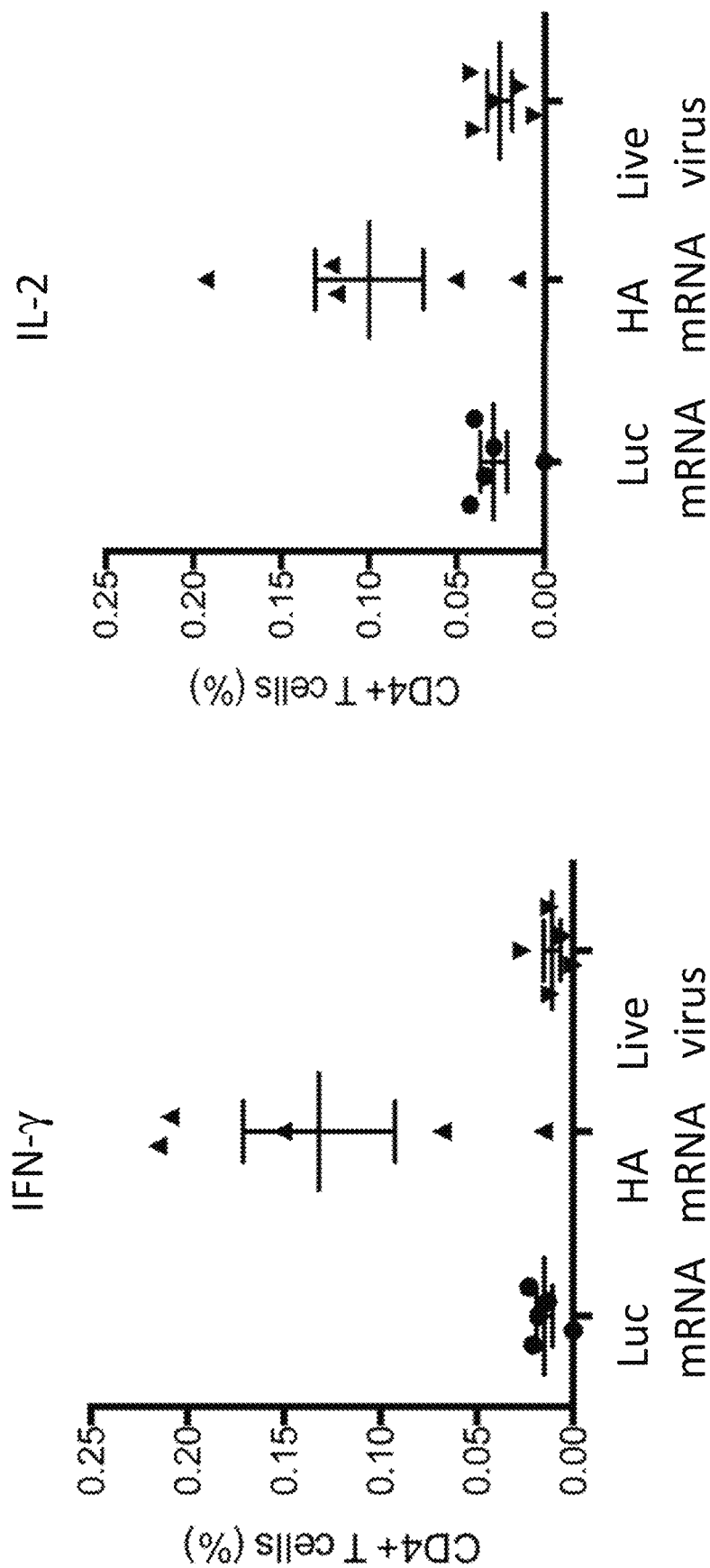
FIG. 30 is a graph depicting the results of example experiments measuring CD8+ Tfh cell responses, as measured by IFN-γ (left) and IL-2 (right) positive CD8+ T cells detected 10 days after a single administration of 30 µg of PR8 HA encoding mRNA-LNPs. Tfh cells were identified by expression of Bcl6.

Additional studies were conducted to examine the effect of administration of HA-encoding modified mRNA on T follicular helper (Tfh) cells, which are critical in driving B cell response and memory. It was observed that a single administration of PR8 HA-encoding modified mRNA-LNP induces an increase in total Tfh cells in the spleen (FIG. 29). Further, administration of 30 μg PR8 HA-encoding modified mRNA-LNP resulted in an increase in the production of IFN-γ and IL-2 in CD4+ Tfh cells, as compared to treatment with luciferase-encoding mRNA and live virus control when spleen cells were stimulated with overlapping HA peptides and Tfh cells were defined as Bcl6+ (FIG. 30).

Figure 31:
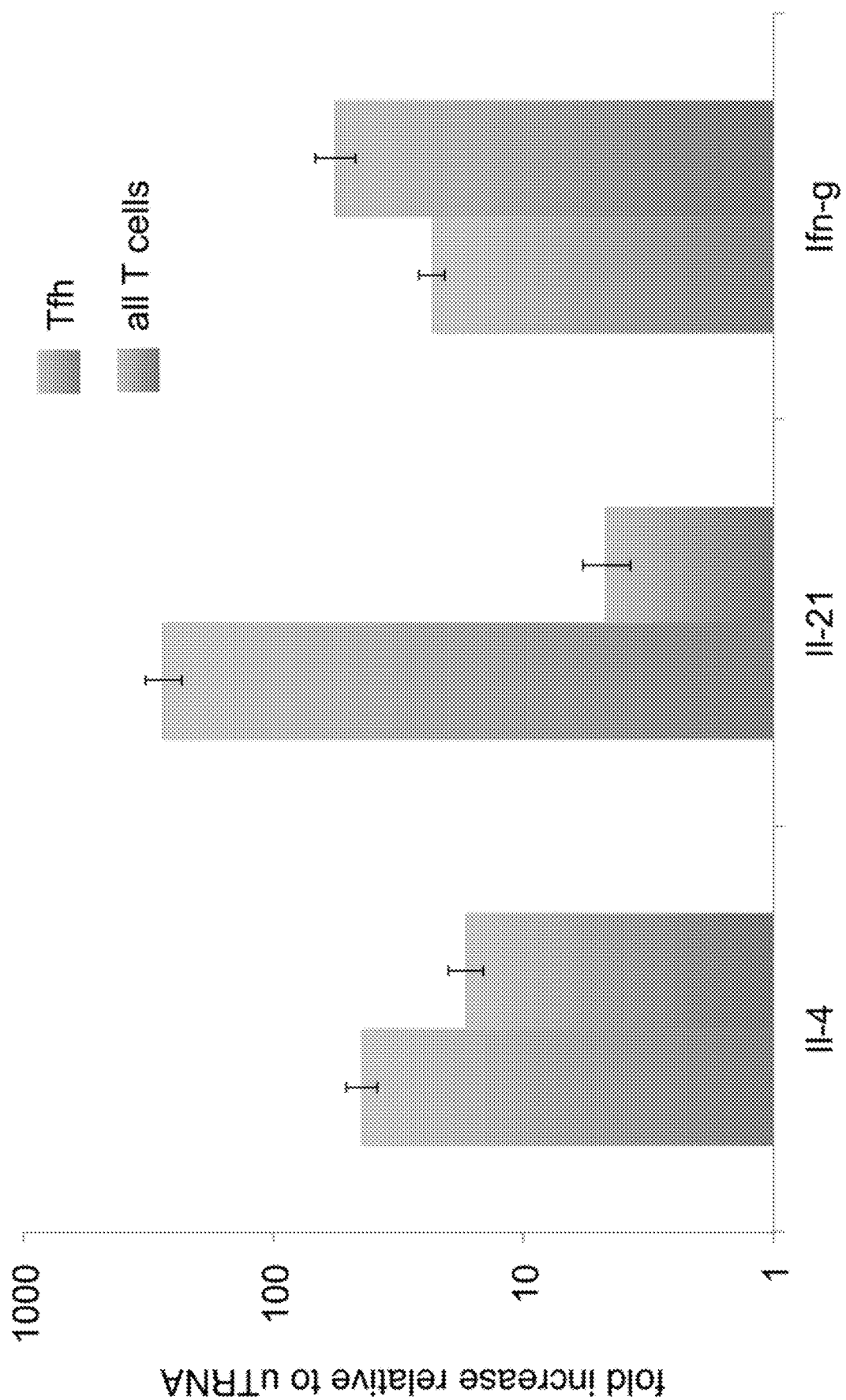
FIG. 31 is a graph depicting the results of example experiments demonstrating the relative amount of cytokine expression in Tfh cells compared to total T cells purified from the spleens of mice immunized with PR8 HA encoding mRNA-LNP. All T cells were selected by negative selection. Tfh cells were further purified by flow cytometric sorting selecting memory+, CXCR5+, PD-1+ cells. mRNA was isolated from the T cell populations and analyzed by real time PCR using specific primers. Values are expressed as compared to universal mRNA.
Figure 32:
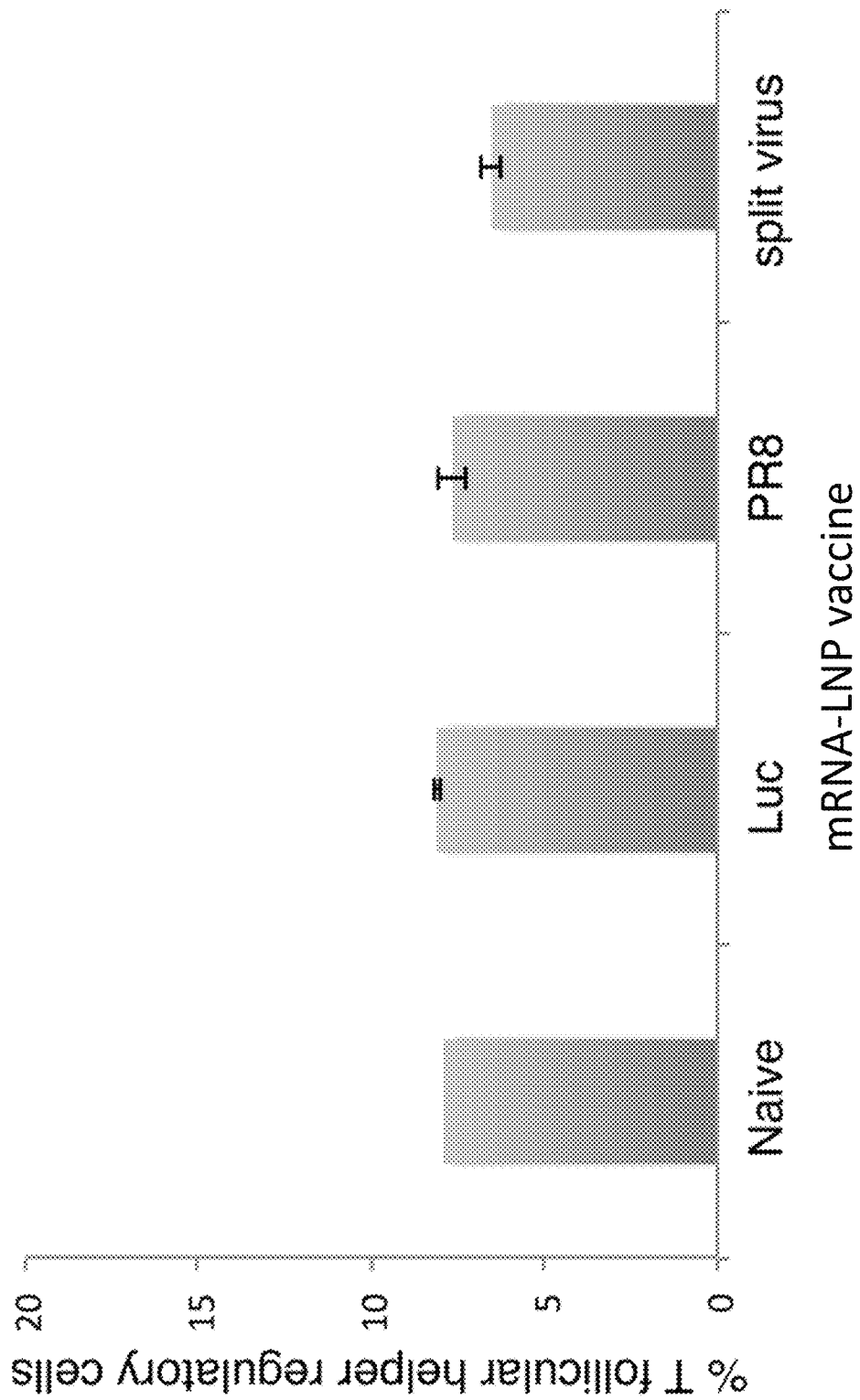
FIG. 32 is a graph depicting the results of example experiments demonstrating that T follicular regulatory cells are not increased by administration of modified mRNA-LNP. Tfh cells were identified as memory+, CXCR5+, PD-1+, Bcl6+ and T follicular regulatory cells were identified as memory+, CXCR5+, PD-1+, Bcl6+, FoxP3+. Data is expressed as the percentage of Tfh cells that were T follicular regulatory cells.

The cytokine expression of IL-4, IL-21, and IFN-γ was measured in Tfh cells purified from the spleens of mice immunized with PR8 HA-encoding modified mRNA-LNP (FIG. 31). Spleen cells 10 days after PRB modified mRNA-LNP immunization were isolated. T cells were selected by either positive selection with CD3 or negative selection with CD14, CD19, CD16, CD56. Total T cells were either directly analyzed (all T cells) or further purified by selection of CXCR5+ and PD-1+ cells, T follicular helper cells. Levels of IL-4, IL-21, and IFN-g were measured by real time PCR using GAPDH as a control. Data are expressed as fold difference compared to a universal standard mRNA. Further, it was observed that administration of the PR8 HA-encoding modified mRNA-LNP does not increase the percentage of Tfh regulatory cells (FIG. 32).

Figure 33:
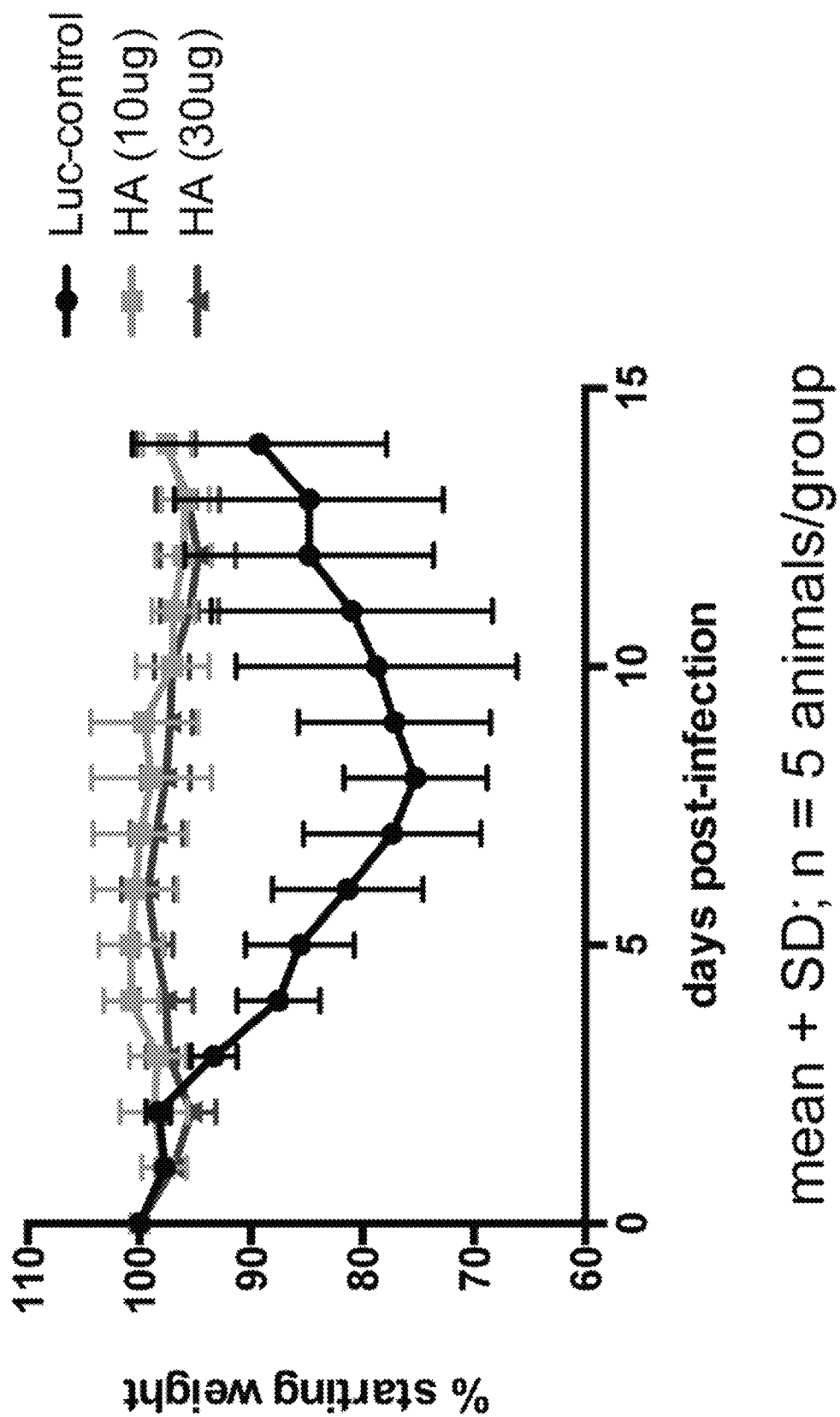
FIG. 33 is a graph depicting the results of example experiments demonstrating the weight loss as a measure of illness after influenza challenge in HA mRNA-LNP or control single immunized mice.

Experiments were also conducted to examine the effects of influenza challenge on mice that were immunized with either 10 μg or 30 μg of PR8 HA-encoding modified mRNA-LNP. It was observed that that challenged mice which were immunized intradermally with either 10 μg or 30 μg of PR8 HA-encoding modified mRNA-LNP maintained their weight throughout the 15 days post-infection study, while control animals exhibited reduced weight (FIG. 33) and significant mortality.

Experiments were conducted to examine the influenza stalk response to evaluate the potential to induce universal protection across influenza strains, and to measure affinity maturation driven by Tfh cells. Current influenza vaccines do not induce stalk responses.

Figure 34:
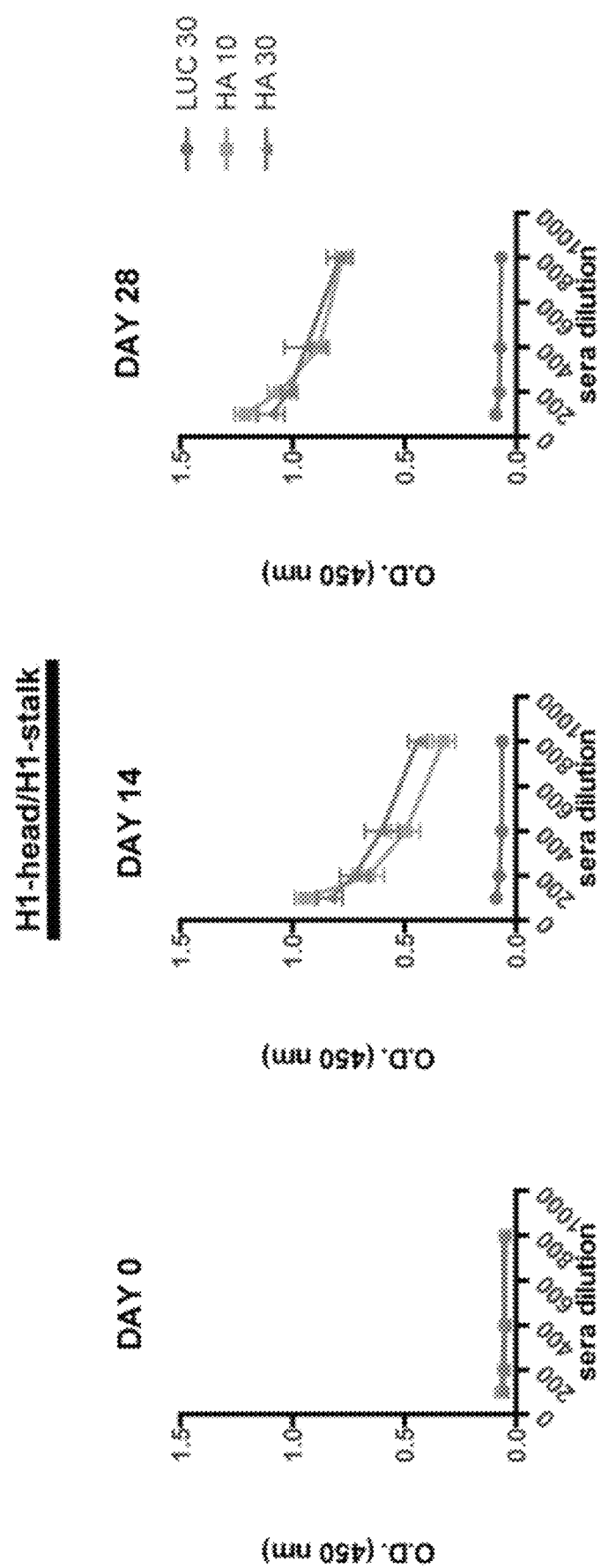
FIG. 34 is a set of graphs depicting the results of example experiments demonstrating HA binding at 2 weeks (center) and 4 weeks (right) to hemagglutinin where both the head and stalk are derived from H1.
Figure 35:
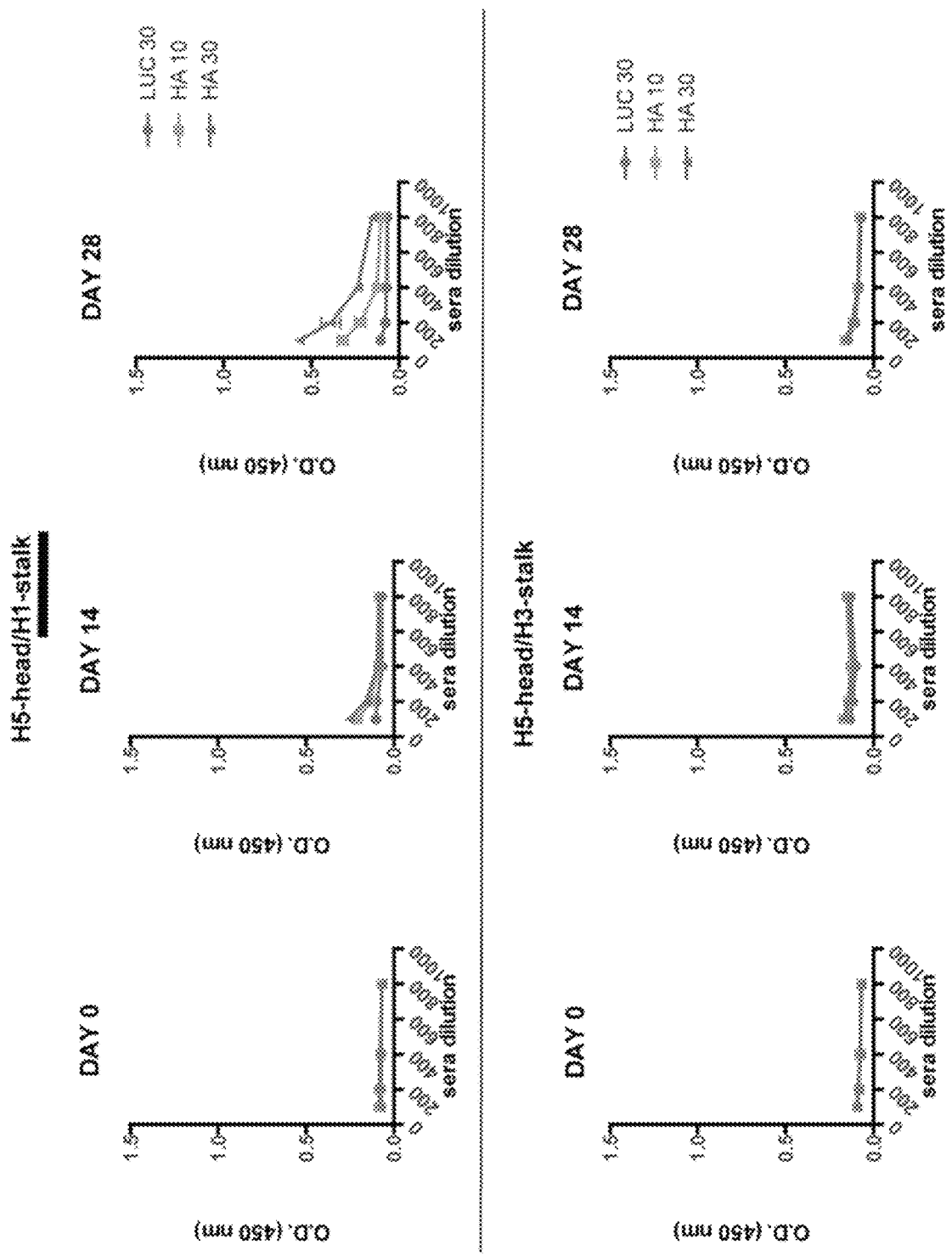
FIG. 35 is a set of graphs depicting the results of example experiments demonstrating specific binding to the stalk region of hemagglutinin. HA binding at 2 weeks (center) and 4 weeks (right) to hybrid hemagglutinin containing H5-head/H1-stalk HA (top) and H5-head/H3-stalk (bottom).
Figure 36:
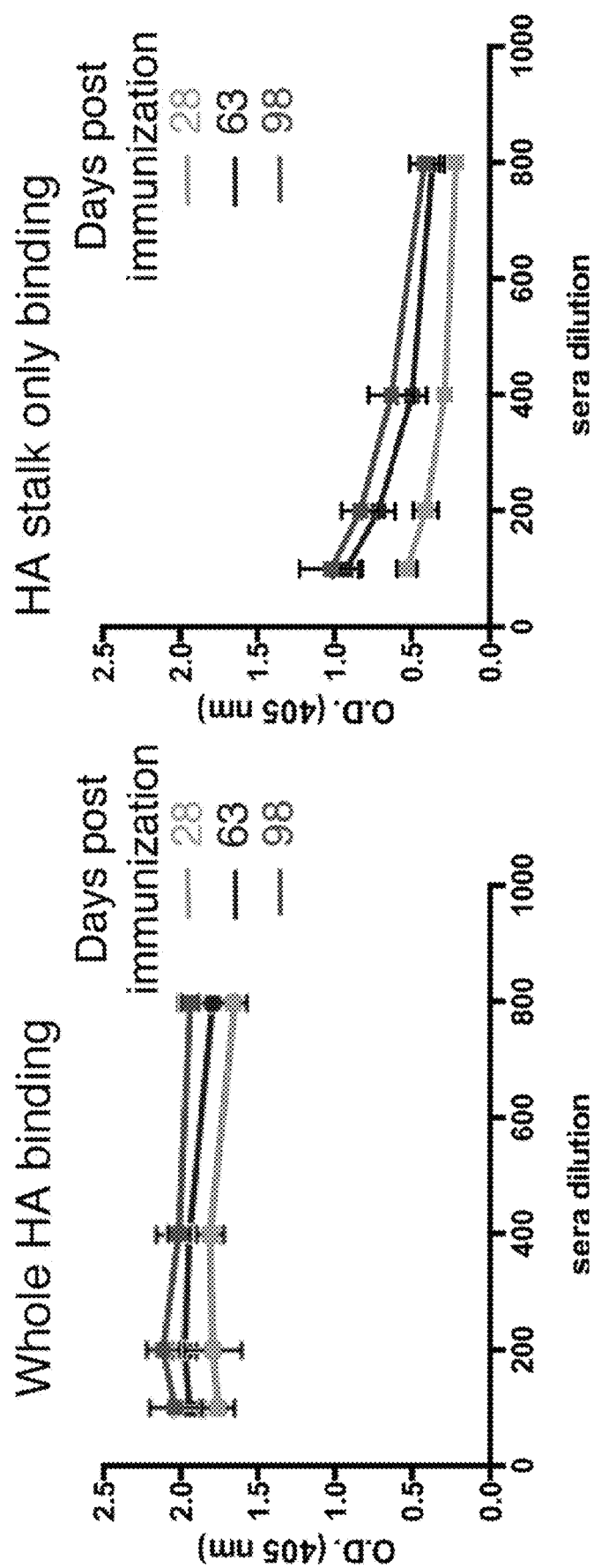
FIG. 36 is a set of graphs depicting the results of example experiments examining binding to whole HA (left) and HA stalk (right) binding over time. It is demonstrated that stalk binding increases over time post immunization.

Experiments were conducted to evaluate HA binding ability of sera of animals treated with a single intradermal administration of either 10 μg or 30 μg of PR8 HA-encoding modified mRNA-LNP. It was observed that binding to H1 HA (H1-head/H1-stalk) was increased 4 weeks after administration, as compared to 2 weeks after administration (FIG. 34). Further, it was observed that administration of either 10 μg or 30 μg of PR8 HA-encoding modified mRNA-LNP induced IgG specific for the stalk, as demonstrated by the ability to bind to H5-head/H1-stalk hybrid HA (FIG. 35). It was also observed that whole HA binding and HA stalk binding increases over time up to 63 days after a single intradermal immunization (FIG. 36).

Figure 37:
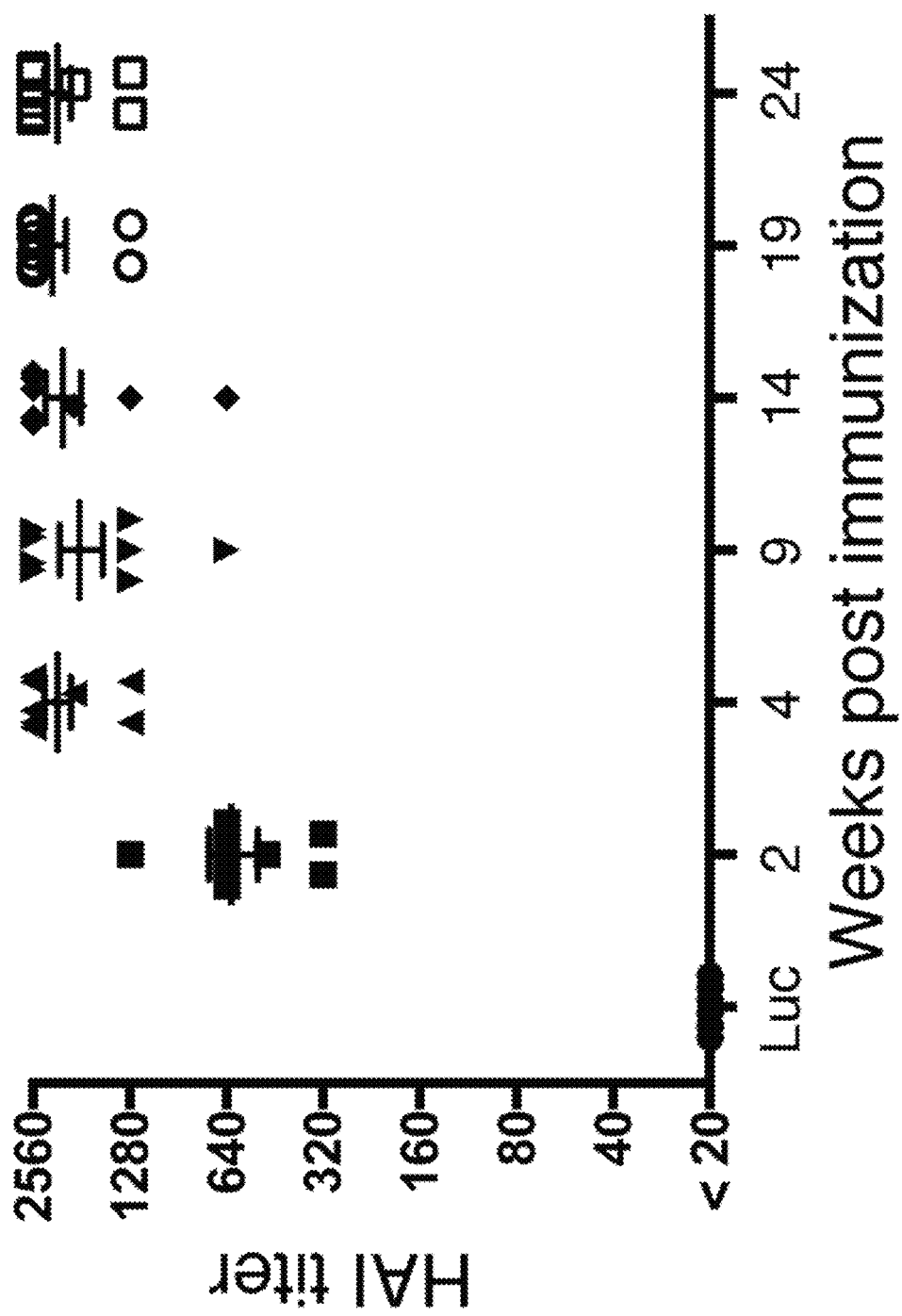
FIG. 37 is a graph depicting the results of experiments demonstrating that the neutralization titer as measured by hemagglutinin inhibition after a single administration of PR8 HA encoding modified mRNA-LNP remains unchanged 6 months after administration.

The persistence of the adaptive immune response induced by the PR8 HA-encoding modified mRNA-LNP was then evaluated. It was observed that the antibody response after single intradermal administration of PR8 HA-encoding modified mRNA-LNP remains unchanged 6 months after administration (FIG. 37).

Figure 38:
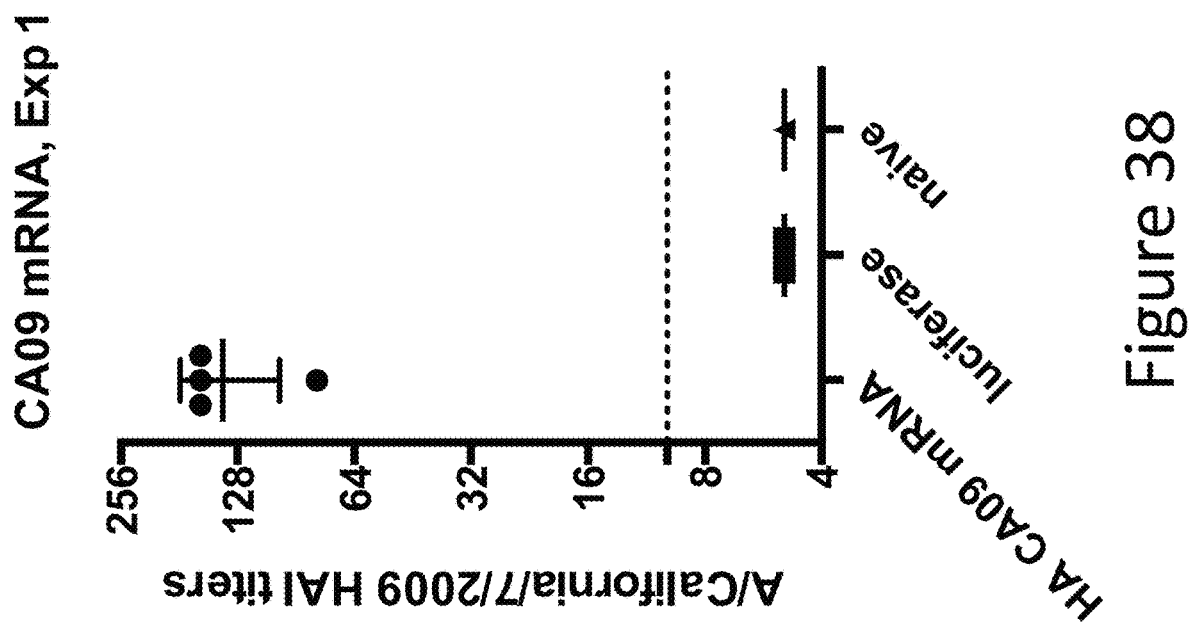
FIG. 38 is a graph depicting the results of experiments depicting HA inhibition titer measured 2 weeks after single administration of Cal/7/2009 HA encoding mRNA-LNPs.

Additional experiments were conducted using m1Ψ modified RNA-LNP, where the m1Ψ modified RNA encodes A/California/7/2009 HA (hereinafter "CA09 HA"). This is a different influenza HA that was used in the 2015-2016 vaccine and is clinically significant. It was observed that a single intradermal administration of 30 μg CA09 HA-encoding mRNA-LNP induced an antigen-specific adaptive immune response, as measured by HA inhibition titer 2 weeks after the single intradermal administration (FIG. 38).

Figure 39:
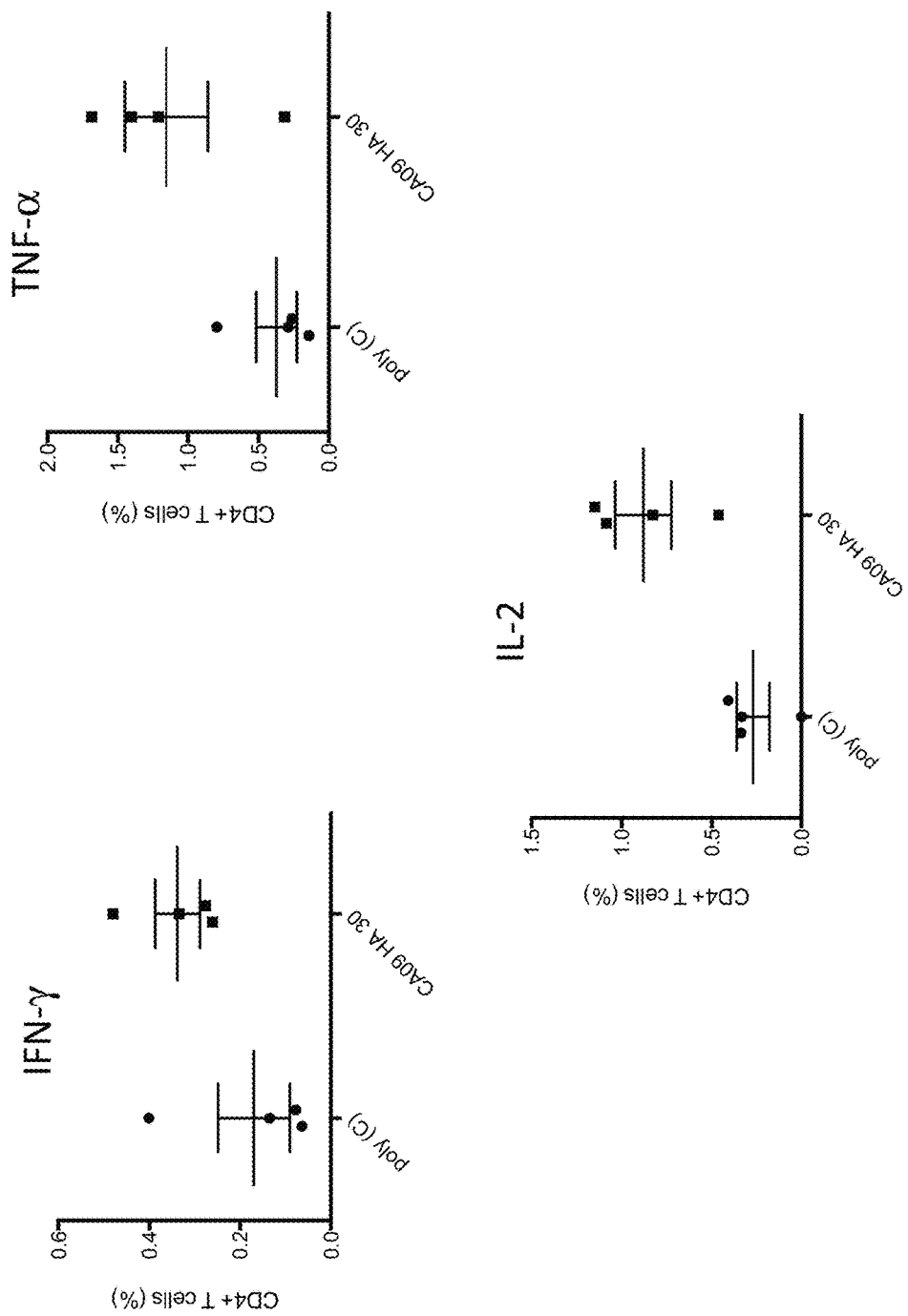
FIG. 39 is a set of graphs depicting the results of example experiments measuring CD4+ T cell responses, as measured by IFN-γ (top left), TNF-α (top right), and IL-2 (bottom) positive CD4+ T cells detected 2 weeks after a single administration of CA09 HA encoding mRNA-LNP. Cytokine production of individual animals is displayed as the percent of total CD4+ T cells in the spleen. Poly(C)=control mice injected with 30 of control poly(C) mRNA-LNPs injected intradermally (ID). All intracellular cytokine measurements were performed using multicolor flow cytometry after stimulation with peptide pools of 15-mers overlapping by 11 amino acids of the complete HA sequence. Standard error of the mean is indicated.
Figure 40:
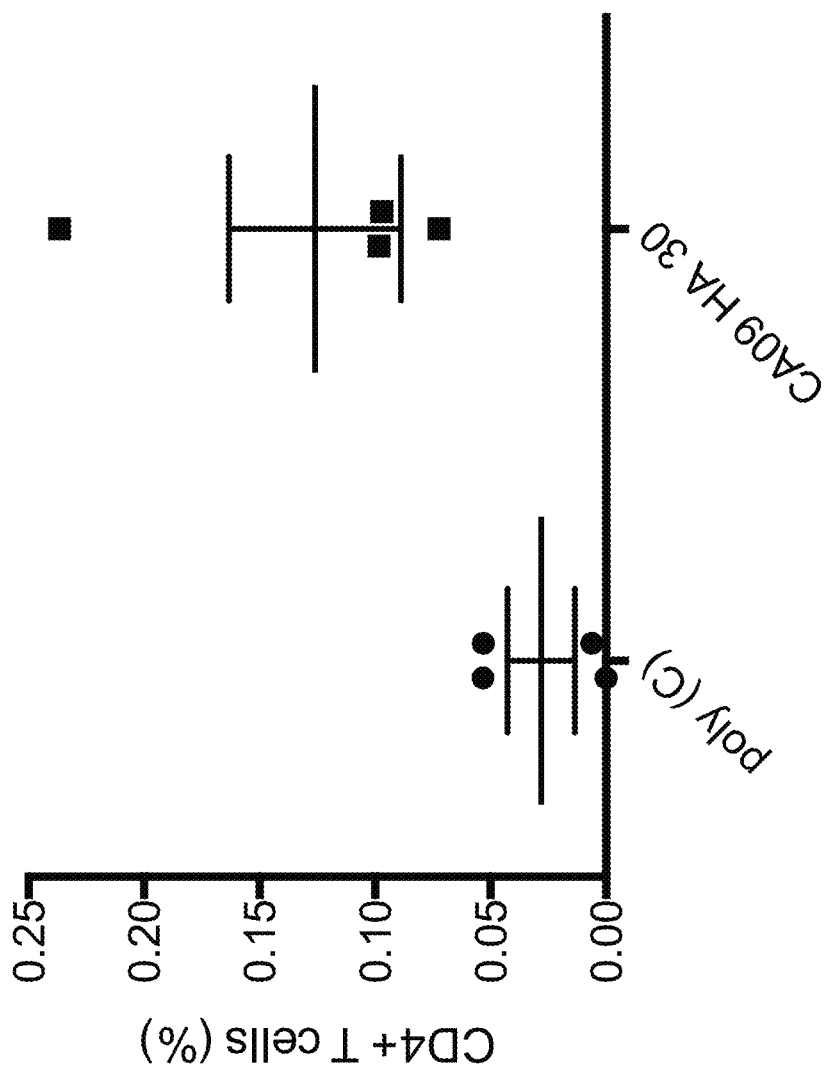
FIG. 40 is a graph depicting the results of example experiments measuring Tfh cell response 2 weeks after single administration of CA09 HA encoding mRNA-LNP. Tfh cells were defined as CD4+, memory+, CXCR5+, PD-1+ cells. Error bars are standard error of the mean.

Further, it was observed that a single administration of 30 μg of CA09 HA-encoding mRNA-LNP induced increased IFN-γ, TNF-α, and IL-2 in CD4+ T cells, measured 2 weeks after the single administration, as compared to poly(C) control (FIG. 39). It was also observed that that single administration of 30 μg of CA09 HA-encoding mRNA-LNP resulted in increased percentage of Tfh cells, measured 2 weeks after single administration (FIG. 40).

Figure 41:
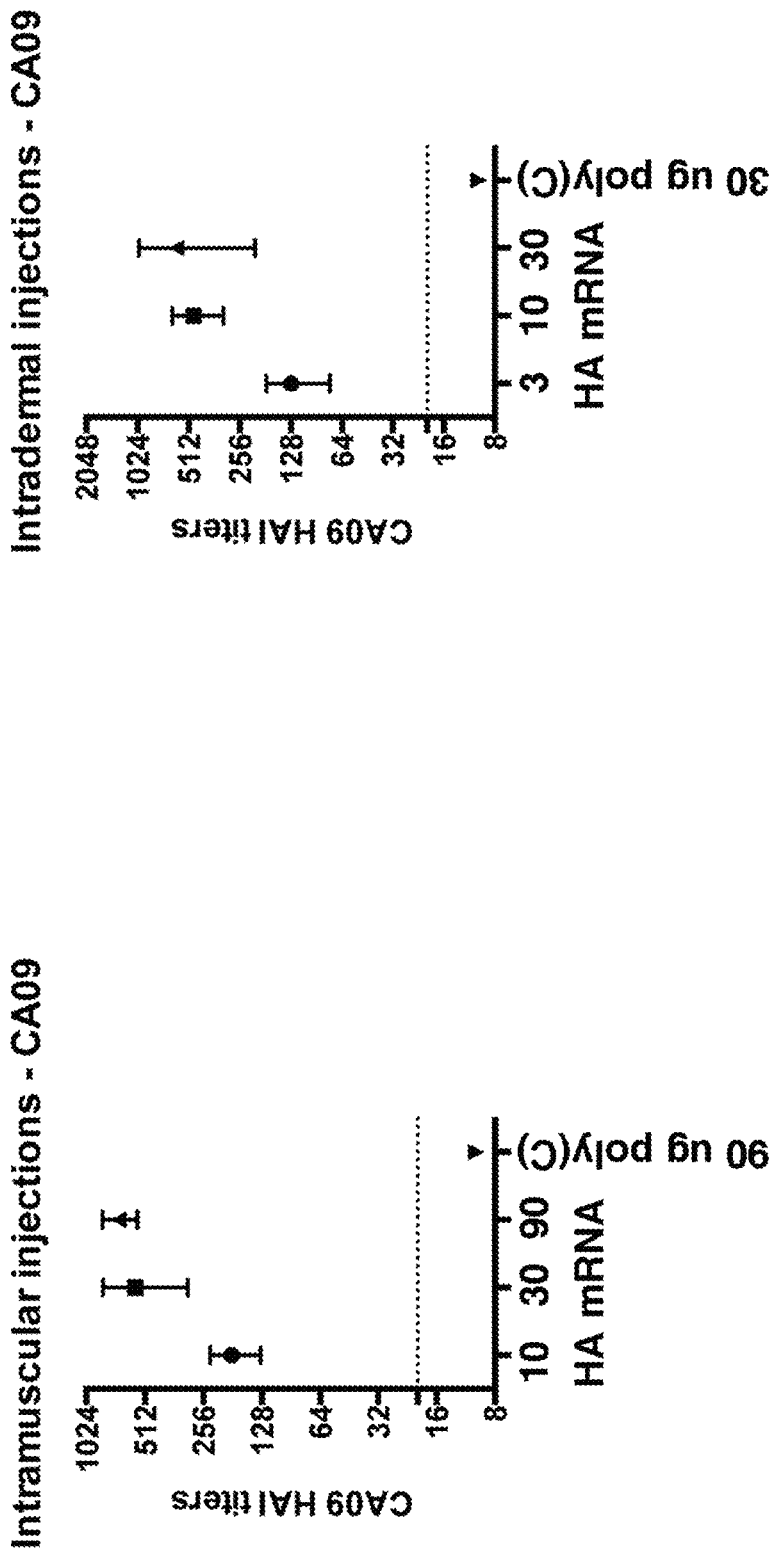
FIG. 41 is a set of graphs depicting the results of example experiments measuring HA inhibition titers after single administration of CA09 HA encoding mRNA administered by intramuscular injection (left) and intradermal injection (right).

An experiment was conducted to examine the effectiveness of intramuscular delivery of CA09 HA-encoding mRNA-LNP. Subjects were administered either 10 μg, 30 μg, or 90 μg of CA09 HA-encoding mRNA-LNPs, administered by intramuscular injection, or with 3 μg, 10 μg, or 30 μg of CA09 HA-encoding mRNA-LNPs administered by intradermal injection. It was observed that intramuscular injection resulted in a similar immune response as compared to intradermal injection but required 3 times as much mRNA (FIG. 41).

The data presented herein demonstrate the clear superiority of the modified mRNA-LNP vaccine for influenza. Importantly, it is shown that only a single immunization in a naïve host is needed for complete protection against influenza. It is understood that this is the first reported demonstration that a single immunization with a non-replicating vaccine is capable of inducing a high titer IgG response and over a quarter of the response is directed at the stalk. While not wishing to be bound by any particular theory, the potent antibody response is likely due to the Tfh response that makes up half of the CD4 helper response. Further, it is demonstrated the mRNA-LNP vaccine can be effective following delivery via different routes, which greatly expands the utility of the mRNA-LNP vaccine.

Example 3: Mechanism of Modified mRNA Induction of Potent Tfh Responses

Nucleoside modified mRNA in LNPs does not induce an innate immune response. It was examined whether it is the lack of adjuvant effect that results in the potent Tfh response. To investigate this, PR8 HA mRNA was manufactured that only differs by the lack of nucleoside modification but contains modification of the nucleoside sequence. This results in similar levels of translation but the unmodified mRNA induces an innate immune response.

Figure 42:
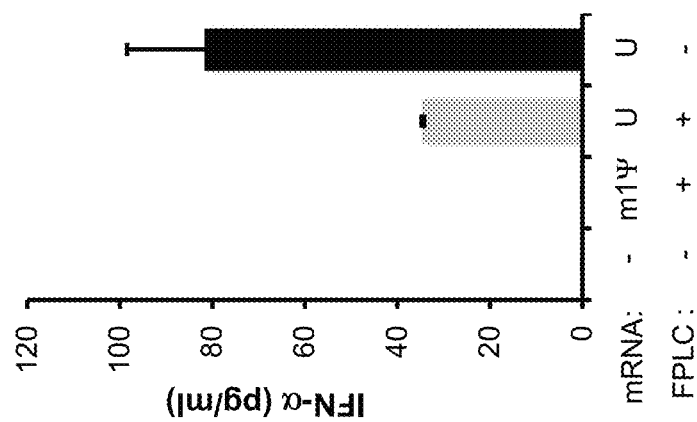
FIG. 42 is a graph depicting the results of example experiments demonstrating INF-α production induced by codon optimized unmodified HA mRNA with none by m1ψ modified mRNA, demonstrating that unmodified codon optimized HA encoding mRNA induces an innate immune response.
Figure 43:
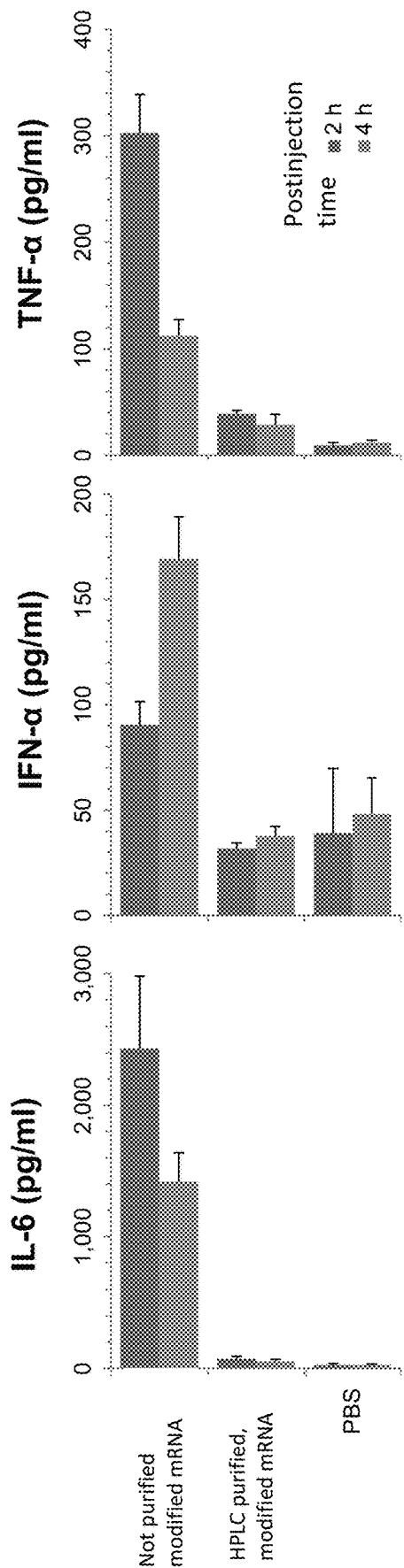
FIG. 43 is a set of graphs depicting the results of example experiments demonstrating that intravenous injection of HPLC purified nucleoside modified mRNA-LNP does not induce proinflammatory cytokines or type I interferons.

It was observed that codon-optimized FPLC-purified, but unmodified HA mRNA induces type 1 interferon production, demonstrating that the unmodified HA mRNA induces an innate immune response. However, the m1Ψ-modified mRNA did not induce an innate immune response (FIG. 42). Further, it was observed that intravenous injection of HPLC purified, nucleoside modified mRNA-LNP does not induce the production of proinflammatory cytokines IL-6, IFN-α, or TNF-α (FIG. 43) demonstrating a lack of innate immune activation.

Figure 44:
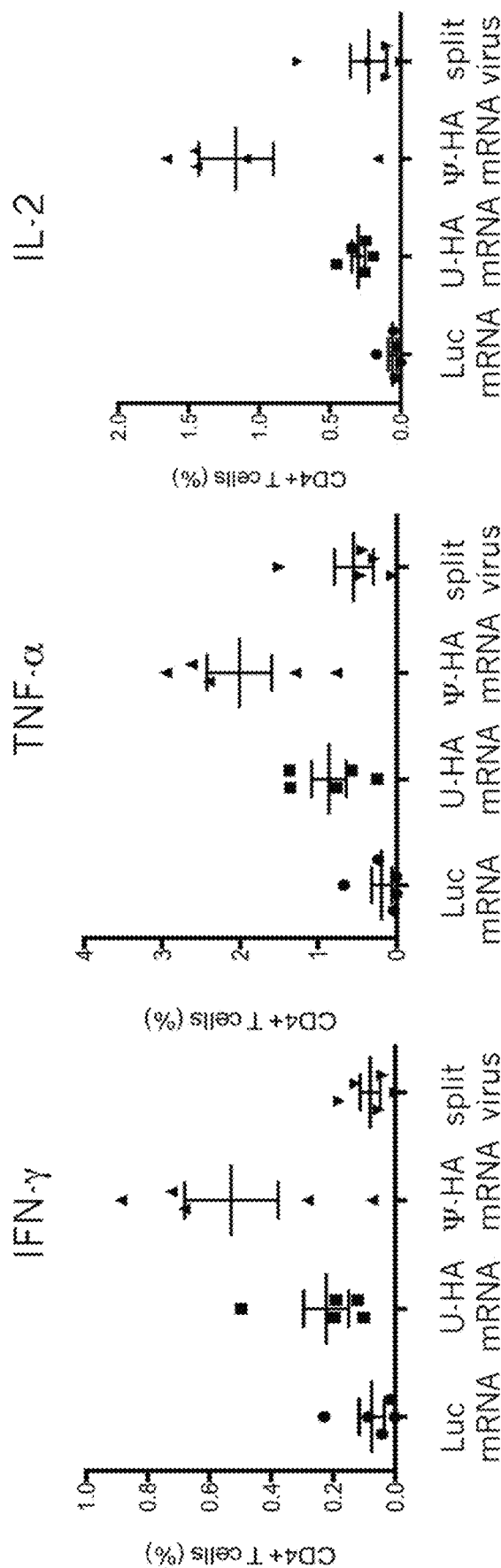
FIG. 44 is a set of graphs depicting the results of example experiments demonstrating that administration of nucleoside modified HA encoding mRNA induces significantly better CD4+ T cell response, as measured by IFN-γ (left), TNF-α (center), and IL-2 (right) production, as compared to unmodified HA encoding mRNA.

Experiments were conducted to compare mlxv modified mRNA with unmodified codon optimized mRNA in their ability to induce a CD4+ T cell response. It was observed that the nucleoside modified HA-encoding mRNA (does not induce innate immune response) induces a better CD4+ T cell response, as measured by the increased production of IFN-γ, TNF-α, and IL-2, as compared to unmodified HA-encoding mRNA (which does induce innate immune response) (FIG. 44).

Figure 45:
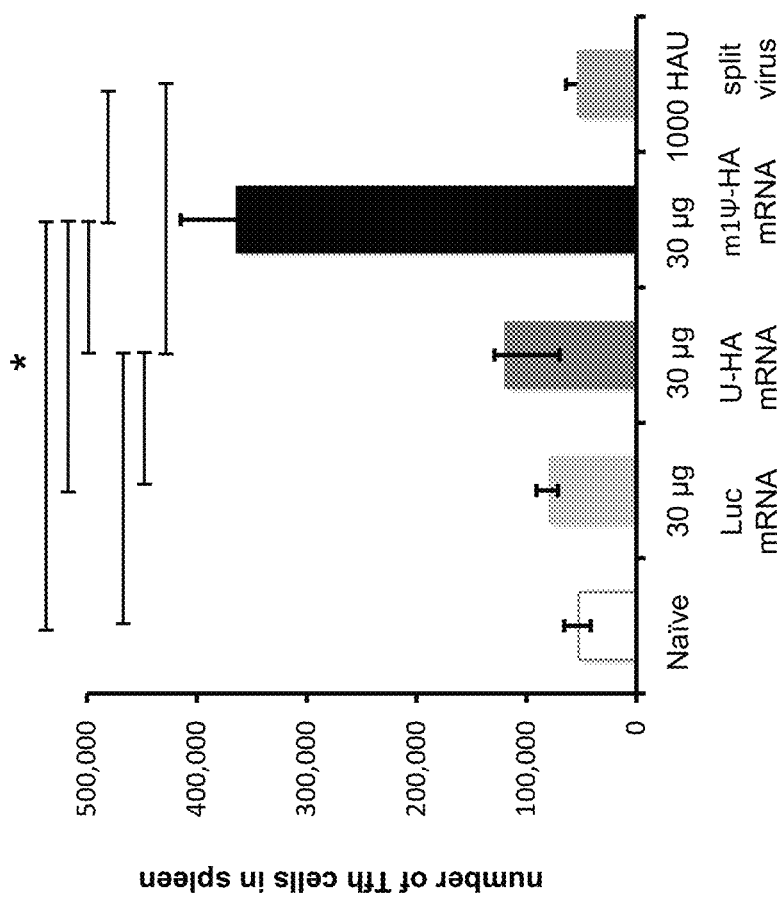
FIG. 45 is a graph depicting the results of example experiments demonstrating that administration of nucleoside modified HA encoding mRNA results in increased numbers of Tfh cells in the spleen, as compared to unmodified HA-encoding mRNA.
Figure 46:
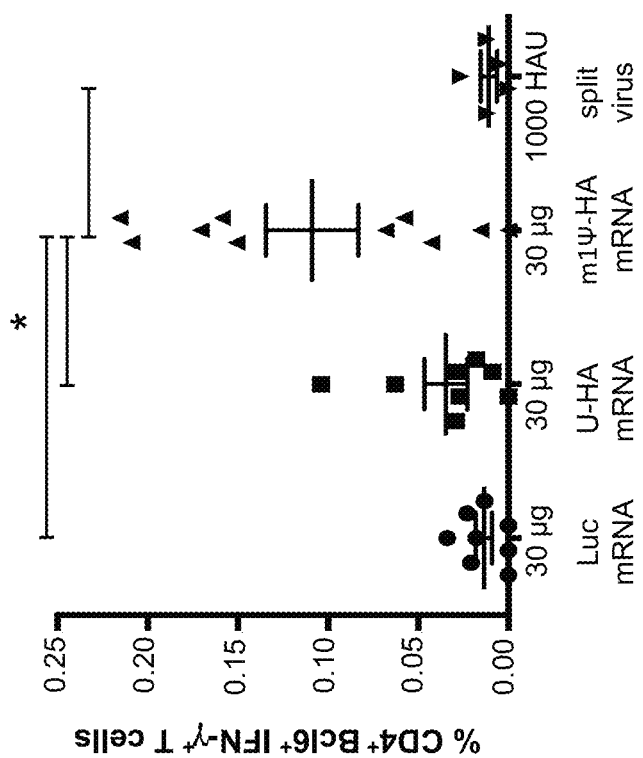
FIG. 46 is a graph depicting the results of example experiments demonstrating that administration of nucleoside modified HA encoding mRNA results in increased frequencies of antigen-specific Tfh cells response, as compared to unmodified HA-encoding mRNA.
Figure 47:
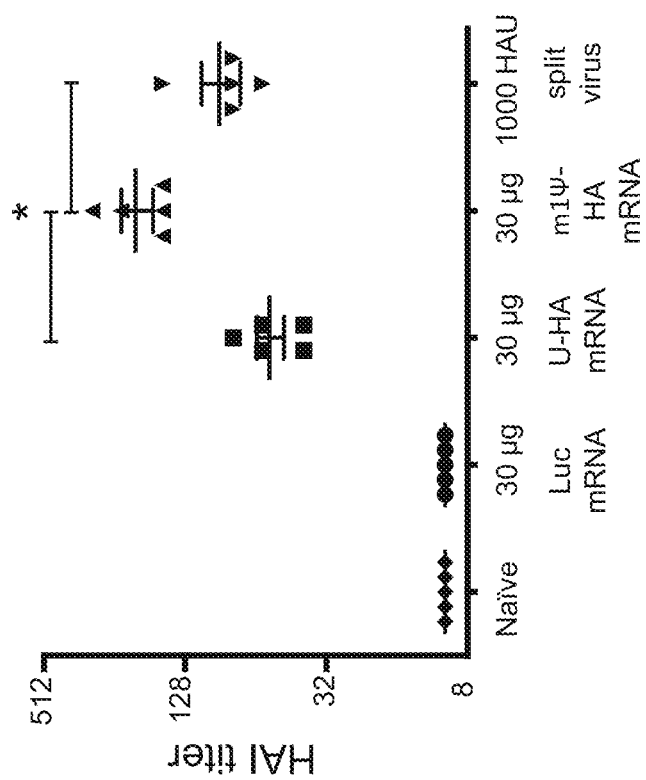
FIG. 47 is a graph depicting the results of example experiments demonstrating that administration of nucleoside modified HA encoding mRNA results in increased HA inhibition titers measured 10 days after a single administration of unmodified codon optimized or m1ψ, as compared to unmodified HA-encoding mRNA.

Experiments were conducted to examine the adaptive immune response generated by intradermal administration of 30 μg of m1Ψ-modified HA-encoding mRNA compared to 30 μg of unmodified codon-optimized PR8 HA-encoding mRNA. It was observed that m1Ψ-modified HA-encoding mRNA produced increased levels of Tfh cells in the spleen, as compared to unmodified HA-encoding mRNA and to controls (FIG. 45). Additionally, administration of m1Ψ-modified HA-encoding mRNA resulted in a greater antigen specific Tfh cell response, as measured by percentage of CD4+ Bcl6+IFN-γ+ T cells, as compared to unmodified HA-encoding mRNA (FIG. 46). Finally, m1Ψ-modified HA-encoding mRNA induced greater HA-specific antibody response, as measured by HA inhibition titers 10 days after single administration (FIG. 47).

These experiments demonstrate that HA-encoding mRNAs that only differed in containing m1Ψ versus unmodified mRNA and the ability to activate RNA sensors (only unmodified), but had similar levels of translation, have a differential ability in inducing an adaptive immune response. The m1Ψ modified mRNA was observed to induce a greater antigen-specific immune response. Most importantly, the lack of innate immune activation or adjuvant activity or induction of IFN-α induced the induction of potent Tfh cells.

Example 4: mRNA Delivery

Figure 48:
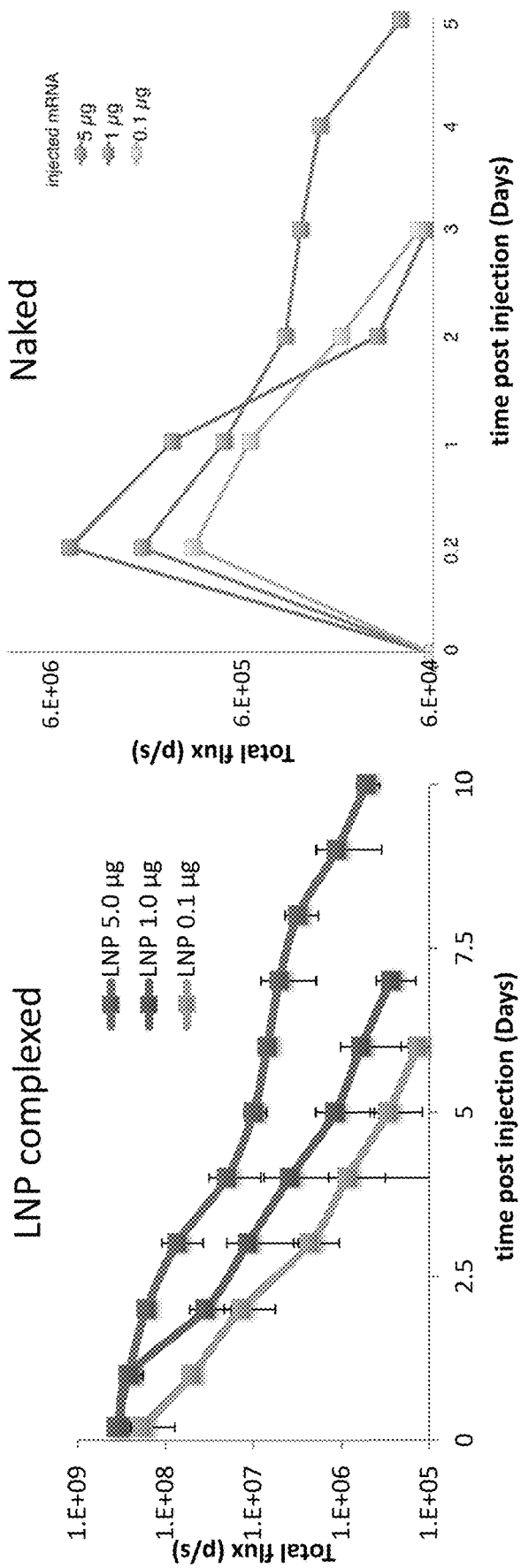
FIG. 48 is a set of graphs depicting the results of example experiments examining mRNA translation of luciferase encoding m1ψ modified mRNA administered as complexed in LNP (left) and naked (right). Translation was measured by injecting luciferase encoding m1ψ-mRNA and then 4 hours later, administering D-luciferin, and imaging on an IVIS spectrum. Activity was quantitated by selecting regions of increased signal and using IVIS software.

Experiments were conducted to visualize the expression of the m1Ψ modified mRNA. Mice were injected with 0.1

µg, 1 µg, or 5 µg of naked or LNP complexed m luciferase encoding mRNA and imaged by In Vivo Imaging (IVIS). mRNA translation was observed in all conditions (FIG. 48). LNP complexing increases the level and duration of mRNA translation (FIG. 48).

Example 5: Comparison of LNP Formulations

Figure 49:
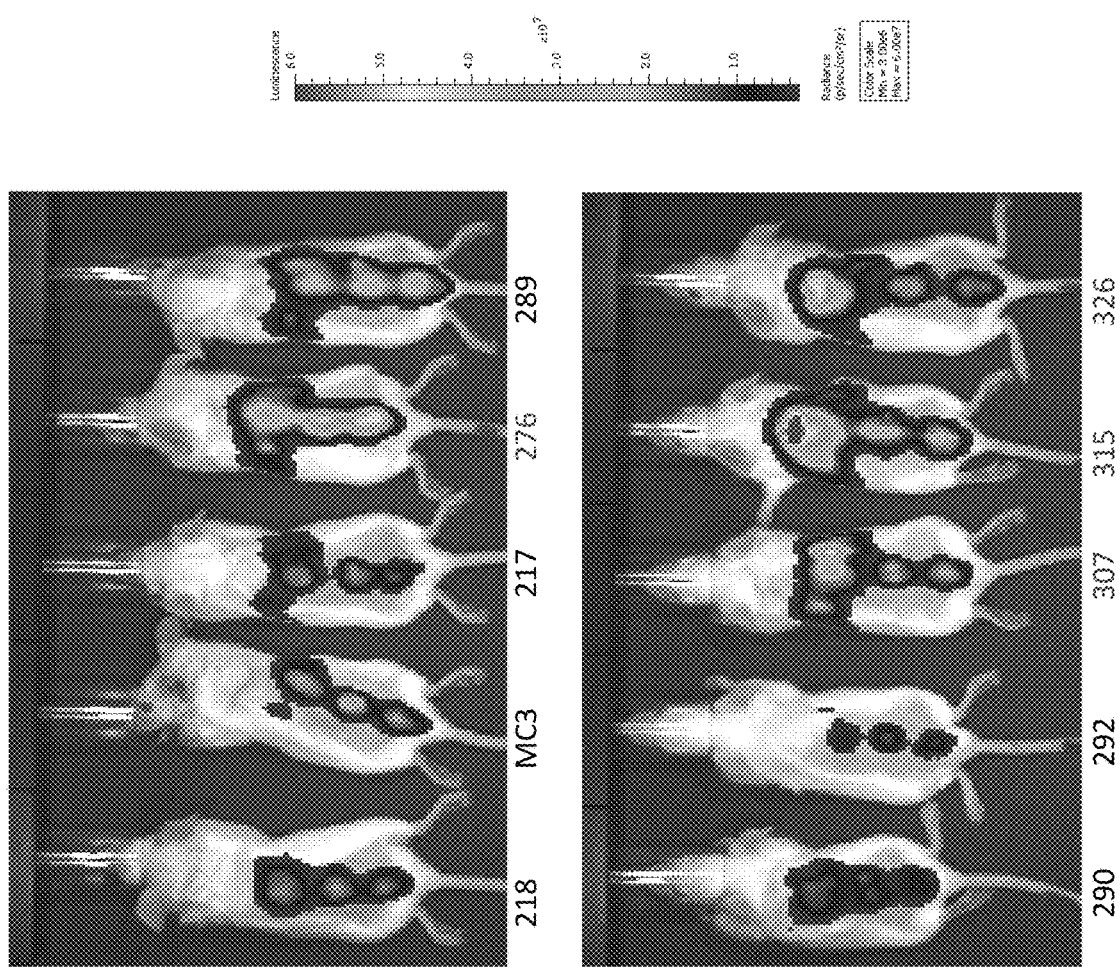
FIG. 49 depicts the results of example experiments which compare different LNP formulations intradermally injected into mice.

Experiments were conducted to examine the effectiveness of various LNP formulations, as measured by the effective translation of the encapsulated mRNA. LNPs comprising Luciferase encoding m-RNA were prepared as described in Example 15. The tested LNPs comprised cationic lipid 1-5, 1-6, 11-9, II-10, II-11, 11-12, 11-32, 111-3 or 111-7. Other components were as described in Example 15. Six week old BALB/c mice were intradermally injected with 3 µg of Luciferase encoding mRNA-LNPs. The expression of luciferase was measured by IVIS. The data show that mRNA can be effectively delivered using a variety of LNPs (FIG. 49). Accordingly, the data provide evidence that a wide variety of LNPs can be used to deliver nucleoside-modified RNA encoding at least one antigen Example 6: Synthesis of Compound I-5

Compound I-5 was prepared according to method B as follows:
A solution of hexan-1,6-diol (10 g) in methylene chloride (40 mL) and tetrahydrofuran (20 mL) was treated with 2-hexyldecanoyl chloride (10 g) and triethylamine (10 mL). The solution was stirred for an hour and the solvent removed. The reaction mixture was suspended in hexane, filtered and the filtrate washed with water. The solvent was removed and the residue passed down a silica gel (50 g) column using hexane, followed by methylene chloride, as the eluent, yielding 6-(2'-hexyldecanoyloxy)hexan-1-ol as an oil (7.4 g).

The purified product (7.4 g) was dissolved in methylene chloride (50 mL) and treated with pyridinum chlorochromate (5.2 g) for two hours. Diethyl ether (200 mL) as added and the supernatant filtered through a silica gel bed. The solvent was removed from the filtrate and resultant oil passed down a silica gel (50 g) column using a ethyl acetate/hexane (0-5%) gradient. 6-(2'-hexyldecanoyloxy) dodecanal (5.4 g) was recovered as an oil.

A solution of the product (4.9 g), acetic acid (0.33 g) and 2-N,N-dimethylaminoethylamine (0.40 g) in methylene chloride (20 mL) was treated with sodium triacetoxyborohydride (2.1 g) for two hours. The solution was washed with aqueous sodium hydroxide. The organic phase was dried over anhydrous magnesium sulfate, filtered and the solvent removed. The residue was passed down a silica gel (50 g) column using a methanol/methylene chloride (0-8%) gradient to yield the desired product (1.4 g) as a colorless oil.

Example 7: Synthesis of Compound I-6

Compound I-6 was prepared according to method B as follows:
A solution of nonan-1,9-diol (12.6 g) in methylene chloride (80 mL) was treated with 2-hexyldecanoic acid (10.0 g), DCC (8.7 g) and DMAP (5.7 g). The solution was stirred for two hours. The reaction mixture was filtered and the solvent removed. The residue was dissolved in warmed hexane (250 mL) and allowed to crystallize. The solution was filtered and the solvent removed. The residue was dissolved in methylene chloride and washed with dilute hydrochloric acid. The organic fraction was dried over anhydrous magnesium sulfate, filtered and the solvent removed. The residue was passed down a silica gel column (75 g) using 0-12% ethyl acetate/hexane as the eluent, yielding 9-(2'-hexyldecanoyloxy)nonan-1-ol (9.5 g) as an oil.

The product was dissolved in methylene chloride (60 mL) and treated with pyridinum chlorochromate (6.4 g) for two hours. Diethyl ether (200 mL) was added and the supernatant filtered through a silica gel bed. The solvent was removed from the filtrate and resultant oil passed down a silica gel (75 g) column using a ethyl acetate/hexane (0-12%) gradient, yielding 9-(2'-ethylhexanoyloxy)nonanal (6.1 g) as an oil.

A solution of the crude product (6.1 g), acetic acid (0.34 g) and 2-N,N-dimethylaminoethylamine (0.46 g) in methylene chloride (20 mL) was treated with sodium triacetoxyborohydride (2.9 g) for two hours. The solution was diluted with methylene chloride washed with aqueous sodium hydroxide, followed by water. The organic phase was dried over anhydrous magnesium sulfate, filtered and the solvent removed. The residue was passed down a silica gel (75 g) column using a methanol/methylene chloride (0-8%) gradient, followed by a second column (20 g) using a methylene chloride/acetic acid/methanol gradient. The purified fractions were dissolved in methylene chloride, washed with dilute aqueous sodium hydroxide solution, dried over anhydrous magnesium sulfate, filtered and the solvent removed, to yield the desired product (1.6 g) as a colorless oil.

Example 8: Synthesis of Compound II-9

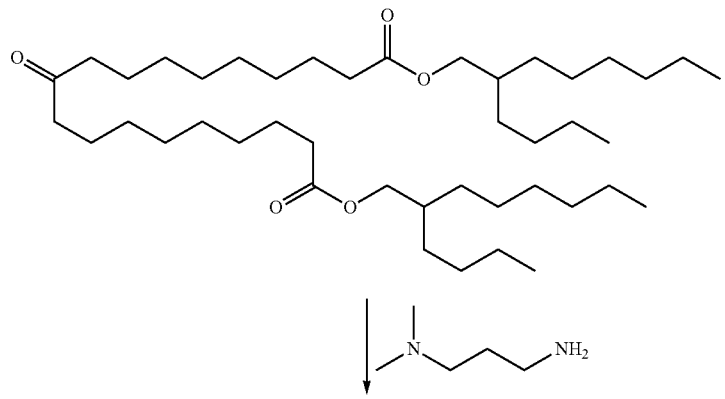

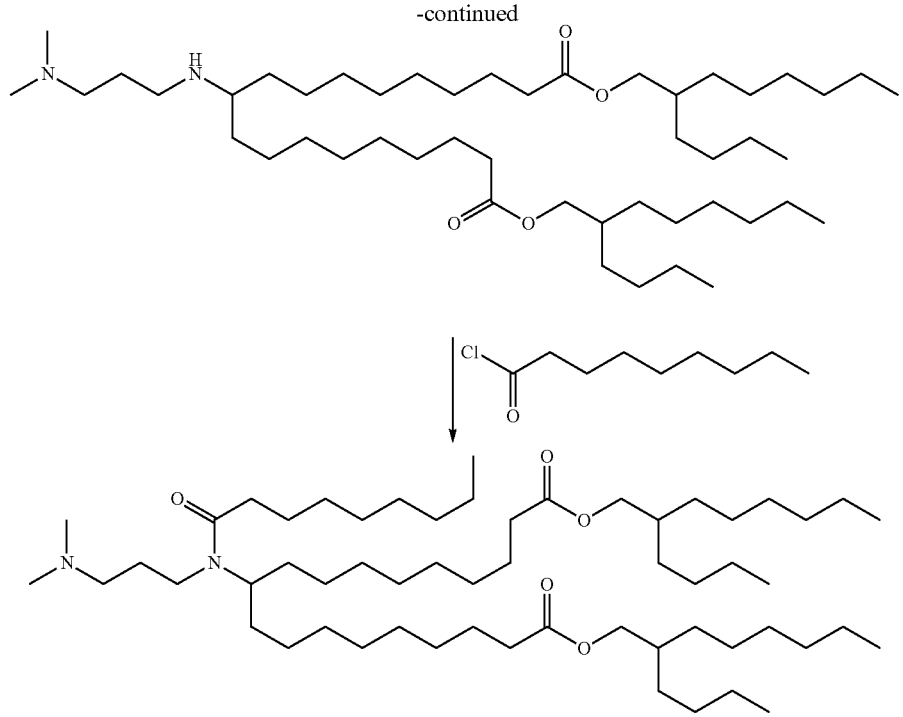

Compound II-9 was prepared according to method D as follows:

Step 1

3-dimethylamine-1-propylamine (1 eq. 1.3 mmol, 133 mg, 163 uL; MW102.18, d 0.812) and the ketone 9a (1 eq., 0.885 g, 1.3 mmol) were mixed in DCE (8 mL) and then treated with sodium triacetoxyborohydride (1.4 eq., 1.82 mmol, 386 mg; MW211.94) and AcOH (1 eq., 1.3 mmol, 78 mg, 74 uL, MW 60.05, d 1.06). The mixture was stirred at RT under an Ar atmosphere for 2 days. The reaction mixture was diluted with hexanes-EtOAc (9:1) and quenched by adding 0.1 N NaOH (20 mL). The organic phase was separated, washed with sat $NaHCO_3$, brine, dried over sodium sulfate, decanted and concentrated to give the desired product 9b as a slightly yellow cloudy oil (1.07 g, 1.398 mmol).

Step 2

A solution of nonanoyl chloride (1.3 eq., 1.27 mmol, 225 mg) in benzene (10 mL) was added via syringe to a solution of the compound 9b from step 1 (0.75 g, 0.98 mmol) and triethylamine (5 eq, 4.90 mmol, 0.68 mL) and DMAP (20 mg) in benzene (10 mL) at RT in 10 min. After addition, the mixture was stirred at RT overnight. Methanol (5.5 mL) was added to remove excess acyl chloride. After 3 h, the mixture was filtered through a pad of silica gel (1.2 cm). Concentration gave a colorless oil (0.70 g).

The crude product (0.70 g) was purified by flash dry column chromatography on silica gel (0 to 4% MeOH in chloroform). This yielded 457 mg of colorless oil, 0.50 mmol, 51%. 1HNMR (400 MHz, $CDCl_3$) δ: 4.54-4.36 (very br., estimated 0.3H, due to slow isomerization about amide bond), 3.977, 3.973 (two sets of doublets, 5.8 Hz, 4H), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 10H), 1.49-1.39 (m, 4H), 1.37-1.11 (62H), 0.92-0.86 (m, 15H).

Example 9: Synthesis of Compound II-10

Compound II-10 was prepared according to the general procedure D to yield 245 mg of colorless oil, 0.27 mmol, total yield 53% for 2 steps. $^1$HNMR (400 MHz, CDCl3) δ: 4.87 (quintet-like, 6.3 Hz, 2H), 4.54-4.36 (very br., estimated 0.3H, due to slow isomerization about amide bond), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 8H), 1.55-1.39 (m, 12H), 1.37-1.11 (60H), 0.92-0.86 (m, 15H).

Example 10: Synthesis of Compound II-11

Compound II-11 was prepared according to the general procedure D to yield 239 mg of colorless oil, 0.26 mmol, total yield 52% for 2 steps. $^1$HNMR (400 MHz, CDCl3) δ: 4.87 (quintet-like, 6.3 Hz, 2H), 4.54-4.36 (very br., estimated 0.3H, due to slow isomerization about amide bond), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 8H), 1.55-1.39 (m, 12H), 1.37-1.11 (62H), 0.92-0.86 (m, 15H).

Example 11: Synthesis of Compound II-12

Compound II-12 was prepared according to the general procedure D to yield 198 mg of colorless oil, 0.20 mmol, total yield 46% for 2 steps. $^1$HNMR (400 MHz, CDCl3) δ: 4.54-4.36 (very br., estimated 0.3H, due to slow isomerization about amide bond), 3.974, 3.971 (two sets of doublets, 5.8 Hz, 4H), 3.63 (quintet-like, 6.8 Hz, 0.7H), 3.14-3.09 (m, 2H), 2.33-2.25 (m, 8H), 2.23, 2.22 (two sets of singlet, 6H), 1.76-1.56 (m, 10H), 1.49-1.39 (m, 4H), 1.37-1.11 (76H), 0.92-0.86 (m, 15H).

Example 12: Synthesis of Compound III-3

A solution of 6-(2'-hexyldecanoyloxy)hexan-1-al (2.4 g), acetic acid (0.33 g) and 4-aminobutan-1-ol (0.23 g) in methylene chloride (20 mL) was treated with sodium triacetoxyborohydride (1.3 g) for two hours. The solution was washed with aqueous sodium bicarbonate solution. The organic phase was dried over anhydrous magnesium sulfate, filtered and the solvent removed. The residue was passed down a silica gel column using a methanol/methylene chloride (0-8/100-92%) gradient, yielding compound 3 as a colorless oil (0.4 g).

Example 13: Synthesis of Compound III-7

A solution of 6-(2'-hexyldecanoyloxy)hexan-1-al (2.4 g), acetic acid (0.14 g) and 5-aminopentan-1-ol (0.24 g) in methylene chloride (20 mL) was treated with sodium triacetoxyborohydride (1.3 g) for two hours. The solution was washed with aqueous sodium hydrogen carbonate solution. The organic phase was dried over anhydrous magnesium sulfate, filtered and the solvent removed. The residue was passed down a silica gel column using a methanol/methylene chloride (0-8/100-92%) gradient, yielding compound 7 as a colorless oil (0.5 g)

Example 14: Synthesis of a Representative PEG Lipid

Pegylated lipid 14-6 ("PEG-DMA") was prepared according to the above reaction scheme, wherein n approximates the center of the range of ethylene oxide repeating units in the pegylated lipid.

Synthesis of 14-1 and 14-2

To a solution of myristic acid (6 g, 26 mmol) in toluene (50 mL) was added oxalyl chloride (39 mmol, 1.5 eq. 5 g) at RT. After the resulting mixture was heated at 70° C. for 2 h, the mixture was concentrated. The residue was taken up in toluene and concentrated again. The residual oil was added via a syringe to a concentrated ammonia solution (20 mL) at 10° C. The reaction mixture was filtered and washed with water. The white solid was dried in vacuo. The desired product was obtained as a white solid (3.47 g, 15 mmol, 58.7%).

Synthesis of 14-3

To suspension of 20-2 (3.47 g, 15 mmol) in THF (70 mL) was added in portions of lithium aluminium hydride (1.14 g, 30 mmol) at RT during 30 min period of time. Then the mixture was heated to reflux gently (oil bath at 65° C.) overnight. The mixture was cooled to 5° C. and sodium sulphate 9 hydrate was added. The mixture was stirred for 2 h, filtered through a layer of celite, washed with 15% of MeOH in DCM (200 mL). The filtrate and washings were

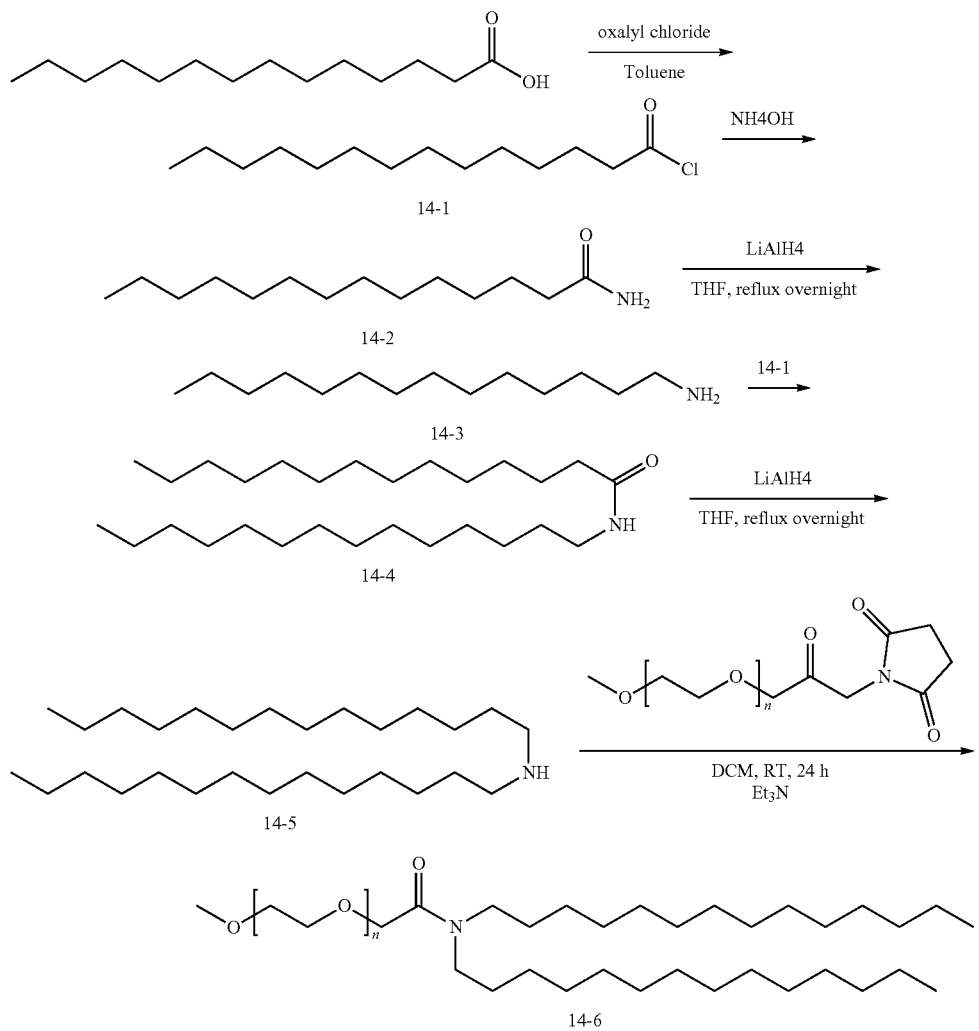

combined and concentrated. The residual solid was dried in vacuo. The desired product was obtained as a white solid (2.86 13.4 mmol, 89.5%).

Synthesis of 14-4

To a solution of myristic acid (3.86 g, 16.9 mmol) in benzene (40 mL) and DMF (1 drop) was added oxalyl chloride (25.35 mmol, 1.5 eq. 3.22 g) at RT. The mixture was stirred at RT for 1.5 h. Heated at 60° C. for 30 min. The mixture was concentrated. The residue was taken up in toluene and concentrated again. The residual oil (light yellow) was taken in 20 mL of benzene and added via syringe to a solution of 20-3 (2.86 13.4 mmol) and triethylamine (3.53 mL, 1.5 eq) in benzene (40 mL) at 10° C. After addition, the resulting mixture was stirred at RT overnight. The reaction mixture was diluted with water and was adjusted to pH 6-7 with 20% H2SO4. The mixture was filtered and washed with water. A pale solid was obtained. The crude product was recrystallized from methanol. This gave the desired product as an off-white solid (5.65 g, 13 mmol, 100%).

Synthesis of 14-5

To suspension of 20-4 (5.65 g, 13 mmol) in THF (60 mL) was added in portions lithium aluminium hydride (0.99 g, 26 mmol) at RT during 30 min period of time. Then the mixture was heated to reflux gently overnight. The mixture was cooled to 0° C. and sodium sulphate 9 hydrate. The mixture was stirred for 2 h, then filtered through a pad of celite and silica gel and washed with ether first. The filtrate turned cloudy and precipitation formed. Filtration gave a white solid. The solid was recrystallized from MeOH and a colorless crystalline solid (2.43 g).

The pad of celite and silica gel was then washed 5% of MeOH in DCM (400 mL) and then 10% of MeOH in DCM with 1% of triethylamine (300 mL). The fractions containing the desired product were combined and concentrated. A white solid was obtained. The solid was recrystallized from MeOH and a colorless crystalline solid (0.79 g). The above two solids (2.43 g and 0.79 g) were combined and dried in vacuo (3.20 g, 60%). 1HNMR (CDCl3 at 7.27 ppm) δ: 2.58 (t-like, 7.2 Hz, 4H), 1.52-1.44 (m, 4H), 1.33-1.24 (m, 44H), 0.89 (t-like, 6.6 Hz, 6H), 2.1-1.3 (very broad, 1H).

Synthesis of 14-6

To a solution of 20-5 (7 mmol, 2.87 g) and triethylamine (30 mmol, 4.18 mL) in DCM (100 mL) was added a solution of mPEG-NHS (from NOF, 5.0 mmol, 9.97 g, PEG MW approx. 2,000, n=about 45) in DCM (120 mL). After 24 h the reaction solution was washed with water (300 mL). The aqueous phase was extracted twice with DCM (100 mL×2). DCM extracts were combined, washed with brine (100 mL). The organic phase was dried over sodium sulfate, filtered, concentrated partially. The concentrated solution (ca 300 mL) was cooled at ca −15 C. Filtration gave a white solid (1.030 g, the unreacted starting amine). To the filtration was added Et$_3$N (1.6 mmol, 0.222 mL, 4 eq) and acetic anhydride (1.6 mmol, 164 mg). The mixture was stirred at RT for 3 h and then concentrated to a solid. The residual solid was purified by column chromatography on silica gel (0-8% methanol in DCM). This gave the desired product as a white solid (9.211 g). 1HNMR (CDCl3 at 7.27 ppm) δ: 4.19 (s, 2H), 3.83-3.45 (m, 180-200H), 3.38 (s, 3H), 3.28 (t-like, 7.6 Hz, 2H, CH$_2$N), 3.18 (t-like, 7.8 Hz, 2H, CH$_2$N), 1.89 (s, 6.6 H, water), 1.58-1.48 (m, 4H), 1.36-1.21 (m, 48-50H), 0.88 (t-like, 6.6 Hz, 6H).

Example 15: Preparation of Lipid Nanoparticle Compositions

LNPs were prepared as follows. Cationic lipid, DSPC, cholesterol and PEG-lipid (compound 14-6) were solubilized in ethanol at a molar ratio of approximately 50:10:38.5:1.5. LNPs for Examples 1, 2, 3 and 4 included cationic lipid compound 1-6 and the foregoing components. LNPs of Example 5 included the indicated cationic lipid and the foregoing components. Lipid nanoparticles (LNP) were prepared at a total lipid to mRNA weight ratio of approximately 10:1 to 30:1. Briefly, the mRNA was diluted to 0.05 to 0.2 mg/mL in 10 to 50 mM citrate buffer, pH 4. Syringe pumps were used to mix the ethanolic lipid solution with the mRNA aqueous solution at a ratio of about 1:5 to 1:3 (vol/vol) with total flow rates above 15 ml/min. The ethanol was then removed and the external buffer replaced with PBS by dialysis. Finally, the lipid nanoparticles were filtered through a 0.2 μm pore sterile filter. Lipid nanoparticle particle size was 70-90 nm diameter as determined by quasi-elastic light scattering using a Malvern Zetasizer Nano (Malvern, UK).

Example 16: Sequences

Table 4 below provides sequence identifiers and description of nucleic acid and amino acid sequences described herein.

TABLE 4

| Sequences | |
|---|---|
| Sequence Description | Number |
| Nucleic acid sequence encoding Env | SEQ ID NO: 1 |
| Entire mRNA encoding Env (with UTRs and poly(A) tail) | SEQ ID NO: 2 |
| PR8 HA amino acid sequence | SEQ ID NO: 3 |
| Native nucleoside sequence encoding PR8 HA | SEQ ID NO: 4 |
| Codon optimized used in mRNA encoding PR8 HA | SEQ ID NO: 5 |
| Cal/7/2009 HA amino acid sequence | SEQ ID NO: 6 |
| Native nucleoside sequence encoding Cal/7/2009 HA | SEQ ID NO: 7 |
| Codon optimized sequence used in mRNA encoding Cal/7/2009 HA | SEQ ID NO: 8 |

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A composition for inducing an adaptive immune response in a subject, the composition comprising at least one nucleoside-modified RNA encoding at least one influenza hemagglutinin (HA) antigen, wherein the mRNA molecule encoding the influenza antigen comprises a sequence selected from SEQ ID NO:5 and SEQ ID NO:8.

2. The composition of claim 1, wherein the at least one isolated nucleoside-modified RNA comprises pseudouridine.

3. The composition of claim 1, wherein the at least one isolated nucleoside-modified RNA comprises 1-methyl-pseudouridine.

4. The composition of claim 1, wherein the composition further comprises an adjuvant.

5. The composition of claim 1, wherein the at least one nucleoside-modified RNA further encodes at least one adjuvant.

6. The composition of claim 1, further comprising a lipid nanoparticle (LNP).

7. The composition of claim 6, wherein the at least one nucleoside-modified RNA is encapsulated within the LNP.

8. The composition of claim 1, wherein the composition is a vaccine.

9. A method of inducing an adaptive immune response in a subject comprising administering to the subject an effective amount of the composition of claim 1.

10. The method of claim 9, wherein the composition is administered by a delivery route selected from the group consisting of intradermal, subcutaneous, and intramuscular.

11. The method of claim 9, wherein the method comprises a single administration of the composition.

12. The method of claim 9, wherein the method comprises a multiple administrations of the composition.

13. The method of claim 9, wherein the method treats an influenza infection.

* * * * *

UNITED STATES PATENT AND TRADEMARK OFFICE
CERTIFICATE OF CORRECTION

| | | |
|---|---|---|
| PATENT NO. | : 12,138,305 B2 | Page 1 of 1 |
| APPLICATION NO. | : 17/705837 | |
| DATED | : November 12, 2024 | |
| INVENTOR(S) | : Drew Weissman and Norbert Pardi | |

It is certified that error appears in the above-identified patent and that said Letters Patent is hereby corrected as shown below:

In the Specification

Column 1 Lines 17-23 Please replace the paragraph under the heading "STATEMENT REGARDING FEDERALLY SPONSORED RESEARCH OR DEVELOPMENT" with the following:
--This invention was made with government support under AI090788 awarded by the National Institutes of Health. The government has certain rights in the invention.--

Signed and Sealed this
Tenth Day of December, 2024

Katherine Kelly Vidal
*Director of the United States Patent and Trademark Office*